United States Patent
Del'Guidice et al.

(10) Patent No.: US 9,982,267 B2
(45) Date of Patent: May 29, 2018

(54) RATIONALLY-DESIGNED SYNTHETIC PEPTIDE SHUTTLE AGENTS FOR DELIVERING POLYPEPTIDE CARGOS FROM AN EXTRACELLULAR SPACE TO THE CYTOSOL AND/OR NUCLEUS OF A TARGET EUKARYOTIC CELL, USES THEREOF, METHODS AND KITS RELATING TO SAME

(71) Applicant: Feldan Bio Inc., Québec (CA)

(72) Inventors: Thomas Del'Guidice, Québec (CA); Jean-Pascal Lepetit-Stoffaes, Québec (CA); David Guay, Québec (CA)

(73) Assignee: FELDAN BIO INC., Quebec (CA)

( * ) Notice: Subject to any disclaimer, the term of this patent is extended or adjusted under 35 U.S.C. 154(b) by 0 days. days.

(21) Appl. No.: 15/666,139

(22) Filed: Aug. 1, 2017

(65) Prior Publication Data
US 2018/0100158 A1 Apr. 12, 2018

Related U.S. Application Data

(60) Provisional application No. 62/407,232, filed on Oct. 12, 2016, provisional application No. 62/535,010, filed on Jul. 20, 2017.

(51) Int. Cl.
*C12Q 1/68* (2018.01)
*C12N 15/62* (2006.01)
(Continued)

(52) U.S. Cl.
CPC .......... *C12N 15/62* (2013.01); *C07K 14/4705* (2013.01); *C07K 16/18* (2013.01);
(Continued)

(58) Field of Classification Search
CPC .............. C07K 14/001; C07K 2319/01; C07K 2319/10; C07K 2319/21; C12N 15/907; C12N 2501/60; C12N 2501/998
See application file for complete search history.

(56) References Cited

U.S. PATENT DOCUMENTS

2016/0298078 A1  10/2016  Guay et al.

FOREIGN PATENT DOCUMENTS

WO  WO-2015089462 A1  6/2015
WO  WO-2016161516 A1  10/2016

OTHER PUBLICATIONS

Aguila, et al., (2011). SALL4 is a robust stimulator for the expansion of hematopoietic stem cells. Blood 118(3):576-585.
(Continued)

*Primary Examiner* — Reza Ghafoorian
(74) *Attorney, Agent, or Firm* — Wilson Sonsini Goodrich & Rosati

(57) ABSTRACT

The present description relates to methods for delivering polypeptide cargos from an extracellular space to the cytosol and/or nucleus of a target eukaryotic cell. The methods involve contacting the cell with the polypeptide cargo in the presence of a peptide shuttle agent at a concentration sufficient to increase the polypeptide cargo's transduction efficiency. Also described here are parameters that may be used in the rational design of such synthetic peptide shuttle agents, peptide shuttle agents that satisfy one or more of these design parameters, as well as methods and compositions relating to the use of the synthetic peptide shuttle agents for delivery of a variety of polypeptide cargos (such as transcription factors, antibodies, CRISPR-associated nucleases and functional genome editing complexes) from an extracellular space to the cytosol and/or nucleus of target eukaryotic cells. Applications and targets for genome-edit-
(Continued)

ing NK cells for improved immunotherapy are also described.

20 Claims, 52 Drawing Sheets

(51) Int. Cl.
C07K 17/06 (2006.01)
C07K 14/47 (2006.01)
C07K 16/18 (2006.01)
C07K 16/46 (2006.01)

(52) U.S. Cl.
CPC .............. *C07K 16/46* (2013.01); *C07K 17/06* (2013.01); *C07K 2319/01* (2013.01); *C07K 2319/03* (2013.01); *C07K 2319/09* (2013.01); *C07K 2319/70* (2013.01)

(56) References Cited

OTHER PUBLICATIONS

Akinci, et al. (2012). Reprogramming of pancreatic exocrine cells towards a beta (beta) cell character using Pdx1, Ngn3 and MafA. Biochem J, 442(3):539-550.
Alford et al., (2009).Toxicity of organic fluorophores used in molecular imaging: literature review. Mol Imaging. 8(6):341-54.
Amand, et al., (2012) Functionalization with C-terminal cysteine enhances transfection efficiency of cell-penetrating peptides through dimer formation. Biochem Biophys Res Commun, 418(3):469-474.
Andreu, et al., (1992) Shortened cecropin A-melittin hybrids. Significant size reduction retains potent antibiotic activity. FEBS Letters, 296:190-194.
Aoukaty, A. & Tan, R. (2005). Role for glycogen synthase kinase-3 in NK cell cytotoxicity and X-linked lymphoproliferative disease. J Immunol 174:4551-8.
Barrangou, R. and Luciano A. Marraffini (2014). CRISPR-Cas Systems: Prokaryotes Upgrade to Adaptive Immunity. Mod. Cell 54(2):234-244.
Bejarano, L. A. and C. Gonzalez (1999) Motif trap: A rapid method to clone motifs that can target proteins to defined subcellular localisations J Cell Sci, 112(Pt 23):4207-4211.
Bikard et al., (2013) Programmable repression and activation of bacterial gene expression using an engineered CRISPR-Cas system. Nucleic Acids Res. 41:7429-7437.
Boman, et al., (1989) Antibacterial and antimalarial properties of peptides that are cecropin-melittin hybrids. FEBS letters, 259:103-106.
Braud, et al., (1998). HLA-E binds to natural killer cell receptors CD94/NKG2A, B and C. Nature 391:795-9.
Buganim et al., (2014) The Developmental Potential of iPSCs Is Greatly Influenced by Reprogramming Factor Selection. Cell stem cell. 15: 295-309.
Burstein et al., (2017), New CRISPR-Cas systems from uncultivated microbes. Nature. 542(7640):237-241.
Chan, C. K. and D. A. Jans (1999) Enhancement of polylysine-mediated transferrinfection by nuclear localization sequences: polylysine does not function as a nuclear localization sequence. Hum Gene Ther., 10(10):1695-1702.
Chan, C. K. and D. A. Jans (2001) Enhancement of MSH receptor- and GAL4-mediated gene transfer by switching the nuclear import pathway. Gene Ther 8(2):166-171.
Cong et al., (2013). Multiplex genome engineering using CRISPR/Cas systems. Science, 339: 819-823.
Cooper, et al., (2001). The biology of human natural killer-cell subsets. Trends Immunol 22:633- 640 (Abstract).
Cox et al. Therapeutic genome editing: prospects and challenges. Nat Med 21:121-131 (2015).

de Kruijf, et al., (2010). HLA-E and HLA-G expression in classical HLA class I-negative tumors is of prognostic value for clinical outcome of early breast cancer patients. J Immunol 185:7452-9.
Delconte, et al., (2016). CIS is a potent checkpoint in NK cell-mediated tumor immunity. Nat Immunol 17:816-24.
Denman, et al., (2012). Membrane-bound IL-21 promotes sustained ex vivo proliferation of human natural killer cells. PLoS ONE 7:e30264.
Dolfini, et al., (2012). The short isoform of NF-YA belongs to the embryonic stem cell transcription factor circuitry. Stem Cells, 30(11):2450-2459.
Drin, et al., (2003) Studies on the internalization mechanism of cationic cell-penetrating peptides. J Biol Chem,278(33):31192-31201.
Eisenberg et al., (1982). "The helical hydrophobic moment: a measure of the amphiphilicity of a helix." Nature 299:371-374. (Abstract only).
El-Andaloussi, et al., (2007). A novel cell-penetrating peptide, M918, for efficient delivery of proteins and peptide nucleic acids. Mol Ther, 15(10):1820-1826.
Elmquist, et al., (2001). "VE-cadherin-derived cell-penetrating peptide, pVEC, with carrier functions." Exp Cell Res 269(2):237-244.
El-Sayed, et al., (2009) Delivery of macromolecules using arginine-rich cell-penetrating peptides: ways to overcome endosomal entrapment. AAPS J, 11(1):13-22.
Erazo-Oliveras et al., (2014) Protein delivery into live cells by incubation with an endosomolytic agent. Nat Methods. (8):861-7.
Fanara, et al., (2000). Quantitative analysis of nuclear localization signal (NLS)-importin alpha interaction through fluorescence depolarization. Evidence for auto-inhibitory regulation of NLS binding. J Biol Chem 275(28):21218-21223.
Fasoli et al., (2014) Mechanistic insight into CM18-Tat11 peptide membrane-perturbing action by whole-cell patch-clamp recording. Molecules. 19(7):9228-39.
Fawell,et al., (1994). Tat-mediated delivery of heterologous proteins into cells. Proc Natl Acad Sci U S A, 91(2):664-668.
Fominaya, et al., (1998). A chimeric fusion protein containing transforming growth factor-alpha mediates gene transfer via binding to the EGF receptor. Gene Ther 5(4):521-530.
Fominaya, J. and W. Wels (1996). Target cell-specific DNA transfer mediated by a chimeric multidomain protein. Novel non-viral gene delivery system. J Biol Chem 271(18):10560-10568.
Fonoudi, et al., (2013). ISL1 protein transduction promotes cardiomyocyte differentiation from human embryonic stem cells. PLoS One 8(1):e55577.
Gao et al., (2016) DNA-guided genome editing using the Natronobacterium gregoryi Argonaute. Nature Biotechnology 34:768-773.
Giguère et al., (2015) Machine learning assisted design of highly active peptides for drug discovery. PLoS Comput Biol. 11(4):e1004074.
Gilbert et al., (2013) CRISPR-mediated modular RNA-guided regulation of transcription in eukaryotes. Cell 154:442-451.
Gilmore, T. D. and H. M. Temin (1988). v-rel oncoproteins in the nucleus and in the cytoplasm transform chicken spleen cells. J Virol 62(3): 703-714.
Glover, et al.,(2009). Multifunctional protein nanocarriers for targeted nuclear gene delivery in non-dividing cells. FASEB J 23(9):2996-3006.
Gomez-Cabrero et al., Use of transduction proteins to target trabecular meshwork cells: outflow modulation by profilin I. Molecular Vision, 11:1071-1082, 2005.
Gordon, et al., (2012). The transcription factors T-bet and Eomes control key checkpoints of natural killer cell maturation. Immunity. 36(1):55-67.
Gottschalk, et al., (1996). A novel DNA-peptide complex for efficient gene transfer and expression in mammalian cells. Gene Ther 3(5):448-457.
Gould, et al., (1989). A conserved tripeptide sorts proteins to peroxisomes. J Cell Biol 108(5): 1657-1664.
Green, M. and P. M. Loewenstein (1988). Autonomous functional domains of chemically synthesized human immunodeficiency virus tat trans-activator protein. Cell 55(6):1179-1188.

(56) References Cited

OTHER PUBLICATIONS

Grimes, et al., (1996). Endocytosis of activated TrkA: evidence that nerve growth factor induces formation of signaling endosomes. J Neurosci 16(24):7950-7964.
Guo, et al., (2015). Predictive value of HLA-G and HLA-E in the prognosis of colorectal cancer patients. Cell Immunol 293:10-6.
Hallbrink, et al., (2001). Cargo delivery kinetics of cell-penetrating peptides. Biochim Biophys Acta 1515(2):101-109.
Herce, H. D. and A. E. Garcia (2007). Molecular dynamics simulations suggest a mechanism for translocation of the HIV-1 TAT peptide across lipid membranes. Proc Natl Acad Sci U S A, 104(52):20805-20810.
Ho et al., (2001). Synthetic protein transduction domains: enhanced transduction potential in vivo. *Cancer Research* 61:474-477.
Horng, et al., (2007). NKG2D signaling is coupled to the interleukin 15 receptor signaling pathway. Nat Immunol 8:1345-52.
Shoya, et al., (1998). Two proline-rich nuclear localization signals in the amino- and carboxyl-terminal regions of the Borna disease virus phosphoprotein. J .Virol, 72(12): 9755-9762.
Hurt, et al., (1985). The first twelve amino acids (less than half of the pre-sequence) of an imported mitochondrial protein can direct mouse cytosolic dihydrofolate reductase into the yeast mitochondrial matrix. EMBO J, 4(8):2061-2068.
Ichii, et al., (2004). Bcl6 acts as an amplifier for the generation and proliferative capacity of central memory CD8+ T cells. J Immunol 173(2):883-891.
Irie, et al., (2000). Molecular cloning and characterization of Amida, a novel protein which interacts with a neuron-specific immediate early gene product arc, contains novel nuclear localization signals, and causes cell death in cultured cells. J Biol Chem 275(4):2647-2653.
Ishigami, et al., (2015). Human leukocyte antigen (HLA)-E and HLA-F expression in gastric cancer. Anticancer Res 35:2279-85.
Kakudo, et al.,(2004). Transferrin-modified liposomes equipped with a pH-sensitive fusogenic peptide: an artificial viral-like delivery system. Biochemistry. 43(19):5618-5628.
Kamiely, S. and O. Pines (2005). Single translation—dual destination: mechanisms of dual protein targeting in eukaryotes. EMBO Rep 6(5):420-425.
Kato, et al., (1992). Max: functional domains and interaction with c-Myc. Genes Dev. 6(1):81-92.
Kichler et al., (2003). Histidine-rich amphipathic peptide antibiotics promote efficient delivery of DNA into mammalian cells. Proc Natl Acad Sci U S A, 100(4)1564-1568.
Kichler, et al., (2006). Cationic amphipathic histidine-rich peptides for gene delivery. Biochim Biophys Acta 1758(3):301-307.
Kirwan, S. E. & Burshtyn, D. N. (2005). Killer cell Ig-like receptor-dependent signaling by Ig-like transcript 2 (ILT2/CD85j/LILRB1/LIR-1). J Immunol 175:5006-15.
Kleinschmidt, J. A. and A. Seiter (1988). Identification of domains involved in nuclear uptake and histone binding of protein N1 of Xenopus laevis. EMBO J, 7(6):1605-1614.
Kohler, et al., (2001). Adenoviral E1A protein nuclear import is preferentially mediated by importin alpha3 in vitro. Virology 289(2):186-191.
Kwon et al., (2010) A truncated HGP peptide sequence that retains endosomolytic activity and improves gene delivery efficiencies.Mol Pharm., 7(4):1260-1265.
Lamiable et al., (2016). PEP-FOLD3: faster de novo structure prediction for linear peptides in solution and in complex. Nucleic Acids Res. 44(W1):W449-454.
Lanford, et al., (1986). Induction of nuclear transport with a synthetic peptide homologous to the SV40 T antigen transport signal. Cell 46(4):575-582.
Lee et al., Delivery of macromolecules into live cells by simple co-incubation with a peptide. Chembiochem., 11(3):325-330, 2010.
Levy, et al., (2008). Human leukocyte antigen-E protein is overexpressed in primary human colorectal cancer. Int J Oncol 32:633-41.

Li, et al., (2004). GALA: a designed synthetic pH-responsive amphipathic peptide with applications in drug and gene delivery. Adv Drug Deliv Rev, 56(7):967-985.
Lin, et al., (2013). "B lymphocyte-induced maturation protein 1 (BLIMP-1) attenuates autoimmune diabetes in NOD mice by suppressing Th1 and Th17 cells." Diabetologia 56(1):136-146.
Liu, et al., (2003). Systemic genetic transfer of p21WAF-1 and GM-CSF utilizing of a novel oligopeptide-based EGF receptor targeting polyplex. Cancer Gene Ther, 10(7):529-539.
Liu, et al., (2014). E3 ubiquitin ligase Cbl-b in innate and adaptive immunity. Cell Cycle 13:1875-84.
Liu et al., Cell-penetrating peptide-mediated delivery of TALEN proteins via bioconjugation for genome engineering. PLoS ONE 9(1):e85755, 2014.
Lo et al., An endosomolytic Tat peptide produced by incorporation of histidine and cysteine residues as a nonviral vector for DNA transfection. ScienceDirect, Biomaterials, 29:2408-2414, 2008.
Loeser, et al., (2007). Spontaneous tumor rejection by cbl-b-deficient CD8+ T cells. J Exp Med 204:879-91.
London, E. (1992). Diphtheria toxin: membrane interaction and membrane translocation. Biochim Biophys Acta 1113(1): 25-51.
Lord-Dufour et al., (2009) Evidence for transcriptional regulation of the glucose-6-phosphate transporter by HIF-1alpha: Targeting G6PT with mumbaistatin analogs in hypoxic mesenchymal stromal cells. Stem cells, 27:489-497.
Lorieau, et al., (2010). The complete influenza hemagglutinin fusion domain adopts a tight helical hairpin arrangement at the lipid:water interface. Proc Natl Acad Sci U S A, 107(25): 11341-11346.
Lu, et al., (2007). Recombinant HoxB4 fusion proteins enhance hematopoietic differentiation of human embryonic stem cells. Stem Cells Dev 16(4):547-559.
Luan et al., (2015). Peptide amphiphiles with multifunctional fragments promoting cellular uptake and endosomal escape as efficient gene vectors.*J. Mater. Chem. B*, 3:1068-1078.
Lutz-Nicoladoni, et al., (2015). Modulation of Immune Cell Functions by the E3 Ligase Cbl-b. Front Oncol 5:58.
Mack, et al., (1998). Aminooxypentane-RANTES induces CCR5 internalization but inhibits recycling: a novel inhibitory mechanism of HIV infectivity. J Exp Med, 187(8):1215-1224.
Maeng, et al., (2013). Effects of single nucleotide polymorphisms on treatment outcomes and toxicity in patients treated with sunitinib. Anticancer Res 33(10):4619-4626.
Mahlum, et al., (2007). Engineering a noncarrier to a highly efficient carrier peptide for noncovalently delivering biologically active proteins into human cells. Anal Biochem. 365(2):215-221.
Makarova et al., (2011) Unification of Cas protein families and a simple scenario for the origin and evolution of CRISPR-Cas systems. Biol Direct. 6:38.
Makkerh, et al., (1996). Comparative mutagenesis of nuclear localization signals reveals the importance of neutral and acidic amino acids. Curr Biol. 6(8):1025-1027.
Martinez-Fong, et al., (1999). Neurotensin-SPDP-poly-L-lysine conjugate: a nonviral vector for targeted gene delivery to neural cells. Brain Res Mol Brain Res. 69(2):249-262.
Matalon, et al., (2016). Dephosphorylation of the adaptor LAT and phospholipase C-gamma by SHP-1 inhibits natural killer cell cytotoxicity. Sci Signal 9:ra54.
Maurer, M. and E. von Stebut (2004). Macrophage inflammatory protein-1. Int J Biochem Cell Biol. 36(10):1882-1886.
McKay, et al., (2002). Secretin-mediated gene delivery, a specific targeting mechanism with potential for treatment of biliary and pancreatic disease in cystic fibrosis. Mol Ther 5(4):447-454.
Midoux, et al., (1998). Membrane permeabilization and efficient gene transfer by a peptide containing several histidines. Bioconjug Chem. 9(2):260-267.
Milenkovic, et al., (2009). Identification of the signal directing Tim9 and Tim10 into the intermembrane space of mitochondria. Mol Biol Cell 20(10):2530-2539.
Miyoshi, et al., (1994). "[Structure and regulation of human thyroid-stimulating hormone (TSH) gene]." Nihon Rinsho 52(4):940-947.
Moede, et al., (1999). Identification of a nuclear localization signal, RRMKWKK, in the homeodomain transcription factor PDX-1. FEBS Lett 461(3):229-234.

(56) References Cited

OTHER PUBLICATIONS

Montrose, et al., (2013). Xentry, a new class of cell-penetrating peptide uniquely equipped for delivery of drugs. Sci Rep 3:1661.
Moreland, et al., (1987). Amino acid sequences that determine the nuclear localization of yeast histone 2B. Mol Cell Biol 7(11):4048-4057.
Morris, et al., (2001). A peptide carrier for the delivery of biologically active proteins into mammalian cells. Nat Biotechnol 19(12):1173-1176.
Morris, et al., (2004). Combination of a new generation of PNAs with a peptide-based carrier enables efficient targeting of cell cycle progression. Gene Ther 11(9):757-764.
Nakanishi, et al., (2002). Interaction of the Vp3 nuclear localization signal with the importin alpha 2/beta heterodimer directs nuclear entry of infecting simian virus 40. J Virol, 76(18):9368-9377.
O'Keefe, D. O. (1992). Characterization of a full-length, active-site mutant of diphtheria toxin. Arch Biochem Biophys 296(2):678-684.
Paolino, et al., (2014). The E3 ligase Cbl-b and TAM receptors regulate cancer metastasis via natural killer cells. Nature 507:508-12.
Parameswaran, et al., (2016). Repression of GSK3 restores NK cell cytotoxicity in AML patients. Nat Commun 7:11154.
Parente, et al., (1990). Mechanism of leakage of phospholipid vesicle contents induced by the peptide GALA Biochemistry, 29(37):8720-8728.
Patel, P. & Woodgett, J. R. (2017). Glycogen Synthase Kinase 3: A Kinase for All Pathways? Curr Top Dev Biol 123:277-302.
Paul, et al., (1997). Gene transfer using a novel fusion protein, GAL4/invasin.Hum Gene Ther,8(10):1253-1262.
Perez, et al., (1992). Antennapedia homeobox as a signal for the cellular internalization and nuclear addressing of a small exogenous peptide. J Cell Sci 102 (Pt 4):717-722.
Pimenta, et al., (2000). Alpha1-antichymotrypsin and kallistatin hydrolysis by human cathepsin D.J Protein Chem, 19(5):411-418.
Poli, et al., (2009). CD56bright natural killer (NK) cells: an important NK cell subset. Immunology 126:458-65.
Prieve, M. G. and M. L. Waterman (1999). Nuclear localization and formation of beta-catenin-lymphoid enhancer factor 1 complexes are not sufficient for activation of gene expression. Mol Cell Biol, 19(6):4503-4515.
Rajagopalan, etal., (2007). Recombinant fusion proteins TAT-Mu, Mu and Mu-Mu mediate efficient non-viral gene delivery. J Gene Med, 9(4):275-286.
Riddell et al., (2014) Reprogramming committed murine blood cells to induced hematopoietic stem cells with defined factors. Cell, 157: 549-564.
Salomone, et al., (2012). A novel chimeric cell-penetrating peptide with membrane-disruptive properties for efficient endosomal escape. J Control Release, 163(3):293-303.
Salomone et al., (2013) In vitro efficient transfection by $CM_{18}$-$Tat_{11}$ hybrid peptide: a new tool for gene-delivery applications. PLoS One 8(7):e70108, 11 pages.
Salomone et al., High-Yield nontoxic gene transfer through conjugation of the CM18-Tat11 chimeric peptide with nanosecond electric pulses. Molecular Pharmaceutics, 9 pages, 2014, available at: http://pubs.acs.org.
Schneider, et al., (1998) A novel peptide, Plaeidgielty, for the targeting of alpha9beta1-integrins.FEBS Lett , 429(3):269-273.
Schreiber, et al., (1992). The human poly(ADP-ribose) polymerase nuclear localization signal is a bipartite element functionally separate from DNA binding and catalytic activity. EMBO J, 11(9): 3263-3269.
Schuster, et al., (1999). Multicomponent DNA carrier with a vesicular stomatitis virus G-peptide greatly enhances liver-targeted gene expression in mice. Bioconjug Chem, 10(6):1075-1083.
Scott, et al., (2010).Characterization and prediction of protein nucleolar localization sequences. Nucleic Acids Res, 38(21): 7388-7399.
Shaw, et al., (2008). Comparison of protein transduction domains in mediating cell delivery of a secreted CRE protein. Biochemistry, 47(4):1157-1166.
Shawe-Taylor and Cristianini (2004) Kernel methods for pattern analysis. Cambridge University Press, 12 pages.
Shen et al., (2014) "Improved PEP-FOLD approach for peptide and miniprotein structure prediction". J. Chem. Theor. Comput. 10:4745-4758.
Somasekaram, et al., (1999). Intracellular localization of human cytidine deaminase. Identification of a functional nuclear localization signal. J Biol Chem. 274(40): 28405-28412.
Stojanovski, et al., (2012). Mechanisms of protein sorting in mitochondria. Cold Spring Harbor Perspect Biol, 4(10):a011320, 18 pages.
Sudbeck, P. and G. Scherer (1997). Two independent nuclear localization signals are present in the DNA-binding high-mobility group domains of SRY and SOX9. J Biol Chem., 272(44): 27848-27852.
Sung, et al., (2013).Efficient myogenic differentiation of human adipose-derived stem cells by the transduction of engineered MyoD protein. Biochem Biophys Res Commun, 437(1):156-161.
Takahashi, K. and S. Yamanaka (2006). Induction of pluripotent stem cells from mouse embryonic and adult fibroblast cultures by defined factors. Cell 126(4):663-676.
Takeda, et al., (2006). NUP98-HOXA9 induces long-term proliferation and blocks differentiation of primary human CD34+ hematopoietic cells. Cancer Res., 66(13):6628-6637.
Tan, et al., (2010). Increased levels of FoxA1 transcription factor in pluripotent P19 embryonal carcinoma cells stimulate neural differentiation. Stem Cells Dev., 19(9):1365-1374.
Tan, et al., (2012). Truncated peptides from melittin and its analog with high lytic activity at endosomal pH enhance branched polyethylenimine-mediated gene transfection. J Gene Med 14(4):241-250.
Thévenet et al., (2012) PEP-FOLD: an updated de novo structure prediction server for both linear and disulfide bonded cyclic peptides. Nucleic Acids Res. 40:W288-293.
Uherek, et al., (1998). A modular DNA carrier protein based on the structure of diphtheria toxin mediates target cell-specific gene delivery. J Biol Chem 273(15):8835-8841.
U.S. Appl. No. 15/094,365 Applicant Initiated Interview Summary dated Jan. 11, 2017.
U.S. Appl. No. 15/094,365 Office Action dated Dec. 15, 2016.
U.S. Appl. No. 15/094,365 Restriction Requirement dated Aug. 2, 2016.
Varkouhi, et al., (2011). Endosomal escape pathways for delivery of biologicals. J Control Release 151(3):220-228.
Veach, et al., (2004). Receptor/transporter-independent targeting of functional peptides across the plasma membrane. J Biol Chem., 279(12):11425-11431.
Vives, et al., (1997). A truncated HIV-1 Tat protein basic domain rapidly translocates through the plasma membrane and accumulates in the cell nucleus. J Biol Chem., 272(25):16010-16017.
Wagstaff, et al., (2007). Histone-mediated transduction as an efficient means for gene delivery. Mol Ther., 15(4):721-731.
Warr, et al., (2013). FOXO3A directs a protective autophagy program in haematopoietic stem cells. Nature 494(7437):323-327.
Welch, et al., (1999). RanBP3 contains an unusual nuclear localization signal that is imported preferentially by importin-alpha3. Mol Cell Biol. 19(12):8400-8411.
Wiedenheft et al., (2011). RNA-guided complex from a bacterial immune system enhances target recognition through seed sequence interactions. Proc. Natl. Acad. Sci. USA, 108:10092-10097.
Witzel, et al., (2013). Androgen receptor expression is a predictive marker in chemotherapy-treated patients with endocrine receptor-positive primary breast cancers. J Cancer Res Clin Oncol., 139(5):809-816.
Wu, et al., (2015). Rescuing lymphocytes from HLA-G immunosuppressive effects mediated by the tumor microenvironment. Oncotarget 6:37385-37397.
Wu, et al., (1999). The quaking I-5 protein (QKI-5) has a novel nuclear localization signal and shuttles between the nucleus and the cytoplasm. J Biol Chem., 274(41):29202-29210.

(56) References Cited

OTHER PUBLICATIONS

Wyman, et al., (1997). Design, synthesis, and characterization of a cationic peptide that binds to nucleic acids and permeabilizes bilayers. Biochemistry, 36(10):3008-3017.

Ye, et al., (2007). Human leukocyte antigen G expression: as a significant prognostic indicator for patients with colorectal cancer. Mod Pathol 20:375-383.

Yie, et al., (2007). Expression of HLA-G is associated with prognosis in esophageal squamous cell carcinoma. Am J Clin Pathol 128:1002-1009.

Yie, et al., (2007). Expression of human leukocyte antigen G (HLA-G) correlates with poor prognosis in gastric carcinoma. Ann Surg Oncol 14: 2721-2729.

Yie, et al., (2007). Expression of human leucocyte antigen G (HLA-G) is associated with prognosis in non-small cell lung cancer. Lung Cancer 58:267-74.

Yu, et al., (1998). A constitutive nuclear localization signal from the second zinc-finger of orphan nuclear receptor TR2. J Endocrinol., 159(1):53-60.

Zetsche et al., (2015). Cpf1 Is a Single RNA-Guided Endonuclease of a Class 2 CRISPR-Cas System. Cell. 25. pii: S0092-8674(15)01200-3[http://dx.doi.org/10.1016/j.cell.2015.09.038].

Zhen, et al., (2013). Impact of HLA-E gene polymorphism on HLA-E expression in tumor cells and prognosis in patients with stage III colorectal cancer. Med Oncol 30:482.

Zhou et al. (2009) Generation of induced pluripotent stem cells using recombinant proteins. Cell Stem Cell 4(5):381-384.

PCT/IB2017/000512 International Search Report and Written Opinion dated Jul. 26, 2017.

Ramakrishna et al., (2014) Gene disruption by cell-penetrating peptide-mediated delivery of Cas9 protein and guide RNA. Genome Research, 24:1020-1027.

Fig. 23A  Fig. 23B  Fig. 23C  Fig. 23D
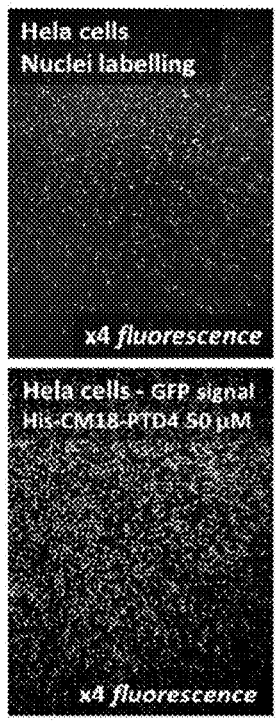
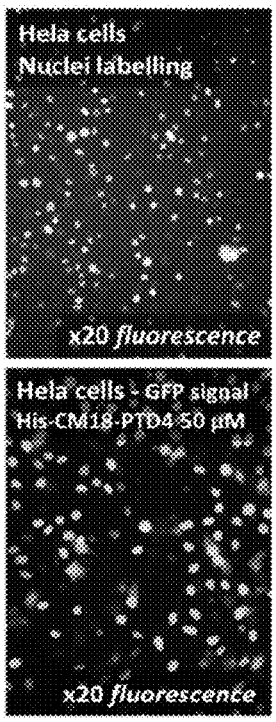
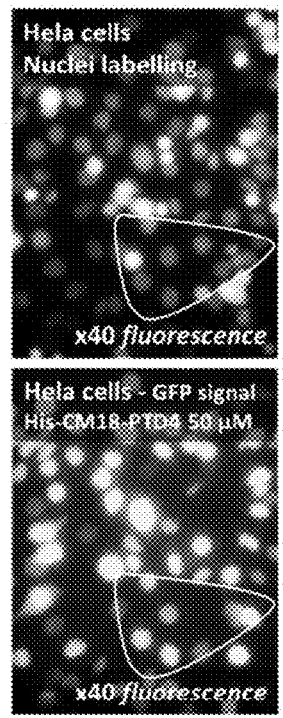
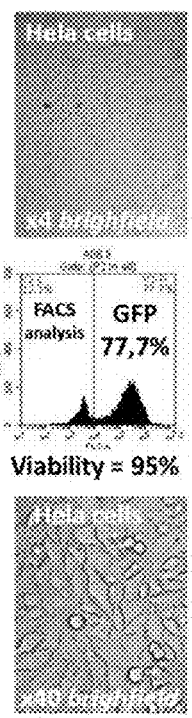
Fig. 24A  Fig. 24B
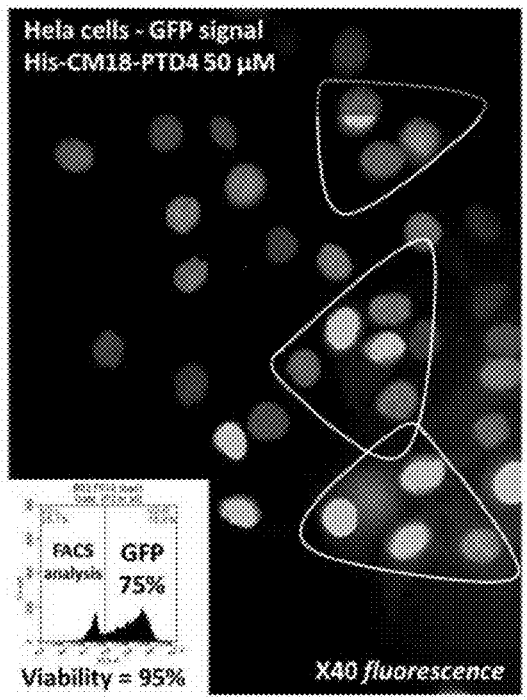

Fig. 25A
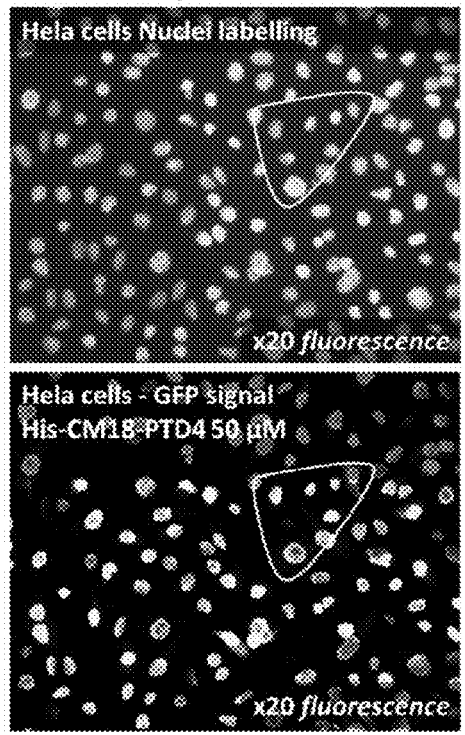
Fig. 25B
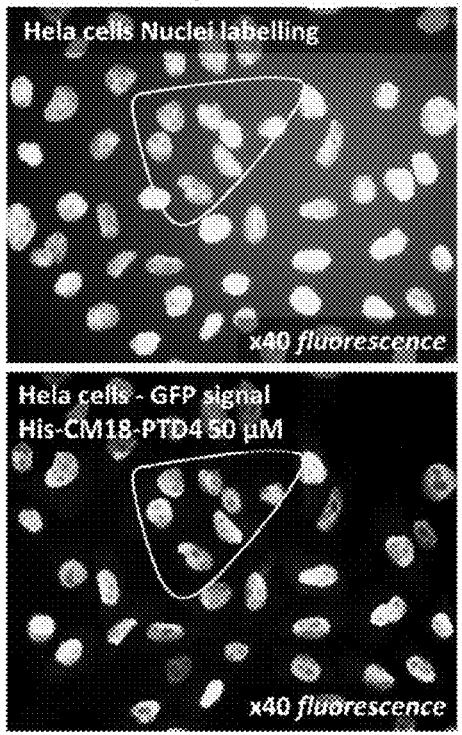
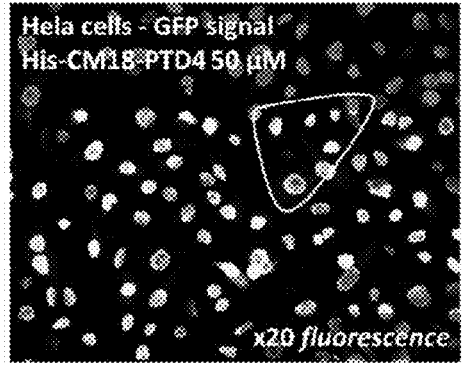
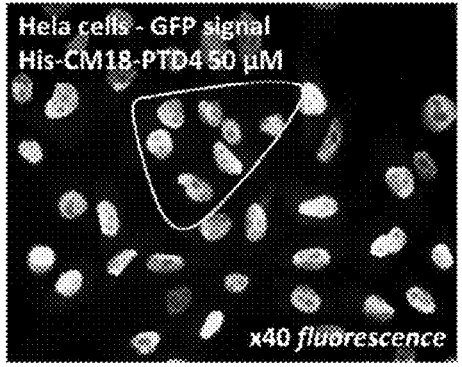
Fig. 26A
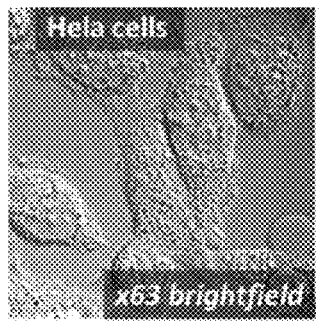
Fig. 26C
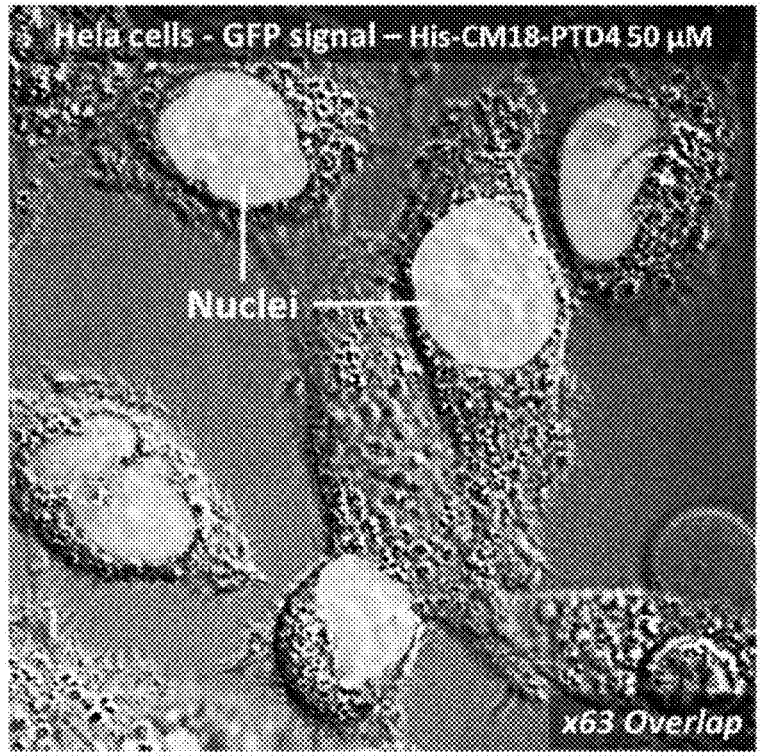
Fig. 26B
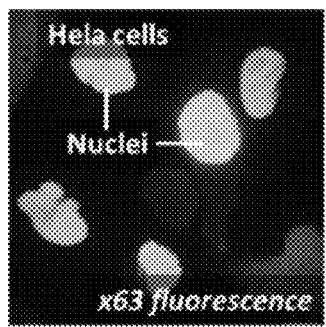

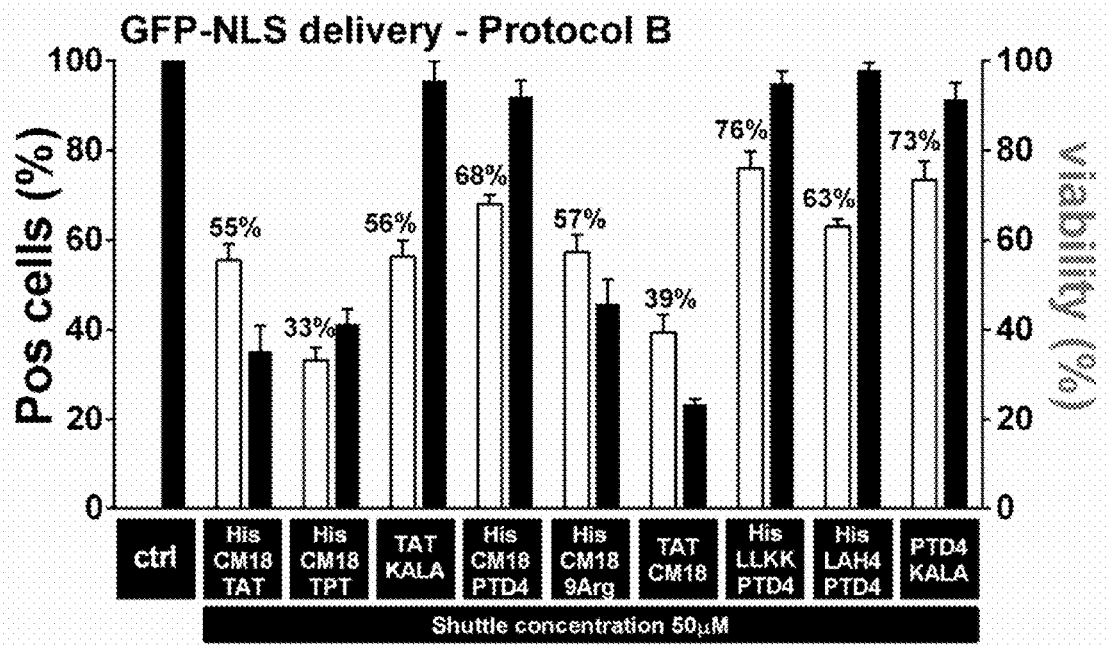
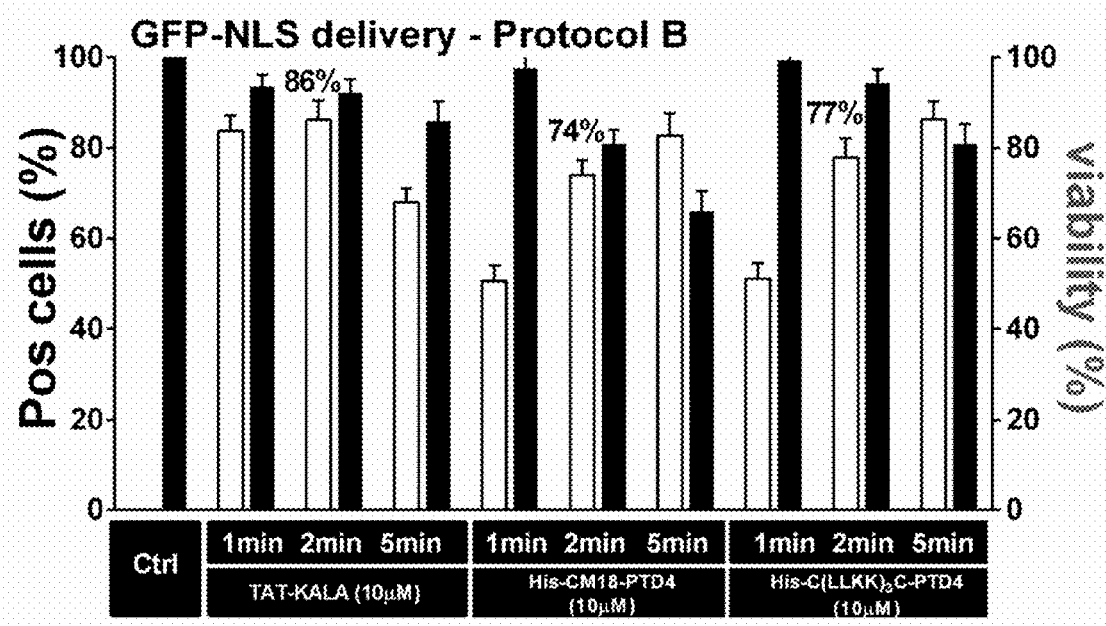

Fig. 32A 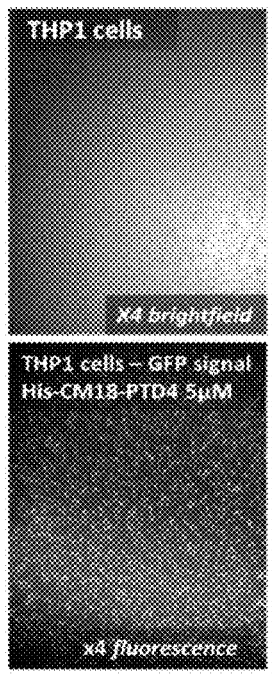 Fig. 32B 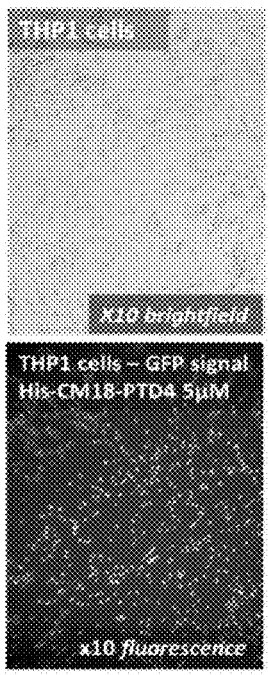 Fig. 32C 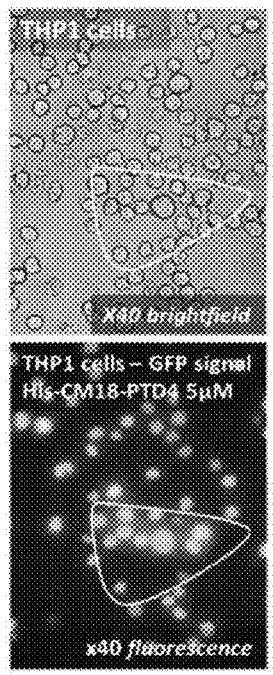

Viability = 95%
Fig. 33A 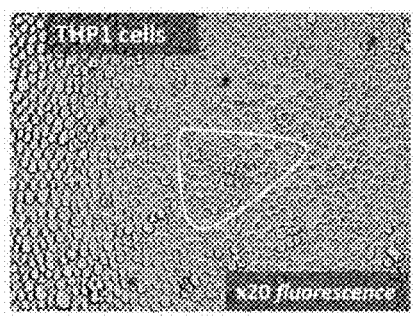 Fig. 33C 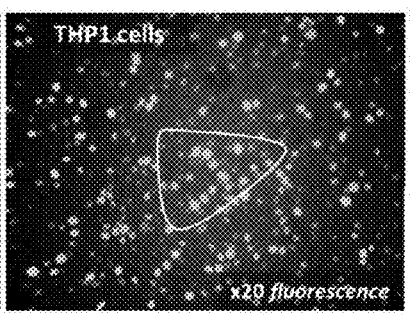
Fig. 33B 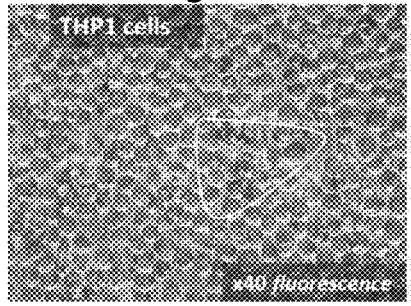 Fig. 33D 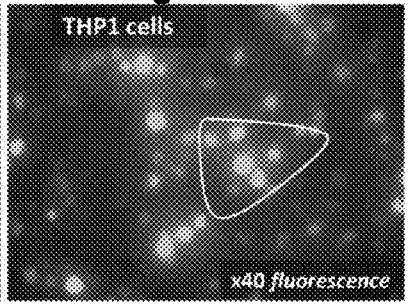
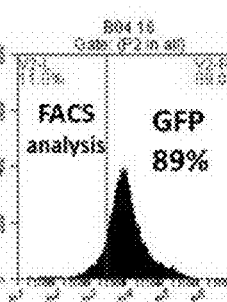
Viability = 75%

Fig. 38A
Fig. 38B
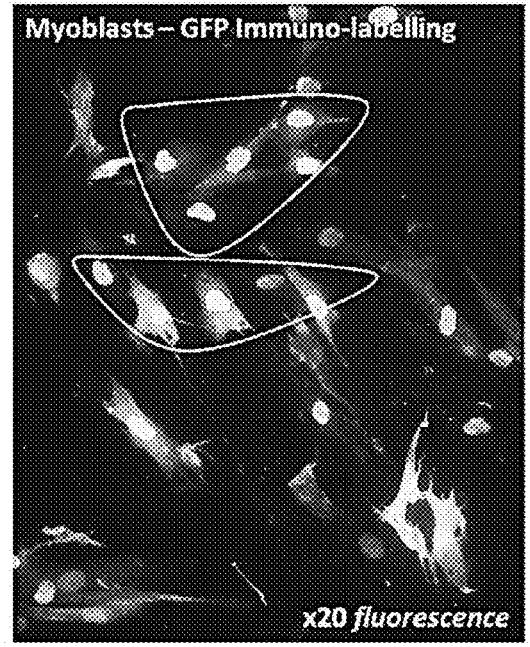
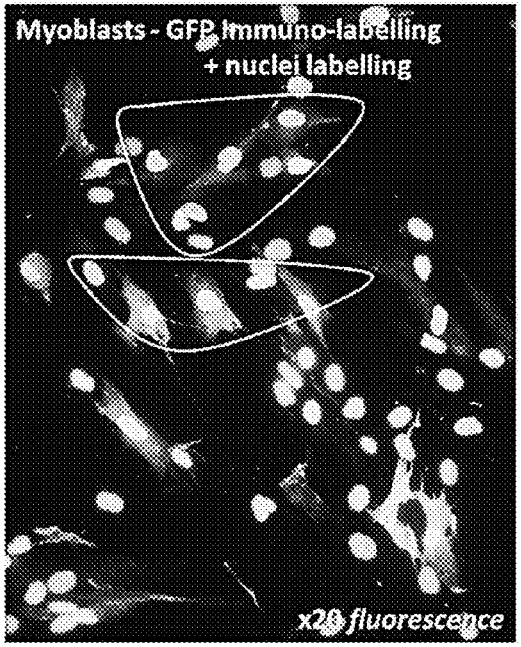
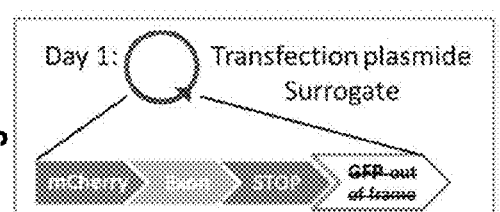
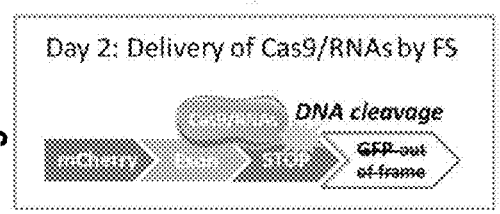
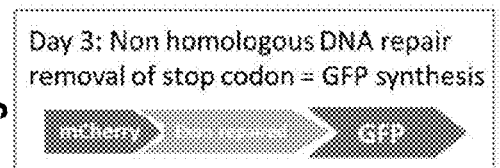
Fig. 39D
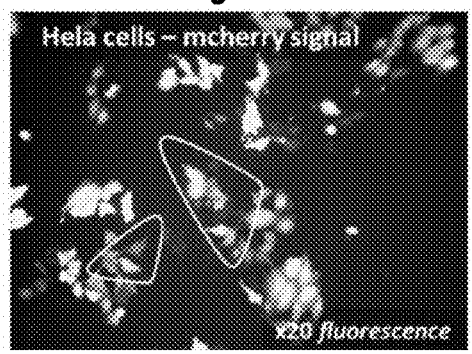
Fig. 39E
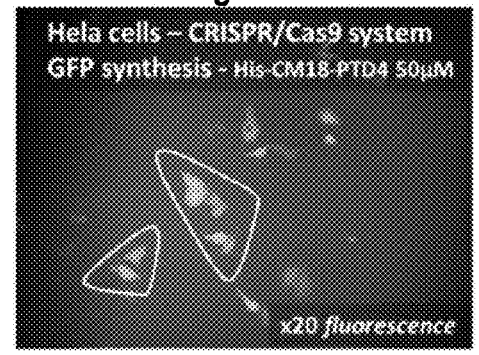

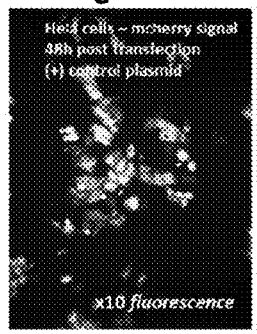 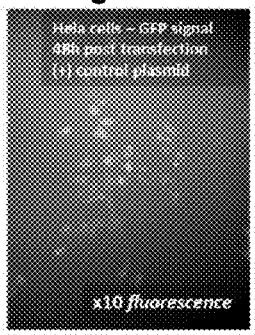  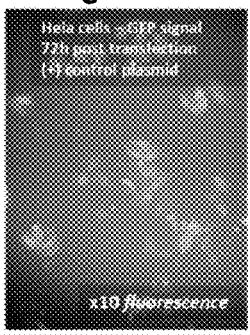
 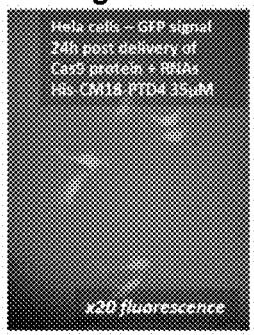  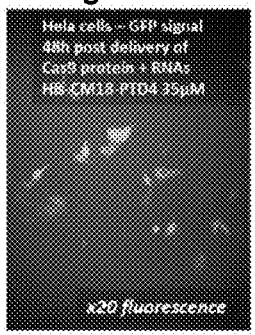
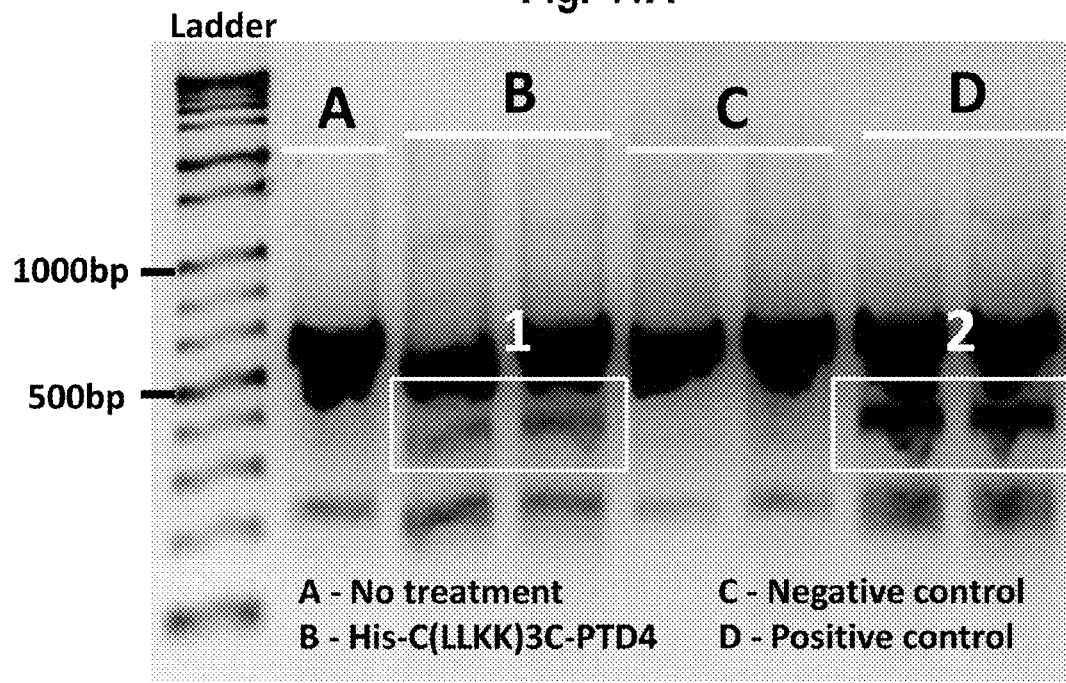

Fig. 49A
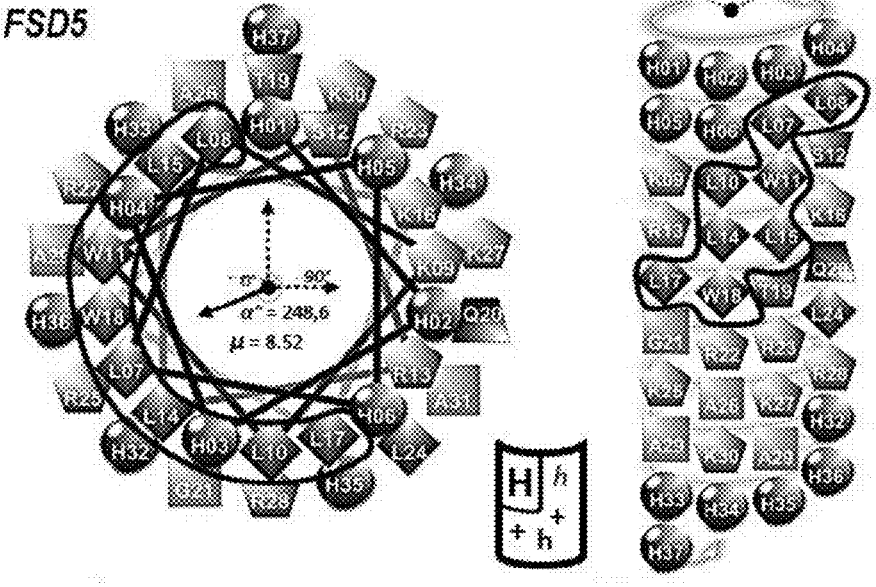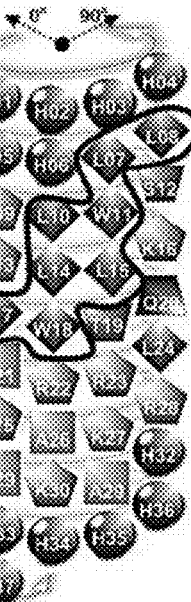
Fig. 49B
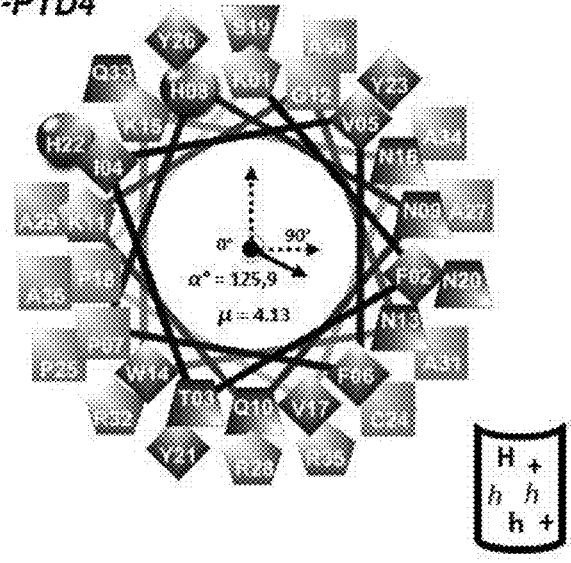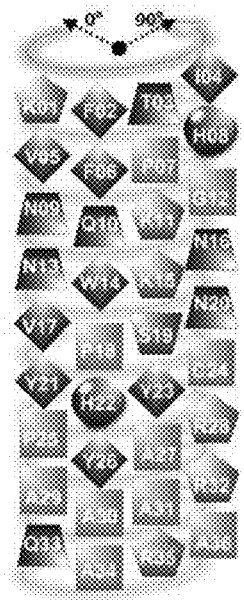

FSD5

FSD18

VSVG-PTD4

FSN7

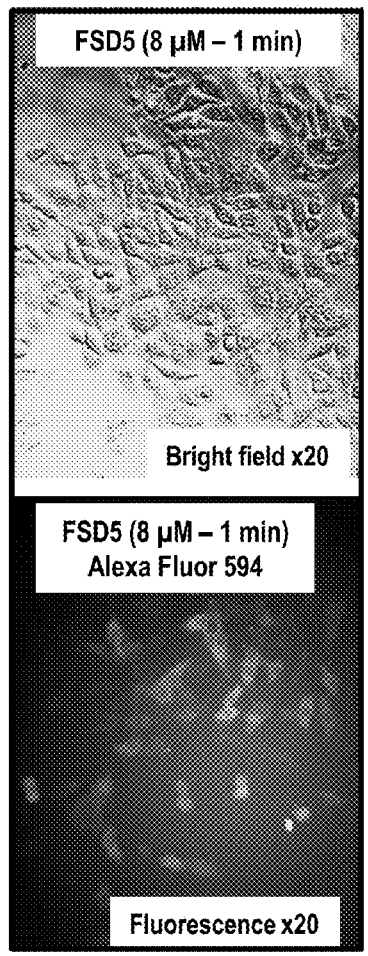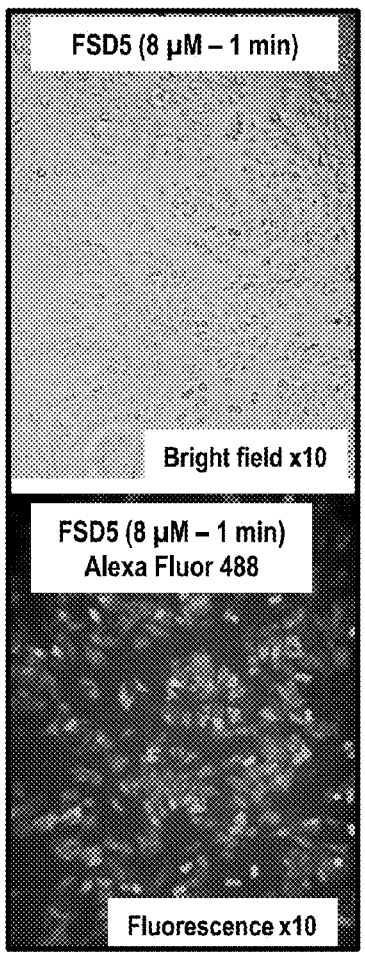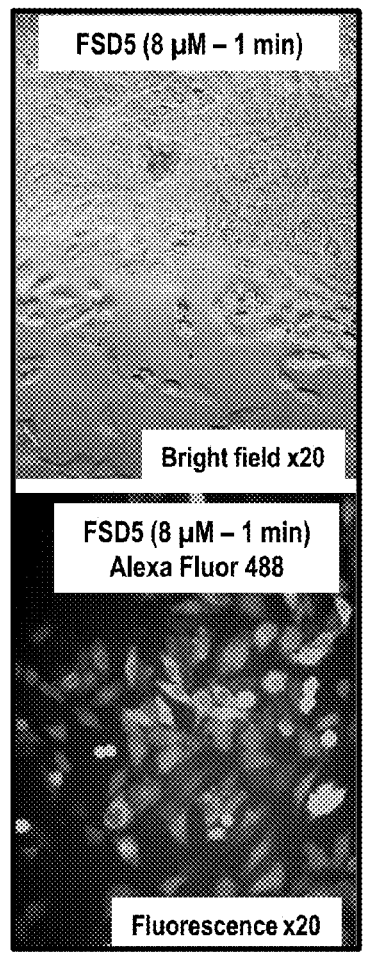

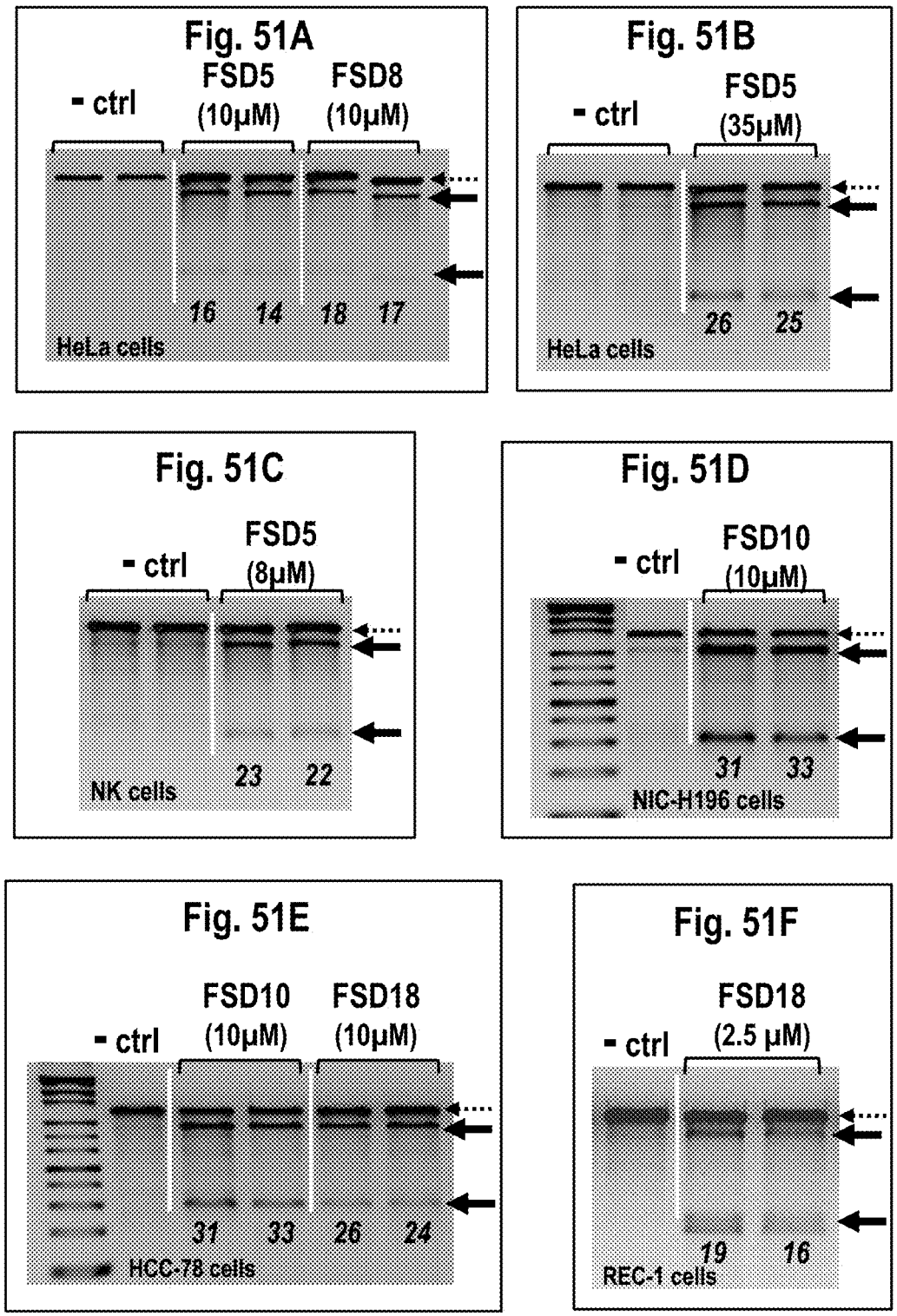

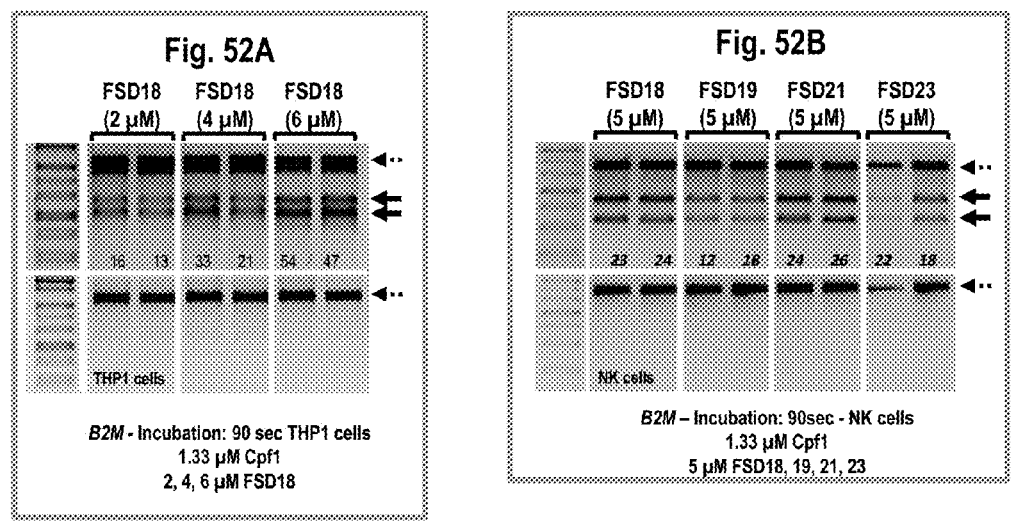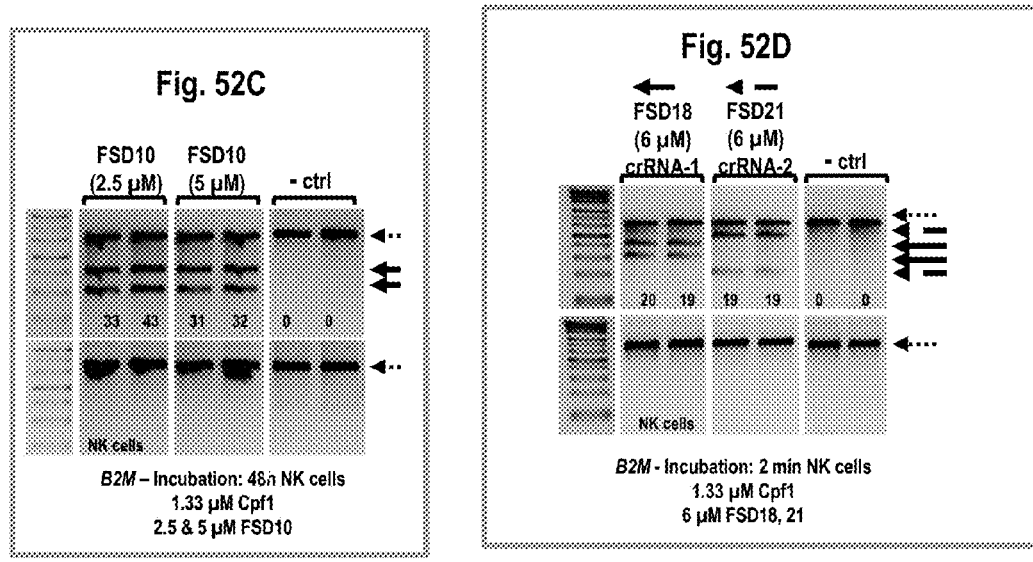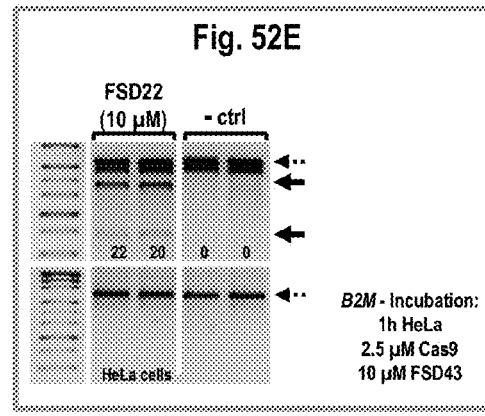

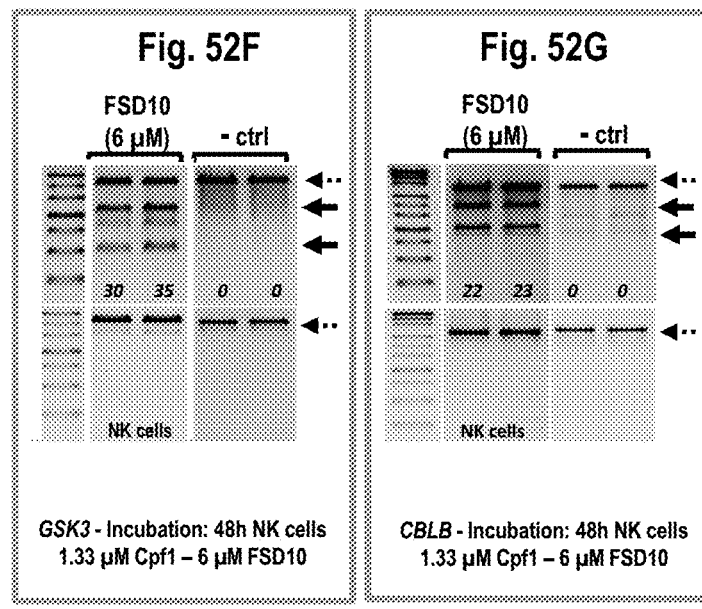
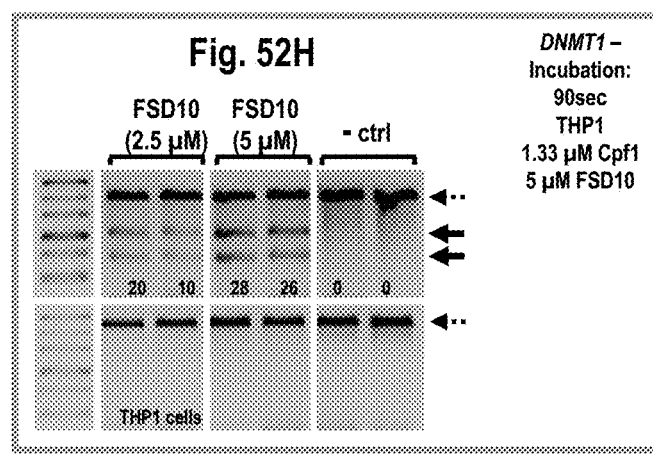
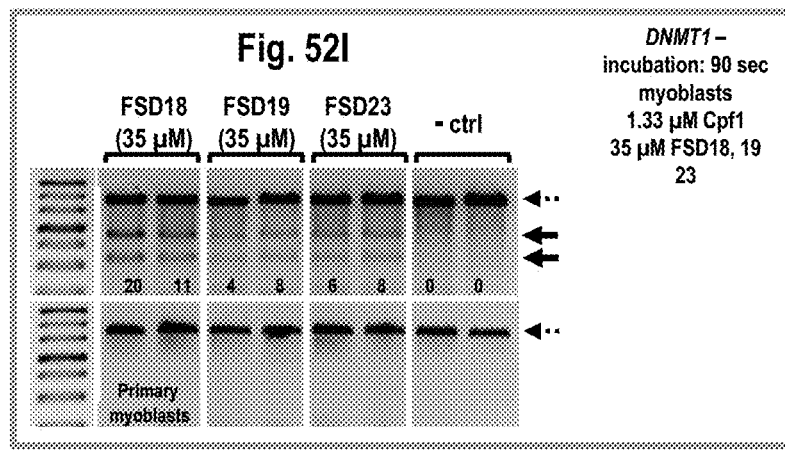

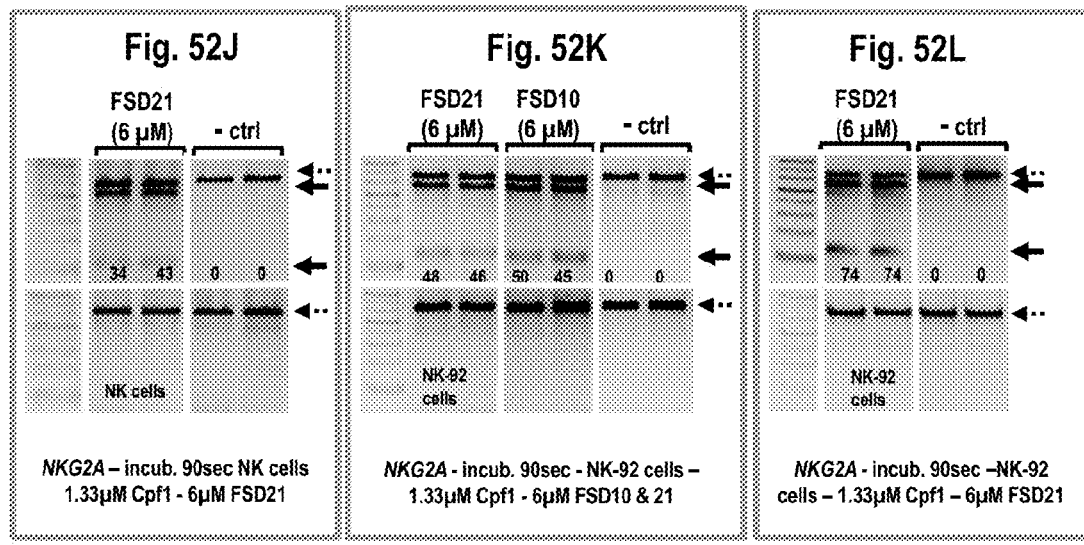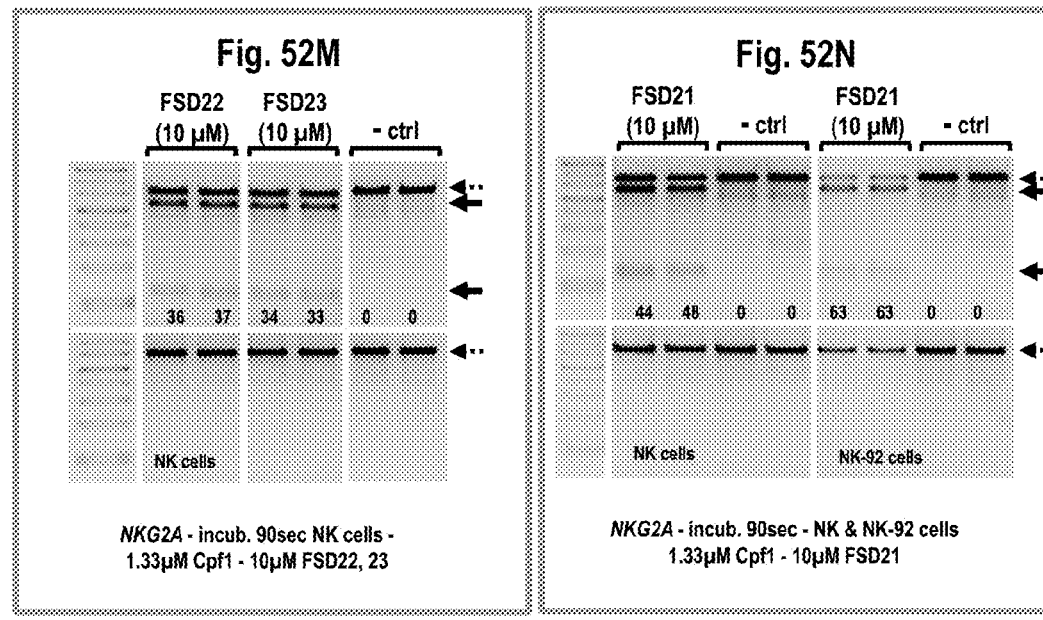

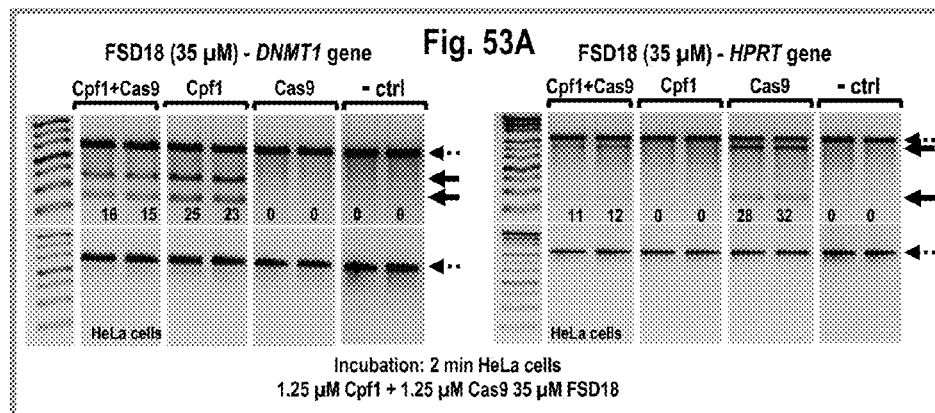
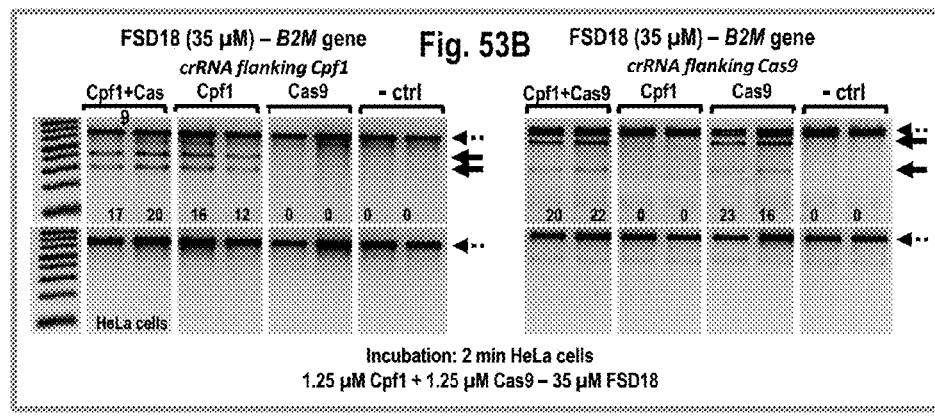
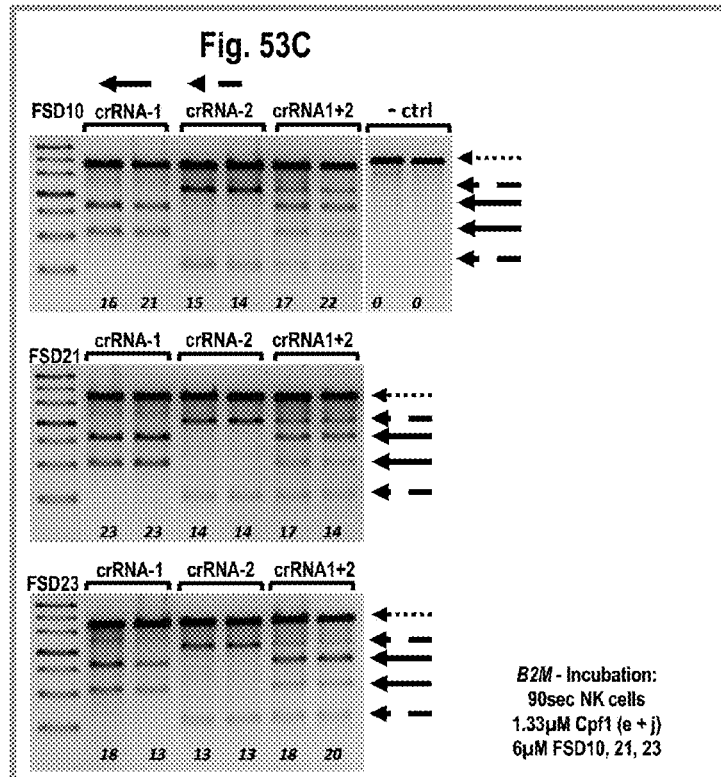

Untreated crRNA E crRNA G crRNA J crRNA E + G + J

RATIONALLY-DESIGNED SYNTHETIC PEPTIDE SHUTTLE AGENTS FOR DELIVERING POLYPEPTIDE CARGOS FROM AN EXTRACELLULAR SPACE TO THE CYTOSOL AND/OR NUCLEUS OF A TARGET EUKARYOTIC CELL, USES THEREOF, METHODS AND KITS RELATING TO SAME

CROSS REFERENCE

This application claims priority under 35 U.S.C section 119 from Provisional Application Ser. No. 62/407,232, filed Oct. 12, 2016 and Provisional Application Ser. No. 62/535,010, filed Jul. 20, 2017, the disclosures of which are each incorporated herein by reference in their entirety.

SEQUENCE LISTING

This application contains a Sequence Listing in computer readable form created Jul. 20, 2017 having a size of about 92 kb. The computer readable form is incorporated herein by reference.

BACKGROUND

Cell delivery technologies to transport large molecules inside eukaryotic cells have a wide range of applications, particularly in the biopharmaceutical industry. While some soluble chemical substances (e.g., small molecule drugs) may passively diffuse through the eukaryotic cell membrane, larger cargos (e.g., biologics, polynucleotides, and polypeptides) require the help of shuttle agents to reach their intracellular targets.

Areas that would greatly benefit from advances in cell delivery technologies include the fields of genome editing and cell therapy, which have made enormous leaps over the last two decades. Deciphering the different growth factors and molecular cues that govern cell expansion, differentiation and reprogramming open the door to many therapeutic possibilities for the treatment of unmet medical needs. For example, induction of pluripotent stem cells directly from adult cells, direct cell conversion (trans-differentiation), and genome editing (Zinc finger nuclease, TALEN™ and CRISPR-associated endonuclease technologies) are examples of methods that have been developed to maximize the therapeutic value of cells for clinical applications. Presently, the production of cells with high therapeutic activity usually requires ex vivo manipulations, mainly achieved by viral transduction, raising important safety and economical concerns for human applications. The ability to directly deliver active proteins such as transcription factors or artificial nucleases, inside these cells, may advantageously circumvent the safety concerns and regulatory hurdles associated with more risky gene transfer methods. In particular, methods of directly delivering active genome editing complexes in immune cells in order to improve immunotherapy would be highly desirable.

Protein transduction approaches involving fusing a recombinant protein cargo directly to a cell-penetrating peptide (e.g., HIV transactivating protein TAT) require large amounts of the recombinant protein and often fail to deliver the cargo to the proper subcellular location, leading to massive endosomal trapping and eventual degradation. Several endosomal membrane-disrupting peptides have been developed to try to facilitate the escape of endosomally-trapped cargos to the cytosol. However, many of these endosomolytic peptides have been used to alleviate endosomal entrapment of cargos that have already been delivered intracellularly, and do not by themselves aid in the initial step of shuttling the cargos intracellularly across the plasma membrane (Salomone et al., 2012; Salomone et al., 2013; Erazo-Oliveras et al., 2014; Fasoli et al., 2014).

In particular, Salomone et al., 2012 described a chimeric peptide $CM_{18}$-$TAT_{11}$, resulting from the fusion of the $Tat_{11}$ cell penetrating motif to the CM18 hybrid (residues 1-7 of Cecropin-A and 2-12 of Melittin). This peptide was reported to be rapidly internalized by cells (due to its TAT motif) and subsequently responsible for destabilizing the membranes of endocytic vesicles (due to the membrane disruptive abilities of the CM18 peptide). Although the peptide $CM_{18}$-$TAT_{11}$ fused to the fluorescent label Atto-633 (molecular weight of 774 Da; 21% of the MW of the peptide) was reported to facilitate the escape of endosomally trapped $TAT_{11}$-EGFP to the cytosol (see FIG. 3 of Salomone et al., 2012), the $CM_{18}$-$TAT_{11}$ peptide (alone or conjugated to Atto-633) was not shown to act as a shuttle agent that can increase delivery of a polypeptide cargo from an extracellular space to inside of the cell—i.e., across the plasma membrane. In fact, Salomone et al., 2012 compared co-treatment (simultaneous treatment of $TAT_{11}$-EGFP and $CM_{18}$-$TAT_{11}$-Atto-633) versus time-shifted treatment (i.e., incubation of cells with $TAT_{11}$-EGFP alone, fluorescence imaging, and then incubation of the same cells with the $CM_{18}$-$TAT_{11}$-Atto-633 peptide alone, and again fluorescence imaging), and the authors reported that "both yielded the same delivery results" (see page 295 of Salomone et al., 2012, last sentence of first paragraph under the heading "2.9 Cargo delivery assays"). In other words, Salomone et al., 2012 described that the peptide $CM_{18}$-$TAT_{11}$ (alone or conjugated to Atto-633) had no effect on delivery of a polypeptide cargo from an extracellular space to inside of the cell (i.e., protein transduction). Thus, there remains a need for improved shuttle agents capable of increasing the transduction efficiency of polypeptide cargos, and delivering the cargos to the cytosol and/or nucleus of target eukaryotic cells.

The present description refers to a number of documents, the content of which is herein incorporated by reference in their entirety.

SUMMARY

The present description relates to synthetic peptide shuttle agents useful for delivering a variety of polypeptide cargos from an extracellular space to the cytosol and/or nucleus of target eukaryotic cells. More specifically, the present description relates to parameters useful in the rational design of such synthetic peptide shuttle agents.

A plurality of different peptides was screened with the goal of identifying polypeptide-based shuttle agents that can deliver independent polypeptide cargos intracellularly to the cytosol/nucleus of eukaryotic cells. On one hand, these large-scale screening efforts led to the surprising discovery that certain domain-based peptide shuttle agents increase the transduction efficiency of polypeptide cargos in eukaryotic cells, by increasing the number and/or proportion of cells that ultimately internalize the polypeptide cargos, and also enable the internalized cargos to gain access to the cytosol/nuclear compartment (thus avoiding or reducing cargo endosomal entrapment). These domain-base shuttle agents comprise an endosome leakage domain (ELD) operably linked to a cell penetrating domain (CPD), and optionally one or more histidine-rich domains. On the other hand, the above screening efforts also revealed some peptides having no or low polypeptide cargo transduction activity, excessive toxicity, and/or other undesirable properties (e.g., poor solubility and/or stability). These empirical data (both positive and negative) were used herein to identify physiochemical properties of successful, less successful, and failed peptides in order to arrive at a set of design parameters that enable the rational design and/or identification of peptides having protein transduction activity.

Accordingly, the present description relates to methods for delivering polypeptide cargos from an extracellular space to the cytosol and/or nucleus of a target eukaryotic cell by contacting the cell with the polypeptide cargo in the presence of a peptide shuttle agent as described herein, at a concentration sufficient to increase the polypeptide cargo's transduction efficiency, as compared to in the absence of the shuttle agent. More particularly, the present description relates to parameters that may be used in the rational design of such synthetic peptide shuttle agents, peptide shuttle agents that satisfy one or more of these design parameters, as well as methods and compositions relating to the use of the synthetic peptide shuttle agents for delivery of a variety of polypeptide cargos from an extracellular space to the cytosol and/or nucleus of target eukaryotic cells.

General Definitions

Headings, and other identifiers, e.g., (a), (b), (i), (ii), etc., are presented merely for ease of reading the specification and claims. The use of headings or other identifiers in the specification or claims does not necessarily require the steps or elements be performed in alphabetical or numerical order or the order in which they are presented.

The use of the word "a" or "an" when used in conjunction with the term "comprising" in the claims and/or the specification may mean "one" but it is also consistent with the meaning of "one or more", "at least one", and "one or more than one".

The term "about" is used to indicate that a value includes the standard deviation of error for the device or method being employed in order to determine the value. In general, the terminology "about" is meant to designate a possible variation of up to 10%. Therefore, a variation of 1, 2, 3, 4, 5, 6, 7, 8, 9 and 10% of a value is included in the term "about". Unless indicated otherwise, use of the term "about" before a range applies to both ends of the range.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, "protein" or "polypeptide" means any peptide-linked chain of amino acids, which may or may not comprise any type of modification (e.g., post-translational modifications such as acetylation, phosphorylation, glycosylation, sulfatation, sumoylation, prenylation, ubiquitination, etc).

As used herein, a "domain" or "protein domain" generally refers to a part of a protein having a particular functionality or function. Some domains conserve their function when separated from the rest of the protein, and thus can be used in a modular fashion. The modular characteristic of many protein domains can provide flexibility in terms of their placement within the shuttle agents of the present description. However, some domains may perform better when engineered at certain positions of the shuttle agent (e.g., at the N- or C-terminal region, or therebetween). The position of the domain within its endogenous protein is sometimes an indicator of where the domain should be engineered within the shuttle agent and of what type/length of linker should be used. Standard recombinant DNA techniques can be used by the skilled person to manipulate the placement and/or number of the domains within the shuttle agents of the present description in view of the present disclosure. Furthermore, assays disclosed herein, as well as others known in the art, can be used to assess the functionality of each of the domains within the context of the shuttle agents (e.g., their ability to facilitate cell penetration across the plasma membrane, endosome escape, and/or access to the cytosol). Standard methods can also be used to assess whether the domains of the shuttle agent affect the activity of the cargo to be delivered intracellularly. In this regard, the expression "operably linked" as used herein refers to the ability of the domains to carry out their intended function(s) (e.g., cell penetration, endosome escape, and/or subcellular targeting) within the context of the shuttle agents of the present description. For greater clarity, the expression "operably linked" is meant to define a functional connection between two or more domains without being limited to a particular order or distance between same.

As used herein, the term "synthetic" used in expressions such as "synthetic peptide" or "synthetic polypeptide" is intended to refer to non-naturally occurring molecules that can be produced in vitro (e.g., synthesized chemically and/or produced using recombinant DNA technology). The purities of various synthetic preparations may be assessed by, for example, high-performance liquid chromatography analysis and mass spectroscopy. Chemical synthesis approaches may be advantageous over cellular expression systems (e.g., yeast or bacteria protein expression systems), as they may preclude the need for extensive recombinant protein purification steps (e.g., required for clinical use). In contrast, longer synthetic polypeptides may be more complicated and/or costly to produce via chemical synthesis approaches and such polypeptides may be more advantageously produced using cellular expression systems. In some embodiments, the peptides or shuttle agent of the present description may be chemically synthesized (e.g., solid- or liquid phase peptide synthesis), as opposed to expressed from a recombinant host cell. In some embodiments, the peptides or shuttle agent of the present description may lack an N-terminal methionine residue. A person of skill in the art may adapt a synthetic peptide or shuttle agent of the present description by using one or more modified amino acids (e.g., non-naturally-occurring amino acids), or by chemically modifying the synthetic peptide or shuttle agent of the present description, to suit particular needs of stability or other needs.

The expression "polypeptide-based" when used here in the context of a shuttle agent of the present description, is intended to distinguish the presently described shuttle agents from non-polypeptide or non-protein-based shuttle agents such as lipid- or cationic polymer-based transduction agents, which are often associated with increased cellular toxicity and may not be suitable for use in human therapy.

As used herein, the term "independent" is generally intended refer to molecules or agents which are not covalently bound to one another. For example, the expression "independent polypeptide cargo" is intended to refer to a polypeptide cargo to be delivered intracellularly that is not covalently bound (e.g., not fused) to a shuttle agent of the present description. In some aspects, having shuttle agents that are independent of (not fused to) a polypeptide cargo may be advantageous by providing increased shuttle agent versatility—e.g., not being required to re-engineer a new fusion protein for different polypeptide cargoes, and/or being able to readily vary the ratio of shuttle agent to cargo (as opposed to being limited to a 1:1 ratio in the case of a fusion protein).

As used herein, the expression "is or is from" or "is from" comprises functional variants of a given protein domain (e.g., CPD or ELD), such as conservative amino acid substitutions, deletions, modifications, as well as variants or function derivatives, which do not abrogate the activity of the protein domain.

Other objects, advantages and features of the present description will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 1A shows the results of a fluorescence microscopy experiment, while FIG. 1B shows the results of a flow cytometry experiment.

FIG. 22A shows a comparison of GFP-NLS transduction efficiencies using different transduction protocols (Protocol A vs. B). FIG. 22B shows the effect of using different concentrations of the shuttle His-CM18-PTD4 when using Protocol B.

FIGS. 23A, 23B, 23C, 23D, 24A, 24B, 24C, 24D, 25A, 25B, 26A, 26B, and 26C are microscopy images showing the results of transduction experiments in which GFP-NLS (FIGS. 23A, 23B, 23C, 23D, 24A, 24B, 25A, 25B, 26A, 26B, and 26C) or FITC-labeled anti-tubulin antibody (FIGS. 24C and 24D) cargo protein was intracellularly delivered with the shuttle His-CM18-PTD4 in HeLa cells. The bright field and fluorescence images of living cells are shown in FIGS. 23A, 23B, 23C, 23D, 24A, 24B, 24C, 24D, 26A, 26B, and 26C. In FIGS. 25A and 25B, the cells were fixed, permeabilized and subjected to immuno-labelling with an anti-GFP antibody and a fluorescent secondary antibody. White triangle windows indicate examples of areas of co-labelling between nuclei (DAPI) and GFP-NLS signals. FIGS. 26A, 26B, and 26C shows images captured by confocal microscopy.

FIGS. 29A-29I show the results of GFP-NLS transduction efficiency experiments in HeLa cells using different shuttle agents or single-domain/control peptides. GFP-NLS transduction efficiency was evaluated by flow cytometry and the percentage of GFP fluorescent cells ("Pos cells (%)"), as well as corresponding cell viability data ("viability (%)") are shown in FIGS. 29A, 29B, 29D-29G and 29I. In FIGS. 29A and 29D-29F, cells were exposed to the cargo/shuttle agent for 10 seconds. In panel I, cells were exposed to the cargo/shuttle agent for 1 minute. In FIGS. 29B, 29C, 29G and 29H, cells were exposed to the cargo/shuttle agent for 1, 2, or 5 min. "Relative fluorescence intensity (FL1-A)" or "Signal intensity" corresponds to the mean of all fluorescence intensities from each cell with a GFP fluorescent signal after GFP-NLS fluorescent protein delivery with the shuttle agent. FIG. 29D shows the results of a control experiment in which only single-domain peptides (ELD or CDP) or the peptide His-PTD4 (His-CPD) were used for the GFP-NLS transduction, instead of the multi-domain shuttle agents.

FIG. 30A: TAT-KALA, FIG. 30B: His-CM18-PTD4, FIG. 30C: His-C (LLKK)$_3$C-PTD4, FIG. 30D: PTD4-KALA, FIG. 30E: EB1-PTD4, and FIG. 30F: His-CM18-PTD4-His. The insets in the bottom row panels show the results of corresponding flow cytometry analyses, indicating the percentage of cells exhibiting GFP fluorescence.

FIGS. 32A-32D shows microscopy images of THP-1 cells transduced with GFP-NLS cargo protein using the shuttle His-CM18-PTD4. Images captured under at 4×, 10× and 40× magnifications are shown in FIGS. 32A, 32B, and 32C, respectively. White triangle windows in FIG. 32C indicate examples of areas of co-labelling between cells (bright field) and GFP-NLS fluorescence. FIG. 32D shows the results of corresponding flow cytometry analyses, indicating the percentage of cells exhibiting GFP fluorescence.

FIG. 33A-33D show microscopy images of THP-1 cells transduced with GFP-NLS cargo protein using the shuttle His-CM18-PTD4. White triangle windows indicate examples of areas of co-labelling between cells (bright field; FIGS. 33A and 33B), and GFP-NLS fluorescence (FIG. 33C and FIG. 33D).

In FIG. 34B, "Relative fluorescence intensity (FL1-A)" corresponds to the mean of all fluorescence intensities from each cell with a GFP fluorescent signal after GFP-NLS fluorescent protein delivery with the shuttle agent.

FIG. 35D shows the metabolic activity index of the THP-1 cells after 1, 2, 4, and 24 h, and FIG. 35E shows the metabolic activity index of the THP-1 cells after 1 to 4 days, for cells exposed to the His-CM18-PTD4 shuttle.

FIGS. 38A-38B show fluorescence microscopy images of primary human myoblasts transduced with GFP-NLS using the shuttle His-CM18-PTD4. Cells were fixed and permeabilized prior to immuno-labelling GFP-NLS with an anti-GFP antibody and a fluorescent secondary antibody. Immuno-labelled GFP is shown in FIG. 38A, and this image is overlaid with nuclei (DAPI) labelling in FIG. 38B.

FIG. 39A-39E show a schematic layout (FIGS. 39A, 39B and 39C) and sample fluorescence images (FIGS. 39D and 39E) of a transfection plasmid surrogate assay used to evaluate the activity of intracellularly delivered CRISPR/Cas9-NLS complex. At Day 1 (FIG. 39A), cells are transfected with an expression plasmid encoding the fluorescent proteins mCherry™ and GFP, with a STOP codon separating their two open reading frames. Transfection of the cells with the expression plasmid results in only mCherry™ expression (FIG. 39D). A CRISPR/Cas9-NLS complex, which has been designed/programmed to cleave the plasmid DNA at the STOP codon, is then delivered intracellularly to the transfected cells expressing mCherry™, resulting double-stranded cleavage of the plasmid DNA at the STOP codon (FIG. 39B). In a fraction of the cells, random non-homologous DNA repair of the cleaved plasmid occurs and results in removal of the STOP codon (FIG. 39C), and thus GFP expression and fluorescence (FIG. 39E). White triangle windows indicate examples of areas of co-labelling of mCherry™ and GFP fluorescence.

FIG. 40A-40H show fluorescence microscopy images of HeLa cells expressing mCherry™ and GFP, indicating CRISPR/Cas9-NLS-mediated cleavage of plasmid surrogate DNA. In panels A-D, HeLa cells were co-transfected with three plasmids: the plasmid surrogate as described in the brief description of FIGS. 39A-39E, and two other expression plasmids encoding the Cas9-NLS protein and crRNA/tracrRNAs, respectively. CRISPR/Cas9-mediated cleavage of the plasmid surrogate at the STOP codon, and subsequent DNA repair by the cell, enables expression of GFP (FIGS. 40B and 40D) in addition to mCherry™ (FIGS. 40A and 40C). In FIGS. 40E-40H, HeLa cells were transfected with the plasmid surrogate and then transduced with an active CRISPR/Cas9-NLS complex using the shuttle His-CM18-PTD4. CRISPR/Cas9-NLS-mediated cleavage of the plasmid surrogate at the STOP codon, and subsequent DNA repair by the cell, enables expression of GFP (FIGS. 40F and 40H) in addition to mCherry™ (panels 40E and 40G).

FIG. 41A (lanes A to D) shows the products of a DNA cleavage assay (T7E1 assay) separated by agarose gel electrophoresis, which is used to measure CRISPR/Cas9-mediated cleavage of cellular genomic DNA. HeLa cells were transduced with a CRISPR-Cas9-NLS complex programmed to cleave the PPIB gene. The presence of the cleavage product framed in white boxes 1 and 2, indicates cleavage of the PPIB gene by the CRISPR-Cas9-NLS complex, which was delivered intracellularly using the shuttle His-C(LLKK)$_3$C-PTD4 (FIG. 41A, lane B) or with a lipidic transfection agent used as a positive control (FIG. 41A, lane D). This cleavage product is absent in negative controls (FIG. 41A, lanes A and C).

FIG. 46A shows the results with the shuttle agents: His-CM18-PTD4, His-CM18-PTD4-His, and His-C(LLKK)3C-PTD4 in HeLa cells. FIG. 46B shows the results with His-CM18-PTD4-His and His-CM18-L2-PTD4 in Jurkat cells. Negative controls (lane 4 in panels A and B) show amplified HPTR DNA sequence after incubation of the cells with the CRISPR/Cas9 complex without the presence of the shuttle agent. Positive controls (lane 5 in panels A and B) show the amplified HPTR DNA sequence after incubation of the cells with the Cas9/RNAs complex in presence of a commercial lipidic transfection agent.

FIG. 48B shows the stereotaxic coordinates of the injection site (black arrows) from the rat brain atlas of Franklin and Paxinos. The injection of GFP-NLS in presence of His-CM18-PTD4 was performed on the left part of the brain, and the negative control (injection of GFP-NLS alone), was done on the contralateral site. The black circle and connected black lines in FIG. 48B show the areas observed in the fluorescent pictures (FIGS. 48A, 48C and 48D).

FIGS. 49A and 49B show helical wheel (left panels) and "open cylinder" (right panels) representations of the peptides FSD5 and VSVG-PTD4, respectively. The geometrical shape of each amino acid residue corresponds to its biochemical property based on the residue's side chain (i.e., hydrophobicity, charge, or hydrophilicity). One of the main differences between the two opened cylindrical representations of FSD5 and VSVG-PTD4 is the presence of a highly hydrophobic core in FSD5 (outlined in FIG. 49A, left and right panels), which is not present in VSVG-PTD4. The cylinder in the lower middle panels of FIGS. 49A and 49B represent simplified versions of the opened cylindrical representations in the right panels, in which: "H" represents the high hydrophobic surface area; "h" represents low hydrophobic surface area; "+" represents positively charged residues; and "h" represent hydrophilic residues.

FIGS. 50A-50C show microscopy images of live HeLa cells successfully transduced by the shuttle agent FSD5 with fluorescently labelled antibodies as cargos. FIG. 50A shows the cytoplasmic transduction of a Goat Anti-Rabbit IgG H&L (Alexa Fluor® 594) antibody visualized by bright field (upper panel) and fluorescence microscopy (lower panel) at 20× magnification. FIGS. 50B and 50C show the cytoplasmic transduction of a Goat Anti-Mouse IgG H&L (Alexa Fluor® 488) antibody visualized by bright field (upper panels) and fluorescence microscopy (lower panels) at 10× and 20× magnifications, respectively.

FIGS. 51A-51F show the results of genome editing experiments in which CRISPR/Cas9-NLS genome editing complexes were transduced into different cell types (HeLa, NK cells, NIC-H196 cells, HCC-78 cells, and REC-1 cells) using different shuttle agent peptides (FSD5, FSD8, FSD10, FSD18), and successful genome editing was verified by genomic DNA cleavage assays. The CRISPR/Cas9-NLS complexes consisted of recombinant Cas9-NLS complexed with a crRNA/tracrRNA designed to cleave the HPRT genomic DNA sequence. Successful genome editing was observed by the detection of genomic DNA cleavage products (thick solid arrows), as compared to the uncleaved genomic target gene (thin dashed arrows). The negative control (–ctrl") were from transduction experiments performed in the absence of any shuttle agent peptide. An imaging software was used to quantify the relative signal intensities of the cleavage product bands directly on gels. The sum of all the bands in a given lane corresponds to 100% of the signal, and the numerical value in italics at the bottom of each lane is the sum of the relative signals (%) of only the two cleavage product bands (thick solid arrows).

FIGS. 52A-52E show the results of the cleavage of a targeted genomic B2M DNA sequence with the CRISPR/Cas9-NLS and the crRNA/tracrRNA, or with the CRISPR/Cpf1-NLS and a single guide RNA in the absence ("−ctrl") or presence of the shuttle agents FSD10, FSD18, FSD19, FSD21, FSD23 or FSD43 used at different concentrations, exposure times, and in different types of cells: THP-1 (FIG. 52A); NK (FIG. 52B-D) and HeLa (FIG. 52E), after separation by agarose gel electrophoresis. Cells were incubated with CRISPR/Cpf1 complexes and FSD shuttle agents at the indicated times and concentrations. Thin dashed arrows indicate the bands corresponding to the target gene, and thicker solid arrows indicate the bands corresponding to the CRISPR system-mediated cleavage products of this target gene, which indicate the successful transduction of fully functional CRISPR/Cas9-NLS genome editing complexes. An imaging software was used to quantify the relative signal intensities of each of the different bands directly on gels. The sum of all the bands in a given lane corresponds to 100% of the signal, and the numerical value in italics at the bottom of each lane is the sum of the relative signals (%) of only the two cleavage product bands (thick solid arrows).

FIGS. 52F-52I show the results of the cleavage of a targeted genomic GSK3 (FIG. 52F), CBLB (FIG. 52G) and DNMT1 (FIG. 52H-I) DNA sequence with the CRISPR/Cpf1-NLS and a single guide crRNA in the absence ("−ctrl") or presence of the shuttle agents FSD10, FSD18, FSD19 or FSD23 used at different concentrations, exposure times, and in different types of cells: NK (FIG. 52F-G); THP-1 (FIG. 52H) and primary myoblasts (FIG. 52I), after separation by agarose gel electrophoresis. Cells were incubated with CRISPR/Cpf1 complexes and FSD at the indicated times and concentrations. Thin dashed arrows indicate the bands corresponding to the target gene, and thicker solid arrows indicate the bands corresponding to the CRISPR system-mediated cleavage products of these target genes, which indicate the successful transduction of fully functional CRISPR/Cpf1-NLS genome editing complexes.

FIGS. 52J-52N show the results of the cleavage of a targeted genomic NKG2A DNA sequence with the CRISPR/Cpf1-NLS and a single guide crRNA in the absence ("−ctrl") or presence of the shuttle agents FSD10, FSD21, FSD22 or FSD23 used at different concentrations, exposure times, and in NK cells (FIG. 52F-52G) and NK-92 cells (FIG. 52H), after separation by agarose gel electrophoresis. Cells were incubated with CRISPR/Cpf1 complexes for the indicated incubation times and concentrations. Thin dashed arrows indicate the bands corresponding to the target gene, and thicker solid arrows indicate the bands corresponding to the CRISPR system-mediated cleavage products of this target gene, which indicate the successful transduction of fully functional CRISPR/Cpf1-NLS genome editing complexes.

FIGS. 53A-53C show the results of the cleavage of the targeted genomic HPRT, DNMT1 and B2M DNA sequences with CRISPR systems. The two genomic HPRT and DNMT1 (FIG. 53A) DNA sequences or two DNA loci on the genomic B2M exon 2 (FIG. 53B) were targeted in HeLa cells using CRISPR/Cas9-NLS and CRISPR/Cpf1-NLS genome editing complexes designed for those purposes, which were transduced using the shuttle agent peptide FSD18. The two DNA loci on the genomic B2M exon 2 (FIG. 53C) were targeted in NK cells with the CRISPR/Cpf1-NLS and single guide crRNA-1, crRNA-2 or both, in the absence ("−ctrl") or presence of the shuttle agents FSD10, FSD21 or FSD23 used at different concentrations, exposure times, after separation by agarose gel electrophoresis. Thin dashed arrows indicate the bands corresponding to the target gene, and thicker solid arrows indicate the bands corresponding to the CRISPR/Cpf1-mediated cleavage products in presence of the crRNA-1 or crRNA2 or both (crRNA1+2) for the B2M exon 2, which indicate the successful transduction of fully functional CRISPR/Cpf1-NLS genome editing complexes.

FIG. 57B shows the results of cytotoxicity assays in which target HeLa cells previously loaded with an intracellular fluorescent dye (calcein) were exposed to either wild-type (solid line) or genome edited NKG2A-KO (dotted line) effector NK-92 cells, at different Effector:Target ratios (E:T ratio). Cytotoxicity was evaluated by the relative release of intracellular calcein into the extracellular space resulting from disruption of the cell membranes of the target HeLa cells (% cell lysis").

SEQUENCE LISTING

Figure 1A:
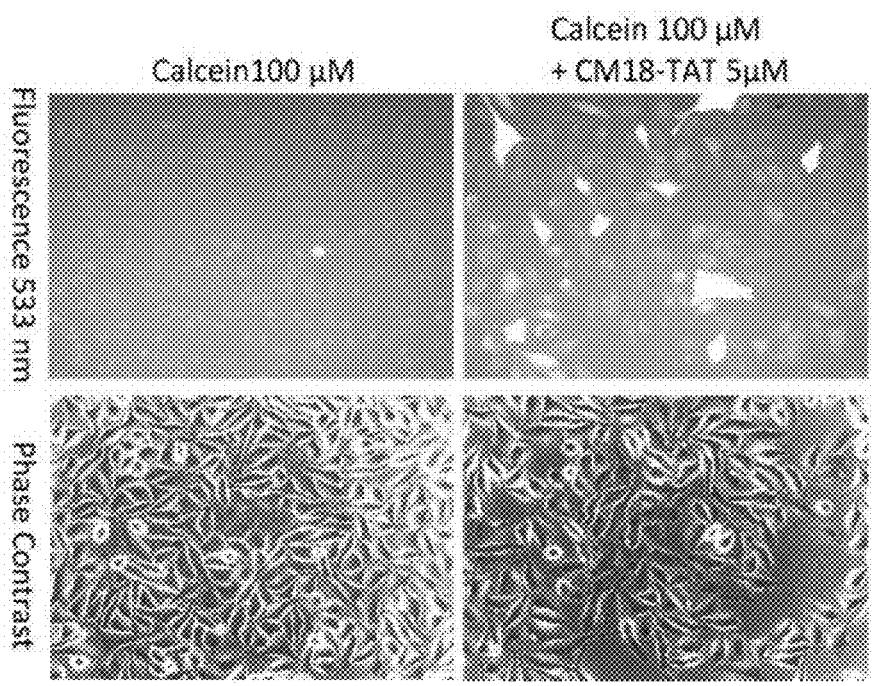
FIGS. 1A and 1B show a typical result of a calcein endosomal escape assay in which HEK293A cells were loaded with the fluorescent dye calcein ("100 μM calcein"), and were then treated (or not) with a shuttle agent that facilitates endosomal escape of the calcein ("100 μM calcein+CM18-TAT 5 μM").

This application contains a Sequence Listing in computer readable form created Jul. 20, 2017 having a size of about 92 kb. The computer readable form is incorporated herein by reference.

| SEQ ID NO: | Description |
|---|---|
| 1 | CM18 |
| 2 | Diphtheria toxin T domain (DT) |
| 3 | GALA |
| 4 | PEA |
| 5 | INF-7 |
| 6 | LAH4 |
| 7 | HGP |
| 8 | H5WYG |
| 9 | HA2 |
| 10 | EB1 |
| 11 | VSVG |
| 12 | Pseudomonas toxin |
| 13 | Melittin |
| 14 | KALA |
| 15 | JST-1 |
| 16 | SP |
| 17 | TAT |
| 18 | Penetratin (Antennapedia) |
| 19 | pVEC |
| 20 | M918 |
| 21 | Pep-1 |
| 22 | Pep-2 |
| 23 | Xentry |
| 24 | Arginine stretch |
| 25 | Transportan |
| 26 | SynB1 |
| 27 | SynB3 |
| 28 | E1a |
| 29 | SV40 T-Ag |
| 30 | c-myc |
| 31 | Op-T-NLS |
| 32 | Vp3 |
| 33 | Nucleoplasmin |
| 34 | Histone 2B NLS |
| 35 | Xenopus N1 |
| 36 | PARP |
| 37 | PDX-1 |
| 38 | QKI-5 |
| 39 | HCDA |
| 40 | H2B |
| 41 | v-Rel |
| 42 | Amida |
| 43 | RanBPS |
| 44 | Pho4p |
| 45 | LEF-1 |
| 46 | TCF-1 |
| 47 | BDV-P |
| 48 | TR2 |
| 49 | SOX9 |
| 50 | Max |
| 51 | Mitochondrial signal sequence from Tim9 |
| 52 | Mitochondrial signal sequence from Yeast cytochrome c oxidase subunit IV |
| 53 | Mitochondrial signal sequence from 18S rRNA |
| 54 | Peroxisome signal sequence - PTS1 |
| 55 | Nucleolar signal sequence from BIRC5 |
| 56 | Nucleolar signal sequence from RECQL4 |
| 57 | CM18-TAT |
| 58 | CM18-Penetratin |
| 59 | His-CM18-TAT |
| 60 | GFP |
| 61 | TAT-GFP |
| 62 | GFP-NLS |
| 63 | C(LLKK)3C |
| 64 | G(LLKK)3G |
| 65 | PTD4 |
| 66 | TAT-CM18 |
| 67 | TAT-KALA |
| 68 | His-CM18-PTD4 |
| 69 | His-CM18-9Arg |
| 70 | His-CM18-Transportan |
| 71 | His-LAH4-PTD4 |
| 72 | His-C(LLKK)3C-PTD4 |
| 73 | mCherryTM-NLS |
| 74 | Cas9-NLS |
| 75 | crRNA (Example 13.3) |
| 76 | tracrRNA (Example 13.3) |
| 77 | Feldan tracrRNA (Example 13.5, 13.6) |
| 78 | PPIB crRNA (Example 13.5) |
| 79 | Dharmacon tracrRNA (Example 13.5) |
| 80 | HOXB4-WT |
| 81 | His-PTD4 |
| 82 | PTD4-KALA |
| 83 | 9Arg-KALA |
| 84 | Pep1-KALA |

-continued

| SEQ ID NO: | Description |
|---|---|
| 85 | Xentry-KALA |
| 86 | SynB3-KALA |
| 87 | VSVG-PTD4 |
| 88 | EB1-PTD4 |
| 89 | JST-PTD4 |
| 90 | CM18-PTD4 |
| 91 | 6Cys-CM18-PTD4 |
| 92 | CM18-L1-PTD4 |
| 93 | CM18-L2-PTD4 |
| 94 | CM18-L3-PTD4 |
| 95 | His-CM18-TAT |
| 96 | His-CM18-PTD4-6Cys |
| 97 | 3His-CM18-PTD4 |
| 98 | 12His-CM18-PTD4 |
| 99 | HA-CM18-PTD4 |
| 100 | 3HA-CM18-PTD4 |
| 101 | CM18-His-PTD4 |
| 102 | His-CM18-PTD4-His |
| 103 | HPRT crRNA (Example 13.6) |
| 104 | FSD1 |
| 105 | FSD2 |
| 106 | FSD3 |
| 107 | FSD4 |
| 108 | FSD5 |
| 109 | FSD6 |
| 110 | FSD7 |
| 111 | FSD8 |
| 112 | FSD9 |
| 113 | FSD10 |
| 114 | FSD11 |
| 115 | FSD12 |
| 116 | FSD13 |
| 117 | FSD14 |
| 118 | FSD15 |
| 119 | FSD16 |
| 120 | FSD17 |
| 121 | FSD18 |
| 122 | FSD19 |
| 123 | FSD20 |
| 124 | FSD21 |
| 125 | FSD22 |
| 126 | FSD23 |
| 127 | FSD24 |
| 128 | FSD25 |
| 129 | FSD26 |
| 130 | FSN1 |
| 131 | FSN2 |
| 132 | FSN3 |
| 133 | FSN4 |
| 134 | FSN5 |
| 135 | FSN6 |
| 136 | FSN7 |
| 137 | FSN8 |
| 138 | FSD27 |
| 139 | FSD28 |
| 140 | FSD29 |
| 141 | FSD30 |
| 142 | FSD31 |
| 143 | FSD32 |
| 144 | FSD33 |
| 145 | FSD34 |
| 146 | FSD35 |
| 147 | FSD36 |
| 148 | FSD37 |
| 149 | FSD38 |
| 150 | FSD39 |
| 151 | FSD40 |
| 152 | FSD41 |
| 153 | FSD42 |
| 154 | Short DNA template |
| 155 | Cpf1-NLS |
| 156 | GFP coding DNA template |
| 157 | DNMT1 crRNA |
| 158 | LKLWXRXLKXXXXG motif |
| 159 | RRXXAKXA motif |
| 160 | B2M crRNA (Cas9) |
| 161 | B2M exon 2 crRNA-1 (Cpf1) |

-continued

| SEQ ID NO: | Description |
|---|---|
| 162 | B2M exon 2 crRNA-2 (Cpf1) |
| 163 | CBLB crRNA |
| 164 | GSK3 crRNA |
| 165 | NKG2A crRNA |
| 166 | B2M crRNA-E |
| 167 | B2M crRNA-J |
| 168 | B2M crRNA-G |

DETAILED DESCRIPTION

Large-scale screening efforts led to the discovery that domain-based peptide shuttle agents, comprising an endosome leakage domain (ELD) operably linked to a cell penetrating domain (CPD), and optionally one or more histidine-rich domains, can increase the transduction efficiency of an independent polypeptide cargo in eukaryotic cells, such that the cargo gains access to the cytosol/nuclear compartment (e.g., see Examples 1-15). Conversely, the above screening efforts also revealed some peptides having no or low polypeptide cargo transduction power, excessive toxicity, and/or other undesirable properties (e.g., poor solubility and/or stability).

Based on these empirical data (both positive and negative), the amino acid sequences and properties of successful, less successful, and failed peptides were compared in order to better understand the physicochemical properties common to the more successful shuttle agents. This comparison involved two main approaches: First, manually stratifying the different screened peptides according to their transduction performance, based on our complied biological characterization data; and second, a more simplified "transduction score" approach, which considered only the transduction efficiency and cellular toxicity of the different peptides, for a given polypeptide cargo and cell line.

For manual stratification, the screened peptides were evaluated individually according to their transduction performance, with due consideration to, for example: their solubility/stability/ease of synthesis; their ability to facilitate escape of endosomally-trapped calcein (e.g., see Example 2); their ability to deliver one or more types of independent polypeptide cargos intracellularly, as evaluated by flow cytometry (e.g., see Examples 3-6 and 8-15) in different types of cells and cell lines (e.g., primary, immortalized, adherent, suspension, etc.) as well as under different transduction protocols; their ability to deliver polypeptide cargos to the cytosol and/or nucleus, as evaluated by fluorescence microscopy (e.g., for fluorescently labelled cargos), increased transcriptional activity (e.g., for transcription factor cargos), or genome editing capabilities (e.g., for nuclease cargos or genome-editing complexes such as CRISPR/Cas9 or CRISPR/Cpf1) (e.g., see Examples 3-6 and 8-15), and toxicity towards different types of cells and cell lines (e.g., primary, immortalized, adherent, suspension, etc.), under different transduction protocols.

For the "transduction score" approach, each peptide was assigned a score corresponding to a given cell line and fluorescently-labelled polypeptide cargo, which combines both transduction efficiency and cellular toxicity data into a single numerical value. The transduction scores were calculated by simply multiplying the highest percentage transduction efficiency observed by flow cytometry for a given peptide, cargo and cell type by the percentage cellular viability for the peptide in the tested cell line. The peptides were then sorted according to their transduction scores as a screening tool to stratify peptides as successful, less successful, or failed shuttle agents.

The above-mentioned manual curation and "transduction score"-based analyses revealed a number of parameters that are generally shared by successful domain-based shuttle agents (e.g. see Example A). These parameters were then successfully used to manually design new peptide shuttle agents having polypeptide cargo transduction activity, which lack and/or are not based on known putative CPDs and/or ELDs (e.g., see Example B). Furthermore, it was observed that peptides satisfying the most number of design parameters had generally the highest transduction scores, while peptides satisfying the least number of design parameters had generally the lowest transduction scores.

The design parameters described herein were further validated by testing a plurality of synthetic peptides whose amino acid sequences were generated using a machine learning algorithm (e.g., see Example C), the algorithm having been "trained" using transduction efficiency and cellular toxicity data of domain-based peptides (but not the design parameters described herein). Interestingly, the peptides generated by the machine learning algorithm demonstrating the highest transduction scores were generally peptides that satisfied all of the design parameters described herein, thereby substantiating their use in actively designing and/or predicting the transduction activity of new peptide shuttle agents (e.g., tailored to particular polypeptide cargos and/or types of cells).

Rationally-designed peptide shuttle agents are shown herein to facilitate escape of an endosomally trapped fluorescent dye, suggesting endosomolytic activity (e.g., see Example D). Furthermore, the ability of rationally-designed peptide shuttle agents to transduce a variety of polypeptide cargos (e.g., fluorescent proteins, transcription factors, antibodies, as well as entire CRISPR-associated genome editing complexes, with or without a DNA template) in a variety of different cell types (both adherent and suspension) is also shown herein (e.g., see Examples E-G).

Rational Design Parameters and Peptide Shuttle Agents

In some aspects, the present description relates to a method for delivering a polypeptide cargo from an extracellular space to the cytosol and/or nucleus of a target eukaryotic cell. The method comprises contacting the target eukaryotic cell with the polypeptide cargo in the presence of a shuttle agent at a concentration sufficient to increase the transduction efficiency of said polypeptide cargo, as compared to in the absence of the shuttle agent. In some aspects, the shuttle agent relates to a peptide that satisfies one or more of the following parameters.

(1) In some embodiments, the shuttle agent is a peptide at least 20 amino acids in length. For example, the peptide may comprise a minimum length of 20, 21, 22, 23, 24, 25, 26, 27, 28, 29, or 30 amino acid residues, and a maximum length of 35, 36, 37, 38, 39, 40, 41, 42, 43, 44, 45, 46, 47, 48, 49, 50, 51, 52, 53, 54, 55, 60, 65, 70, 75, 80, 85, 90, 95, 100, 105, 110, 115, 120, 125, 130, 135, 140, 145, or 150 amino acid residues. In some embodiments, shorter peptides (e.g., in the 20-50 amino acid range) may be particularly advantageous because they may be more easily synthesized and purified by chemical synthesis approaches, which may be more suitable for clinical use (as opposed to recombinant proteins that must be purified from cellular expression systems). While numbers and ranges in the present description are often listed as multiples of 5, the present description should not be so limited. For example, the maximum length described herein should be understood as also encompassing a length of 56, 57, 58 . . . 61, 62, etc., in the present description, and that their non-listing herein is only for the sake of brevity. The same reasoning applies to the % of identities listed herein.

(2) In some embodiments, the peptide shuttle agent comprises an amphipathic alpha-helical motif. As used herein, the expression "alpha-helical motif" or "alpha-helix", unless otherwise specified, refers to a right-handed coiled or spiral conformation (helix) having angle of rotation between consecutive amino acids of 100 degrees and/or an alpha-helix having 3.6 residues per turn. As used herein, the expression "comprises an alpha-helical motif" or "an amphipathic alpha-helical motif" and the like, refers to the three-dimensional conformation that a peptide (or segment of a peptide) of the present description is predicted to adopt when in a biological setting based on the peptide's primary amino acid sequence, regardless of whether the peptide actually adopts that conformation when used in cells as a shuttle agent. Furthermore, the peptides of the present description may comprise one or more alpha-helical motifs in different locations of the peptide. For example, the shuttle agent FSD5 is predicted to adopt an alpha-helix over the entirety of its length (see FIG. 49C), while the shuttle agent FSD18 is predicted to comprise two separate alpha-helices towards the N and C terminal regions of the peptide (see FIG. 49D). In some embodiments, the shuttle agents of the present description are not predicted to comprise a beta-sheet motif, for example as shown in FIGS. 49E and 49F. Methods of predicting the presence of alpha-helices and beta-sheets in proteins and peptides are well known in the art. For example, one such method is based on 3D modeling using PEP-FOLD™, an online resource for de novo peptide structure prediction (http://bioserv.rpbs.univ-paris-diderot.fr/services/PEP-FOLD/) (Lamiable et al., 2016; Shen et al., 2014; Thévenet et al., 2012). Other methods of predicting the presence of alpha-helices in peptides and protein are known and readily available to the skilled person.

As used herein, the expression "amphipathic" refers to a peptide that possesses both hydrophobic and hydrophilic elements (e.g., based on the side chains of the amino acids that comprise the peptide). For example, the expression "amphipathic alpha helix" or "amphipathic alpha-helical motif" refers to a peptide predicted to adopt an alpha-helical motif having a non-polar hydrophobic face and a polar hydrophilic face, based on the properties of the side chains of the amino acids that form the helix.

(3) In some embodiments, peptide shuttle agents of the present description comprise an amphipathic alpha-helical motif having a positively-charged hydrophilic outer face, such as one that is rich in R and/or K residues. As used herein, the expression "positively-charged hydrophilic outer face" refers to the presence of at least three lysine (K) and/or arginine (R) residues clustered to one side of the amphipathic alpha-helical motif, based on alpha-helical wheel projection (e.g., see FIG. 49A, left panel). Such helical wheel projections may be prepared using a variety of programs, such as the online helical wheel projection tool available at: http://rzlab.ucr.edu/scripts/wheel/wheel.cgi. In some embodiments, the amphipathic alpha-helical motif may comprise a positively-charged hydrophilic outer face that comprises: (a) at least two, three, or four adjacent positively-charged K and/or R residues upon helical wheel projection; and/or (b) a segment of six adjacent residues comprising three to five K and/or R residues upon helical wheel projection, based on an alpha helix having angle of rotation between consecutive amino acids of 100 degrees and/or an alpha-helix having 3.6 residues per turn.

In some embodiments, peptide shuttle agents of the present description comprise an amphipathic alpha-helical motif comprising a hydrophobic outer face, the hydrophobic outer face comprising: (a) at least two adjacent L residues upon helical wheel projection; and/or (b) a segment of ten adjacent residues comprising at least five hydrophobic residues selected from: L, I, F, V, W, and M, upon helical wheel projection, based on an alpha helix having angle of rotation between consecutive amino acids of 100 degrees and/or an alpha-helix having 3.6 residues per turn.

(4) In some embodiments, peptide shuttle agents of the present description comprise an amphipathic alpha-helical motif having a highly hydrophobic core composed of spatially adjacent highly hydrophobic residues (e.g., L, I, F, V, W, and/or M). In some embodiments, the highly hydrophobic core may consist of spatially adjacent L, I, F, V, W, and/or M amino acids representing 12 to 50% of the amino acids of the peptide, calculated while excluding any histidine-rich domains (see below), based on an open cylindrical representation of the alpha-helix having 3.6 residues per turn, as shown for example in FIG. 49A, right panel. In some embodiments, the highly hydrophobic core may consist of spatially adjacent L, I, F, V, W, and/or M amino acids representing from 12.5%, 13%, 13.5%, 14%, 14.5%, 15%, 15.5%, 16%, 16.5%, 17%, 17.5%, 18%, 18.5%, 19%, 19.5%, or 20%, to 25%, 30%, 35%, 40%, or 45% of the amino acids of the peptide. More particularly, highly hydrophobic core parameter may be calculated by first arranging the amino acids of the peptide in an opened cylindrical representation, and then delineating an area of contiguous highly hydrophobic residues (L, I, F, V, W, M), as shown in FIG. 49A, right panel. The number of highly hydrophobic residues comprised in this delineated highly hydrophobic core is then divided by the total amino acid length of the peptide, excluding any histidine-rich domains (e.g., N- and/or C-terminal histidine-rich domains). For example, for the peptide shown in FIG. 49A, there are 8 residues in the delineated highly hydrophobic core, and 25 total residues in the peptide (excluding the terminal 12 histidines). Thus, the highly hydrophobic core is 32% (8/25).

(5) Hydrophobic moment relates to a measure of the amphiphilicity of a helix, peptide, or part thereof, calculated from the vector sum of the hydrophobicities of the side chains of the amino acids (Eisenberg et al., 1982). An online tool for calculating the hydrophobic moment of a polypeptide is available from: http://rzlab.ucr.edu/scripts/wheel/wheel.cgi. A high hydrophobic moment indicates strong amphiphilicity, while a low hydrophobic moment indicates poor amphiphilicity. In some embodiments, peptide shuttle agents of the present description may consist of or comprise a peptide or alpha-helical domain having have a hydrophobic moment ($\mu$) of 3.5 to 11. In some embodiments, the shuttle agent may be a peptide comprising an amphipathic alpha-helical motif having a hydrophobic moment between a lower limit of 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, and an upper limit of 9.5, 9.6, 9.7, 9.8, 9.9, 10.0, 10.1, 10.2, 10.3, 10.4, 10.5, 10.6, 10.7, 10.8, 10.9, or 11.0. In some embodiments, the shuttle agent may be a peptide having a hydrophobic moment between a lower limit of 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, and an upper limit of 9.5, 9.6, 9.7, 9.8, 9.9, 10.0, 10.1, 10.2, 10.3, 10.4, or 10.5. In some embodiments, the hydrophobic moment is calculated excluding any histidine-rich domains that may be present in the peptide.

(6) In some embodiments, peptide shuttle agents of the present description may have a predicted net charge of at least +4 at physiological pH, calculated from the side chains of K, R, D, and E residues. For example, the net charge of the peptide may be at least +5, +6, +7, at least +8, at least +9, at least +10, at least +11, at least +12, at least +13, at least +14, or at least +15 at physiological pH. These positive charges are generally conferred by the greater presence of positively-charged lysine and/or arginine residues, as opposed to negatively charged aspartate and/or glutamate residues.

(7) In some embodiments, peptide shuttle agents of the present description may have a predicted isoelectric point (pI) of 8 to 13, preferably from 10 to 13. Programs and methods for calculating and/or measuring the isoelectric point of a peptide or protein are known in the art. For example, pI may be calculated using the Prot Param software available at: http://web.expasy.org/protparam/

(8) In some embodiments, peptide shuttle agents of the present description may be composed of 35 to 65% of hydrophobic residues (A, C, G, I, L, M, F, P, W, Y, V). In particular embodiments, the peptide shuttle agents may be composed of 36% to 64%, 37% to 63%, 38% to 62%, 39% to 61%, or 40% to 60% of any combination of the amino acids: A, C, G, I, L, M, F, P, W, Y, and V.

(9) In some embodiments, peptide shuttle agents of the present description may be composed of 0 to 30% of neutral hydrophilic residues (N, Q, S, T). In particular embodiments, the peptide shuttle agents may be composed of 1% to 29%, 2% to 28%, 3% to 27%, 4% to 26%, 5% to 25%, 6% to 24%, 7% to 23%, 8% to 22%, 9% to 21%, or 10% to 20% of any combination of the amino acids: N, Q, S, and T.

(10) In some embodiments, peptide shuttle agents of the present description may be composed of 35 to 85% of the amino acids A, L, K and/or R In particular embodiments, the peptide shuttle agents may be composed of 36% to 80%, 37% to 75%, 38% to 70%, 39% to 65%, or 40% to 60% of any combination of the amino acids: A, L, K, or R.

(11) In some embodiments, peptide shuttle agents of the present description may be composed of 15 to 45% of the amino acids A and/or L, provided there being at least 5% of L in the peptide. In particular embodiments, the peptide shuttle agents may be composed of 15% to 40%, 20% to 40%, 20 to 35%, or 20 to 30% of any combination of the amino acids: A and L, provided there being at least 5% of L in the peptide.

(12) In some embodiments, peptide shuttle agents of the present description may be composed of 20 to 45% of the amino acids K and/or R In particular embodiments, the peptide shuttle agents may be composed of 20% to 40%, 20 to 35%, or 20 to 30% of any combination of the amino acids: K and R.

(13) In some embodiments, peptide shuttle agents of the present description may be composed of 0 to 10% the amino acids D and/or E. In particular embodiments, the peptide shuttle agents may be composed of 5 to 10% any combination of the amino acids: D and E.

(14) In some embodiments, the absolute difference between the percentage of A and/or L and the percentage of K and/or R in the peptide shuttle agent may be less than or equal to 10%. In particular embodiments, the absolute difference between the percentage of A and/or L and the percentage of K and/or R in the peptide shuttle agent may be less than or equal to 9%, 8%, 7%, 6%, or 5%.

(15) In some embodiments, peptide shuttle agents of the present description may be composed of 10 to 45% of the amino acids Q, Y, W, P, I, S, G, V, F, E, D, C, M, N, T, or H (i.e., not A, L, K, or R). In particular embodiments, the peptide shuttle agents may be composed of 15 to 40%, 20% to 35%, or 20% to 30% of any combination of the amino acids: Q, Y, W, P, I, S, G, V, F, E, D, C, M, N, T, and H.

In some embodiments, peptide shuttle agents of the present description respect at least one, at least two, at least three, at least four, at least five, at least six, at least seven, at least eight, at least nine, at least ten, at least eleven, at least twelve, at leave thirteen, at least fourteen, or all of parameters (1) to (15) described herein. In particular embodiments, peptide shuttle agents of the present description respect all of parameters (1) to (3), and at least six, at least seven, at least eight, at least nine, at least ten, at least eleven, or all of parameters (4) to (15) described herein.

In some embodiments, peptide shuttle agents of the present description may comprise or consist of any one of the amino acid sequences of SEQ ID NOs: 104, 105, 107, 108, 110-131, 133-135, 138, 140, 142, 145, 148, 151, and 152. In some embodiments, peptide shuttle agents of the present description may comprise the amino acid sequence motifs of SEQ ID NOs: 158 and/or 159, which were found in each of peptides FSD5, FSD16, FSD18, FSD19, FSD20, FSD22, and FSD23. In some embodiments, peptide shuttle agents of the present description may comprise the amino acid sequence motif of SEQ ID NO: 158 operably linked to the amino acid sequence motif of SEQ ID NO: 159. In some embodiments, peptide shuttle agents of the present description may comprise or consist of a peptide which is at least 50%, 55%, 60%, 65%, 70%, 75%, 80%, 85%, 90%, or 95% identical to the amino acid sequence of any one of SEQ ID NOs: 104, 105, 107, 108, 110-131, 133-135, 138, 140, 142, 145, 148, 151, and 152, or a functional variant of any one of SEQ ID NOs: 104, 105, 107, 108, 110-131, 133-135, 138, 140, 142, 145, 148, 151, and 152. As used herein, a "functional variant" refers to a peptide having polypeptide cargo transduction activity, which differs from the reference peptide by one or more conservative amino acid substitutions. As used herein, a "conservative amino acid substitution" is one in which one amino acid residue is replaced with another amino acid residue having a similar side chain. Families of amino acid residues having similar side chains have been well defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

In some embodiments, peptide shuttle agents of the present description may comprise or consist of the amino acid sequence of any one of SEQ ID NOs: 57-59, 66-72, or 82-102, or a functional variant thereof having at least 65%, 66%, 67%, 68%, 69%, 70%, 71%, 72%, 73%, 74%, 75%, 76%, 77%, 78%, 79%, 80%, 81% 82%, 83%, 84%, 85%, 86%, 87%, 88%, 89%, 90%, 91%, 92%, 93%, 94%, or 95% identity to any one of SEQ ID NOs: 57-59, 66-72, or 82-102. In some embodiments, peptide shuttle agents of the present description do not comprise one or more of the amino acid sequences of any one of SEQ ID NOs: 57-59, 66-72, or 82-102.

In some embodiments, shuttle agents of the present description may comprise oligomers (e.g., dimers, trimers, etc.) of peptides described herein. Such oligomers may be constructed by covalently binding the same or different types of shuttle agent monomers (e.g., using disulfide bridges to link cysteine residues introduced into the monomer sequences). In some embodiments, shuttle agents of the present description may comprise an N-terminal and/or a C-terminal cysteine residue.

Histidine-Rich Domains

In some embodiments, peptide shuttle agents of the present description may further comprise one or more histidine-rich domains. In some embodiments, the histidine-rich domain may be a stretch of at least 2, at least 3, at least 4, at least 5, or at least 6 amino acids comprising at least 30%, at least 35%, at least 40%, at least 45%, at least 50%, at least 55%, at least 60%, at least 65%, at least 70%, at least 75%, at least 80%, at least 85%, or at least 90% histidine residues. In some embodiments, the histidine-rich domain may comprise at least 2, at least 3, at least 4 at least 5, at least 6, at least 7, at least 8, or at least 9 consecutive histidine residues. Without being bound by theory, the histidine-rich domain in the shuttle agent may act as a proton sponge in the endosome through protonation of their imidazole groups under acidic conditions of the endosomes, providing another mechanism of endosomal membrane destabilization and thus further facilitating the ability of endosomally-trapped cargos to gain access to the cytosol. In some embodiments, the histidine-rich domain may be located at or towards the N and/or C terminus of the peptide shuttle agent.

Linkers

In some embodiments, peptide shuttle agents of the present description may comprise one or more suitable linkers (e.g., flexible polypeptide linkers). In some embodiments, such linkers may separate two or more amphipathic alpha-helical motifs (e.g., see the shuttle agent FSD18 in FIG. 49D). In some embodiments, linkers can be used to separate two more domains (CPDs, ELDs, or histidine-rich domains) from one another. In some embodiments, linkers may be formed by adding sequences of small hydrophobic amino acids without rotatory potential (such as glycine) and polar serine residues that confer stability and flexibility. Linkers may be soft and allow the domains of the shuttle agents to move. In some embodiments, prolines may be avoided since they can add significant conformational rigidity. In some embodiments, the linkers may be serine/glycine-rich linkers (e.g., GGS, GGSGGGS, GGSGGGSGGGS, or the like). In some embodiments, the use shuttle agents comprising a suitable linker may be advantageous for delivering an independent polypeptide cargo to suspension cells, rather than to adherent cells.

Endosome Leakage Domains (ELDs)

In some aspects, peptide shuttle agents of the present description may comprise an endosome leakage domain (ELD) for facilitating endosome escape and access to the cytoplasmic compartment. As used herein, the expression "endosome leakage domain" refers to a sequence of amino acids which confers the ability of endosomally-trapped macromolecules to gain access to the cytoplasmic compartment. Without being bound by theory, endosome leakage domains are short sequences (often derived from viral or bacterial peptides), which are believed to induce destabilization of the endosomal membrane and liberation of the endosome contents into the cytoplasm. As used herein, the expression "endosomolytic peptide" is intended to refer to this general class of peptides having endosomal membrane-destabilizing properties. Accordingly, in some embodiments, synthetic peptide or polypeptide-based shuttle agents of the present description may comprise an ELD which is an endosomolytic peptide. The activity of such peptides may be assessed for example using the calcein endosome escape assays described in Example 2.

In some embodiments, the ELD may be a peptide that disrupts membranes at acidic pH, such as pH-dependent membrane active peptide (PMAP) or a pH-dependent lytic peptide. For example, the peptides GALA and INF-7 are amphiphilic peptides that form alpha helices when a drop in pH modifies the charge of the amino acids which they contain. More particularly, without being bound by theory, it is suggested that ELDs such as GALA induce endosomal leakage by forming pores and flip-flop of membrane lipids following conformational change due to a decrease in pH (Kakudo, Chaki et al., 2004, Li, Nicol et al., 2004). In contrast, it is suggested that ELDs such as INF-7 induce endosomal leakage by accumulating in and destabilizing the endosomal membrane (El-Sayed, Futaki et al., 2009). Accordingly in the course of endosome maturation, the concomitant decline in pH causes a change in the conformation of the peptide and this destabilizes the endosome membrane leading to the liberation of the endosome contents. The same principle is thought to apply to the toxin A of *Pseudomonas* (Varkouhi, Scholte et al., 2011). Following a decline in pH, the conformation of the domain of translocation of the toxin changes, allowing its insertion into the endosome membrane where it forms pores (London 1992, O'Keefe 1992). This eventually favors endosome destabilization and translocation of the complex outside of the endosome. The above described ELDs are encompassed within the ELDs of the present description, as well as other mechanisms of endosome leakage whose mechanisms of action may be less well defined.

In some embodiments, the ELD may be an antimicrobial peptide (AMP) such as a linear cationic alpha-helical antimicrobial peptide (AMP). These peptides play a key role in the innate immune response due to their ability to strongly interact with bacterial membranes. Without being bound by theory, these peptides are thought to assume a disordered state in aqueous solution, but adopt an alpha-helical secondary structure in hydrophobic environments. The latter conformation thought to contribute to their typical concentration-dependent membrane-disrupting properties. When accumulated in endosomes at a certain concentrations, some antimicrobial peptides may induce endosomal leakage.

In some embodiments, the ELD may be an antimicrobial peptide (AMP) such as Cecropin-A/Melittin hybrid (CM series) peptide. Such peptides are thought to be among the smallest and most effective AMP-derived peptides with membrane-disrupting ability. Cecropins are a family of antimicrobial peptides with membrane-perturbing abilities against both Gram-positive and Gram-negative bacteria. Cecropin A (CA), the first identified antibacterial peptide, is composed of 37 amino acids with a linear structure. Melittin (M), a peptide of 26 amino acids, is a cell membrane lytic factor found in bee venom. Cecropin-melittin hybrid peptides have been shown to produce short efficient antibiotic peptides without cytotoxicity for eukaryotic cells (i.e., non-hemolytic), a desirable property in any antibacterial agent. These chimeric peptides were constructed from various combinations of the hydrophilic N-terminal domain of Cecropin A with the hydrophobic N-terminal domain of Melittin, and have been tested on bacterial model systems. Two 26-mers, CA(1-13)M(1-13) and CA(1-8) M(1-18) (Boman et al., 1989), have been shown to demonstrate a wider spectrum and improved potency of natural Cecropin A without the cytotoxic effects of melittin.

In an effort to produce shorter CM series peptides, the authors of Andreu et al., 1992 constructed hybrid peptides such as the 26-mer (CA(1-8)M(1-18)), and compared them with a 20-mer (CA(1-8)M(1-12)), a 18-mer (CA(1-8)M(1-10)) and six 15-mers ((CA(1-7)M(1-8), CA(1-7)M(2-9), CA(1-7)M(3-10), CA(1-7)M(4-11), CA(1-7)M(5-12), and CA(1-7)M(6-13)). The 20 and 18-mers maintained similar activity comparatively to CA(1-8)M(1-18). Among the six 15-mers, CA(1-7)M(1-8) showed low antibacterial activity, but the other five showed similar antibiotic potency compared to the 26-mer without hemolytic effect. Accordingly, in some embodiments, synthetic peptide or polypeptide-based shuttle agents of the present description may comprise an ELD which is or is from CM series peptide variants, such as those described above.

In some embodiments, the ELD may be the CM series peptide CM18 composed of residues 1-7 of Cecropin-A (KWKLFKKIGAVLKVLTTG) fused to residues 2-12 of Melittin (YGRKKRRQRRR), [C(1-7)M(2-12)]. When fused to the cell penetrating peptide TAT, CM18 was shown to independently cross the plasma membrane and destabilize the endosomal membrane, allowing some endosomally-trapped cargos to be released to the cytosol (Salomone et al., 2012). However, the use of a CM18-TAT11 peptide fused to a fluorophore (atto-633) in some of the authors' experiments, raises uncertainty as to the contribution of the peptide versus the fluorophore, as the use of fluorophores themselves have been shown to contribute to endosomolysis— e.g., via photochemical disruption of the endosomal membrane (Erazo-Oliveras et al., 2014).

In some embodiments, the ELD may be CM18 having the amino acid sequence of SEQ ID NO: 1, or a variant thereof having at least 70%, 71%, 72%, 73%, 74%, 75%, 76%, 77%, 78%, 79%, 80%, 81%, 82%, 83%, 84%, 85%, 86%, 87%, 88%, 89%, 85%, 90%, 91%, 92%, 93%, 94%, or 95% identity to SEQ ID NO: 1 and having endosomolytic activity.

In some embodiments, the ELD may be a peptide derived from the N terminus of the HA2 subunit of influenza hemagglutinin (HA), which may also cause endosomal membrane destabilization when accumulated in the endosome.

In some embodiments, synthetic peptide or polypeptide-based shuttle agents of the present description may comprise an ELD which is or is from an ELD set forth in Table I, or a variant thereof having endosome escape activity and/or pH-dependent membrane disrupting activity.

TABLE I

Examples of endosome leakage domains

| Name | Amino acid sequence | SEQ ID NO: | Reference(s) |
|---|---|---|---|
| CM18 | KWKLFKKIGAVLKVLTTG | 1 | (Salomone, Cardarelli et al., 2012) |
| Diphtheria toxin T domain | VGSSLSCINLDWDVIRDKTKTKIESL KEHGPIKNKMSESPNKTVSEEKAKQ | 2 | (Uherek, Fominaya et al., 1998, Glover, Ng |

TABLE I-continued

Examples of endosome leakage domains

| Name | Amino acid sequence | SEQ ID NO: | Reference(s) |
|---|---|---|---|
| (DT) | YLEEFHQTALEHPELSELKTVTGTNP VFAGANYAAWAVNVAQVIDSETAD NLEKTTAALSILPGIGSVMGIADGAV HHNTEEIVAQSIALSSLMVAQAIPLV GELVDIGFAAYNFVESIINLFQVVHN SYNRPAYSPG | | et al., 2009) |
| GALA | WEAALAEALAEALAEHLAEALAEA LEALAA | 3 | (Parente, Nir et al., 1990) (Li, Nicol et al., 2004) |
| PEA | VLAGNPAKHDLDIKPTVISHRLHFPE GGSLAALTAHQACHLPLETFTRHRQ PRGWEQLEQCGYPVQRLVALYLAA RLSWNQVDQVIRNALASPGSGGDLG EAIREQPEQARLALT | 4 | (Fominaya and Wels 1996) |
| INF-7 | GLFEAIEGFIENGWEGMIDGWYGC | 5 | (El-Sayed, Futaki et al., 2009) |
| LAH4 | KKALLALALHHLAHLALHLALALK KA | 6 | (Kichler, Mason et al., 2006) Kichler et al., 2003 |
| HGP | LLGRRGWEVLKYWWNLLQYWSQEL | 7 | (Zhang, Cui et al., 2006) |
| H5WYG | GLFHAIAHFIHGGWHGLIHGWYG | 8 | (Midoux, Kichler et al., 1998) |
| HA2 | GLFGAIAGFIENGWEGMIDGWYG | 9 | (Lorieau, Louis et al., 2010) |
| EB1 | LIRLWSHLIHIWFQNRRLKWKKK | 10 | (Amand, Norden et al., 2012) |
| VSVG | KFTIVFPHNQKGNWKNVPSNYHYCP | 11 | (Schuster, Wu et al., 1999) |
| Pseudomonas toxin | EGGSLAALTAHQACHLPLETFTRHR QPRGWEQLEQCGYPVQRLVALYLA ARLSWNQVDQVIRNALASPGSGGDL GEAIREQPEQARLALTLAAAESERFV RQGTGNDEAGAANAD | 12 | (Fominaya, Uherek et al., 1998) |
| Melittin | GIGAVLKVLTTGLPALISWIKRKRQQ | 13 | (Tan, Chen et al., 2012) |
| KALA | WEAKLAKALAKALAKHLAKALAKA LKACEA | 14 | (Wyman, Nicol et al., 1997) |
| JST-1 | GLFEALLELLESLWELLLEA | 15 | (Gottschalk, Sparrow et al., 1996) |
| C(LLKK)₃C | CLLKKLLKKLLKKC | 63 | (Luan et al., 2014) |
| G(LLKK)₃G | GLLKKLLKKLLKKG | 64 | (Luan et al., 2014) |

In some embodiments, shuttle agents of the present description may comprise one or more ELD or type of ELD. More particularly, they can comprise at least 2, at least 3, at least 4, at least 5, or more ELDs. In some embodiments, the shuttle agents can comprise between 1 and 10 ELDs, between 1 and 9 ELDs, between 1 and 8 ELDs, between 1 and 7 ELDs, between 1 and 6 ELDs, between 1 and 5 ELDs, between 1 and 4 ELDs, between 1 and 3 ELDs, etc.

In some embodiments, the order or placement of the ELD relative to the other domains (CPD, histidine-rich domains) within the shuttle agents of the present description may be varied provided the shuttling ability of the shuttle agent is retained.

In some embodiments, the ELD may be a variant or fragment of any one those listed in Table I, and having endosomolytic activity. In some embodiments, the ELD may comprise or consist of the amino acid sequence of any one of SEQ ID NOs: 1-15, 63, or 64, or a sequence which is at least 70%, 71%, 72%, 73%, 74%, 75%, 76%, 77%, 78%, 79%, 80%, 81%, 82%, 83%, 84%, 85%, 86%, 87%, 88%, 89%, 85%, 90%, 91%, 92%, 93%, 94%, or 95% identical to any one of SEQ ID NOs: 1-15, 63, or 64, and having endosomolytic activity.

In some embodiments, shuttle agents of the present description do not comprise one or more of the amino acid sequence of any one of SEQ ID NOs: 1-15, 63, or 64.

Cell Penetration Domains (CPDs)

In some aspects, the shuttle agents of the present description may comprise a cell penetration domain (CPD). As used herein, the expression "cell penetration domain" refers to a sequence of amino acids which confers the ability of a macromolecule (e.g., peptide or protein) containing the CPD to be transduced into a cell.

In some embodiments, the CPD may be (or may be from) a cell-penetrating peptide or the protein transduction domain of a cell-penetrating peptide. Cell-penetrating peptides can serve as carriers to successfully deliver a variety of cargos intracellularly (e.g., polynucleotides, polypeptides, small molecule compounds or other macromolecules/compounds that are otherwise membrane-impermeable). Cell-penetrating peptides often include short peptides rich in basic amino acids that, once fused (or otherwise operably linked) to a macromolecule, mediate its internalization inside cells (Shaw, Catchpole et al., 2008). The first cell-penetrating peptide was identified by analyzing the cell penetration ability of the HIV-1 trans-activator of transcription (Tat) protein (Green and Loewenstein 1988, Vives, Brodin et al., 1997). This protein contains a short hydrophilic amino acid sequence, named "TAT", which promotes its insertion within the plasma membrane and the formation of pores. Since this discovery, many other cell-penetrating peptides have been described. In this regard, in some embodiments, the CPD can be a cell-penetrating peptide as listed in Table II, or a variant thereof having cell-penetrating activity.

Without being bound by theory, cell-penetrating peptides are thought to interact with the cell plasma membrane before crossing by pinocytosis or endocytosis. In the case of the TAT peptide, its hydrophilic nature and charge are thought to promote its insertion within the plasma membrane and the formation of a pore (Herce and Garcia 2007). Alpha helix motifs within hydrophobic peptides (such as SP) are also thought to form pores within plasma membranes (Veach, Liu et al., 2004).

In some embodiments, shuttle agents of the present description may comprise one or more CPD or type of CPD. More particularly, they may comprise at least 2, at least 3, at least 4, or at least 5 or more CPDs. In some embodiments, the shuttle agents can comprise between 1 and 10 CPDs, between 1 and 6 CPDs, between 1 and 5 CPDs, between 1 and 4 CPDs, between 1 and 3 CPDs, etc.

In some embodiments, the CPD may be TAT having the amino acid sequence of SEQ ID NO: 17, or a variant thereof having at least 70%, 71%, 72%, 73%, 74%, 75%, 76%, 77%, 78%, 79%, 80%, 81% 82%, 83%, 84%, 85%, 86%, 87%, 88%, 89%, 90%, 91%, 92%, 93%, 94%, or 95% identity to SEQ ID NO: 17 and having cell penetrating activity; or Penetratin having the amino acid sequence of SEQ ID NO: 18, or a variant thereof having at least 70%, 71%, 72%, 73%, 74%, 75%, 76%, 77%, 78%, 79%, 80%, 81% 82%, 83%, 84%, 85%, 86%, 87%, 88%, 89%, 85%, 86%, 87%, 88%, 89%, 90%, 91%, 92%, 93%, 94%, or 95% identity to SEQ ID NO: 18 and having cell penetrating activity.

TABLE II

Examples of cell-penetrating peptides

| Name | Amino acid sequence | SEQ ID NO: | Reference(s) |
|---|---|---|---|
| SP | AAVALLPAVLLALLAP | 16 | (Mahlum, Mandal et al., 2007) |
| TAT | YGRKKRRQRRR | 17 | (Green and Loewenstein 1988, Fawell, Seery et al., 1994, Vives, Brodin et al., 1997) |
| Penetratin (Antennapedia) | RQIKIWFQNRRMKWKK | 18 | (Perez, Joliot et al., 1992) |
| pVEC | LLIILRRRIRKQAHAHSK | 19 | (Elmquist, Lindgren et al., 2001) |
| M918 | MVTVLFRRLRIRRACGPPRVRV | 20 | (El-Andaloussi, Johansson et al., 2007) |
| Pep-1 | KETWWETWWTEWSQPKKKRKV | 21 | (Morris, Depollier et al., 2001) |
| Pep-2 | KETWFETWFTEWSQPKKKRKV | 22 | (Morris, Chaloin et al., 2004) |
| Xentry | LCLRPVG | 23 | (Montrose, Yang et al., 2013) |
| Arginine stretch | RRRRRRRR | 24 | (Zhou, Wu et al., 2009) |
| Transportan | WTLNSAGYLLGKINLKALAALAKKIL | 25 | (Hallbrink, Floren et al., 2001) |
| SynB1 | RGGRLSYSRRRFSTSTGR | 26 | (Drin, Coffin et al., 2003) |
| SynB3 | RRLSYSRRRF | 27 | (Drin, Coffin et al., 2003) |
| PTD4 | YARAAARQARA | 65 | (Ho et al, 2001) |

In some embodiments, the CPD may be PTD4 having the amino acid sequence of SEQ ID NO: 65, or a variant thereof having at least 70%, 71%, 72%, 73%, 74%, 75%, 76%, 77%, 78%, 79%, 80%, 81% 82%, 83%, 84%, 85%, 86%, 87%, 88%, 89%, 90%, 91%, 92%, 93%, 94%, or 95% identity to SEQ ID NO: 65.

In some embodiments, the order or placement of the CPD relative to the other domains (ELD, histidine-rich domains) within the shuttle agents of the present description may be varied provided the shuttling ability of the shuttle agent is retained.

In some embodiments, the CPD may be a variant or fragment of any one those listed in Table II, and having cell penetrating activity. In some embodiments, the CPD may comprise or consist of the amino acid sequence of any one of SEQ ID NOs: 16-27 or 65, or a sequence which is at least 70%, 71%, 72%, 73%, 74%, 75%, 76%, 77%, 78%, 79%, 80%, 81%, 82%, 83%, 84%, 85%, 86%, 87%, 88%, 89%, 85%, 90%, 91%, 92%, 93%, 94%, or 95% identical to any one of SEQ ID NOs: 16-27 or 65, and having cell penetrating activity.

In some embodiments, shuttle agents of the present description do not comprise any one of the amino acid sequences of SEQ ID NOs: 16-27 or 65.

Cargos

In some aspects, peptide shuttle agents of the present description may be useful for delivering a polypeptide cargo (e.g., an independent polypeptide cargo) from an extracellular space to the cytosol and/or nucleus of a target eukaryotic cell. In some embodiments, the polypeptide cargo may be fused to one or more CPDs to further facilitate intracellular delivery. In some embodiments, the CPD fused to the polypeptide cargo may be the same or different from a CPD that may be present in the shuttle agent of the present description. Such fusion proteins may be constructed using standard recombinant technology. In some embodiments, the independent polypeptide cargo may be fused, complexed with, or covalently bound to a second biologically active cargo (e.g., a biologically active polypeptide or compound). Alternatively or simultaneously, the polypeptide cargo may comprise a subcellular targeting domain.

In some embodiments, the polypeptide cargo must be delivered to the nucleus for it to carry out its intended biological effect. One such example is when the cargo is a polypeptide intended for nuclear delivery (e.g., a transcription factor). In this regard, studies on the mechanisms of translocation of viral DNA have led to the identification of nuclear localization signals (NLSs). The NLS sequences are recognized by proteins (importins α and β), which act as transporters and mediators of translocation across the nuclear envelope. NLSs are generally enriched in charged amino acids such as arginine, histidine, and lysine, conferring a positive charge which is partially responsible for their recognition by importins. Accordingly, in some embodiments, the polypeptide cargo may comprise an NLS for facilitating nuclear delivery, such as one or more of the NLSs as listed in Table III, or a variant thereof having nuclear targeting activity. Of course, it is understood that, in certain embodiments, the polypeptide cargo may comprise its natural NLS.

TABLE III

Nuclear localization signals

| Name | Amino acid sequence | SEQ ID NO: | Reference(s) |
|---|---|---|---|
| E1a | KRPRP | 28 | (Kohler, Gorlich et al., 2001) |
| SV40 T-Ag | PKKKRKV | 29 | (Lanford, Kanda et al., 1986) |
| c-myc | PAAKRVKLD | 30 | (Makkerh, Dingwall et al., 1996) |
| Op-T-NLS | SSDDEATADSQHAAPPKKKRKV | 31 | (Chan and Jans 1999) |
| Vp3 | KKKRK | 32 | (Nakanishi, Shum et al., 2002) |
| Nucleoplasmin | KRPAATKKAGQAKKKK | 33 | (Fanara, Hodel et al., 2000) |
| Histone 2B NLS | DGKKRKRSRK | 34 | (Moreland, Langevin et al., 1987) |
| Xenopus N1 | VRKKRKTEEESPLKDKDAKKSKQE | 35 | (Kleinschmidt and Seiter 1988) |
| PARP | KRKGDEVDGVDECAKKSKK | 36 | (Schreiber, Molinete et al., 1992) |
| PDX-1 | RRMKWKK | 37 | (Moede, Leibiger et al., 1999) |
| QKI-5 | RVHPYQR | 38 | (Wu, Zhou et al., 1999) |
| HCDA | KRPACTLKPECVQQLLVCSQEAKK | 39 | (Somasekaram, Jarmuz et al., 1999) |

TABLE III-continued

Nuclear localization signals

| Name | Amino acid sequence | SEQ ID NO: | Reference(s) |
|---|---|---|---|
| H2B | GKKRSKA | 40 | (Moreland, Langevin et al., 1987) |
| v-Rel | KAKRQR | 41 | (Gilmore and Temin 1988) |
| Amida | RKRRR | 42 | (Irie, Yamagata et al., 2000) |
| RanBP3 | PPVKRERTS | 43 | (Welch, Franke et al., 1999) |
| Pho4p | PYLNKRKGKP | 44 | (Welch, Franke et al., 1999) |
| LEF-1 | KKKKRKREK | 45 | (Prieve and Waterman 1999) |
| TCF-1 | KKKRRSREK | 46 | (Prieve and Waterman 1999) |
| BDV-P | PRPRKIPR | 47 | (Shoya, Kobayashi et al., 1998) |
| TR2 | KDCVINKHHRNRCQYCRLQR | 48 | (Yu, Lee et al., 1998) |
| SOX9 | PRRRK | 49 | (Sudbeck and Scherer 1997) |
| Max | PQSRKKLR | 50 | (Kato, Lee et al., 1992) |

Once delivered to the cytoplasm, recombinant proteins are exposed to protein trafficking system of eukaryotic cells. Indeed, all proteins are synthesized in the cell's cytoplasm and are then redistributed to their final subcellular localization by a system of transport based on small amino acid sequences recognized by shuttle proteins (Karniely and Pines 2005, Stojanovski, Bohnert et al., 2012). In addition to NLSs, other localization sequences can mediate subcellular targeting to various organelles following intracellular delivery of the polypeptide cargos of the present description. Accordingly, in some embodiments, polypeptide cargos of the present description may comprise a subcellular localization signal for facilitating delivery of the shuttle agent and cargo to specific organelles, such as one or more of the sequences as listed in Table IV, or a variant thereof having corresponding subcellular targeting activity.

TABLE IV

Subcellular localization signals

| Name | Amino acid sequence | SEQ ID NO: | Reference(s) |
|---|---|---|---|
| Mitochondrial signal sequence from Tim9 | NLVERCFTD | 51 | (Milenkovic, Ramming et al., 2009) |
| Mitochondrial signal sequence from Yeast cytochrome c oxidase subunit IV | MLSLRQSIRFFK | 52 | (Hurt, Pesold-Hurt et al., 1985) |
| Mitochondrial signal sequence from 18S rRNA | MLISRCKWSRFPGNQR | 53 | (Bejarano and Gonzalez 1999) |
| Peroxisome signal sequence - PTS1 | SKL | 54 | (Gould, Keller et al., 1989) |
| Nucleolar signal sequence from BIRC5 | MQRKPTIRRKNLRLRRK | 55 | (Scott, Boisvert et al., 2010) |
| Nucleolar signal sequence from RECQL4 | KQAWKQKWRKK | 56 | (Scott, Boisvert et al., 2010) |

In some embodiments, the cargo can be a biologically active compound such as a biologically active (recombinant) polypeptide (e.g., a transcription factor, a cytokine, or a nuclease) intended for intracellular delivery. As used herein, the expression "biologically active" refers to the ability of a compound to mediate a structural, regulatory, and/or biochemical function when introduced in a target cell.

In some embodiments, the cargo may be a recombinant polypeptide intended for nuclear delivery, such as a transcription factor. In some embodiments, the transcription factor can be HOXB4 (Lu, Feng et al., 2007), NUP98-HOXA9 (Takeda, Goolsby et al., 2006), Oct3/4, Sox2, Sox9, Klf4, c-Myc (Takahashi and Yamanaka 2006), MyoD (Sung, Mun et al., 2013), Pdx1, Ngn3 and MafA (Akinci, Banga et al., 2012), Blimp-1 (Lin, Chou et al., 2013), Eomes, T-bet (Gordon, Chaix et al., 2012), FOXO3A (Warr, Binnewies et al., 2013), NF-YA (Dolfini, Minuzzo et al., 2012), SALL4 (Aguila, Liao et al., 2011), ISL1 (Fonoudi, Yeganeh et al., 2013), FoxA1 (Tan, Xie et al., 2010), Nanog, Esrrb, Lin28 (Buganim et al., 2014), HIF1-alpha (Lord-Dufour et al., 2009), Hlf, Runxlt1, Pbx1, Lmo2, Zfp37, Prdm5 (Riddell et al., 2014), or Bcl-6 (Ichii, Sakamoto et al., 2004).

In some embodiments, the cargo may be a recombinant polypeptide intended for nuclear delivery, such as a nuclease useful for genome editing technologies. In some embodiments, the nuclease may be an RNA-guided endonuclease, a CRISPR endonuclease, a type I CRISPR endonuclease, a type II CRISPR endonuclease, a type m CRISPR endonuclease, a type IV CRISPR endonuclease, a type V CRISPR endonuclease, a type VI CRISPR endonuclease, CRISPR associated protein 9 (Cas9), Cpf1 (Zetsche et al., 2015), CasX and/or CasY (Burstein et al., 2016) a zinc-finger nuclease (ZFN), a Transcription activator-like effector nuclease (TALEN) (Cox et al., 2015), a homing endonuclease, a meganuclease, a DNA-guided nuclease such as *Natronobacterium gregoryi* Argonaute (NgAgo; Gao et al., 2016), or any combination thereof. In some embodiments, the nuclease may be a catalytically dead endonuclease, such as a catalytically dead CRISPR associated protein 9 (dCas9), dCpf1, dCasX, dCasY, or any combination thereof. Other nucleases not explicitly mentioned here may nevertheless be encompassed in the present description. In some embodiments, the nuclease may be fused to a nuclear localization signal (e.g., Cas9-NLS; Cpf1-NLS; ZFN-NLS; TALEN-NLS). In some embodiments, the nuclease may be complexed with a nucleic acid (e.g., one or more guide RNAs, a crRNA, a tracrRNAs, or both a crRNA and a tracrRNA). In some embodiments, the nuclease may possess DNA or RNA-binding activity, but may lack the ability to cleave DNA.

In some embodiments, the shuttle agents of the present description may be used for intracellular delivery (e.g., nuclear delivery) of one or more CRISPR endonucleases, for example one or more of the CRISPR endonucleases described below.

Type I and its subtypes A, B, C, D, E, F and I, including their respective Cas1, Cas2, Cas3, Cas4, Cas6, Cas7 and Cas8 proteins, and the signature homologs and subunits of these Cas proteins including Cse1, Cse2, Cas7, Cas5, and Cas6e subunits in *E. coli* (type I-E) and Csy1, Csy2, Csy3, and Cas6f in *Pseudomonas aeruginosa* (type I-F) (Wiedenheft et al., 2011; Makarova et al, 2011). Type II and its subtypes A, B, C, including their respective Cas1, Cas2 and Cas9 proteins, and the signature homologs and subunits of these Cas proteins including Csn complexes (Makarova et al, 2011). Type II and its subtypes A, B and MTH326-like module, including their respective Cas1, Cas2, Cas6 and Cas10 proteins, and the signature homologs and subunits of these Cas proteins including Csm and CMR complexes (Makarova et al, 2011). Type IV represents the Csf3 family of Cas proteins. Members of this family show up near CRISPR repeats in *Acidithiobacillus ferrooxidans* ATCC 23270, *Azoarcus* sp. (strain EbN1), and *Rhodoferox ferrireducens* (strain DSM 15236/ATCC BAA-621/T118). In the latter two species, the CRISPR/Cas locus is found on a plasmid. Type V and it subtypes have only recently been discovered and include Cpf1, C2c1, and C2c3. Type VI includes the enzyme C2c2, which reported shares little homology to known sequences.

In some embodiments, the shuttle agents of the present description may be used in conjunction with one or more of the nucleases, endonucleases, RNA-guided endonuclease, CRISPR endonuclease described above, for a variety of applications, such as those described herein. CRISPR systems interact with their respective nucleic acids, such as DNA binding, RNA binding, helicase, and nuclease motifs (Makarova et al, 2011; Barrangou & Marraffini, 2014). CRISPR systems may be used for different genome editing applications including:

- a Cas-mediated genome editing method conducting to non-homologous end-joining (NHEJ) and/or Homologous-directed recombination (HDR) (Cong et al, 2013);
- a catalytically dead Cas (dCas) that can repress and/or activate transcription initiation when bound to promoter sequences, to one or several gRNA(s) and to a RNA polymerase with or without a complex formation with others protein partners (Bikard et al, 2013);
- a catalytically dead Cas (dCas) that can also be fused to different functional proteins domains as a method to bring enzymatic activities at specific sites of the genome including transcription repression, transcription activation, chromatin remodeling, fluorescent reporter, histone modification, recombinase system acetylation, methylation, ubiquitylation, phosphorylation, sumoylation, ribosylation and citrullination (Gilbert et al, 2013).

The person of ordinary skill in the art will understand that the present shuttle agents, although exemplified with Cas9 and Cpf1 in the present examples, may be used with other nucleases as described herein. Thus, nucleases such as Cpf1, Cas9, and variants of such nucleases or others, are encompassed by the present description. It should be understood that, in one aspect, the present description may broadly cover any cargo having nuclease activity, such an RNA-guided endonuclease, or variants thereof (e.g., those that can bind to DNA or RNA, but have lost their nuclease activity; or those that have been fused to a transcription factor).

In some embodiments, the polypeptide cargo may be a cytokine such as a chemokine, an interferon, an interleukin, a lymphokine, or a tumour necrosis factor. In some embodiments, the polypeptide cargo may be a hormone or growth factor. In some embodiments, the cargo may be an antibody (e.g., a labelled antibody, a therapeutic antibody, an anti-apoptotic antibody, an antibody that recognizes an intracellular antigen). In some embodiments, the cargo can be a detectable label (fluorescent polypeptide or reporter enzyme) that is intended for intracellular delivery, for example, for research and/or diagnostic purposes.

In some embodiments, the cargo may be a globular protein or a fibrous protein. In some embodiments, the cargo may have a molecule weight of any one of about 5, 10, 15, 20, 25, 30, 35, 40, 45, to 50 to about 150, 200, 250, 300, 350, 400, 450, 500 kDa or more. In some embodiments, the cargo may have a molecule weight of between about 20 to 200 kDa.

In some embodiments, the polypeptide cargo may be a peptide cargo, such as peptide that recognizes an intracellular molecule.

In some embodiments, peptide shuttle agents of the present description may be useful for delivering a polypeptide cargo from an extracellular space to the cytosol and/or nucleus of different types of target eukaryotic cells. The target eukaryotic cells may be an animal cell, a mammalian cell, or a human cell. In some embodiments, the target eukaryotic cells may be a stem cell (e.g., embryonic stem cells, pluripotent stem cells, induced pluripotent stem cells, neural stem cells, mesenchymal stem cells, hematopoietic stem cells, peripheral blood stem cells), a primary cell (e.g., myoblast, fibroblast), or an immune cell (e.g., NK cell, T cell, dendritic cell, antigen presenting cell). It will be understood that cells that are often resistant or not amenable to protein transduction may be interesting candidates for the synthetic peptides or polypeptide-based shuttle agents of the present description.

Non-Toxic, Metabolizable Shuttle Agents

In some embodiments, the shuttle agents of the present description may be non-toxic to the intended target eukaryotic cells at concentrations up to 50 µM, 45 µM, 40 µM, 35 µM, 30 µM, 25 µM, 20 µM, 15 µM, 10 µM, 9 µM, 8 µM, 7 µM, 6 µM, 5 µM, 4 µM, 3 µM, 2 µM, 1 µM, 0.5 µMm 0.1 µM, or 0.05 µM. Cellular toxicity of shuttle agents of the present description may be measured using any suitable method. Furthermore, transduction protocols may be adapted (e.g., concentrations of shuttle and/or cargo used, shuttle/cargo exposure times, exposure in the presence or absence of serum), to reduce or minimize toxicity of the shuttle agents, and/or to improve/maximize transfection efficiency.

In some embodiments, shuttle agents of the present description may be readily metabolizable by intended target eukaryotic cells. For example, the shuttle agents may consist entirely or essentially of peptides or polypeptides, for which the target eukaryotic cells possess the cellular machinery to metabolize/degrade. Indeed, the intracellular half-life of the synthetic peptides and polypeptide-based shuttle agents of the present description is expected to be much lower than the half-life of foreign organic compounds such as fluorophores. However, fluorophores can be toxic and must be investigated before they can be safely used clinically (Alford et al., 2009). In some embodiments, shuttle agents of the present description may be suitable for clinical use. In some embodiments, the shuttle agents of the present description may avoid the use of domains or compounds for which toxicity is uncertain or has not been ruled out.

Cocktails

In some embodiments, the present description relates to a composition comprising a cocktail of at least 2, at least 3, at least 4, or at least 5 different types of the synthetic peptides or polypeptide-based shuttle agents as defined herein. In some embodiments, combining different types of synthetic peptides or peptide shuttle agents (e.g., different shuttle agents comprising different types of domains) may provide increased versatility for delivering different polypeptide cargos intracellularly. Furthermore, without being bound by theory, combining lower concentrations of different types of shuttle agents may help reduce cellular toxicity associated with using a single type of shuttle agent (e.g., at higher concentrations).

Methods, Kits, Uses and Cells

In some embodiments, the present description relates to methods for delivering a polypeptide cargo from an extracellular space to the cytosol and/or nucleus of a target eukaryotic cell. The methods comprise contacting the target eukaryotic cell with the polypeptide cargo in the presence of a shuttle agent at a concentration sufficient to increase the transduction efficiency of said polypeptide cargo, as compared to in the absence of said shuttle agent. In some embodiments, contacting the target eukaryotic cell with the polypeptide cargo in the presence of the shuttle agent results in an increase in the transduction efficiency of said polypeptide cargo by at least 10-fold, 20-fold, 30-fold, 40-fold, 50-fold, or 100-fold, as compared to in the absence of said shuttle agent.

In some embodiments, the present description relates to a method for increasing the transduction efficiency of a polypeptide cargo to the cytosol of a target eukaryotic cell. As used herein, the expression "increasing transduction efficiency" refers to the ability of a shuttle agent of the present description to improve the percentage or proportion of a population of target cells into which a cargo of interest (e.g., a polypeptide cargo) is delivered intracellularly across the plasma membrane. Immunofluorescence microscopy, flow cytometry, and other suitable methods may be used to assess cargo transduction efficiency. In some embodiments, a shuttle agent of the present description may enable a transduction efficiency of at least 25%, 30%, 35%, 40%, 45%, 50%, 55%, 60%, 65%, 70%, 75%, 80%, or 85%, for example as measure by immunofluorescence microscopy, flow cytometry, FACS, and other suitable methods. In some embodiments, a shuttle agent of the present description may enable one of the aforementioned transduction efficiencies together wish a cell viability of at least 25%, 30%, 35%, 40%, 45%, 50%, 55%, 60%, 65%, 70%, 75%, 80%, 85%, 90%, or 95%, for example as measure by the assay described in Example 3.3a, or by another suitable assay known in the art.

In addition to increasing target cell transduction efficiency, shuttle agents of the present description may facilitate the delivery of a cargo of interest (e.g., a polypeptide cargo) to the cytosol of target cells. In this regard, efficiently delivering an extracellular cargo to the cytosol of a target cell using peptides can be challenging, as the cargo often becomes trapped in intracellular endosomes after crossing the plasma membrane, which may limit its intracellular availability and may result in its eventual metabolic degradation. For example, use of the protein transduction domain from the HIV-1 Tat protein has been reported to result in massive sequestration of the cargo into intracellular vesicles. In some aspects, shuttle agents of the present description may facilitate the ability of endosomally-trapped cargo to escape from the endosome and gain access to the cytoplasmic compartment. In this regard, the expression "to the cytosol" in the phrase "increasing the transduction efficiency of an independent polypeptide cargo to the cytosol," is intended to refer to the ability of shuttle agents of the present description to allow an intracellularly delivered cargo of interest to escape endosomal entrapment and gain access to the cytoplasmic compartment. After a cargo of interest has gained access to the cytosol, it may be subsequently targeted to various subcellular compartments (e.g., nucleus, nucleolus, mitochondria, peroxisome). In some embodiments, the expression "to the cytosol" is thus intended to encompass not only cytosolic delivery, but also delivery to other subcellular compartments that first require the cargo to gain access to the cytoplasmic compartment.

In some embodiments, the methods of the present description are in vitro methods. In other embodiments, the methods of the present description are in vivo methods.

In some embodiments, the methods of the present description may comprise contacting the target eukaryotic cell with the shuttle agent, or composition as defined herein, and the polypeptide cargo. In some embodiments, the shuttle agent, or composition may be pre-incubated with the polypeptide cargo to form a mixture, prior to exposing the target eukaryotic cell to that mixture. In some embodiments, the type of shuttle agent may be selected based on the amino acid sequence of the polypeptide cargo to be delivered intracellularly. In other embodiments, the type of shuttle agent may be selected to take into account the amino acid sequence of the polypeptide cargo to be delivered intracellularly, the type of cell, the type of tissue, etc.

In some embodiments, the method may comprise multiple treatments of the target cells with the shuttle agent, or composition (e.g., 1, 2, 3, 4 or more times per day, and/or on a predetermined schedule). In such cases, lower concentrations of the shuttle agent, or composition may be advisable (e.g., for reduced toxicity). In some embodiments, the cells may be suspension cells or adherent cells. In some embodiments, the person of skill in the art will be able to adapt the teachings of the present description using different combinations of shuttles, domains, uses and methods to suit particular needs of delivering a polypeptide cargo to particular cells with a desired viability.

In some embodiments, the methods of the present description may apply to methods of delivering a polypeptide cargo intracellularly to a cell in vivo. Such methods may be accomplished by parenteral administration or direct injection into a tissue, organ, or system.

In some embodiments, the shuttle agent, or composition, and the polypeptide cargo may be exposed to the target cell in the presence or absence of serum. In some embodiments, the method may be suitable for clinical or therapeutic use.

In some embodiments, the present description relates to a kit for delivering a polypeptide cargo from an extracellular space to the cytosol and/or nucleus of a target eukaryotic cell. In some embodiments, the present description relates to a kit for increasing the transduction efficiency of a polypeptide cargo to the cytosol of a target eukaryotic cell. The kit may comprise the shuttle agent, or composition as defined herein, and a suitable container.

In some embodiments, the target eukaryotic cells may be an animal cell, a mammalian cell, or a human cell. In some embodiments, the target eukaryotic cells may be a stem cell (e.g., embryonic stem cells, pluripotent stem cells, induced pluripotent stem cells, neural stem cells, mesenchymal stem cells, hematopoietic stem cells, peripheral blood stem cells), a primary cell (e.g., myoblast, fibroblast), or an immune cell (e.g., NK cell, T cell, dendritic cell, antigen presenting cell). In some embodiments, the present description relates to an isolated cell comprising a synthetic peptide or polypeptide-based shuttle agent as defined herein. In some embodiments, the cell may be a protein-induced pluripotent stem cell. It will be understood that cells that are often resistant or not amenable to protein transduction may be interesting candidates for the synthetic peptides or polypeptide-based shuttle agents of the present description.

In some embodiments, the present description relates to a method for producing a synthetic peptide shuttle agent that delivers a polypeptide cargo from an extracellular space to the cytosol and/or nucleus of a target eukaryotic cell, the method comprising synthesizing a peptide which is:
  (1) a peptide at least 20 amino acids in length comprising
  (2) an amphipathic alpha-helical motif having
  (3) a positively-charged hydrophilic outer face, and a hydrophobic outer face,
wherein at least five of the following parameters (4) to (15) are respected:
  (4) the hydrophobic outer face comprises a highly hydrophobic core consisting of spatially adjacent L, I, F, V, W, and/or M amino acids representing 12 to 50% of the amino acids of the peptide, based on an open cylindrical representation of the alpha-helix having 3.6 residues per turn;
  (5) the peptide has a hydrophobic moment (µ) of 3.5 to 11;
  (6) the peptide has a predicted net charge of at least +4 at physiological pH;
  (7) the peptide has an isoelectric point (pI) of 8 to 13;
  (8) the peptide is composed of 35% to 65% of any combination of the amino acids: A, C, G, I, L, M, F, P, W, Y, and V;
  (9) the peptide is composed of 0% to 30% of any combination of the amino acids: N, Q, S, and T;
  (10) the peptide is composed of 35% to 85% of any combination of the amino acids: A, L, K, or R;
  (11) the peptide is composed of 15% to 45% of any combination of the amino acids: A and L, provided there being at least 5% of L in the peptide;
  (12) the peptide is composed of 20% to 45% of any combination of the amino acids: K and R;
  (13) the peptide is composed of 0% to 10% of any combination of the amino acids: D and E;
  (14) the difference between the percentage of A and L residues in the peptide (% A+L), and the percentage of K and R residues in the peptide (% K+R), is less than or equal to 10%; and
  (15) the peptide is composed of 10 to 45% of any combination of the amino acids: Q, Y, W, P, I, S, G, V, F, E, D, C, M, N, T, and H.

In some embodiments, the present description relates to a method for identifying a shuttle agent that delivers a polypeptide cargo from an extracellular space to the cytosol and/or nucleus of a target eukaryotic cell, the method comprising: (a) synthesizing a peptide which is the peptide as defined herein; (b) contacting the target eukaryotic cell with the polypeptide cargo in the presence of said peptide; (c) measuring the transduction efficiency of the polypeptide cargo in the target eukaryotic cell; and (d) identifying the peptide as being a shuttle agent that transduces the polypeptide cargo, when an increase in the transduction efficiency of said polypeptide cargo in the target eukaryotic cell is observed.

In some embodiments, the present description relates to a genome editing system comprising: (a) the shuttle agent as defined herein; (b) a CRISPR-associated endonuclease; and (c) one or more guide RNAs. In some embodiments, the genome editing system may further comprise a linear DNA template for controlling the genome editing.

Genome Editing for Improved Cell Therapy

In some embodiments, the shuttle agents, synthetic peptides, compositions, and methods described herein may be used for transducing genome-editing complexes (e.g., the CRISPR-based genome editing complexes) to genetically engineer cells for improved cell therapy, as compared to native cells or unengineered cells. Such improvements may include, for example, reducing the immunogenicity of the engineered cells and/or improving the activity/efficacy of the engineered cells.

Particularly attractive immune cells for genome engineering may be natural killer (NK) cells, given their natural ability to recognize and kill tumor cells. Accordingly, in some embodiments, the present description relates to the use of the shuttle agents, synthetic peptides, compositions, and methods described herein for transducing genome-editing complexes (e.g., the CRISPR-based genome editing complexes) to genetically engineer NK (or other immune cells that would benefit from the same modifications) for improved cell-based immunotherapy. For example, the present description may relate to the intracellular delivery of one or more CRISPR-based genome editing complexes that comprise a guide RNA and/or linear DNA template targeting the CBLB gene, c-CBL gene, GSK3 gene, ILT2 gene, CISH gene, NKG2a gene, B2M gene, or any combination thereof. Such gene targets may potentiate NK-mediated cellular cytotoxicity following knockout, as discussed below.

1. NKG2A (KLRC1, CD159A, Killer Cell Lectin-Like Receptor C1)

CD94/NKG2A acts as an MHC class-I specific NK inhibitory receptor (Braud et al., 1998; Lee et al., 1998). It is expressed by a subset of NK cells known as $CD56^{bright}$ $CD16^{dim}$ (~10% of peripheral NK), which are typically less cytotoxic (Cooper et al., 2001; Poli et al., 2009). NKG2A ligands are the non-classical MHC class-I HLA-E molecules that are expressed in every human cell. The recognition of HLA-E by the NKG2A receptor is part of the "self-tolerance" mechanism (also including KIR receptors), resulting in negative modulation of NK cell cytotoxicity (Lee et al., 1998).

There exists clinical evidence demonstrating the role of non-classical HLA class I, mainly HLA-E and HLA-G (see ILT-2 target), in evading immune surveillance resulting in higher cancer relapses and decrease overall survival following surgery (de Kruijf et al., 2010; Levy et al., 2008; Ye et al., 2007a; Yie et al., 2007b; Yie et al., 2007c; Yie et al., 2007d; Guo et al., 2015; Ishigami et al., 2015; Zhen et al., 2013). The use of NKG2A-KO NK cells during adoptive cell therapy may counteract the presence of HLA-E molecules (membrane-bound or solubles) in tumor microenvironment. In addition, NK cells expanded from IL15 or IL21-expressing K562 feeder cells lead to a high percentage of $NKG2A^{pos}$ cells (Denman et al., 2012), and it may be desirable to knockout this inhibitory receptor during the expansion process. Furthermore, the results in Example G.9 demonstrate that NKG2A-KO NK92 cells are significantly more cytotoxic against IFN-gamma-treated HeLa cells.

2. ILT2 (Ig-Like Transcript 2 Gene)

ILT2 is an inhibitory receptor expressed on several immune cells, including NK cells (Kirwan et al., 2005). The ligands for this receptor are HLA-G molecules, which are naturally expressed only in thymus and trophoblasts. However, many tumors gain the capacity to express HLA-G to escape immune cell attack by inhibition through ILT2 receptor activation. In fact, $NKL^{ILT2-}$ cells are more potent than parental NKL against HLA-G-overexpressing K562 cells (Wu et al., 2015). Moreover, overexpression of HLA-G in OVCAR-3 cancer cells impaired NK cell-mediated cytotoxicity (Lin et al., 2007). As for HLA-E, expression of HLA-G on cancer cells is generally associated with poor prognosis.

3. c-Cbl and Cbl-b (Casitas B-Lineage Lymphoma Proto-Oncogene Family).

These genes (from the Casitas B-lineage lymphoma proto-oncogene, Cbl family) encode for E3 ligases, which are function in the protein ubiquitylation pathway (regulation of cellular protein content). E3 ligases catalyze the formation of a covalent bond between Ub (ubiquitin) and specific lysine residues on targeted proteins (more than thousand E3 ligases in mammalians). Cbl family members are involved in negative regulation of signaling by receptor tyrosine kinases on immune cells by binding and ubiquitylating phosphorylated receptor and adaptors (Liu et al., 2014; utz-Nicoladoni, 2015). One demonstrated that both c-cbl and Cbl-b ubiquitylate phosphorylated LAT adaptor. Phosphorylation of LAT following NK cell activation is required to recruit other mediators, especially PLC-□□□ and siRNA-mediated c-cbl and Cbl-b knockdown increased NK cell activity against B cell lymphoma 721.221-Cw4 (Matalon et al., 2016).

Others identified TAM (Tyro3, Axl, Mer) receptors as targets for Cbl-b ubiquitylation (Paolino et al., 2014). However, assuming that TAM receptors are proposed to negatively regulate NK cells, Cbl-b knockout should rather be associated to a decrease in NK cell activity. Therefore, TAM receptors may be considered as a good target to enhance NK cells but unlikely via Cbl-b knockout.

In vivo studies demonstrated that $Cbl-b^{-/-}$ mice prevent primary tumor growth (Loeser et al., 2007). In addition, NK cells isolated from these mice have increased proliferation and IFN-□□ production when activated (Paolino et al., 2014).

4. GSK3B (Glycogen Synthase Kinase Beta)

GSK3b is a Ser/Thr kinase involved in several cellular functions, such as proliferation, apoptosis, inflammatory response, stress, and others (Patel et al., 2017). Inhibition of GSK3b (using small inhibitors) in NK cells leads to increase cytotoxicity (likely through IFN-g, TNF-□ production, 2B4 stimulation and up-regulation of LFA-1) against AML (OCI-AML3) (Parameswaran et al., 2016; Aoukaty et al., 2005). We have recently demonstrated that the GSK3□ inhibitor, SB216763, enhances the cytotoxic activity of NK92 against HeLa cells (data not shown). This effect is increased by co-incubation with IL-15.

5. CISH (Cytokine-Inducible SH2-Containing Protein)

CIS protein is a member of the suppressor of cytokine signaling (SOCS) proteins, which bind to phosphorylated JAKs and inhibit JAK-STAT signaling pathways. Recently, Cish−/− mice demonstrated that CIS is a key suppressor of IL15 signaling in NK cells (Delconte et al., 2016). Following IL15 exposure, these cells have prolonged IL15 responses, an elevated IFN-g production, and an increased cytotoxic potential. Moreover, there is a clear relationship between IL15 responsiveness and NKG2D-dependent cytotoxicity (Homg et al., 2007).

In clinical trials, co-injection of cytokines, such as IL2 and IL15, during adoptive NK-cell therapy is strongly recommended to sustain NK cell activity. However, such a co-injection induces serious side effects to patients. The use of IL15-hypersensitive NK cells (CISH knockout) would benefit the treatment.

In some embodiments, disrupting the B2M gene encoding β2 microglobulin (B2M), a component of MHC class I molecules, may substantially reduce the immunogenicity of every cell expressing MHC class I. In other aspects, the genome of NK cells can be modified after the delivery of a genome editing system as described herein. More specifically, the cytotoxicity of NK cells can be improved after the delivery of a genome editing system targeting specific putative targets that may potentiate NK-mediated cellular cytotoxicity such as the NKG2A, ILT2, c-Cbl, Cbl-b, GSK3B and CISH genes.

Items

In some embodiments, the present description may relate to the following items:

1. A method for delivering a polypeptide cargo from an extracellular space to the cytosol and/or nucleus of a target eukaryotic cell, said method comprising contacting the target eukaryotic cell with the polypeptide cargo in the presence of a shuttle agent at a concentration sufficient to increase the transduction efficiency of said polypeptide cargo, as compared to in the absence of said shuttle agent, wherein said shuttle agent is
   (1) a peptide at least 20 amino acids in length comprising
   (2) an amphipathic alpha-helical motif having
   (3) a positively-charged hydrophilic outer face, and a hydrophobic outer face,
   wherein at least five of the following parameters (4) to (15) are respected:

(4) the hydrophobic outer face comprises a highly hydrophobic core consisting of spatially adjacent L, I, F, V, W, and/or M amino acids representing 12 to 50% of the amino acids of the peptide, based on an open cylindrical representation of the alpha-helix having 3.6 residues per turn;

(5) the peptide has a hydrophobic moment (µ) of 3.5 to 11;

(6) the peptide has a predicted net charge of at least +4 at physiological pH;

(7) the peptide has an isoelectric point (pI) of 8 to 13;

(8) the peptide is composed of 35% to 65% of any combination of the amino acids: A, C, G, I, L, M, F, P, W, Y, and V;

(9) the peptide is composed of 0% to 30% of any combination of the amino acids: N, Q, S, and T;

(10) the peptide is composed of 35% to 85% of any combination of the amino acids: A, L, K, or R;

(11) the peptide is composed of 15% to 45% of any combination of the amino acids: A and L, provided there being at least 5% of L in the peptide;

(12) the peptide is composed of 20% to 45% of any combination of the amino acids: K and R;

(13) the peptide is composed of 0% to 10% any combination of the amino acids: D and E;

(14) the difference between the percentage of A and L residues in the peptide (% A+L), and the percentage of K and R residues in the peptide (K+R), is less than or equal to 10%; and

(15) the peptide is composed of 10 to 45% of any combination of the amino acids: Q, Y, W, P, I, S, G, V, F, E, D, C, M, N, T, and H.

2. The method of item 1, wherein the shuttle agent respects at least six of parameters (4) to (15).

3. The method of item 1, wherein the shuttle agent respects at least seven of parameters (4) to (15).

4. The method of item 1, wherein the shuttle agent respects at least eight of parameters (4) to (15).

5. The method of item 1, wherein the shuttle agent respects at least nine of parameters (4) to (15).

6. The method of item 1, wherein the shuttle agent respects at least ten of parameters (4) to (15).

7. The method of item 1, wherein the shuttle agent respects at least eleven of parameters (4) to (15).

8. The method of item 1, wherein the shuttle agent respects all of parameters (4) to (15).

9. The method of any one of items 1 to 8, wherein said shuttle agent is a peptide having a minimum length of 20, 21, 22, 23, 24, 25, 26, 27, 28, 29, or 30 amino acids, and a maximum length of 40, 41, 42, 43, 44, 45, 46, 47, 48, 49, 50, 51, 52, 53, 54, 55, 60, 65, 70, 80, 90, 100, 110, 120, 130, 140, or 150 amino acids.

10. The method of any one of items 1 to 9, wherein said amphipathic alpha-helical motif has a hydrophobic moment (µ) between a lower limit of 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, and an upper limit of 9.5, 9.6, 9.7, 9.8, 9.9, 10.0, 10.1, 10.2, 10.3, 10.4, 10.5, 10.6, 10.7, 10.8, 10.9, or 11.0.

11. The method of any one of items 1 to 10, wherein said amphipathic alpha-helical motif comprises a positively-charged hydrophilic outer face comprising: (a) at least two, three, or four adjacent positively-charged K and/or R residues upon helical wheel projection; and/or (b) a segment of six adjacent residues comprising three to five K and/or R residues upon helical wheel projection, based on an alpha helix having angle of rotation between consecutive amino acids of 100 degrees and/or an alpha-helix having 3.6 residues per turn.

12. The method of any one of items 1 to 11, wherein said amphipathic alpha-helical motif comprises a hydrophobic outer face comprising: (a) at least two adjacent L residues upon helical wheel projection; and/or (b) a segment of ten adjacent residues comprising at least five hydrophobic residues selected from: L, I, F, V, W, and M, upon helical wheel projection, based on an alpha helix having angle of rotation between consecutive amino acids of 100 degrees and/or an alpha-helix having 3.6 residues per turn.

13. The method of any one of items 1 to 12, wherein said hydrophobic outer face comprises a highly hydrophobic core consisting of spatially adjacent L, I, F, V, W, and/or M amino acids representing from 12.5%, 13%, 13.5%, 14%, 14.5%, 15%, 15.5%, 16%, 16.5%, 17%, 17.5%, 18%, 18.5%, 19%, 19.5%, or 20%, to 25%, 30%, 35%, 40%, or 45% of the amino acids of the peptide.

14. The method of any one of items 1 to 13, wherein said peptide has a hydrophobic moment (µ) between a lower limit of 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, and an upper limit of 9.5, 9.6, 9.7, 9.8, 9.9, 10.0, 10.1, 10.2, 10.3, 10.4, or 10.5.

15. The method of any one of items 1 to 14, wherein said peptide has a predicted net charge of between +4, +5, +6, +7, +8, +9, to +10, +11, +12, +13, +14, or +15.

16. The method of any one of items 1 to 15, wherein said peptide has a predicted pI of 10-13.

17. The method of any one of items 1 to 16, wherein said shuttle agent respects at least one, at least two, at least three, at least four, at least five, at least six, or all of the following parameters:

(8) the peptide is composed of 36% to 64%, 37% to 63%, 38% to 62%, 39% to 61%, or 40% to 60% of any combination of the amino acids: A, C, G, I, L, M, F, P, W, Y, and V;

(9) the peptide is composed of 1% to 29%, 2% to 28%, 3% to 27%, 4% to 26%, 5% to 25%, 6% to 24%, 7% to 23%, 8% to 22%, 9% to 21%, or 10% to 20% of any combination of the amino acids: N, Q, S, and T;

(10) the peptide is composed of 36% to 80%, 37% to 75%, 38% to 70%, 39% to 65%, or 40% to 60% of any combination of the amino acids: A, L, K, or R;

(11) the peptide is composed of 15% to 40%, 20% to 40%, 20 to 35%, or 20 to 30% of any combination of the amino acids: A and L;

(12) the peptide is composed of 20% to 40%, 20 to 35%, or 20 to 30% of any combination of the amino acids: K and R;

(13) the peptide is composed of 5 to 10% of any combination of the amino acids: D and E;

(14) the difference between the percentage of A and L residues in the peptide (% A+L), and the percentage of K and R residues in the peptide (K+R), is less than or equal to 9%, 8%, 7%, 6%, or 5%; and

(15) the peptide is composed of 15 to 40%, 20% to 35%, or 20% to 30% of any combination of the amino acids: Q, Y, W, P, I, S, G, V, F, E, D, C, M, N, T, and H.

18. The method of any one of items 1 to 17, wherein said peptide comprises a histidine-rich domain.

19. The method of item 18, wherein said histidine-rich domain is positioned towards the N terminus and/or towards the C terminus of the peptide.

20. The method of any one of items 17 to 19, wherein said histidine-rich domain is a stretch of at least 3, at least 4, at least 5, or at least 6 amino acids comprising at least 50%, at least 55%, at least 60%, at least 65%, at least 70%, at least 75%, at least 80%, at least 85%, or at least 90% histidine residues; and/or comprises at least 2, at least 3, at least 4, at least 5, at least 6, at least 7, at least 8, or at least 9 consecutive histidine residues.
21. The method of any one of items 1 to 20, wherein said peptide comprises a flexible linker domain rich in serine and/or glycine residues.
22. The method of any one of items 1 to 21, wherein said peptide is at least 50%, 55%, 60%, 65%, 70%, 75%, 80%, 85%, 90%, or 95% identical to the amino acid sequence of any one of SEQ ID NOs: 104, 105, 107, 108, 110-131, 133-135, 138, 140, 142, 145, 148, 151, and 152.
23. The method of any one of items 1 to 21, wherein said peptide comprises or consists of a functional variant of any one of SEQ ID NOs: 104, 105, 107, 108, 110-131, 133-135, 138, 140, 142, 145, 148, 151, and 152.
24. The method of any one of items 1 to 22, wherein said peptide: (a) comprises or consists of the amino acid sequence of any one of SEQ ID NOs: 104, 105, 107, 108, 110-131, 133-135, 138, 140, 142, 145, 148, 151, and 152; (b) comprises the amino acid sequence motifs of SEQ ID NOs: 158 and/or 159; or (c) comprises the amino acid sequence motif of SEQ ID NO: 158 operably linked to the amino acid sequence motif of SEQ ID NO: 159.
25. The method of any one of items 1 to 24, wherein the peptide comprises an endosome leakage domain (ELD), and/or a cell penetrating domain (CPD).
26. The method of item 25, wherein said ELD is or is from: an endosomolytic peptide; an antimicrobial peptide (AMP); a linear cationic alpha-helical antimicrobial peptide; a Cecropin-A/Melittin hybrid (CM series) peptide; pH-dependent membrane active peptide (PAMP); a peptide amphiphile; a peptide derived from the N terminus of the HA2 subunit of influenza hemagglutinin (HA); CM18; Diphtheria toxin T domain (DT); GALA; PEA; INF-7; LAH4; HGP; H5WYG; HA2; EB1; VSVG; *Pseudomonas* toxin; melittin; KALA; JST-1; C(LLKK)$_3$C; G(LLKK)$_3$G; or any combination thereof.
27. The method of item 25 or 26, wherein said CPD is or is from: a cell-penetrating peptide or the protein transduction domain from a cell-penetrating peptide; TAT; PTD4; Penetratin (Antennapedia); pVEC; M918; Pep-1; Pep-2; Xentry; arginine stretch; transportan; SynB1; SynB3; or any combination thereof.
28. The method of any one of items 25 to 27, wherein said peptide comprises: (a) an ELD comprising the amino acid sequence of any one of SEQ ID NOs: 1-15, 63, or 64, or a variant or fragment thereof having endosomolytic activity; (b) a CPD comprising the amino acid sequence of any one of SEQ ID NOs: 16-27 or 65, or a variant or fragment thereof having cell penetrating activity; or (c) both (a) and (b).
29. The method of any one of items 25 to 28, wherein said peptide comprises an ELD which is CM18, KALA, or C(LLKK)$_3$C having the amino acid sequence of SEQ ID NO: 1, 14, or 63, or a variant thereof having at least 50%, 55%, 60%, 65%, 70%, 75%, 80%, 85%, 90%, or 95% identity to SEQ ID NO: 1, 14, or 63, and having endosomolytic activity.
30. The method of any one of items 25 to 29, wherein said peptide comprises a CPD which is TAT or PTD4 having the amino acid sequence of SEQ ID NO: 17 or 65, or a variant thereof having at least 50%, 55%, 60%, 65%, 70%, 75%, 80%, 85%, 90%, or 95% identity to SEQ ID NO: 17 or 65 and having cell penetrating activity.

30. The method of any one of items 1 to 24, wherein said peptide comprises the amino acid sequence of any one of SEQ ID NOs: 57-59, 66-72, or 82-102, or a functional variant thereof having at least 85%, 90%, or 95% identity to any one of SEQ ID NOs: 57-59, 66-72, or 82-102.
31. The method of any one of items 1 to 30, wherein said shuttle agent is completely metabolizable by the target eukaryotic cell.
32. The method of any one of items 1 to 31, wherein contacting the target eukaryotic cell with the polypeptide cargo in the presence of the shuttle agent at said concentration results in an increase in the transduction efficiency of said polypeptide cargo by at least 10-fold, 20-fold, 30-fold, 40-fold, 50-fold, or 100-fold, as compared to in the absence of said shuttle agent.
33. The method of any one of items 1 to 32, which is an in vitro method.
34. A synthetic peptide shuttle agent which is the peptide as defined in any one of items 1 to 32.
35. The synthetic peptide of item 34, which is a peptide between 20 and 100 amino acids in length comprising the amino acid sequence of any one of SEQ ID NOs: 104, 105, 107, 108, 110, 111, 112, 113, 114, 115, 116, 117, 118, 119, 120, 121, 122, 123, 124, 125, 126, 127, 128, 129, 130, 131, 133, 134, 135, 138, 140, 142, 145, 148, 151, and 152, or comprises the amino acid sequence motifs of SEQ ID NOs: 158 and/or 159.
36. The synthetic peptide shuttle agent of item 34 or 35 for use in delivering a polypeptide cargo from an extracellular space to the cytosol and/or nucleus of a target eukaryotic cell in vitro.
37. The synthetic peptide shuttle agent of item 34 or 35 for use in delivering a polypeptide cargo from an extracellular space to the cytosol and/or nucleus of a target eukaryotic cell in vivo.
38. A composition comprising the shuttle agent as defined in any one of items 1 to 32, or a cocktail of at least 2, at least 3, at least 4, or at least 5 different types of the shuttle agents as defined in any one of items 1 to 32; and a polypeptide cargo to be delivered from an extracellular space to the cytosol and/or nucleus of a target eukaryotic cell.
39. Use of the shuttle agent as defined in any one of items 1 to 32, or the synthetic peptide as defined in item 35, for delivering a polypeptide cargo from an extracellular space to the cytosol and/or nucleus of a target eukaryotic cell.
40. A kit for delivering a polypeptide cargo from an extracellular space to the cytosol and/or nucleus of a target eukaryotic cell, said kit comprising the shuttle agent as defined in any one of items 1 to 32 or the synthetic peptide as defined in item 35, and a suitable container.
41. The method of any one of items 1 to 33, the synthetic peptide shuttle agent of any one of items 34 to 38, the composition of item 38, the use of item 39, or the kit of item 40, wherein said polypeptide cargo lacks a cell penetrating domain.
42. The method of any one of items 1 to 33, the synthetic peptide shuttle agent of any one of items 34 to 38, the composition of item 38, the use of item 39, or the kit of item 40, wherein said polypeptide cargo comprises a cell penetrating domain.
43. The method of any one of items 1 to 33, 41 and 42, the synthetic peptide shuttle agent of any one of items 34 to 38, 41 and 42, the composition of item 38, 41 and 42, the use of any one of items 39 to 42, wherein said polypeptide cargo comprises a subcellular targeting domain.

44. The method, the synthetic peptide shuttle agent, composition, use, or kit of item 43, wherein said subcellular targeting domain is: (a) a nuclear localization signal (NLS); (b) a nucleolar signal sequence; (c) a mitochondrial signal sequence; or (d) a peroxisome signal sequence.

45. The method, the synthetic peptide shuttle agent, composition, use, or kit of item 44, wherein: (a) said NLS is from: Ela, T-Ag, c-myc, T-Ag, op-T-NLS, Vp3, nucleoplasmin, histone 2B, *Xenopus* N1, PARP, PDX-1, QKI-5, HCDA, H2B, v-Rel, Amida, RanBP3, Pho4p, LEF-1, TCF-1, BDV-P, TR2, SOX9, or Max; (b) said nucleolar signal sequence is from BIRC5 or RECQL4; (c) said mitochondrial signal sequence is from Tim9 or Yeast cytochrome c oxidase subunit IV; or (d) said peroxisome signal sequence is from PTS1.

46. The method, the synthetic peptide shuttle agent, composition, use, or kit of any one of items 41 to 45, wherein said polypeptide cargo is complexed with a DNA and/or RNA molecule.

47. The method, the synthetic peptide shuttle agent, composition, use, or kit of any one of items 41 to 46, wherein said polypeptide cargo is a transcription factor, a nuclease, a cytokine, a hormone, a growth factor, an antibody, a peptide cargo, or any combination thereof.

48. The method, the synthetic peptide shuttle agent, composition, use, or kit of item 47, wherein:
 (a) said transcription factor is: HOXB4, NUP98-HOXA9, Oct3/4, Sox2, Sox9, Klf4, c-Myc, MyoD, Pdx1, Ngn3, MafA, Blimp-1, Eomes, T-bet, FOXO3A, NF-YA, SALL4, ISL1, FoxA1, Nanog, Esrrb, Lin28, HIF1-alpha, Hlf, Runxlt1, Pbx1, Lmo2, Zfp37, Prdm5, Bcl-6, or any combination thereof;
 (b) said nuclease is a catalytically active or catalytically dead: an RNA-guided endonuclease, a CRISPR endonuclease, a type I CRISPR endonuclease, a type II CRISPR endonuclease, a type II CRISPR endonuclease, a type IV CRISPR endonuclease, a type V CRISPR endonuclease, a type VI CRISPR endonuclease, CRISPR associated protein 9 (Cas9), Cpf1, CasY, CasX, a zinc-finger nuclease (ZFNs), a Transcription activator-like effector nucleases (TALENs), a homing endonuclease, a meganuclease, a DNA-guided nuclease, *Natronobacterium gregoryi* Argonaute (NgAgo), or any combination thereof;
 (c) said antibody recognizes an intracellular antigen; and/or
 (d) said peptide cargo recognizes an intracellular molecule.

49. The method, the synthetic peptide shuttle agent, composition, use, or kit of any one of items 41 to 47, for use in cell therapy, genome editing, adoptive cell transfer, and/or regenerative medicine.

50. The method, the synthetic peptide shuttle agent, composition, use, or kit of any one of items 41 to 49, wherein said target eukaryotic cell is an animal cell, a mammalian cell, a human cell, a stem cell, a primary cell, an immune cell, a T cell, an NK cell, or a dendritic cell.

51. A eukaryotic cell comprising the shuttle agent as defined in any one of items 1 to 33, the synthetic peptide shuttle agent as defined in item 35, or the composition as defined in item 38.

52. The eukaryotic cell of item 51, which is an animal cell, a mammalian cell, a human cell, a stem cell, a primary cell, an immune cell, a T cell, an NK cell, or a dendritic cell.

53. A method for delivering one or more CRISPR-associated endonucleases alone or with one or more corresponding guide RNA and/or linear DNA templates, to a target eukaryotic cell, said method comprising contacting the target eukaryotic cell with the endonuclease in the presence of a shuttle agent at a concentration sufficient to increase the transduction efficiency of said endonuclease, as compared to in the absence of said shuttle agent, wherein said shuttle agent is as defined in any one of items 1 to 32.

54. The method of item 53, which is an in vitro method.

55. The method of item 53, which is an in vivo method.

56. The method of any one of items 53 to 55, wherein said one or more endonuclease is: a type I CRISPR endonuclease, a type II CRISPR endonuclease, a type m CRISPR endonuclease, a type IV CRISPR endonuclease, a type V CRISPR endonuclease, a type VI CRISPR endonuclease, or any combination thereof.

57. The method of any one of items 53 to 55, wherein said one or more endonuclease is CRISPR associated protein 9 (Cas9), Cpf1, CasX, CasY, or any combination thereof; or a catalytically dead CRISPR associated protein 9 (dCas9), dCpf1, dCasX, dCasY, or any combination thereof.

58. The method of any one of items 53 to 57, wherein said target eukaryotic cell is an animal cell, a mammalian cell, a human cell, a stem cell, a primary cell, an immune cell, a T cell, an NK cell, or a dendritic cell.

59. The method of item 58, wherein said target eukaryotic cell is an NK cell.

60. The method of item 58 or 59, wherein said one or more corresponding guide RNA and/or linear DNA template targets one or more genes to reduce the immunogenicity, improve cytotoxicity, and/or otherwise improve the effectiveness of the target eukaryotic cell for cell-based therapy, as compared to a corresponding parent eukaryotic cell that has not been subjected to said method.

61. The method of item 60, wherein said cell-based therapy is cell-based cancer immunotherapy.

62. The method of any one of items 58 to 61, wherein said one or more corresponding guide RNA and/or linear DNA template targets the CBLB gene, c-CBL gene, GSK3 gene, ILT2 gene, CISH gene, NKG2a gene, B2M gene, or any combination thereof.

63. A method for producing a synthetic peptide shuttle agent that delivers a polypeptide cargo from an extracellular space to the cytosol and/or nucleus of a target eukaryotic cell, said method comprising synthesizing a peptide which is:
 (1) a peptide at least 20 amino acids in length comprising
 (2) an amphipathic alpha-helical motif having
 (3) a positively-charged hydrophilic outer face, and a hydrophobic outer face,
 wherein at least five of the following parameters (4) to (15) are respected:
 (4) the hydrophobic outer face comprises a highly hydrophobic core consisting of spatially adjacent L, I, F, V, W, and/or M amino acids representing 12 to 50% of the amino acids of the peptide, based on an open cylindrical representation of the alpha-helix having 3.6 residues per turn;
 (5) the peptide has a hydrophobic moment ($\mu$) of 3.5 to 11;
 (6) the peptide has a predicted net charge of at least +4 at physiological pH;
 (7) the peptide has an isoelectric point (pI) of 8 to 13;

(8) the peptide is composed of 35% to 65% of any combination of the amino acids: A, C, G, I, L, M, F, P, W, Y, and V;
(9) the peptide is composed of 0% to 30% of any combination of the amino acids: N, Q, S, and T;
(10) the peptide is composed of 35% to 85% of any combination of the amino acids: A, L, K, or R;
(11) the peptide is composed of 15% to 45% of any combination of the amino acids: A and L, provided there being at least 5% of L in the peptide;
(12) the peptide is composed of 20% to 45% of any combination of the amino acids: K and R;
(13) the peptide is composed of 0% to 10% any combination of the amino acids: D and E;
(14) the difference between the percentage of A and L residues in the peptide (% A+L), and the percentage of K and R residues in the peptide (K+R), is less than or equal to 10%; and
(15) the peptide is composed of 10 to 45% of any combination of the amino acids: Q, Y, W, P, I, S, G, V, F, E, D, C, M, N, T, and H.
64. The method of item 63, wherein the peptide is as defined in any one of items 2 to 32.
65. A method for identifying a shuttle agent that delivers a polypeptide cargo from an extracellular space to the cytosol and/or nucleus of a target eukaryotic cell, said method comprising:
(a) synthesizing a peptide which is the peptide as defined in any one items 1 to 32 or 35;
(b) contacting the target eukaryotic cell with the polypeptide cargo in the presence of said peptide;
(c) measuring the transduction efficiency of the polypeptide cargo in the target eukaryotic cell; and
(d) identifying the peptide as being a shuttle agent that transduces the polypeptide cargo, when an increase in the transduction efficiency of said polypeptide cargo in the target eukaryotic cell is observed.
66. The method of item 65, wherein said polypeptide cargo is as defined in any one of items 41 to 48.
67. A genome editing system comprising:
(a) the shuttle agent as defined in any one items 1 to 32 or 35;
(b) one or more CRISPR-associated endonucleases; and
(c) one or more guide RNAs.
68. The genome editing system of item 67, further comprising a linear DNA template for controlling the genome editing.
69. The genome editing system of item 67 or 68, wherein said one or more CRISPR-associated endonucleases is: a type I CRISPR endonuclease, a type II CRISPR endonuclease, a type III CRISPR endonuclease, a type IV CRISPR endonuclease, a type V CRISPR endonuclease, a type VI CRISPR endonuclease, CRISPR associated protein 9 (Cas9), Cpf1, CasX, CasY, or any combination thereof.

Other objects, advantages and features of the present description will become more apparent upon reading of the following non-restrictive description of specific embodiments thereof, given by way of example only with reference to the accompanying drawings.

EXAMPLES

Example 1

Materials and Methods 1.1 Materials

All chemicals were purchased from Sigma-Aldrich (St. Louis, Mo., USA or Oakville, ON, Canada) or equivalent grade from BioShop Canada Inc. (Mississauga, ON, Canada) or VWR (Ville Mont-Royal, QC, Canada), unless otherwise noted.

1.2 Reagents

TABLE 1.1

Reagents

| Material | Company | City, Province-State, Country |
| --- | --- | --- |
| RPMI 1640 media | Sigma-Aldrich | Oakville, ON, Canada |
| DMEM | Sigma-Aldrich | Oakville, ON, Canada |
| Alpha MEM | Stem Cell Technology | Oakville, ON, Canada |
| Fetal bovine serum (FBS) | NorthBio | Toronto, ON, Canada |
| Horse serum | Invitrogen | Burlington, ON, Canada |
| L-glutamine-Penicillin-Streptomycin | Sigma-Aldrich | Oakville, ON, Canada |
| Trypsin-EDTA solution | Sigma-Aldrich | Oakville, ON, Canada |
| Inositol | Sigma-Aldrich | Oakville, ON, Canada |
| Folic acid | Sigma-Aldrich | Oakville, ON, Canada |
| pEGFP-C1 | CLONTECH Laboratories | Palo Alto, CA, USA |
| FITC-Antibody α-tubulin | Abcam ab64503 | Cambridge, MA, USA |
| ITS | Invitrogen/41400-045 | Burlington, ON, Canada |
| FGF 2 | Feldan Bio/1D-07-017 | Quebec, QC, Canada |
| Dexamethasone | Sigma-Aldrich/D8893 | Oakville, ON, Canada |
| Bovine serum albumin (BSA) | Sigma-Aldrich/A-1933 | Oakville, ON, Canada |
| MB1 media | GE Healthcare HyClone | Logan, Utah, USA |
| Calcein | Sigma-Aldrich/C0875 | Oakville, ON, Canada |
| HisTrap ™ FF column | GE Healthcare | Baie d'Urfe, QC, Canada |
| Q Sepharose ™ | GE Healthcare | Baie d'Urfe, QC, Canada |
| SP Sepharose ™ | GE Healthcare | Baie d'Urfe, QC, Canada |
| Amicon Ultra centrifugal filters | EMD Millipore | Etobicoke, ON Canada |
| Label IT ® Cy ®5 kit | Mirus Bio LLC | Madison, WI, USA |
| Calf serum | NorthBio | Toronto, ON, Canada |
| beta-mercaptoethanol | Sigma-Aldrich or Gibco-ThermoFisher | Oakville, ON, Canada |
| IL-2 | Feldan Bio/rhIL-2 Research | Quebec, QC, Canada |
| Resazurin sodium salt | Sigma-Aldrich/R7017-1G | Oakville, ON, Canada |
| Anti-HOXB4 monoclonal antibody | Novus Bio #NBP2-37257 | Oakville, ON, Canada |
| Alexa ™-594 Anti-Mouse | Abcam #150116 | Toronto, ON, Canada |

TABLE 1.1-continued

Reagents

| Material | Company | City, Province-State, Country |
| --- | --- | --- |
| Fluoroshield ™ with DAPI | Sigma #F6057 | Oakville, ON, Canada |
| GFP Monoclonal antibody | Feldan Bio #A017 | Quebec, QC, Canada |
| Phusion ™ High-Fidelity DNA polymerase | (NEB #M0530S) | Whitby, ON, Canada |
| Edit-R ™ Synthetic crRNA Positive Controls | (Dharmacon #U-007000-05) | Ottawa, ON, Canada |
| T7 Endonuclease I | (NEB, Cat #M0302S) | Whitby, ON, Canada |
| FastFect ™ transfection reagent | (Feldan Bio #9K-010-0001) | Quebec, QC, Canada |
| Goat Anti-Mouse IgG H&L (Alexa Fluor ® 488) | Abcam ab150113 | Toronto, ON, Canada |
| Goat Anti-Rabbit IgG H&L (Alexa Fluor ® 594) | Abcam ab150080 | Toronto, ON, Canada |
| Opti-MEM ™ | Sigma-Aldrich | Oakville, ON, Canada |
| Anti-NUP98 | Abcam #ab50610 | Toronto, ON, Canada |
| PARP (Cleaved) [214/215] Human ELISA Kit | ThermoFisher #KHO0741 | Burlington, ON, Canada |
| Purified Rabbit Anti- Active Caspase-3 | BD Biosciences #559565 | Mississauga, ON, Canada |
| Active Caspace-3 antibody | | Burlington, ON, Canada |
| TNF-alpha Antibody | | Milpitas, CA, USA |
| APC Mouse Anti-Human HLA-ABC | | Mississauga, ON, Canada |
| Anti-CD3 | | San Diego, CA, USA |
| Anti-CD28 | | Burlington, ON, Canada |

1.3 Cell Lines

HeLa, HEK293A, HEK293T, THP-1, CHO, NIH3T3, CA46, Balb3T3, HT2, KMS-12, DOHH2, REC-1, HCC-78, NCI-H196 and HT2 cells were obtained from American Type Culture Collection (Manassas, Va., USA) and cultured following the manufacturer's instructions. Myoblasts are primary human cells kindly provided by Professor J. P. Tremblay (Université Laval, Quebec, Canada).

TABLE 1.2

Cell lines and culture conditions

| Cell lines | Description | ATCC/others | Culture media | Serum | Additives |
| --- | --- | --- | --- | --- | --- |
| HeLa (adherent cells) | Human cervical carcinoma cells | ATCC ™ CCL-2 | DMEM | 10% FBS | L-glutamine 2 mM Penicillin 100 units Streptomycin 100 µg/mL |
| HEK 293A (adherent cells) | Human embryonic Epithelial kidney cells | ATCC ™ CRL-1573 | DMEM | 10% FBS | L-glutamine 2 mM Penicillin 100 units Streptomycin 100 µg/mL |
| HEK 293T (adherent cells) | Human embryonic Epithelial kidney cells | ATCC ™ CRL-3216 | DMEM | 10% FBS | L-glutamine 2 mM Penicillin 100 units Streptomycin 100 µg/mL |
| THP-1 (suspension cells) | Acute monocytic leukemia | ATCC ™ TIB202 | RPMI 1640 | 10% FBS | β-mercaptoethanol 0.05 mM L-glutamine 2 mM Penicillin 100 units Streptomycin 100 µg/mL |
| Myoblasts (primary adherent cells) | Human (13 months) myoblasts | Kindly provided by Professor J P Tremblay | MB1 | 15% FBS | ITS 1x, FGF 2 10 ng/mL, Dexamethasone 0.39 µg/mL, BSA 0.5 mg/mL, MB1 85% |
| CHO (adherent cells) | Chinese hamster ovary cells | ATCC ™ CCL-61 | DMEM | 10% FBS | L-glutamine 2 mM Penicillin 100 units Streptomycin 100 µg/mL |
| NIH3T3 (adherent cells) | Fibroblasts | ATCC ™ CRL-1658 | DMEM | 10% Calf serum | L-glutamine 2 mM Penicillin 100 units Streptomycin 100 µg/mL |
| HT2 (suspension cells) | T lymphocytes | ATCC ™ CRL-1841 | RPMI 1640 | 10% FBS | 200 IU/mL IL-2 β-mercaptoethanol 0.05 mM L-glutamine 2 mM Penicillin 100 units Streptomycin 100 µg/mL |
| CA46 (suspension cells) | *Homo sapiens* Burkitt's lymphoma | ATCC ™ CRL-1648 | RPMI 1640 | 20% FBS | L-glutamine 2 mM Penicillin 100 units Streptomycin 100 µg/mL |
| Balb3T3 (adherent cells) | Fibroblasts | ATCC ™ CCL-163 | DMEM | 10% Calf serum | L-glutamine 2 mM Penicillin 100 units Streptomycin 100 µg/mL |

TABLE 1.2-continued

Cell lines and culture conditions

| Cell lines | Description | ATCC/others | Culture media | Serum | Additives |
|---|---|---|---|---|---|
| Jurkat (suspension cells) | Human T cells | ATCC™ TIB-152 | RPMI 1640 | 10% FBS | L-glutamine 2 mM Penicillin 100 units Streptomycin 100 μg/mL |
| DOHH2 (suspension cells) | Human B cell lymphoma | Gift from Horizon Inc. | RPMI 1640 | 10% FBS | L-glutamine 2 mM Penicillin 100 units Streptomycin 100 μg/mL |
| KMS-12 (suspension cells) | Myeloma bone marrow | Gift from Horizon Inc. | Advanced RPMI 1640 | 10% FBS | L-glutamine 2 mM Penicillin 100 units Streptomycin 100 μg/mL |
| REC-1 (suspension cells) | Human lymph node mantel cell | Gift from Horizon Inc. | RPMI 1640 | 10% FBS | L-glutamine 2 mM Penicillin 100 units Streptomycin 100 μg/mL |
| HCC-78 (adherent cells) | Human adenocarcinoma lung cell | Gift from Horizon Inc. | RPMI 1640 | 20% FBS | L-glutamine 2 mM Penicillin 100 units Streptomycin 100 μg/mL |
| NCI-H196 (adherent cells) | Human small cell lung cancer | Gift from Horizon Inc. | RPMI 1640 | 10% FBS | L-glutamine 2 mM Penicillin 100 units Streptomycin 100 μg/mL |
| NK (suspension cells) | Human normal Peripheral Blood CD56+ lymphocyte | All cells™ #PB012-PF | RPMI 1640 | 10% FBS | 200 IU/mL IL-2 L-glutamine 2 mM Penicillin 100 units Streptomycin 100 μg/mL |
| NK-92 (suspension cells) | Human normal Peripheral Blood CD56+ lymphocyte | Gift from CETC | Alpha MEM | 12.5% FBS 12.5% Horse serum | L-glutamine 200 nM IL-2 25000 U/mL Inositol 1M Folic acid 100 nM B-ME 55 mM |

FBS: Fetal bovine serum 1.4 Protein Purification

Fusion proteins were expressed in bacteria (*E. coli* BL21DE3) under standard conditions using an isopropyl β-D-1-thiogalactopyranoside (IPTG) inducible vector containing a T5 promoter. Culture media contained 24 g yeast extract, 12 g tryptone, 4 mL glycerol, 2.3 g $KH_2PO_4$, and 12.5 g $K_2HPO_4$ per liter. Bacterial broth was incubated at 37° C. under agitation with appropriate antibiotic (e.g., ampicillin). Expression was induced at optical density (600 nm) between 0.5 and 0.6 with a final concentration of 1 mM IPTG for 3 hours at 30° C. Bacteria were recuperated following centrifugation at 5000 RPM and bacterial pellets were stored at −20° C.

Bacterial pellets were resuspended in Tris buffer (Tris 25 mM pH 7.5, NaCl 100 mM, imidazole 5 mM) with phenylmethylsulfonyl fluoride (PMSF) 1 mM, and lysed by passing 3 times through the homogenizer Panda 2K™ at 1000 bar. The solution was centrifuged at 15000 RPM, 4° C. for 30 minutes. Supernatants were collected and filtered with a 0.22 μM filtration device.

Solubilized proteins were loaded, using a FPLC (AKTA Explorer 100R), on HisTrap™ FF column previously equilibrated with 5 column volumes (CV) of Tris buffer. The column was washed with 30 column volumes (CV) of Tris buffer supplemented with 0.1% Triton™ X-114 followed with 30 CV of Tris buffer with imidazole 40 mM Proteins were eluted with 5 CV of Tris buffer with 350 mM Imidazole and collected. Collected fractions corresponding to specific proteins were determined by standard denaturing SDS-PAGE.

Purified proteins were diluted in Tris 20 mM at the desired pH according to the protein's pI and loaded on an appropriate ion exchange column (Q Sepharose™ or SP Sepharose™) previously equilibrated with 5 CV of Tris 20 mM, NaCl 30 mM The column was washed with 10 CV of Tris 20 mM, NaCl 30 mM and proteins were eluted with a NaCl gradient until 1 M on 15 CV. Collected fractions corresponding to specific proteins were determined by standard denaturing SDS-PAGE. Purified proteins were then washed and concentrated in PBS IX on Amicon Ultra™ centrifugal filters 10,000 MWCO. Protein concentration was evaluated using a standard Bradford assay.

1.5 Synthetic Peptides and Shuttle Agents

All peptides used in this study were purchased from GLBiochem (Shanghai, China) and their purities were confirmed by high-performance liquid chromatography analysis and mass spectroscopy. In some cases, peptides were synthesized to contain a C-terminal cysteine residue to allow the preparation of peptide dimers. These dimeric peptides were directly synthesized with a disulfide bridge between the C-terminal cysteines of two monomers. The amino acid sequences and characteristics of each of the synthetic peptides and shuttle agents tested in the present examples are summarized in Table 1.3, Table B1, and Table C1.

TABLE 1.3

Synthetic peptides and shuttle agents

| Domain(s) | Peptide or Shuttle agent | Amino acid (a.a.) sequence [SEQ ID NO; not including C-terminal Cys, unless indicated with an *] | a.a. | MW (kDa) | pI | Charge | Hydropathicity index |
|---|---|---|---|---|---|---|---|
| ELD | CM18 | KWKLFKKIGAVLKVLTTG[1] | 18 | 2.03 | 10.60 | 5+/0- | 0.350 |
|  | C(LLKK)3C | CLLKKLLKKLLKKC [63] | 14 | 1.69 | 10.05 | 6+/0- | 0.314 |
|  | LAH4 | KKALLALALHHLAHLALHLALALKKA [6] | 26 | 2.78 | 10.48 | 4+/0- | 0.923 |
|  | KALA | WEAKLAKALAKALAKHLAKALAKALKACEA [14] | 30 | 3.13 | 9.9 | 7+/2- | 0.283 |
| CPD | TAT-cys | YGRKKRRQRRRC [17] | 12 | 1.66 | 12.01 | 8+/0- | -3.125 |
|  | Penetratin-cys | RQIKIWFQNRRMKWKKC [18] | 17 | 2.35 | 11.75 | 7+/0- | -1.482 |
|  | PTD4 | YARAAARQARA [65] | 11 | 1.2 | 11.72 | 3+/0- | -0.682 |
| His-PTD4 | His-PTD4 | HHHHHHYARAAARQARA [81] | 17 | 2.03 | 11.71 | 3+/0- | -1.57 |
| CPD-ELD | TAT-CM18 | YGRKKRRQRRRCKWLFKKIGAVLKVLTTG [66] | 30 | 3.68 | 12.02 | 13+/0- | -1.041 |
|  | TAT-KALA | YGRKKRRQRRRCWEAKLAKALAKALAKHLAKALAKALKACEA [67] | 42 | 4.67 | 11.46 | 15+/2- | -0.768 |
|  | PTD4-KALA | YARAAARQARAWEAKLAKALAKALAKHLAKALAKALKACEA [82] | 41 | 4.32 | 10.46 | 10+/2- | 0.024 |
|  | 9Arg-KALA | RRRRRRRRRWEAKLAKALAKALAKHLAKALAKALKACEA [83] | 39 | 4.54 | 12.11 | 16+/2- | -0.821 |
|  | Pep1-KALA | KETWWETWWTEWSQPKKKRKVWEAKLAKALAKALAKHLAKALAKALKACEA [84] | 51 | 5.62 | 10.01 | 13+/5- | -0.673 |
|  | Xentry-KALA | LCLRPVGWEAKLAKALAKALAKHLAKALAKALKACEA [85] | 37 | 3.87 | 9.93 | 8+/2- | 0.441 |
|  | SynB3-KALA | RRLSYSRRRFWEAKLAKALAKALAKHLAKALAKALKACEA [86] | 40 | 4.51 | 11.12 | 12+/2- | -0.258 |
| ELD-CPD | CM18-TAT-Cys | KWKLFKKIGAVLKVLTTGYGRKKRRQRRRC [57] | 30 | 3.67 | 12.02 | 13+/0- | -1.04 |
|  | CM18-Penetratin-Cys | KWKLFKKIGAVLKVLTTGRQIKIWFQNRRMKWKKC [58] | 35 | 4.36 | 11.36 | 12+/0- | -0.54 |
|  | dCM18-TAT-Cys (CM18-TAT-cys dimer) | KWKLFKKIGAVLKVLTTGYGRKKRRQRRRC [57] KWKLFKKIGAVLKVLTTGYGRKKRRQRRRC [57] | 60 | 7.34 | 12.16 | 26+/0- | -1.04 |
|  | dCM18-Penetratin-Cys (CM18-Penetratin-Cys dimer) | KWKLFKKIGAVLKVLTTGRQIKIWFQNRRMKWKKC [58] KWKLFKKIGAVLKVLTTGRQIKIWFQNRRMKWKKC [58] | 70 | 8.72 | 12.05 | 24+/0- | -0.54 |
|  | VSVG-PTD4 | KFTIVFPHNQKGNWKNVPSNYHYCPYARAAARQARA [87] | 36 | 4.2 | 10.3 | 6+/0- | -0.89 |
|  | EB1-PTD4 | LIRLWSHLIHIWFQNRRLKWKKKYARAAARQARA [88] | 34 | 4.29 | 12.31 | 10+/0- | -0.647 |
|  | JST-PTD4 | GLFEALLELLESLWELLLEAYARAAARQARA [89] | 31 | 3.49 | 4.65 | 5+/3- | 0.435 |
|  | CM18-PTD4 | KWKLFKKIGAVLKVLTTGYARAAARQARA [90] | 29 | 3.217 | 11.76 | 8+/0- | -0.041 |
|  | 6Cys-CM18-PTD4 | CCCCCCKWKLFKKIGAVLKVLTTGYARAAARQARA [91] | 35 | 3.835 | 9.7 | 8+/0- | 0.394 |
|  | CM18-L1-PTD4 | KWKLFKKIGAVLKVLTTGGGSYARAAARQARA [92] | 32 | 3.42 | 11.76 | 8+/0- | -0.087 |
|  | CM18-L2-PTD4 | KWKLFKKIGAVLKVLTTGGGSGGGSYARAAARQARA [93] | 36 | 3.68 | 11.76 | 8+/0- | -0.133 |

TABLE 1.3-continued

Synthetic peptides and shuttle agents

| Domain(s) | Peptide or Shuttle agent | Amino acid (a.a.) sequence [SEQ ID NO; not including C-terminal Cys, unless indicated with an *] | a.a. | MW (kDa) | pI | Charge | Hydropathicity index |
|---|---|---|---|---|---|---|---|
| | CM18-L3-PTD4 | KWKLFKKIGAVLKVLTT GGGSGGGSGGGSGYAR AAARQARA [94] | 41 | 3.99 | 11.76 | 8+/0 | −0.176 |
| His-ELD-CPD | Met-His-CM18-TAT-Cys | MHHHHHHKWKLFKKIG AVLKVLTTGYGRKKRR QRRRC [59*] | 37 | 4.63 | 12.02 | 13+/0− | −1.311 |
| | His-CM18-TAT | HHHHHHKWKLFKKIGA VLKVLTTGYGRKKRRQ RRR[95] | 35 | 4.4 | 12.31 | 13+/0− | −1.208 |
| | His-CM18-PTD4 | HHHHHHKWKLFKKIGA VLKVLTTGYARAAARQ ARA[68] | 35 | 4.039 | 11.76 | 8+/0− | −0.583 |
| | His-CM18-PTD4-6Cys | HHHHHHKWKLFKKIGA VLKVLTTGYARAAARQ ARACCCCCC [96*] | 41 | 4.659 | 9.7 | 8+/0− | −0.132 |
| | His-CM18-9Arg | HHHHHHKWKLFKKIGA VLKVLTTGRRRRRRRRR [69] | 33 | 4.26 | 12.91 | 14+/0− | −1.618 |
| | His-CM18-Transportan | HHHHHHKWKLFKKIGA VLKVLTTGGWTLNSAG YLLKINLKALAALAKKIL [70] | 50 | 5.62 | 10.6 | 9+/0− | 0.092 |
| | His--PTD4 | HHHHHHKKALLALALH HLAHLALHLALALKKA YARAAARQARA [71] | 43 | 4.78 | 11.75 | 7+/0− | −0.63 |
| | His-C(LLKK)₃C-PTD4 | HHHHHHCLLKKLLKKLL KKCYARAAARQARA [72] | 31 | 3.56 | 11.21 | 9+/0− | −0.827 |
| | 3His-CM18-PTD4 | HHHKWKLFKKIGAVLK VLTTGYARAAARQARA [97] | 32 | 3.63 | 11.76 | 8+/0− | −0.338 |
| | 12His-CM18-PTD4 | HHHHHHHHHHHHKWK LFKKIGAVLKVLTTGYA RAAARQARA [98] | 41 | 4.86 | 11.76 | 8+/0− | −0.966 |
| | HA-CM18-PTD4 | HHHAHHHKWKLFKKIG AVLKVLTTGYARAAAR QARA [99] | 36 | 4.11 | 11.76 | 8+/0− | −0.517 |
| | 3HA-CM18-PTD4 | HAHHAHHAHKWKLFKK IGAVLKVLTTGYARAAA RQARA [100] | 38 | 4.25 | 11.76 | 8+/0− | −0.395 |
| ELD-His-CPD | CM18-His-PTD4 | KWKLFKKIGAVLKVLTT GHHHHHHYARAAARQA RA [101] | 35 | 4.04 | 11.76 | 8+/0− | −0.583 |
| His-ELD-CPD-His | His-CM18-PTD4-His | HHHHHHKWKLFKKIGA VLKVLTTGYARAAARQ ARAHHHHHH [102] | 41 | 4.86 | 11.76 | 8+/0− | −0.966 |

Results computed using the ProtParam ™ online tool available from ExPASy ™ Bioinformatics Resource Portal (http://web.expasy.org/protparam/)
MW: Molecular weight
pI: Isoelectric point
Charge: Total number of positively (+) and negatively (−) charged residues Example 2

Peptide Shuttle Agents Facilitate Escape of Endosomally-Trapped Calcein 2.1 Endosome Escape Assays Microscopy-based and flow cytometry-based fluorescence assays were developed to study endosome leakage and to determine whether the addition of the shuttle agents facilitates endosome leakage of the polypeptide cargo. These methods are described in Example 2 of PCT/CA2016/050403.

2.1.1 Endosomal Leakage Visualization by Microscopy

Calcein is a membrane-impermeable fluorescent molecule that is readily internalized by cells when administered to the extracellular medium. Its fluorescence is pH-dependent and calcein self-quenches at higher concentrations. Once internalized, calcein becomes sequestered at high concentrations in cell endosomes and can be visualized by fluorescence microscopy as a punctate pattern. Following endosomal leakage, calcein is released to the cell cytoplasm and this release can be visualized by fluorescence microscopy as a diffuse pattern.

One day before the calcein assay was performed, cells in exponential growth phase were harvested and plated in a 24-well plate (80,000 cells per well). The cells were allowed to attach by incubating overnight in appropriate growth media, as described in Example 1. The next day, the media was removed and replaced with 300 μL of fresh media without FBS containing 62.5 μg/mL (100 μM) of calcein, except for HEK293A (250 μg/mL, 400 μM). At the same time, the shuttle agent(s) to be tested was added at a predetermined concentration. The plate was incubated at 37° C. for 30 minutes. The cells were washed with 1×PBS (37° C.) and fresh media containing FBS was added. The plate was incubated at 37° C. for 2.5 hours. The cells were washed three times and were visualized by phase contrast and fluorescence microscopy (IX81™, Olympus).

A typical result is shown in FIG. 1A, in which untreated HEK293A cells loaded with calcein ("100 μM calcein") show a low intensity, punctate fluorescent pattern when visualized by fluorescence microscopy (upper left panel). In contrast, HeLa cells treated with a shuttle agent that facilitates endosomal escape of calcein ("100 μM calcein+CM18-TAT 5 μM") show a higher intensity, more diffuse fluorescence pattern in a greater proportion of cells (upper right panel).

2.1.2 Endosomal Leakage Quantification by Flow Cytometry

In addition to microscopy, flow cytometry allows a more quantitative analysis of the endosomal leakage as the fluorescence intensity signal increases once the calcein is released in the cytoplasm. Calcein fluorescence is optimal at physiological pH (e.g., in the cytosol), as compared to the acidic environment of the endosome.

One day before the calcein assay was performed, cells in exponential growth phase were harvested and plated in a 96-well plate (20,000 cells per well). The cells were allowed to attach by incubating overnight in appropriate growth media, as described in Example 1. The next day, the media in wells was removed and replaced with 50 μL of fresh media without serum containing 62.5 μg/mL (100 μM) of calcein, except for HEK293A (250 μg/mL, 400 μM). At the same time, the shuttle agent(s) to be tested was added at a predetermined concentration. The plate was incubated at 37° C. for 30 minutes. The cells were washed with 1×PBS (37° C.) and fresh media containing 5-10% serum was added. The plate was incubated at 37° C. for 2.5 hours. The cells were washed with 1×PBS and detached using trypsinization. Trypsinization was stopped by addition of appropriate growth media, and calcein fluorescence was quantified using flow cytometry (Accuri C6, Becton, Dickinson and Company (BD)).

Untreated calcein-loaded cells were used as a control to distinguish cells having a baseline of fluorescence due to endosomally-trapped calcein from cells having increased fluorescence due to release of calcein from endosomes. Fluorescence signal means ("mean counts") were analyzed for endosomal escape quantification. In some cases, the "Mean Factor" was calculated, which corresponds to the fold-increase of the mean counts relative to control (untreated calcein-loaded cells). Also, the events scanned by flow cytometry corresponding to cells (size and granularity) were analyzed. The cellular mortality was monitored with the percentage of cells in the total events scanned. When it became lower than the control, it was considered that the number of cellular debris was increasing due to toxicity and the assay was discarded.

Figure 1B:
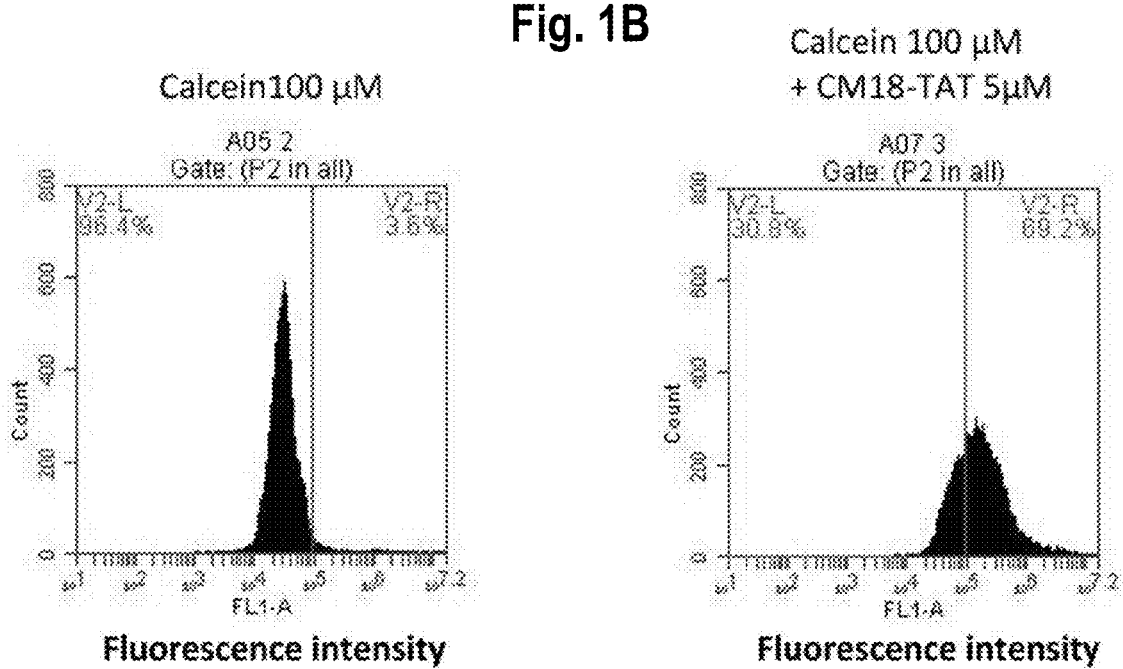

A typical result is shown in FIG. 1B, in which an increase in fluorescence intensity (right-shift) is observed for calcein-loaded HeLa cells treated with a shuttle agent that facilitates endosomal escape ("Calcein 100 μM+CM18-TAT 5 μM", right panel), as compared to untreated calcein-loaded HeLa cells ("Calcein 100 μM", left panel). The increase in calcein fluorescence is caused by the increase in pH associated with the release of calcein from the endosome (acidic) to the cytoplasm (physiological).

2.2 Results from Endosome Escape Assays 2.2.1 HeLa Cells

HeLa cells were cultured and tested in the endosomal escape assays as described in Example 2.1. The results of flow cytometry analyses are summarized below. In each case, the flow cytometry results were also confirmed by fluorescence microscopy (data not shown).

TABLE 2.1

CM18-Penetratin-Cys v. Controls in HeLa cells

| Domains | Peptide | Cells | Concentration (μM) | Mean Counts (±St. Dev.; n = 3) | Mean Factor |
|---|---|---|---|---|---|
| — | No peptide | HeLa | 0 | 55 359 ± 6844 | 1.0 |
| ELD | CM18 | HeLa | 5 | 46 564 ± 9618 | 0.8 |
| CPD | TAT-Cys | HeLa | 5 | 74 961 ± 9337 | 1.3 |
|  | Penetratin-Cys | HeLa | 5 | 59 551 ± 7119 | 1.1 |
| ELD + CPD | CM18 + TAT-Cys | HeLa | 5 + 5 | 64 333 ± 6198 | 1.2 |
|  | CM18 + Penetratin-Cys | HeLa | 5 + 5 | 40 976 ± 8167 | 0.7 |
| ELD-CPD | CM18-Penetratin-Cys | HeLa | 5 | 262 066 ± 28 146 | 4.7 |

TABLE 2.2

CM18-TAT-Cys v. Control in HeLa cells

| Domains | Peptide | Cells | Concentration (μM) | Mean counts (n = 3) | Stand. dev. | Mean Factor |
|---|---|---|---|---|---|---|
| — | No peptide | HeLa | 0 | 53 369 | 4192 | 1.0 |
| ELD-CPD | CM18-TAT-Cys | HeLa | 5 | 306 572 | 46 564 | 5.7 |

The results in Tables 2.1 and 2.2 show that treating calcein-loaded HeLa cells with the shuttle agents CM18-Penetratin-Cys and CM18-TAT-Cys (having the domain structure ELD-CPD) results in increased mean cellular calcein fluorescence intensity, as compared to untreated control cells or cells treated with single-domain peptides used alone (CM18, TAT-Cys, Penetratin-Cys) or together (CM18+TAT-Cys, CM18+Penetratin-Cys). These results suggest that CM18-Penetratin-Cys and CM18-TAT-Cys facilitate escape of endosomally-trapped calcein, but that single domain peptides (used alone or together) do not.

TABLE 2.3

Figure 2:
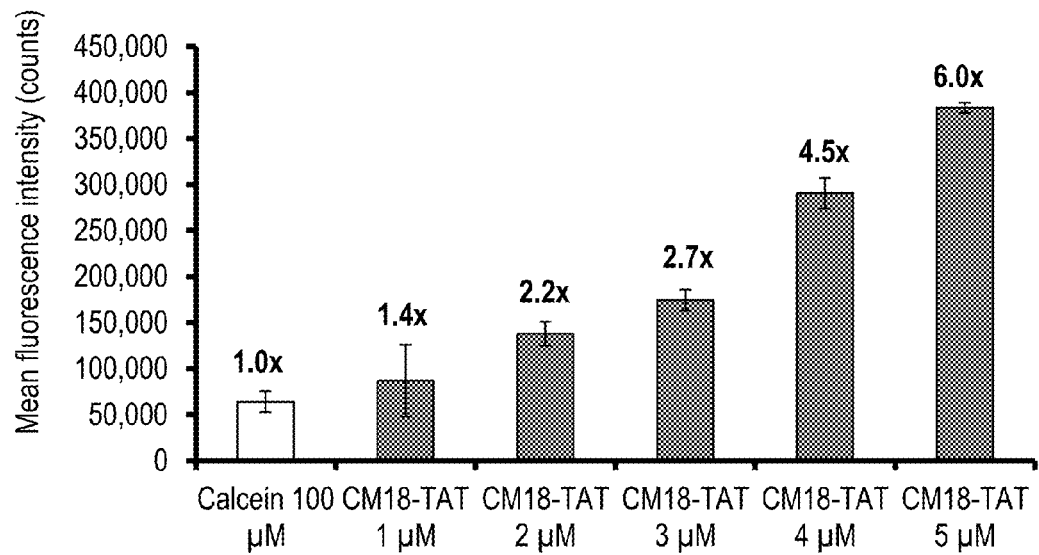
FIG. 2 shows the results of a calcein endosomal escape flow cytometry assay in which HeLa cells were loaded with calcein ("calcein 100 μM"), and were then treated with increasing concentrations of the shuttle agent CM18-TAT-Cys (labeled "CM18-TAT").

Dose response of CM18-TAT-Cys in HeLa cells, data from FIG. 2

| Domains | Peptide | Cells | Concentration (μM) | Mean counts (n = 3) | Stand. dev. | Mean Factor |
|---|---|---|---|---|---|---|
| — | No peptide ("calcein 100 μM") | HeLa | 0 | 63 872 | 11 587 | 1.0 |
| ELD-CPD | CM18-TAT-Cys | HeLa | 1 | 86 919 | 39 165 | 1.4 |
| | CM18-TAT-Cys | HeLa | 2 | 137 887 | 13 119 | 2.2 |
| | CM18-TAT-Cys | HeLa | 3 | 174 327 | 11 519 | 2.7 |
| | CM18-TAT-Cys | HeLa | 4 | 290 548 | 16 593 | 4.5 |
| | CM18-TAT-Cys | HeLa | 5 | 383 685 | 5578 | 6.0 |

TABLE 2.4

Dose response of CM18-TAT-Cys in HeLa cells

| Domains | Peptide | Cells | Concentration (μM) | Mean counts (n = 3) | Stand. dev. | Mean Factor |
|---|---|---|---|---|---|---|
| — | No peptide | HeLa | 0 | 81 013 | 14 213 | 1.0 |
| ELD-CPD | CM18-TAT-Cys | HeLa | 3 | 170 652 | 63 848 | 2.1 |
| | CM18-TAT-Cys | HeLa | 4 | 251 799 | 33 880 | 3.1 |
| | CM18-TAT-Cys | HeLa | 5 | 335 324 | 10 651 | 4.1 |

TABLE 2.5

Figure 3:
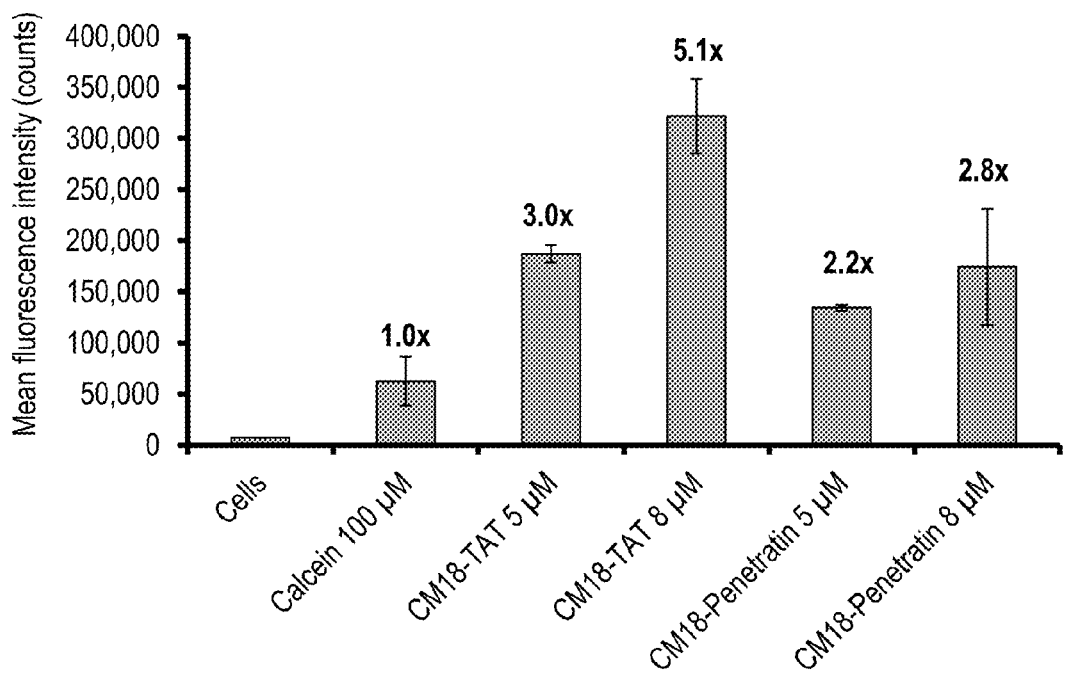
FIGS. 3 and 4 show the results of calcein endosomal escape flow cytometry assays in which HeLa cells (FIG. 3) or primary myoblasts (FIG. 4) were loaded with calcein ("calcein 100 μM"), and were then treated with 5 μM or 8 μM of the shuttle agents CM18-TAT-Cys or CM18-Penetratin-Cys (labeled "CM18-TAT" and "CM18-Penetratin", respectively).

Dose response of CM18-TAT-Cys and CM18-Penetratin-Cys in HeLa cells, data from FIG. 3

| Domains | Peptide | Cells | Concentration (μM) | Mean counts (n = 3) | Stand. dev. | Mean Factor |
|---|---|---|---|---|---|---|
| — | No peptide | HeLa | 0 | 62 503 | 23 752 | 1.0 |
| ELD-CPD | CM18-TAT-Cys | HeLa | 5 | 187 180 | 8593 | 3.0 |
| | CM18-TAT-Cys | HeLa | 8 | 321 873 | 36 512 | 5.1 |
| | CM18-Penetratin-Cys | HeLa | 5 | 134 506 | 2992 | 2.2 |
| | CM18-Penetratin-Cys | HeLa | 8 | 174 233 | 56 922 | 2.8 |

The results in Tables 2.3 (FIG. 2), 2.4, and 2.5 (FIG. 3) suggest that CM18-TAT-Cys and CM18-Penetratin-Cys facilitate escape of endosomally-trapped calcein in HeLa cells in a dose-dependent manner. In some cases, concentrations of CM18-TAT-Cys or CM18-Penetratin-Cys above 10 μM were associated with an increase in cell toxicity in HeLa cells.

TABLE 2.6

Dimers v. monomers of CM18-TAT-Cys and CM18-Penetratin-Cys in HeLa cells

| Domains | Peptide | Cells | Concentration (μM) | Mean counts (n = 4) | Stand. dev. | Mean Factor |
|---|---|---|---|---|---|---|
| — | No peptide | HeLa | 0 | 60 239 | 9860 | 1.0 |
| ELD-CPD | CM18-TAT-Cys | HeLa | 4 | 128 461 | 25 742 | 2.1 |
| | CM18-Penetratin-Cys | HeLa | 4 | 116 873 | 3543 | 1.9 |
| ELD-CPD dimer | dCM18-TAT-Cys | HeLa | 2 | 79 380 | 4297 | 1.3 |
| | dCM18-Penetratin-Cys | HeLa | 2 | 128 363 | 8754 | 2.1 |

TABLE 2.7

Monomers v. dimers of CM18-TAT-Cys and CM18-Penetratin-Cys in HeLa cells

| Domains | Peptide | Cells | Concentration (μM) | Mean counts (n = 3) | Stand. dev. | Mean Factor |
|---|---|---|---|---|---|---|
| — | No peptide | HeLa | 0 | 55 834 | 1336 | 1.0 |
| ELD-CPD | CM18-TAT-Cys | HeLa | 4 | 159 042 | 16 867 | 2.8 |
| ELD-CPD dimer | dCM18-TAT-Cys | HeLa | 2 | 174 274 | 9 553 | 3.1 |

The results in Table 2.6 and 2.7 suggest that shuttle peptide dimers (which are molecules comprising more than one ELD and CPD) are able to facilitate calcein endosomal escape levels that are comparable to the corresponding monomers.

2.2.3 HEK293A Cells

To examine the effects of the shuttle agents on a different cell line, HEK293A cells were cultured and tested in the endosomal escape assays as described in Example 2.1. The results of flow cytometry analyses are summarized below in Table 2.8 and in FIG. 1B.

TABLE 2.8

CM18-TAT-Cys in HEK293A cells

| Domains | Peptide | Cells | Concentration (μM) | Mean counts (n = 2) | Stand. dev. | Mean Factor |
|---|---|---|---|---|---|---|
| — | No peptide | HEK293A | 0 | 165 819 | 7693 | 1.0 |
| ELD-CPD | CM18-TAT-Cys | HEK293A | 0.5 | 196 182 | 17 224 | 1.2 |
| | CM18-TAT-Cys | HEK293A | 5 | 629 783 | 1424 | 3.8 |

The results in Table 2.8 and in FIG. 1B show that treating calcein-loaded HEK293A cells with the shuttle agent CM18-TAT-Cys results in increased mean cellular calcein fluorescence intensity, as compared to untreated control cells.

2.2.2 Myoblasts

To examine the effects of the shuttle agents on primary cells, primary myoblast cells were cultured and tested in the endosomal escape assays as described in Example 2.1. The results of flow cytometry analyses are summarized below in Tables 2.9 and 2.10, and in FIG. 4. In each case, the flow cytometry results were also confirmed by fluorescence microscopy.

TABLE 2.9

Figure 4:
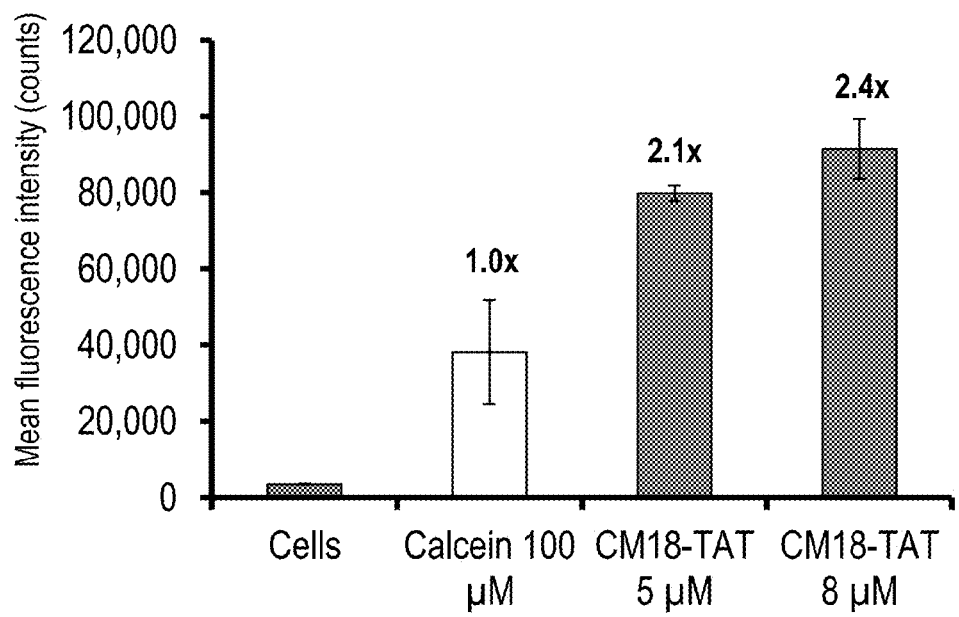

Dose response of CM18-TAT-Cys in primary myoblasts, data from FIG. 4

| Domains | Peptide | Cells | Peptide Conc. (μM) | Mean counts (n = 3) | Stand. dev. | Mean Factor |
|---|---|---|---|---|---|---|
| — | No peptide; no calcein ("Cells") | Myoblasts | 0 | 863 | 61 | n/a |
| — | No peptide ("Calcein 100 μM") | Myoblasts | 0 | 38 111 | 13 715 | 1.0 |
| ELD-CPD | CM18-TAT-Cys | Myoblasts | 5 | 79 826 | 12 050 | 2.1 |
| CPD | CM18-TAT-Cys | Myoblasts | 8 | 91 421 | 10 846 | 2.4 |

TABLE 2.10

Dose response of CM18-TAT-Cys in primary myoblasts

| Domains | Peptide | Cells | Peptide Conc. (μM) | Mean counts (n = 3) | Stand. dev. | Mean Factor |
|---|---|---|---|---|---|---|
| — | No peptide | Myoblasts | 0 | 31 071 | 21 075 | 1.0 |
| ELD-CPD | CM18-TAT-Cys | Myoblasts | 5 | 91 618 | 10 535 | 2.9 |
| CPD | CM18-TAT-Cys | Myoblasts | 7.5 | 95 289 | 11 266 | 3.1 |

The results in Table 2.9 (shown graphically in FIG. 4) and Table 2.10 suggest that CM18-TAT-Cys facilitates escape of endosomally-trapped calcein in a dose-dependent manner in primary myoblasts. Concentrations of CM18-TAT-Cys above 10 μM were associated with an increase in cell toxicity in myoblast cells, as for HeLa cells.

TABLE 2.11

Monomers v. dimers CM18-TAT-Cys and CM18-Penetratin-Cys in primary myoblasts

| Domains | Peptide | Cells | Concentration (μM) | Mean counts | Stand. dev. | Mean Factor |
|---|---|---|---|---|---|---|
| — | No peptide | Myoblasts | 0 | 30 175 | 4687 | 1.0 |
| ELD-CPD | CM18-TAT-Cys | Myoblasts | 5 | 88 686 | 19 481 | 2.9 |
| ELD-CPD dimer | dCM18-TAT-Cys | Myoblasts | 2.5 | 64 864 | 1264 | 2.1 |
| ELD-CPD | CM18-Penetratin-Cys | Myoblasts | 5 | 65 636 | 3288 | 2.2 |

TABLE 2.11-continued

Monomers v. dimers CM18-TAT-Cys and CM18-Penetratin-Cys in primary myoblasts

| Domains | Peptide | Cells | Concentration (μM) | Mean counts | Stand. dev. | Mean Factor |
|---|---|---|---|---|---|---|
| ELD-CPD dimer | dCM18-Penetratin-Cys | Myoblasts | 2.5 | 71 547 | 10 975 | 2.4 |

The results in Table 2.11 suggest that shuttle peptide dimers are able to facilitate calcein endosomal escape levels that are comparable to the corresponding monomers in primary myoblasts.

Example 3

Peptide Shuttle Agents Increase GFP Transduction Efficiency 3.1 Protein Transduction Assay One day before the transduction assay was performed, cells in exponential growth phase were harvested and plated in a 96-well plate (20,000 cells per well). The cells were incubated overnight in appropriate growth media containing FBS (see Example 1). The next day, in separate sterile 1.5 mL tubes, cargo protein at the indicated concentration was pre-mixed (pre-incubated) for 1 or 10 min (depending on the protocol) at 37° C. with the peptide(s) to be tested shuttle agents (0.5 to 5 μM) in 50 μL of fresh medium without serum (unless otherwise specified). The media in wells was removed and the cells were washed three times with freshly prepared phosphate buffered saline (PBS) previously warmed at 37° C. The cells were incubated with the cargo protein/shuttle agent mixture at 37° C. for the indicated time (e.g., 1, 5 or 60 min). After the incubation, the cells were quickly washed three times with freshly prepared PBS and/or heparin (0.5 mg/mL) previously warmed at 37° C. The washes with heparin were required for human THP-1 blood cells to avoid undesired cell membrane-bound protein background in subsequent analyses (microscopy and flow cytometry). The cells were finally incubated in 50 μL of fresh medium with serum at 37° C. before analysis.

3.1a Protocol A: Protein Transduction Assay for Adherent Cells

One day before the transduction assay was performed, cells in exponential growth phase were harvested and plated in a 96-well plate (20,000 cells per well). The cells were incubated overnight in appropriate growth media containing serum (see Example 1). The next day, in separate sterile 1.5-mL tubes, peptides were diluted in sterile distilled water at room temperature (if the cargo is or comprised a nucleic acid, nuclease-free water was used). Cargo protein(s) were then added to the peptides and, if necessary, sterile PBS or cell culture medium (serum-free) was added to obtain the desired concentrations of shuttle agent and cargo in a sufficient final volume to cover the cells (e.g., 10 to 100 μL per well for a 96-well plate). The peptides/cargo mixture was then immediately used for experiments. At least three controls were included for each experiment, including: (1) peptides alone (e.g., at highest concentration tested); (2) cargo alone; and (3) without any cargo or shuttle agent. The media in wells was removed, cells were washed once with PBS previously warmed at 37° C., and the cells were incubated with the cargo protein/peptide mixture at 37° C. for the desired length of time. The peptide/cargo mixture in wells was removed, the cells were washed once with PBS, and fresh complete medium was added. Before analysis, the cells were washed once with PBS one last time and fresh complete medium was added.

3.1b Protocol B: Protein Transduction Assay for Suspension Cells

One day before the transduction assay was performed, suspension cells in exponential growth phase were harvested and plated in a 96-well plate (20,000 cells per well). The cells were incubated overnight in appropriate growth media containing serum (see Example 1). The next day, in separate sterile 1.5-mL tubes, peptides were diluted in sterile distilled water at room temperature (if the cargo is or comprised a nucleic acid, nuclease-free water was used). Cargo protein(s) were then added to the peptides and, if necessary, sterile PBS or cell culture medium (serum-free) was added to obtain the desired concentrations of shuttle agent and cargo in a sufficient final volume to resuspend the cells (e.g., 10 to 100 μL per well in a 96-well plate). The shuttle agent/peptide was then immediately used for experiments. At least three controls were included for each experiment, including: (1) peptide alone (e.g., at highest concentration tested); (2) cargo alone; and (3) without any cargo or shuttle agent. The cells were centrifuged for 2 minutes at 400 g, the medium was then removed and the cells were resuspended in PBS previously warmed at 37° C. The cells were centrifuged again 2 minutes at 400 g, the PBS removed, and the cells were resuspended with the cargo protein/peptide mixture at 37° C. for the desired length of time. After that, 200 μL of complete medium was added directly on the cells. Cells were centrifuged for 2 minutes at 400 g and the medium was removed. The pellet was resuspended and washed in 200 μL of PBS previously warmed at 37° C. After another centrifugation, the PBS was removed and the cells were resuspended in 50 μL of trypsin-EDTA solution for 2 min. 200 of complete medium was directly added and cells were centrifuged for 2 minutes at 400 g. The medium was removed and the cells were resuspended in 200 μL of complete medium.

3.2 Fluorescence Microscopy Analysis

The delivery of fluorescent protein cargo in cytosolic and nuclear cell compartments was observed with an Olympus IX70™ microscope (Japan) equipped with a fluorescence lamp (Model U-LH100HGAPO) and different filters. The Olympus filter U-MF2™ (C54942-Exc495/Em510) was used to observe GFP and FITC-labeled antibody fluorescent signals. The Olympus filter HQ-TR™ (V-N41004-Exc555-60/Em645-75) was used to observe mCherry™ and GFP antibody fluorescent signals. The Olympus filter U-MWU2™ (Exc330/Em385) was used to observe DAPI or Blue Hoechst fluorescent signals. The cells incubated in 50 μL of fresh medium were directly observed by microscopy (Bright-field and fluorescence) at different power fields (4× to 40×). The cells were observed using a CoolSNAP-PRO™ camera (Series A02D874021) and images were acquired using the Image-Proplus™ software.

3.2a Cell Immuno-Labelling

Adherent cells were plated on a sterile glass strip at 1.5×10⁵ cells per well in a 24-plate well and incubated overnight at 37° C. For fixation, cells were incubated in 500 JAL per well of formaldehyde (3.7% v/v) for 15 minutes at room temperature, and washed 3 times for 5 minutes with PBS. For permeabilization, cells were incubated in 500 µL per well of Triton™ X-100 (0.2%) for 10 minutes at room temperature, and washed 3 times for 5 minutes with PBS. For blocking, cells were incubated in 500 µL per well of PBS containing 1% BSA (PBS/BSA) for 60 minutes at room temperature. Primary mouse monoclonal antibody was diluted PBS/BSA (1%). Cells were incubated in 30 µL of primary antibody overnight at 4° C. Cells were washed 3 times for 5 minutes with PBS. Secondary antibody was diluted in PBS/BSA (1%) and cells were incubated in 250 µL of secondary antibody 30 minutes at room temperature in the dark. Cells were washed 3 times for 5 minutes with PBS. Glass strips containing the cells were mounted on microscope glass slides with 10 µL of the mounting medium Fluoroshield™ with DAPI.

3.3 Flow Cytometry Analysis:

The fluorescence of GFP was quantified using flow cytometry (Accuri C6, Becton, Dickinson and Company (BD)). Untreated cells were used to establish a baseline in order to quantify the increased fluorescence due to the internalization of the fluorescent protein in treated cells. The percentage of cells with a fluorescence signal above the maximum fluorescence of untreated cells, "mean %" or "Pos cells (%)", is used to identify positive fluorescent cells. "Relative fluorescence intensity (FL1-A)" corresponds to the mean of all fluorescence intensities from each cell with a fluorescent signal after fluorescent protein delivery with the shuttle agent. Also, the events scanned by flow cytometry corresponding to cells (size and granularity) were analyzed. The cellular toxicity (% cell viability) was monitored comparing the percentage of cells in the total events scanned of treated cells comparatively to untreated cells.

3.3a Viability Analysis

Where indicated, the viability of cells was assessed with a resazurin test. Resazurin is a sodium salt colorant that is converted from blue to pink by mitochondrial enzymes in metabolically active cells. This colorimetric conversion, which only occurs in viable cells, can be measured by spectroscopy analysis in order to quantify the percentage of viable cells. The stock solution of resazurin was prepared in water at 1 mg/100 mL and stored at 4° C. 25 µL of the stock solution was added to each well of a 96-well plate, and cells were incubated at 37° C. for one hour before spectrometry analysis. The incubation time used for the resazurine enzymatic reaction depended on the quantity of cells and the volume of medium used in the wells.

3.4 Construction and Amino Acid Sequence of GFP

The GFP-encoding gene was cloned in a T5 bacterial expression vector to express a GFP protein containing a 6× histidine tag and a serine/glycine rich linker in the N-terminal end, and a serine/glycine rich linker and a stop codon (−) at the C-terminal end. Recombinant GFP protein was purified as described in Example 1.4. The sequence of the GFP construct was:

[SEQ ID NO: 60]
MHHHHHHGGGGSGGGGSGGASTGTGIRMVSKGEELFTGVVPILVELDGDV

NGHKFSVSGEGEGDATYGKLTLKFICTTGKLPVPWPTLVTTLTYGVQCFS

-continued
RYPDHMKQHDFFKSAMPEGYVQERTIFFKDDGNYKTRAEVKFEGDTLVNR

IELKGIDFKEDGNILGHKLEYNYNSHNVYIMADKQKNGIKVNFKIRHNIE

DGSVQLADHYQQNTPIGDGPVLLPDNHYLSTQSALSKDPNEKRDEIMVLL

Figure 5:
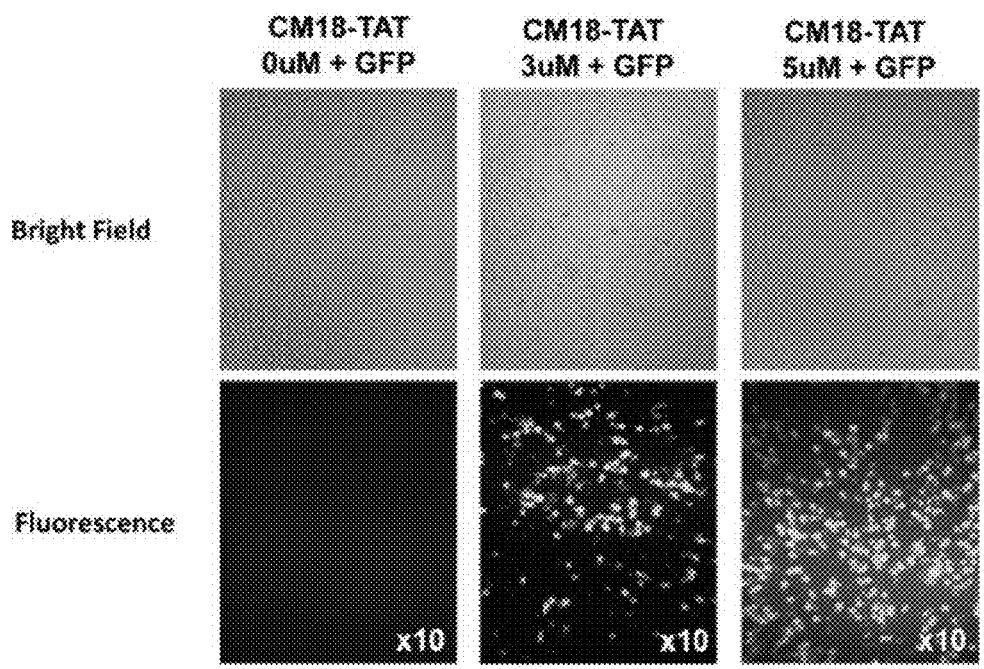
FIG. 5 shows the results of a GFP transduction experiment visualized by fluorescence microscopy in which a GFP cargo protein was co-incubated with 0, 3 or 5 μM of CM18-TAT-Cys (labeled "CM18-TAT"), and then exposed to HeLa cells. The cells were observed by bright field (upper panels) and fluorescence microscopy (lower panels).

EFVTAAGITLGMDELYKGGSGGGSGGGSGWIRASSGGREIS-
(MW = 31.46 kDa; pI = 6.19)
Serine/glycine rich linkers are in bold
GFP sequence is underlined 3.5 GFP Transduction by CM18-TAT-Cys in HeLa Cells: Fluorescence Microscopy HeLa cells were cultured and tested in the protein transduction assay described in Example 3.1. Briefly, GFP recombinant protein was co-incubated with 0, 3 or 5 µM of CM18-TAT, and then exposed to HeLa cells for 1 hour. The cells were observed by bright field and fluorescence microscopy as described in Example 3.2. The results presented in FIG. 5 show that GFP was delivered intracellularly to HeLa cells in the presence of the shuttle agent CM18-TAT.

3.6 GFP Transduction by Shuttle Agents in HeLa Cells: Dose Responses (CM18-TAT-Cys, dCM18-TAT-Cys, GFP) and Cell Viability HeLa cells were cultured and tested in the protein transduction assay described in Examples 3.1-3.3. Briefly, GFP recombinant protein was co-incubated with different concentrations of CM18-TAT-Cys or dimerized CM18-TAT-Cys (dCM18-TAT-Cys), and then exposed to HeLa cells for 1 hour. The results are shown in Table 3.1 and FIGS. 6A-6B.

TABLE 3.1

Figure 6A:
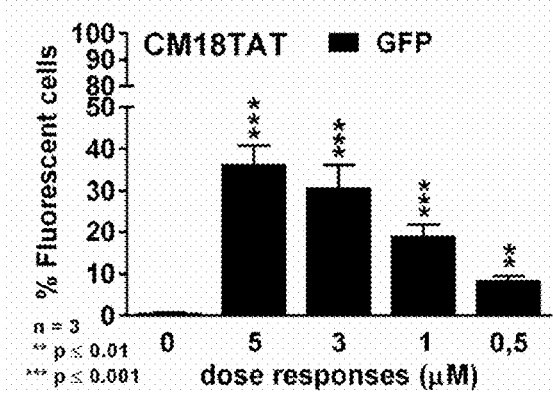
FIGS. 6A and 6B show the results of a GFP transduction efficiency experiment in which GFP cargo protein (10 μM) was co-incubated with different concentrations of CM18-TAT-Cys (labeled "CM18-TAT"), prior to being exposed to HeLa cells. Cells were evaluated by flow cytometry and the percentage of fluorescent (GFP-positive) cell is shown in FIG. 6A, and corresponding cell toxicity data is shown in FIG. 6B.
Figure 6B:
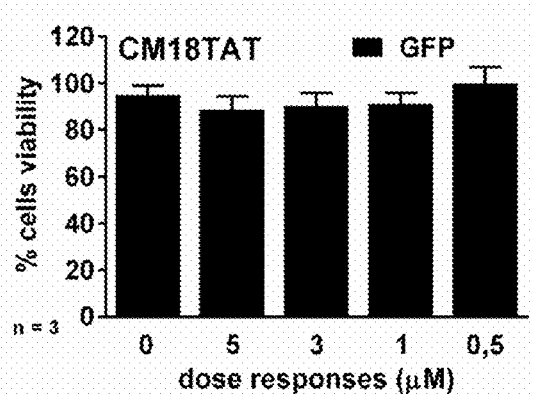

Dose response (CM18-TAT) and cell viability, data from FIGS. 6A and 6B

| Shuttle | Cells | Concentration (µM) | FIG. 6A Mean (%) (n = 3) | Standard deviation | FIG. 6B Cell viability (%) (±St. Dev.; n = 3) |
|---|---|---|---|---|---|
| CM18-TAT-Cys | HeLa | 0 | 0.69 | 0.12 | 95 ± 4 |
| | HeLa | 0.5 | 8.67 | 0.96 | 88.4 ± 6 |
| | HeLa | 1 | 20.03 | 2.55 | 90 ± 6 |
| | HeLa | 3 | 31.06 | 5.28 | 91 ± 5 |
| | HeLa | 5 | 36.91 | 4.33 | 90 ± 7 |

Table 3.1 and FIG. 6A show the results of flow cytometry analysis of the fluorescence intensity of HeLa cells transduced with GFP (5 µM) without or with 5, 3, 1, and 0.5 µM of CM18-TAT-Cys. Corresponding cellular toxicity data are presented in Table 3.1 and in FIG. 6B. These results suggest that the shuttle agent CM18-TAT-Cys increases the transduction efficiency of GFP in a dose-dependent manner.

TABLE 3.2

Figure 7A:
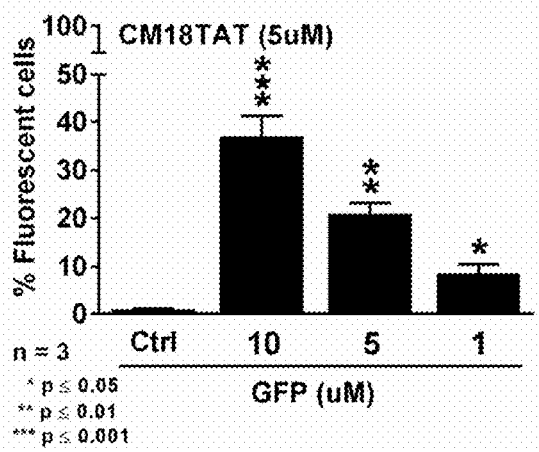
FIGS. 7A and 7B shows the results of a GFP transduction efficiency experiment in which different concentrations of GFP cargo protein (10, 5 or 1 μM) were co-incubated with either 5 μM of CM18-TAT-Cys (FIG. 7A, labeled "CM18TAT"), or 2.5 μM of dCM18-TAT-Cys (FIG. 7B, labeled "dCM18TAT"), prior to being exposed to HeLa cells. Cells were evaluated by flow cytometry and the percentages of fluorescent (GFP-positive) cells are shown.
Figure 7B:
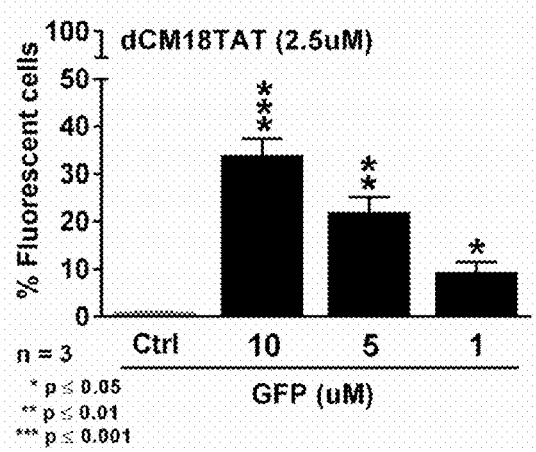

Dose response (GFP), data from FIGS. 7A and 7B

| Shuttle | Cells | Conc. of shuttle agent (µM) | Conc. of GFP (µM) | Mean (%) (n = 3) | Standard deviation |
|---|---|---|---|---|---|
| Control | HeLa | 0 | 10 | 0.93 | 0.08 |
| CM18-TAT-Cys | HeLa | 5 | 10 | 37.1 | 4.29 |
| | HeLa | 5 | 5 | 21.1 | 2.19 |
| | HeLa | 5 | 1 | 8.56 | 1.91 |
| Control | HeLa | 0 | 10 | 0.91 | 0.09 |
| dCM18- | HeLa | 2.5 | 10 | 34.2 | 3.42 |

TABLE 3.2-continued

Dose response (GFP), data from FIGS. 7A and 7B

| Shuttle | Cells | Conc. of shuttle agent (µM) | Conc. of GFP (µM) | Mean (%) (n = 3) | Standard deviation |
|---|---|---|---|---|---|
| TAT-Cys | HeLa | 2.5 | 5 | 22.2 | 3.17 |
|  | HeLa | 2.5 | 1 | 9.38 | 2.11 |

Table 3.2 and FIG. 7 show the results of flow cytometry analysis of the fluorescence intensity of HeLa cells transduced with different concentrations of GFP (1 to 10 µM) without or with 5 µM of CM18-TAT-Cys (FIG. 7A) or 2.5 µM dCM18-TAT-Cys (FIG. 7B).

3.7 GFP Transduction in HeLa Cells: Dose Responses of CM18-TAT-Cys and CM18-Penetratin-Cys, and Dimers Thereof HeLa cells were cultured and tested in the protein transduction assay described in Example 3.1. Briefly, GFP recombinant protein (5 µM) was co-incubated with different concentrations and combinations of CM18-TAT-Cys, CM18-Penetratin-Cys, and dimers of each (dCM18-TAT-Cys, dCM18-Penetratin-Cys), and then exposed to HeLa cells for 1 hour. The cells were subjected to flow cytometry analysis as described in Example 3.3. The results are shown in Table 3.3 and FIG. 8, as well as in Table 3.4 and FIG. 9.

TABLE 3.3

Figure 8:
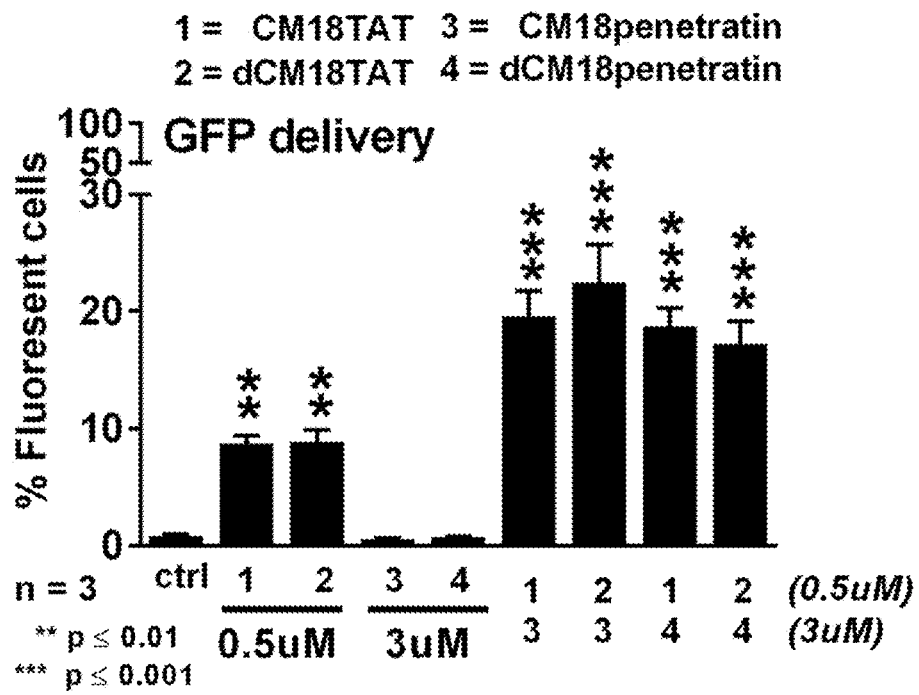
FIGS. 8 and 9 show the results of GFP transduction efficiency experiments in which GFP cargo protein (10 μM) was co-incubated with different concentrations and combinations of CM18-TAT-Cys (labeled "CM18TAT"), CM18-Penetratin-Cys (labeled "CM18penetratin"), and dimers of each (dCM18-TAT-Cys (labeled "dCM18TAT"), dCM18-Penetratin-Cys (labeled "dCM18penetratin"), prior to being exposed to HeLa cells. Cells were evaluated by flow cytometry and the percentages of fluorescent (GFP-positive) cells are shown.

Data in FIG. 8

| No. in FIG. 8 | Shuttle agent | Cells | Concentration (µM) | Mean (%) (n = 3) | Standard deviation |
|---|---|---|---|---|---|
| Control ("ctrl") | No shuttle | HeLa | 0 | 0.43 | 0.08 |
| 1 | CM18-TAT-Cys | HeLa | 0.5 | 8.75 | 0.63 |
| 2 | dCM18-TAT-Cys | HeLa | 0.5 | 8.86 | 1.03 |
| 3 | CM18-Penetratin-Cys | HeLa | 3 | 0.59 | 0.11 |
| 4 | dCM18-Penetratin-Cys | HeLa | 3 | 0.73 | 0.08 |
| 1 + 3 | CM18-TAT-Cys + CM18-Penetratin-Cys | HeLa | 0.5 3 | 19.52 | 2.18 |
| 2 + 3 | dCM18-TAT-Cys + CM18-Penetratin-Cys | HeLa | 0.5 3 | 22.44 | 3.29 |
| 1 + 4 | CM18-TAT-Cys + dCM18-Penetratin-Cys | HeLa | 0.5 3 | 18.73 | 1.55 |
| 2 + 4 | dCM18-TAT-Cys + dCM18-Penetratin-Cys | HeLa | 0.5 3 | 17.19 | 1.93 |

The results in Table 3.3 and FIG. 8 show that the transduction efficiency of GFP is increased in HeLa cells using the shuttle agents CM18-TAT-Cys and dCM18-TAT-Cys (see bars "1" and "2" in FIG. 8). Although no GFP intracellular delivery was observed using CM18-Penetratin-Cys or dCM18-Penetratin-Cys alone (see bars "3" or "4" in FIG. 8), combination of CM18-TAT-Cys with CM18-Penetratin-Cys (monomer or dimer) improved GFP protein delivery (see four right-most bars in FIG. 8).

TABLE 3.4

Figure 9:
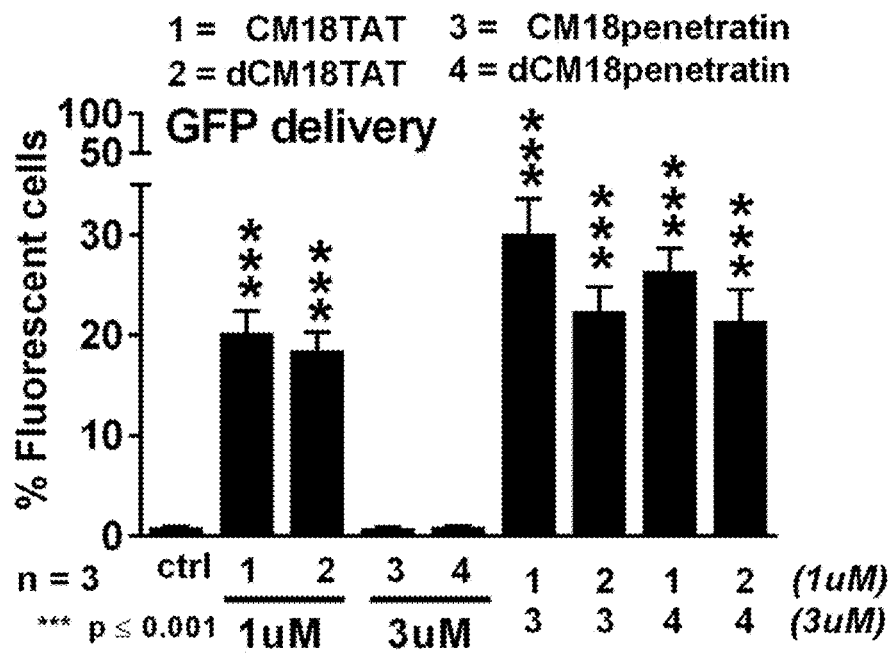

Data in FIG. 9

| No. in FIG. 9 | Shuttle | Cells | Concentration (µM) | Mean (%) (n = 3) | Standard deviation |
|---|---|---|---|---|---|
| Control ("ctrl") | No shuttle | HeLa | 0 | 0.51 | 0.07 |
| 1 | CM18-TAT-Cys | HeLa | 1 | 20.19 | 2.19 |
| 2 | dCM18-TAT-Cys | HeLa | 1 | 18.43 | 1.89 |
| 3 | CM18-Penetratin-Cys | HeLa | 3 | 0.81 | 0.07 |
| 4 | dCM18-Penetratin-Cys | HeLa | 3 | 0.92 | 0.08 |
| 1 + 3 | CM18-TAT-Cys + CM18-Penetratin-Cys | HeLa | 1 3 | 30.19 | 3.44 |
| 2 + 3 | dCM18-TAT-Cys + CM18-Penetratin-Cys | HeLa | 1 3 | 22.36 | 2.46 |
| 1 + 4 | CM18-TAT-Cys + dCM18-Penetratin-Cys | HeLa | 1 3 | 26.47 | 2.25 |
| 2 + 4 | dCM18-TAT-Cys + dCM18-Penetratin-Cys | HeLa | 1 3 | 21.44 | 3.11 |

The results in Table 3.4 and FIG. 9 show that the transduction efficiency of GFP is increased in HeLa cells using the shuttle agents CM18-TAT-Cys and dCM18-TAT-Cys (see bars "1" and "2" in FIG. 9). Although no GFP intracellular delivery was observed using CM18-Penetratin-Cys or dCM18-Penetratin-Cys alone (see bars "3" or "4" in FIG. 9), combination of CM18-TAT-Cys with CM18-Penetratin-Cys (monomer or dimer) improved GFP protein delivery (see four right-most bars in FIG. 9).

3.8 GFP Transduction by Shuttle Agents in HeLa Cells: Controls

HeLa cells were cultured and tested in the protein transduction assay described in Example 3.1. Briefly, GFP recombinant protein (5 µM) was co-incubated with 5 µM of each of the following peptide(s): TAT-Cys; CM18; Penetratin-Cys; TAT-Cys+CM18; Penetratin-Cys+CM18; and CM18-TAT-Cys, and then exposed to HeLa cells for 1 hour. GFP fluorescence was visualized by bright field and fluorescence microscopy. The microscopy results (data not shown) showed that GFP was successfully delivered intracellularly using CM18-TAT-Cys. However, GFP was not successfully delivered intracellularly using single-domain peptides used alone (CM18, TAT-Cys, Penetratin-Cys) or together (CM18+TAT-Cys, CM18+Penetratin-Cys). These results are consistent with those presented in Tables 2.1 and 2.2 with respect to the calcein endosome escape assays.

Example 4

Peptide Shuttle Agents Increase TAT-GFP Transduction Efficiency

The experiments in Example 3 showed the ability of shuttle agents to deliver GFP intracellularly. The experiments presented in this example show that the shuttle agents can also increase the intracellular delivery of a GFP cargo protein that is fused to a CPD (TAT-GFP).

4.1 Construction and Amino Acid Sequence of TAT-GFP

Construction was performed as described in Example 3.4, except that a TAT sequence was cloned between the 6x histidine tag and the GFP sequences. The 6x histidine tag, TAT, GFP and a stop codon (−) are separated by serine/glycine rich linkers. The recombinant TAT-GFP protein was purified as described in Example 1.4. The sequence of the TAT-GFP construct was:

[SEQ ID NO: 61]
MHHHHHHGGGGSGGGGSGGASTGT<u>GRKKRRQRRRPPQ</u>GGGGSGGGGSGGG

TGIRMVSKGEELFTGVVPILVELDGDVNGEIKFSVSGEGEGDATYGKLTL

-continued

KFICTTGKLPVPWPTLVTTLTYGVQCFSRYPDHMKQHDFFKSAMPEGYVQ

ERTIFFKDDGNYKTRAEVKFEGDTLVNRIELKGIDFKEDGNILGHKLEYN

YNSHNVYIMADKQKNGIKVNFKIRHNIEDGSVQLADHYQQNTPIGDGPVL

LPDNHYLSTQSALSKDPNEKRDHMVLLEFVTAAGITLGMDELYKGGSGGG

Figure 10:
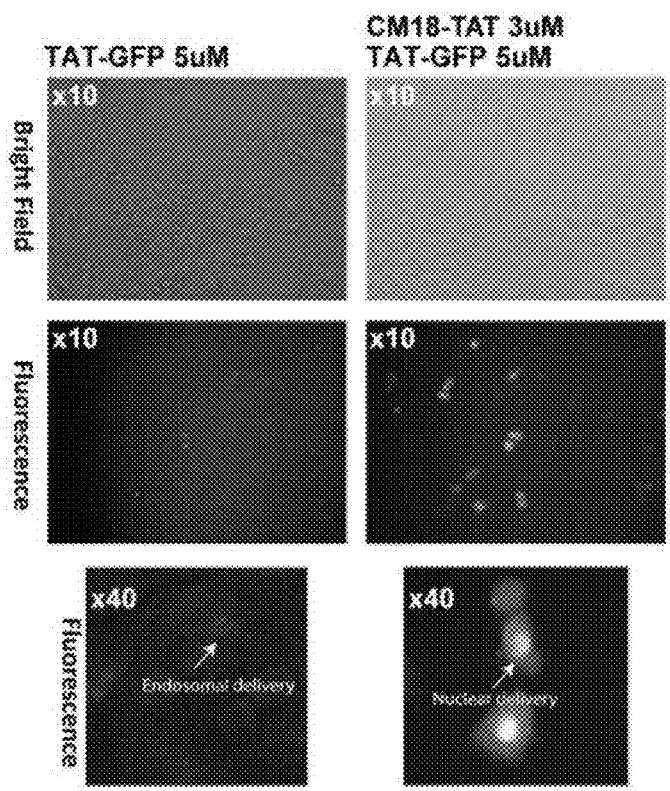
FIG. 10 shows typical results of a TAT-GFP transduction experiment in which TAT-GFP cargo protein (5 μM) was co-incubated with 3 μM of CM18-TAT-Cys (labeled "CM18-TAT"), prior to being exposed to HeLa cells. Cells and GFP fluorescence were visualized by bright field and fluorescence microscopy at 10× and 40× magnifications. Arrows indicate the endosome delivery of TAT-GFP in the absence of CM18-TAT-Cys, as well as its nuclear delivery in the presence of CM18-TAT-Cys.

SGGGSGWIRASSGGREIS-
(MW = 34.06 kDa; pI = 8.36)
TAT sequence is underlined
Serine/glycine rich linkers are in bold 4.2 TAT-GFP Transduction by CM18-TAT-Cys in HeLa Cells: Visualisation by Fluorescence Microscopy HeLa cells were cultured and tested in the protein transduction assay described in Example 3.1. Briefly, TAT-GFP recombinant protein (5 µM) was co-incubated with 3 µM of CM18-TAT-Cys and then exposed to HeLa cells for 1 hour. Cells and GFP fluorescence were visualized by bright field and fluorescence microscopy (as described in Example 3.2) at 10× and 40× magnifications, and sample results are shown in FIG. 10. The microscopy results revealed that in the absence of CM18-TAT-Cys, TAT-GFP shows a low intensity, endosomal distribution as reported in the literature. In contrast, TAT-GFP is delivered to the cytoplasm and to the nucleus in the presence of the shuttle agent CM18-TAT-Cys. Without being bound by theory, the TAT peptide itself may act as a nuclear localization signal (NLS), explaining the nuclear localization of TAT-GFP. These results show that CM18-TAT-Cys is able to increase TAT-GFP transduction efficiency and allow endosomally-trapped TAT-GFP to gain access to the cytoplasmic and nuclear compartments.

4.3 TAT-GFP Transduction by CM18-TAT-Cys in HeLa Cells: Dose Responses and Viability of Cells Transduced HeLa cells were cultured and tested in the protein transduction assay described in Example 3.1. Briefly, TAT-GFP recombinant protein (5 µM) was co-incubated with different concentrations of CM18-TAT-Cys (0, 0.5, 1, 3, or 5 µM) and then exposed to HeLa cells for 1 hour. The cells were subjected to flow cytometry analysis as described in Example 33. Results are shown in Table 4.3 and FIG. 11A. Corresponding cellular toxicity data are presented in FIG. 11B.

TABLE 4.3

Figure 11A:
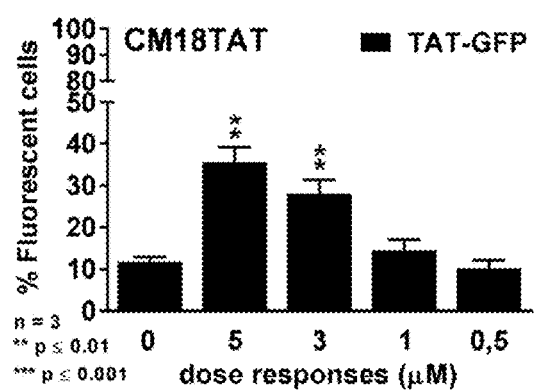
FIGS. 11A and 11B show the results of a TAT-GFP transduction efficiency experiment in which TAT-GFP cargo protein (5 μM) was co-incubated with different concentrations of CM18-TAT-Cys (labeled "CM18TAT"), prior to being exposed to HeLa cells. Cells were evaluated by flow cytometry and the percentage of fluorescent (GFP-positive) cell is shown in FIG. 11A, and corresponding cell toxicity data is shown in FIG. 11B.
Figure 11B:
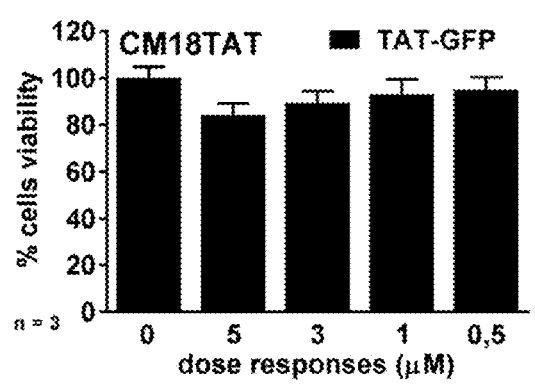

Data from FIG. 11A and 11B

| Shuttle agent | Cells | Concentration (µM) | FIG. 11A Mean (%) (n = 3) | Standard deviation | FIG. 11B Cell viability (%) (±St. Dev.; n = 3) |
|---|---|---|---|---|---|
| CM18-TAT-Cys | HeLa | 0 | 11.79[1] | 1.16 | 100 |
| | HeLa | 0.5 | 10.19 | 1.94 | 84.36 ± 5 |
| | HeLa | 1 | 14.46 | 2.59 | 89.26 ± 5.26 |
| | HeLa | 3 | 28.12 | 3.27 | 93.18 ± 6.28 |
| | HeLa | 5 | 35.5[2] | 3.59 | 95.14 ± 5.28 |

[1] The fluorescence was mostly endosomal, as confirmed by fluorescence microscopy.
[2] Fluorescence was more diffuse and also nuclear, as confirmed by fluorescence microscopy.

Example 5

Peptide Shuttle Agents Increase GFP-NLS Transduction Efficiency and Nuclear Localization The experiments in Examples 3 and 4 showed the ability of shuttle agents to deliver GFP and TAT-GFP intracellularly. The experiments presented in this example show that the shuttle agents can facilitate nuclear delivery of a GFP protein cargo fused to a nuclear localization signal (NLS).

5.1 Construction and Amino Acid Sequence of GFP-NLS

Construction was performed as described in Example 3.4, except that an optimized NLS sequence was cloned between the GFP sequence and the stop codon (−). The NLS sequence is separated from the GFP sequence and the stop codon by two serine/glycine rich linkers. The recombinant GFP-NLS protein was purified as described in Example 1.4. The sequence of the GFP-NLS construct was:

[SEQ ID NO: 62]
MHHHHHHGGGSGGGGSGGASTGIRMVSKGEELFTGVVPILVELDGDVNG

HKFSVSGEGEGDATYGKLTLKFICTTGKLPVPWPTLVTTLTYGVQCFSRY

PDHMKQEMFFKSAMPEGYVQERTIFFKDDGNYKTRAEVKFEGDTLVNRIE

LKGIDFKEDGNILGHKLEYNYNSHNVYIMADKQKNGIKVNFKIRHNIEDG

SVQLADHYQQNTPIGDGPVLLPDNHYLSTQSALSKDPNEKRDHMVLLEFV

TAAGITLGMDELYKGGSGGGSGGGSGWIRASSGGRSSDDEATADSQHAAP

Figure 12:
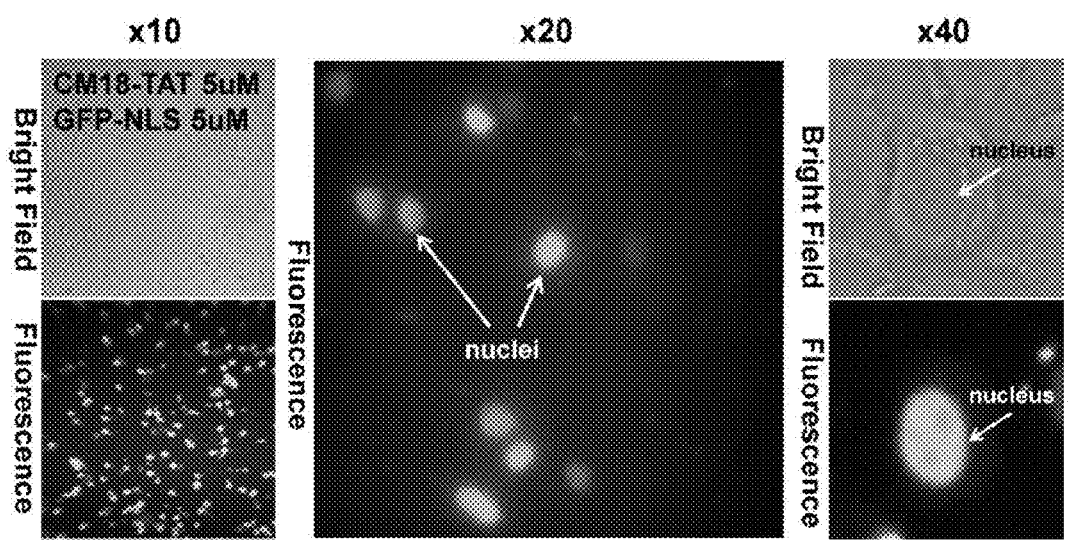
FIG. 12 shows typical results of a GFP-NLS transduction experiment in which GFP-NLS cargo protein (5 μM) was co-incubated with 5 μM of CM18-TAT-Cys (labeled "CM18-TAT"), prior to being exposed to HeLa cells for 5 minutes. Cells and GFP fluorescence were visualized by bright field and fluorescence microscopy at 10×, 20×, and 40× magnifications. Arrows indicate areas of nuclear delivery of GFP-NLS.

PKKKRKVGGSGGGSGGGSGGGRGTEIS-
(MW = 34.85 kDa; pI = 6.46)
NLS sequence is underlined
Serine/glycine rich linkers are in bold 5.2 Nuclear Delivery of GFP-NLS by CM18-TAT-Cys in HeLa Cells in 5 Minutes: Visualisation by Fluorescence Microscopy HeLa cells were cultured and tested in the protein transduction assay described in Example 3.1. Briefly, GFP-NLS recombinant protein (5 µM) was co-incubated with 5 µM of CM18-TAT-Cys, and then exposed to HeLa cells. GFP fluorescence was visualized by bright field and fluorescence microscopy after 5 minutes (as described in Example 3.2) at 10×, 20× and 40× magnifications, and sample results are shown in FIG. 12. The microscopy results revealed that GFP-NLS is efficiently delivered to the nucleus in the presence of the shuttle agent CM18-TAT-Cys, after only 5 minutes of incubation.

5.3 GFP-NLS Transduction by CM18-TAT-Cys in HeLa Cells: Dose Responses and Viability of Cells Transduced HeLa cells were cultured and tested in the protein transduction assay described in Example 3.1. GFP-NLS recombinant protein (5 µM) was co-incubated with 0, 0.5, 1, 3, or 5 µM of CM18-TAT-Cys, and then exposed to HeLa cells for 1 hour. The cells were subjected to flow cytometry analysis as described in Example 3.3. Results are shown in Table 5.1 and FIG. 13A. Corresponding cellular toxicity data are presented in FIG. 13B.

TABLE 5.1

Figure 13A:
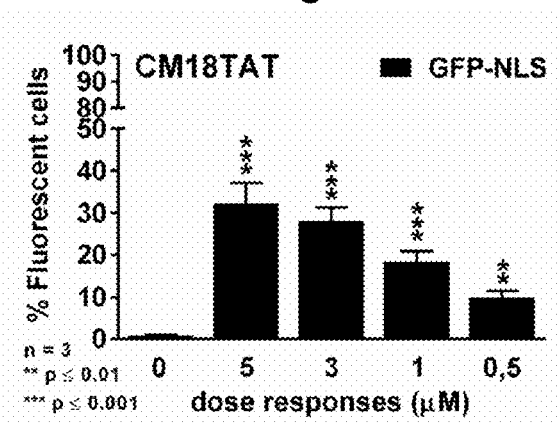
FIGS. 13A and 13B show the results of a GFP-NLS transduction efficiency experiment in which GFP-NLS cargo protein (5 μM) was co-incubated with different concentrations of CM18-TAT-Cys (labeled "CM18TAT"), prior to being exposed to HeLa cells. Cells were evaluated by flow cytometry and the percentage of fluorescent (GFP-positive) cell is shown in FIG. 13A, and corresponding cell toxicity data is shown in FIG. 13B.
Figure 13B:
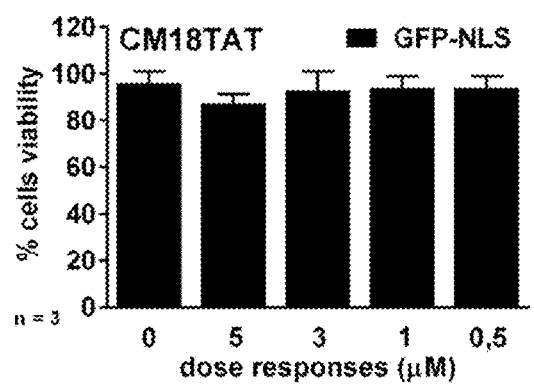

Data from FIG. 13A and 13B

| Shuttle agent | Cells | Concentration (µM) | FIG. 13A Mean (%) (n = 3) | Standard deviation | FIG. 13B Cell viability (%) (±St. Dev.; n = 3) |
|---|---|---|---|---|---|
| CM18-TAT-Cys | HeLa | 0 | 0.90 | 0.12 | 100 |
| | HeLa | 0.5 | 9.81 | 1.63 | 87.6 ± 4 |
| | HeLa | 1 | 18.42 | 2.47 | 93 ± 8 |
| | HeLa | 3 | 28.09 | 3.24 | 94 ± 5 |
| | HeLa | 5 | 32.26 | 4.79 | 93 ± 4 |

These results show that CM18-TAT-Cys is able to increase GFP-NLS transduction efficiency in HeLa cells in a dose-dependent manner.

5.4 GFP-NLS Transduction by CM18-TAT-Cys, CM18-Penetratin-Cys, and Dimers Thereof in HeLa Cells HeLa cells were cultured and tested in the protein transduction assay described in Example 3.1. GFP-NLS recombinant protein (5 µM) was co-incubated with different concentrations and combinations of CM18-TAT-Cys, CM18-Penetratin-Cys, and dimers of each (dCM18-TAT-Cys, dCM18-Penetratin-Cys), and then exposed to HeLa cells for 1 hour. The cells were subjected to flow cytometry analysis as described in Example 3.3. The results are shown in Tables 5.2 and 5.3, and in FIGS. 14 and 15.

TABLE 5.2

Figure 14:
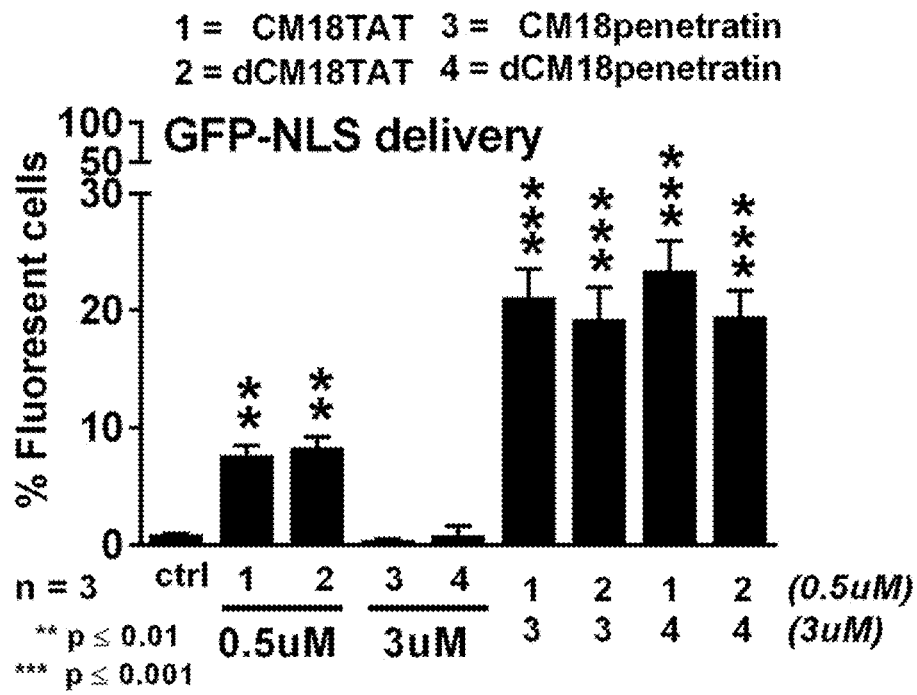
FIGS. 14 and 15 show the results of GFP-NLS transduction efficiency experiments in which GFP-NLS cargo protein (5 μM) was co-incubated with different concentrations and combinations of CM18-TAT (labeled "CM18TAT"), CM18-Penetratin (labeled "CM18penetratin"), and dimers of each (dCM18-TAT-Cys, dCM18-Penetratin-Cys; labeled "dCM18TAT" and "dCM18penetratin", respectively), prior to being exposed to HeLa cells. Cells were evaluated by flow cytometry and the percentages of fluorescent (GFP-positive) cells are shown.

Data in FIG. 14

| No. in FIG. 14 | Shuttle agent | Cells | Concentration (µM) | Mean (%) (n = 3) | Standard deviation |
|---|---|---|---|---|---|
| ctrl | No shuttle | HeLa | 0 | 0.41 | 0.10 |
| 1 | CM18-TAT-Cys | HeLa | 0.5 | 7.64 | 0.85 |
| 2 | dCM18-TAT-Cys | HeLa | 0.5 | 8.29 | 0.91 |
| 3 | CM18-Penetratin-Cys | HeLa | 3 | 0.43 | 0.08 |
| 4 | dCM18-Penetratin-Cys | HeLa | 3 | 0.85 | 0.07 |
| 1 + 3 | CM18-TAT-Cys + CM18-Penetratin-Cys | HeLa | 0.5 3 | 21.1 | 2.47 |
| 2 + 3 | dCM18-TAT-Cys + CM18-Penetratin-Cys | HeLa | 0.5 3 | 19.22 | 2.73 |
| 1 + 4 | CM18-TAT-Cys + dCM18-Penetratin-Cys | HeLa | 0.5 3 | 23.44 | 2.51 |
| 2 + 4 | dCM18-TAT-Cys + dCM18-Penetratin-Cys | HeLa | 0.5 3 | 19.47 | 2.16 |

TABLE 5.3

Figure 15:
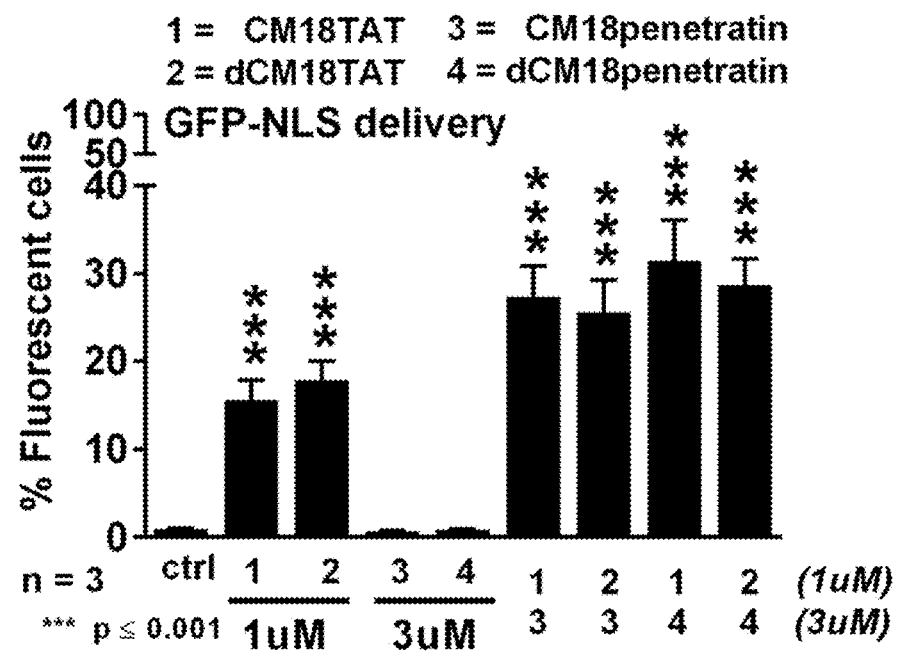

Data in FIG. 15

| No. in FIG. 15 | Shuttle agent | Cells | Concentration (µM) | Mean (%) (n = 3) | Standard deviation |
|---|---|---|---|---|---|
| ctrl | No shuttle | HeLa | 0 | 0.44 | 0.12 |
| 1 | CM18-TAT-Cys | HeLa | 1 | 15.56 | 2.24 |
| 2 | dCM18-TAT-Cys | HeLa | 1 | 17.83 | 2.13 |
| 3 | CM18-Penetratin-Cys | HeLa | 3 | 0.68 | 0.05 |
| 4 | dCM18-Penetratin-Cys | HeLa | 3 | 0.84 | 0.07 |
| 1 + 3 | CM18-TAT-Cys + CM18-Penetratin-Cys | HeLa | 1 3 | 27.26 | 3.61 |
| 2 + 3 | dCM18-TAT-Cys + CM18-Penetratin-Cys | HeLa | 1 3 | 25.47 | 3.77 |
| 1 + 4 | CM18-TAT-Cys + dCM18-Penetratin-Cys | HeLa | 1 3 | 31.47 | 4.59 |
| 2 + 4 | dCM18-TAT-Cys + dCM18-Penetratin-Cys | HeLa | 1 3 | 28.74 | 2.93 |

The results in Tables 5.2 and 5.3 and FIGS. 14 and 15 show that the transduction efficiency of GFP-NLS is increased in HeLa cells using the shuttle agents CM18-TAT-Cys and dCM18-TAT-Cys (see bars "1" and "2" in FIGS. 14 and 15). Although no GFP-NLS intracellular delivery was observed using CM18-Penetratin-Cys or dCM18-Penetratin-Cys alone (see bars "3" and "4" in FIGS. 14 and 15), combination of CM18-TAT-Cys with CM18-Penetratin-Cys (monomer or dimer) improved GFP-NLS intracellular delivery (see four right-most bars in FIGS. 14 and 15).

5.5 GFP-NLS Transduction by Shuttle Agents in HeLa Cells: 5 Min v. 1 h Incubation; with or without FBS HeLa cells were cultured and tested in the protein transduction assay described in Example 3.1. GFP-NLS recombinant protein (5 µM) was co-incubated with either CM18-TAT-Cys (3.5 µM) alone or with dCM18-Penetratin-Cys (1 µM). Cells were incubated for 5 minutes or 1 hour in plain DMEM media ("DMEM") or DMEM media containing 10% FBS ("FBS"), before being subjected to flow cytometry analysis as described in Example 3.3. The results are shown in Table 5.4, and in FIG. 16. Cells that were not treated with shuttle agent or GFP-NLS ("ctrl"), and cells that were treated with GFP-NLS without shuttle agent ("GFP-NLS 5 µM") were used as controls.

TABLE 5.4

Figure 16:
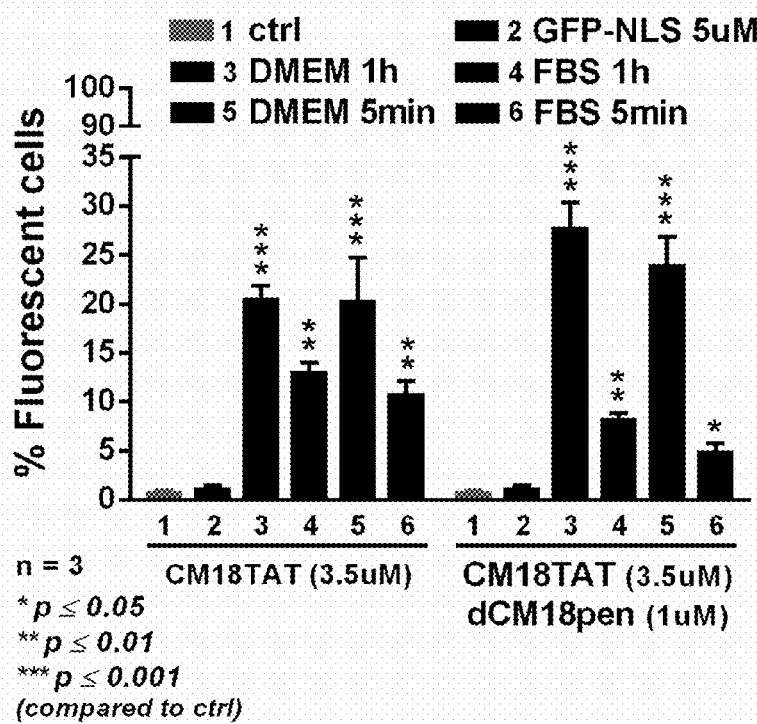
FIG. 16 shows the results of a GFP-NLS transduction efficiency experiment in which GFP-NLS cargo protein (5 μM) was co-incubated with either CM18-TAT-Cys (3.5 μM, labeled "CM18TAT") alone or with dCM18-Penetratin-Cys (1 μM, labeled "dCM18pen") for 5 minutes or 1 hour in plain DMEM media ("DMEM") or DMEM media containing 10% FBS ("FBS"), before being subjected to flow cytometry analysis. The percentages of fluorescent (GFP-positive) cells are shown. Cells that were not treated with shuttle agent or GFP-NLS ("ctrl"), and cells that were treated with GFP-NLS without shuttle agent ("GFP-NLS 5 μM") were used as controls.

Data in FIG. 16

| Shuttle | No. in FIG. 16 | Cells | Medium | Incubation time | Shuttle Conc. (µM) | Mean (%) (n = 3) | Standard deviation |
|---|---|---|---|---|---|---|---|
| No shuttle (Ctrl) | 1 | HeLa | DMEM | 1 h | 0 | 0.59 | 0.09 |
| GFP-NLS alone | 2 | HeLa | DMEM | 1 h | 0 | 1.19 | 0.31 |
| CM18-TAT-Cys | 3 | HeLa | DMEM | 1 h | 3.5 | 20.69 | 1.19 |
| CM18-TAT-Cys | 4 | HeLa | FBS | 1 h | 3.5 | 13.20 | 0.82 |
| CM18-TAT-Cys | 5 | HeLa | DMEM | 5 min | 3.5 | 20.45 | 4.26 |
| CM18-TAT-Cys | 6 | HeLa | FBS | 5 min | 3.5 | 10.83 | 1.25 |
| No shuttle (Ctrl) | 1 | HeLa | DMEM | 1 h | 0 | 0.53 | 0.11 |
| GFP-NLS alone | 2 | HeLa | DMEM | 1 h | 0 | 1.25 | 0.40 |
| CM18-TAT-Cys + dCM18-Penetratin-Cys | 3 | HeLa | DMEM | 1 h | 3.51 | 27.90 | 2.42 |
| CM18-TAT-Cys + dCM18-Penetratin-Cys | 4 | HeLa | FBS | 1 h | 3.51 | 8.35 | 0.46 |

TABLE 5.4-continued

Data in FIG. 16

| Shuttle | No. in FIG. 16 | Cells | Medium | Incubation time | Shuttle Conc. (μM) | Mean (%) (n = 3) | Standard deviation |
|---|---|---|---|---|---|---|---|
| CM18-TAT-Cys + dCM18-Penetratin-Cys | 5 | HeLa | DMEM | 5 min | 3.51 | 24.10 | 2.76 |
|  | 6 | HeLa | FBS | 5 min | 3.51 | 5.02 | 0.72 |

The results in Table 5.4 and FIG. 16 show that the addition of even a relatively low amount of the dimer dCM18-Penetratin-Cys (1 μM; "dCM18pen") to the CM18-TAT-Cys monomer improved GFP-NLS transduction efficiency. Interestingly, intracellular GFP-NLS delivery was achieved in as little as 5 minutes of incubation, and delivery was still achievable (although reduced) in the presence of FBS.

5.6 GFP-NLS Transduction by Shuttle Agents in THP-1 Suspension Cells

The ability of the shuttle agents to deliver GFP-NLS intracellularly was tested in THP-1 cells, which is an acute monocytic leukemia cell line that grows in suspension. THP-1 cells were cultured (see Example 1) and tested in the protein transduction assay described in Example 3.1. GFP-NLS recombinant protein (5 μM) was co-incubated with or without 1 μM CM18-TAT-Cys, and exposed to the THP-1 cells for 5 minutes, before being subjected to flow cytometry analysis as described in Example 3.3. The results are shown in Table 5.5 and in FIG. 17A. Corresponding cellular toxicity data are presented in FIG. 17B.

TABLE 5.5

Figure 17A:
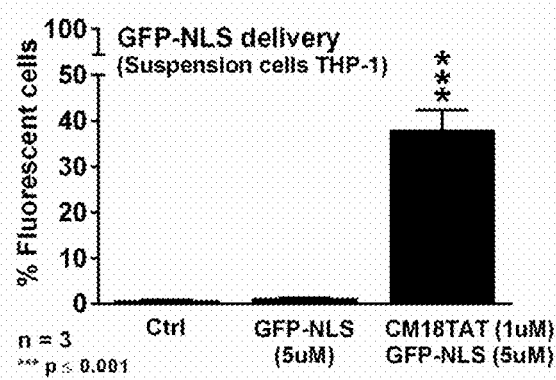
FIGS. 17A and 17B show the results of a GFP-NLS transduction efficiency experiment in which GFP-NLS cargo protein (5 μM) was co-incubated with or without 1 μM CM18-TAT-Cys (labeled "CM18TAT"), prior to being exposed to THP-1 cells. Cells were evaluated by flow cytometry and the percentage of fluorescent (GFP-positive) cells is shown in FIG. 17A, and corresponding cell toxicity data is shown in FIG. 17B.
Figure 17B:
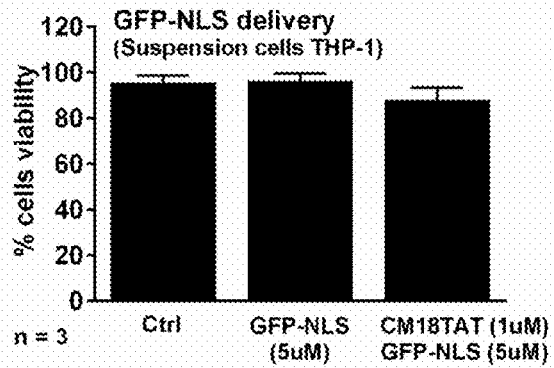

Data in FIG. 17A and 17B

|  |  |  | FIG. 17A |  | FIG. 17B Cell viability (%) |
|---|---|---|---|---|---|
| Shuttle | Cells | Conc. (μM) | Mean (%) (n = 3) | Standard deviation | (±St. Dev.; n = 3) |
| No shuttle (Ctrl) | THP-1 | 0 | 1.23 | 0.16 | 95 ± 4 |
| GFP-NLS alone |  | 0 | 2.49 | 0.37 | 96 ± 3 |
| CM18-TAT-Cys |  | 1 | 38.1 | 4.16 | 85 ± 6 |

The results in Table 5.5 and FIG. 17 demonstrate the ability of the shuttle agents to deliver protein cargo intracellularly to a human monocytic cell line grown in suspension.

Example 6

Peptide Shuttle Agents Increase Transduction Efficiency of an FITC-Labeled Anti-Tubulin Antibody The experiments in Examples 3-5 showed the ability of shuttle agents to increase the transduction efficiency of GFP, TAT-GFP, and GFP-NLS. The experiments presented in this example show that the shuttle agents can also deliver a larger protein cargo: an FITC-labeled anti-tubulin antibody. The FITC-labeled anti-tubulin antibody was purchased from (Abcam, ab64503) and has an estimated molecular weight of 150 KDa. The delivery and microscopy protocols are described in Example 3.

Figure 18:
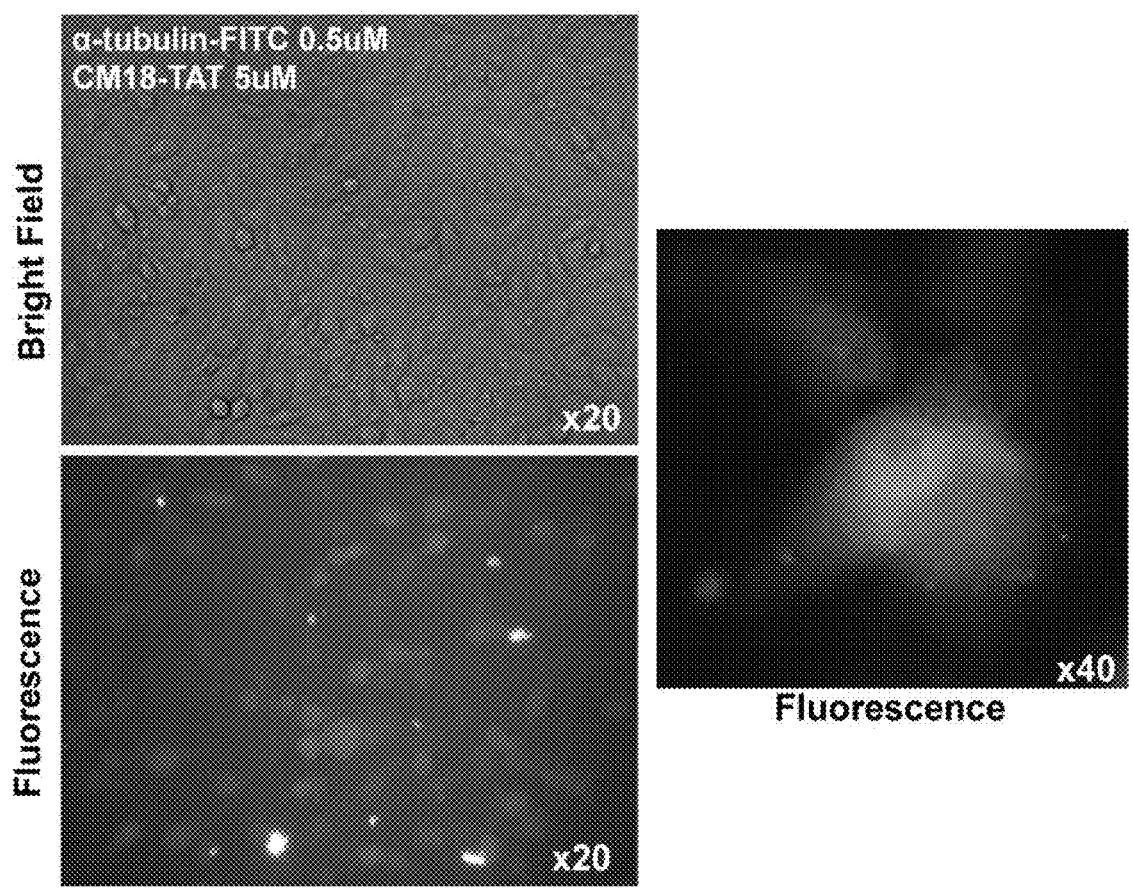
FIG. 18 shows the results of a transduction efficiency experiment in which the cargo protein, FITC-labeled anti-tubulin antibody (0.5 μM), was co-incubated with 5 μM of CM18-TAT-Cys (labeled "CM18-TAT"), prior to being exposed to HeLa cells. Functional antibody delivery was visualized by bright field (20×) and fluorescence microscopy (20× and 40×), in which fluorescent tubulin fibers in the cytoplasm were visualized.

6.1 Transduction of a Functional Antibody by CM18-TAT-Cys in HeLa Cells: Visualization by Microscopy FITC-labeled anti-tubulin antibody (0.5 μM) was co-incubated with 5 μM of CM18-TAT-Cys and exposed to HeLa cells for 1 hour. Antibody delivery was visualized by bright field (20×) and fluorescence microscopy (20× and 40×). As shown in FIG. 18, fluorescent tubulin fibers in the cytoplasm were visualized, demonstrating the functionality of the antibody inside the cell.

6.2 Transduction of a Functional Antibody by CM18-TAT-Cys, CM18-Penetratin-Cys, and Dimers in HeLa Cells: Flow Cytometry HeLa cells were cultured and tested in the protein transduction assay described in Example 3.1. FITC-labeled anti-tubulin antibody (0.5 μM) was co-incubated with 3.5 μM of CM18-TAT-Cys, CM18-Penetratin-Cys or dCM18-Penetratin-Cys, or a combination of 3.5 μM of CM18-TAT-Cys and 0.5 μM of dCM18-Penetratin-Cys, and exposed to HeLa cells for 1 hour. The cells were subjected to flow cytometry analysis as described in Example 33. Results are shown in Table 6.1 and FIG. 19A. Corresponding cellular toxicity data are presented in FIG. 19B.

TABLE 6.1

Figure 19A:
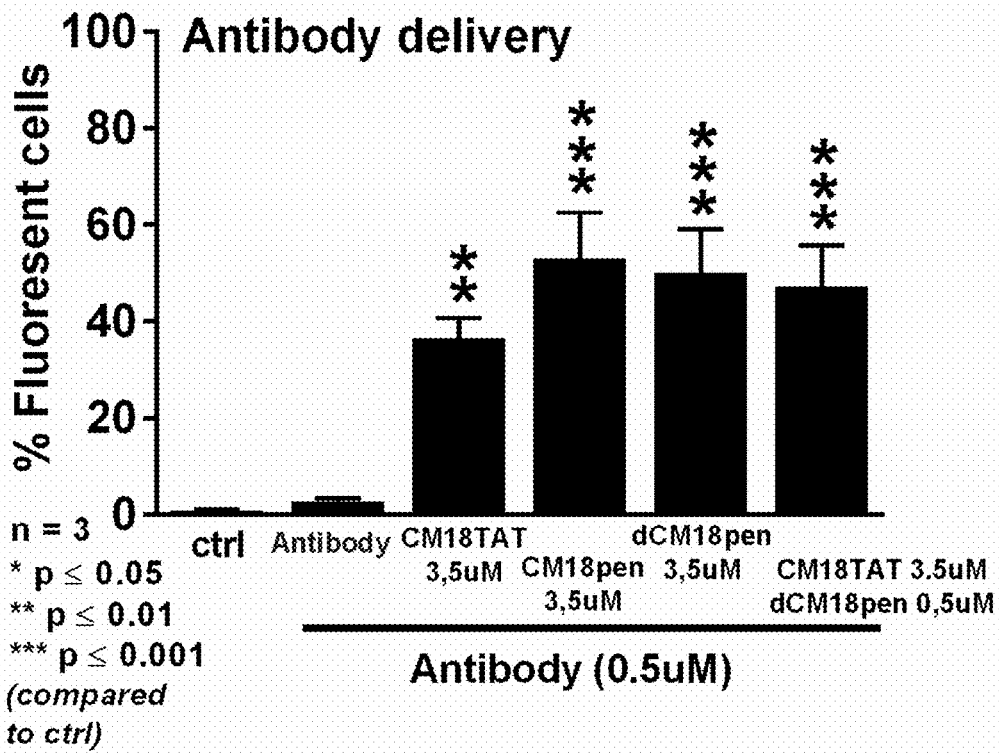
FIGS. 19A and 19B shows the results of an FITC-labeled anti-tubulin antibody transduction efficiency experiment in which the antibody cargo protein (0.5 μM) was co-incubated with 3.5 μM of CM18-TAT-Cys (labeled "CM18TAT"), CM18-Penetratin-Cys (labeled "CM18pen") or dCM18-Penetratin-Cys (labeled "dCM18pen"), or a combination of 3.5 μM of CM18-TAT-Cys and 0.5 μM of dCM18-Penetratin-Cys, prior to being exposed to HeLa cells. Cells were evaluated by flow cytometry and the percentage of fluorescent (FITC-positive) cell is shown in FIG. 19A, and corresponding cell toxicity data is shown in FIG. 19B.
Figure 19B:
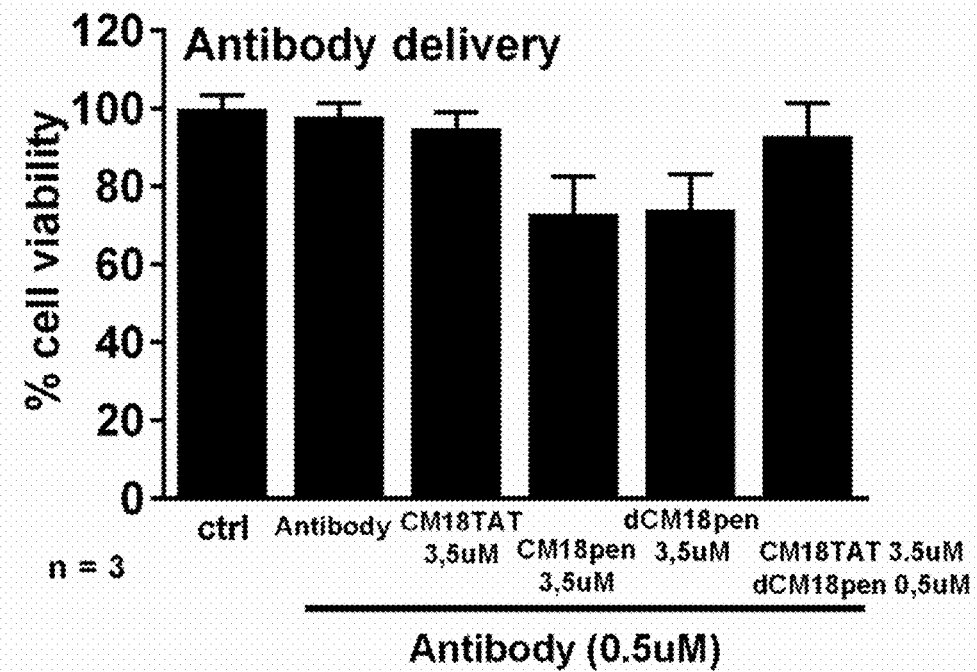

Data from FIG. 19A and 19B

|  |  |  |  | FIG. 19A |  | FIG. 19B |
|---|---|---|---|---|---|---|
| Domains | Shuttle agent | Cells | Shuttle Conc. (μM) | Mean (%) (n = 3) | Standard deviation | Cell viability (%) (±St. Dev.; n = 3) |
| — | No shuttle ("Ctrl") | HeLa | 0 | 0.9 | 0.06 | 98 ± 1.0 |
| — | Antibody alone ("antibody") | HeLa | 0 | 2.66 | 0.61 | 96 ± 3.4 |
| ELD-CPD | CM18-TAT-Cys | HeLa | 3.5 | 36.56 | 4.06 | 95 ± 4.06 |
|  | CM18-Penetratin-Cys | HeLa | 3.5 | 53.05 | 9.5 | 73 ± 9.5 |

TABLE 6.1-continued

Data from FIG. 19A and 19B

| | | | | FIG. 19A | | FIG. 19B |
|---|---|---|---|---|---|---|
| Domains | Shuttle agent | Cells | Shuttle Conc. (µM) | Mean (%) (n = 3) | Standard deviation | Cell viability (%) (±St. Dev.; n = 3) |
| ELD-CPD dimer | dCM18-Penetratin-Cys | HeLa | 3.5 | 50.23 | 9.12 | 74 ± 9.0 |
| ELD-CPD + ELD-CPD dimer | CM18-TAT-Cys + dCM18-Penetratin-Cys | HeLa | 3.5 0.5 | 47.19 | 8.5 | 93 ± 8.5 |

The results in Table 6.1 and FIGS. 18 and 19 show that both CM18-TAT-Cys and CM18-Penetratin-Cys facilitate intracellular delivery of an FITC-labeled anti-tubulin antibody. In contrast to the results with GFP, TAT-GFP, and GFP-NLS in Examples 3-5, CM18-Penetratin-Cys was able to deliver the antibody cargo intracellularly when used alone (without CM18-TAT-Cys). However, combination of CM18-TAT-Cys and dCM18-Penetratin-Cys allowed for higher intracellular delivery as compared with CM18-TAT-Cys alone, and with less cell toxicity as compared to CM18-Penetratin-Cys and dCM18-Penetratin-Cys (see FIGS. 19A and 19B).

Example 7

CM18-TAT-Cys Enables Intracellular Plasmid DNA Delivery but Poor Plasmid Expression The ability of the CM18-TAT-Cys shuttle agent to deliver plasmid DNA intracellularly was tested in this example on HEK293A cells using a plasmid encoding GFP.

7.1 Transfection Assay in HEK293A Cells

One day before the transfection assay was performed, mammalian cells (HEK293A) in exponential growth phase were harvested and plated in a 24-well plate (50,000 cells per well). The cells were incubated overnight in appropriate growth media containing FBS. The next day, in separate sterile 1.5 mL tubes, pEGFP labeled with a Cy5™ fluorochrome was mixed for 10 min at 37° C. with CM18-TAT-Cys (0.05, 0.5, or 5 µM) in fresh PBS at a final 100 µL volume. The media in wells was removed and the cells were quickly washed three times with PBS and 500 µL of warm media without FBS was added. The pEGFP and CM18-TAT-Cys solution was added to the cells and incubated at 37° C. for 4 hours. After the incubation, cells were washed with PBS and fresh media containing FBS was added. Cells were incubated at 37° C. before being subjected to flow cytometry analysis as described in Example 3.

7.2 Plasmid DNA Delivery with CM18-TAT-Cys

Plasmid DNA (pEGFP) was labeled with a Cy5™ dye following the manufacturer's instructions (Mirus Bio LLC). Cy5™ Moiety did not influence transfection efficiency when compared to unlabelled plasmid using standard transfection protocol (data not shown). Flow cytometry analysis allowed quantification of Cy5™ emission, corresponding to DNA intracellular delivery, and GFP emission, corresponding to successful nuclear delivery, DNA transcription and protein expression. The results are shown in Table 7.1 and in FIG. 20.

TABLE 7.1

Figure 20:
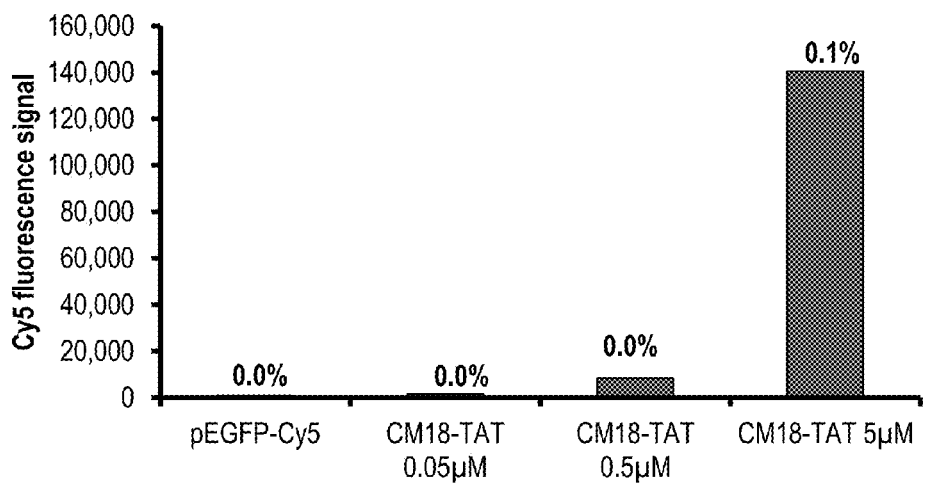
FIG. 20 shows the results of DNA transfection efficiency experiment in which plasmid DNA (pEGFP) was labeled with a Cy5™ dye was co-incubated with 0, 0.05, 0.5, or 5 μM of CM18-TAT-Cys (labeled "CM18-TAT"), prior to being exposed to HEK293A cells. Flow cytometry analysis allowed quantification of Cy5™ emission (corresponding to DNA intracellular delivery; y-axis) and GFP emission (corresponding to successful nuclear delivery of DNA; percentage indicated above each bar).

Data from FIG. 20

| | | Cy5 ™ fluorescence | | GFP expression | |
|---|---|---|---|---|---|
| Sample | DNA (ng) | Mean Cy5 ™ signal (n = 3) | Standard deviation | Mean (% of cells with GFP signal; n = 3) | Standard deviation |
| pEGFP-Cy5 alone | 500 | 914 | 0 | 0.0% | n/a |
| CM18-TAT-Cys, 0.05 µM | 500 | 1450 | 120 | 0.0% | n/a |
| CM18-TAT-Cys, 0.5 µM | 500 | 8362 | 294 | 0.0% | n/a |
| CM18-TAT-Cys, 5 µM | 500 | 140 497 | 3977 | 0.1% | n/a |

The results shown in Table 7.1 and in FIG. 20 show that CM18-TAT-Cys was able to increase the intracellular delivery the plasmid DNA when used at 0.05, 0.5 and 5 µM concentrations, as compared to cell incubated with DNA alone ("pEGFP-Cy5"). However, no expression of GFP was detected in the cells, which suggests that very little of the plasmid DNA gained access to the cytoplasmic compartment, allowing nuclear localization. Without being bound by theory, it is possible that the plasmid DNA was massively sequestered in endosomes, preventing escape to the cytoplasmic compartment. Salomone et al., 2013 reported the use of a CM18-TAT11 hybrid peptide to deliver plasmid DNA intracellularly. They used the luciferase enzyme reporter assay to assess transfection efficiency, which may not be ideal for quantifying the efficiency of cytoplasmic/nuclear delivery, as the proportion of plasmid DNA that is successfully released from endosomes and delivered to the nucleus may be overestimated due to the potent activity of the luciferase enzyme. In this regard, the authors of Salomone et al., 2013 even noted that the expression of luciferase occurs together with a massive entrapment of (naked) DNA molecules into vesicles, which is consistent with the results shown in Table 7.1 and in FIG. 20.

7.3 Plasmid DNA Delivery by Peptides in HeLa Cells

Following the poor transfection efficiency of the peptide CM18-TAT-Cys (0.1%, see Table 7.1) observed in HEK293A cells, the experiment was repeated with CM18-TAT-Cys in another cell line (HeLa), along with other peptides listed in Table 1.3, Table B1, and Table C1.

One day before the transfection assay was performed, HeLa cells in exponential growth phase were harvested and plated in a 96-well plate (10,000 cells per well). The cells were incubated overnight in appropriate growth media containing FBS. The next day, in separate sterile 1.5 mL tubes, the peptide to be tested and the polynucleotide cargo (pEGFP-C1) were mixed for 10 min at 37° C. in serum-free medium at a final volume of 50 μL. The media in wells was removed and the cells were quickly washed one time with PBS at 37° C. The mix containing the peptide to be tested and the polynucleotide cargo was added to the cells and incubated at 37° C. for the indicated period of time (e.g., 1 min, 1 h or 4 h). After the incubation, cells were washed one time with PBS at 37° C. and fresh media containing FBS was added. Cells were incubated at 37° C. before being subjected to flow cytometry analysis as described in Example 3.2, to qualify transfection efficiency (i.e., cells expression EGFP) and viability. Results are shown in Table 7.2.

TABLE 7.2

DNA transfection in HeLa cells using peptides

| Peptide | Mean % cells with GFP signal (±St. Dev.; n = 3) | Cell viability (%) (±St. Dev.; n = 3) |
|---|---|---|
| No peptide (neg. control) | 0.0 ± 0.0 | 100 |
| PTD4-KALA | 0.85 ± 0.04 | 53.64 ± 3.91 |
| FSD9 | 0.81 ± 0.09 | 36.1 ± 3.41 |
| KALA | 0.79 ± 0.06 | 90.62 ± 4.16 |
| His-CM18-Transportan | 0.55 ± 0.01 | 11.89 ± 1.07 |
| FSD12 | 0.37 ± 0.14 | 58.6 ± 2.07 |
| dCM18-Pen-Cys | 0.35 ± 0.02 | 3.36 ± 0.26 |
| His-CM18-PTD4-His | 0.34 ± 0.03 | 29.4 ± 2.38 |
| FSD2 | 0.34 ± 0.00 | 55.77 ± 4.19 |
| Pep1-KALA | 0.31 ± 0.03 | 92.47 ± 3.42 |
| FSD25 | 0.31 ± 0.02 | 98.19 ± 1.19 |
| FSD7 | 0.29 ± 0.07 | 60.9 ± 7.59 |
| CM18-PTD4-His | 0.26 ± 0.01 | 29.5 ± 0.21 |
| FSD19 | 0.24 ± 0.00 | 97.41 ± 2.07 |
| FSD10 | 0.21 ± 0.01 | 72.36 ± 8.61 |
| FSD24 | 0.20 ± 0.00 | 96.45 ± 3.02 |
| FSD15 | 0.18 ± 0.02 | 98.3 ± 1.07 |
| 12His-CM18-PTD4 | 0.18 ± 0.01 | 97.55 ± 1.57 |
| CM18-L1-PTD4 | 0.16 ± 0.01 | 84.3 ± 5.64 |
| FSD33 | 0.15 ± 0.01 | 75.3 ± 4.19 |
| TAT-LAH4 | 0.15 ± 0.00 | 96.17 ± 2.70 |
| CM18-L2-PTD4 | 0.14 ± 0.01 | 93.7 ± 3.07 |
| M-His-CM18-TAT-Cys | 0.13 ± 0.01 | 33.1 ± 0.4 |
| FSD42 | 0.12 ± 0.02 | 96.67 ± 1.96 |
| FSD11 | 0.11 ± 0.01 | 46.2 ± 1.35 |
| Xentry-KALA | 0.1 ± 0.02 | 75.3 ± 4.29 |
| FSD5 | 0.1 ± 0.01 | 93.24 ± 8.63 |
| 3HA-CM18-PTD4 | 0.09 ± 0.01 | 51.48 ± 4.83 |
| FSD32 | 0.08 ± 0.02 | 98.36 ± 0.15 |
| CM18-TAT-Cys | 0.08 ± 0.01 | 96.28 ± 1.86 |
| FSD8 | 0.06 ± 0.84 | 42.3 ± 6.42 |
| CM18-L3-PTD4 | 0.06 ± 0.01 | 98.4 ± 0.83 |
| 3His-CM18-PTD4 | 0.06 ± 0.01 | 82.05 ± 6.81 |
| CM18-PTD4 | 0.06 ± 0.01 | 49.64 ± 5.06 |
| TAT-CM18 | 0.06 ± 0.01 | 44.79 ± 4.17 |
| HA-CM18-PTD4 | 0.06 ± 0.0 | 53.21 ± 4.62 |
| His-CM18-TAT | 0.05 ± 0.01 | 13.6 ± 0.18 |
| VSVG-PTD4 | 0.05 ± 0.01 | 96.21 ± 2.57 |
| 9His-CM18-PTD4 | 0.04 ± 0.01 | 98.72 ± 0.93 |
| JST-PTD4 | 0.04 ± 0.01 | 70.2 ± 5.39 |
| His-CM18-PTD4 | 0.04 ± 0.01 | 63.2 ± 4.07 |
| FSD23 | 0.04 ± 0.00 | 98.18 ± 1.03 |
| FSD20 | 0.04 ± 0.00 | 20.49 ± 3.53 |
| FSD38 | 0.02 ± 0.00 | 95 ± 2.78 |
| FSD16 | 0.02 ± 0.00 | 99.07 ± 0.73 |
| FSD26 | 0.02 ± 0.00 | 97.2 ± 1.53 |
| FSD27 | 0.02 ± 0.00 | 98 ± 0.63 |
| FSD35 | 0.02 ± 0.00 | 96.14 ± 1.67 |
| CM18 | 0.02 ± 0.00 | 99.4 ± 0.14 |
| FSD30 | 0.02 ± 0.00 | 97.41 ± 2.06 |
| His-CM18-9Arg | 0.02 ± 0.0 | 31.63 ± 0.11 |
| FSD21 | 0.01 ± 0.00 | 96.17 ± 1.69 |
| 6His-PTD4 | 0.01 ± 0.00 | 97.25 ± 1.34 |
| FSD31 | 0.01 ± 0.00 | 98.43 ± 0.43 |
| FSD34 | 0.01 ± 0.00 | 96.43 ± 2.41 |
| FSD36 | 0.01 ± 0.00 | 97.05 ± 1.99 |
| FSD40 | 0.01 ± 0.00 | 98.63 ± 1.08 |
| FSD41 | 0.01 ± 0.00 | 94.38 ± 2.81 |
| FSD28 | 0.01 ± 0.00 | 97 ± 1.11 |
| CM18-Pen-Cys | 0.01 ± 0.0 | 16.1 ± 0.12 |
| PTD4 | 0.00 ± 0.01 | 98.2 ± 0.69 |
| FSD39 | 0.00 ± 0.00 | 99.2 ± 0.61 |
| His-CMH18-PTD4 | 0.00 ± 0.00 | 95.15 ± 2.33 |
| Penetratin | 0.00 ± 0.00 | 97.42 ± 1.03 |
| C(LLKK)3 | 0.00 ± 0.00 | 81.74 ± 2.34 |

All the peptides tested in Table 7.2 showed transfection efficiencies lower than 1%. Furthermore, the low transfection efficiency of CM18-TAT-Cys was confirmed in HeLa cells (0.08%). These results show that peptides which are suitable for delivering polypeptide cargos may not necessarily be suitable for delivering plasmid DNA. For example, the shuttle agent His-CM18-PTD4-His is shown herein to effectively transduce polypeptide cargos (e.g., see Example 10), yet this peptide displayed only a DNA plasmid transfection efficiency of 0.34% (Table 7.2).

Example 8

Addition of a Histidine-Rich Domain to Shuttle Agents Further Improves GFP-NLS Transduction Efficiency 8.1 GFP-NLS Transduction by His-CM18-TAT-Cys in HeLa Cells: Visualization by Microscopy GFP-NLS (5 μM; see Example 5) was co-incubated with 5 μM of CM18-TAT-Cys or His-CM18-TAT and exposed to HeLa cells for 1 hour. Nuclear fluorescence of intracellularly delivered GFP-NLS was confirmed by fluorescence microscopy (data not shown), indicating successful delivery of GFP-NLS to the nucleus.

8.2 GFP-NLS Transduction by His-CM18-TAT in HeLa Cells: Flow Cytometry

HeLa cells were cultured and tested in the protein transduction assay described in Example 3.1. GFP-NLS (5 μM) was co-incubated with 0, 1, 3, or 5 μM of CM18-TAT-Cys or His-CM18-TAT, and exposed to HeLa cells for 1 hour. The cells were subjected to flow cytometry analysis as described in Example 3.3. Results are shown in Table 8.1 and FIG. 21A. Corresponding cellular toxicity data are presented in FIG. 21B.

TABLE 8.1

Figure 21A:
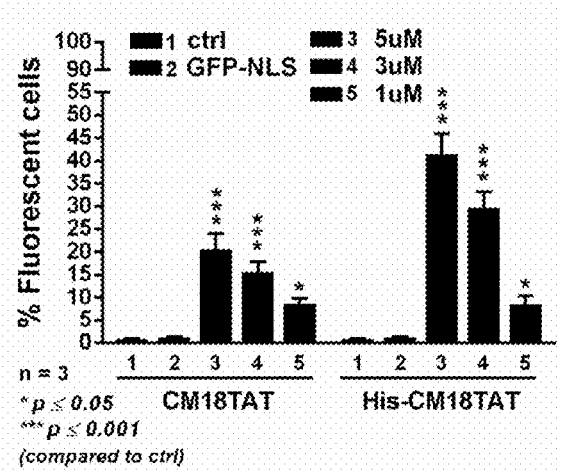
FIGS. 21A and 21B show the results of a GFP-NLS transduction efficiency experiment in which the GFP-NLS cargo protein (5 μM) was co-incubated with 1, 3, or 5 μM of CM18-TAT-Cys (labeled "CM18TAT"), of His-CM18-TAT (labeled "His-CM18TAT"), prior to being exposed to HeLa cells. Cells were evaluated by flow cytometry and the percentage of fluorescent (GFP-positive) cell is shown in FIG. 21A, and corresponding cell toxicity data is shown in FIG. 21B.
Figure 21B:
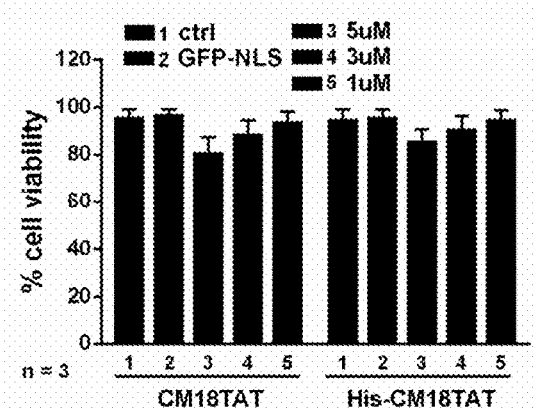

Data from FIG. 21A and 21B

| | | | FIG. 21A | | FIG. 21B |
|---|---|---|---|---|---|
| Shuttle agent | Cells | Shuttle Conc. (µM) | Mean (%) cell with GFP signal (n = 3) | Standard deviation | Cell viability (%) (±St. Dev.; n = 3) |
| Ctrl (no shuttle, no GFP-NLS) | HeLa | 0 | 0.63 | 0.10 | 96 ± 3.17 |
| GFP-NLS alone | | 0 | 0.93 | 0.26 | 97 ± 2.05 |
| CM18-TAT-Cys | | 5 | 20.54 | 3.51 | 81 ± 6.34 |
| | | 3 | 15.66 | 2.18 | 89 ± 5.37 |
| | | 1 | 8.64 | 1.11 | 94 ± 4.28 |
| Ctrl (no shuttle, no GFP-NLS) | HeLa | 0 | 0.51 | 0.28 | 95 ± 4.19 |
| GFP-NLS alone | | 0 | 1.07 | 0.42 | 96 ± 3.16 |
| His-CM18-TAT | | 5 | 41.38 | 4.59 | 86 ± 4.59 |
| | | 3 | 29.58 | 3.61 | 91 ± 5.18 |
| | | 1 | 8.45 | 1.83 | 95 ± 3.55 |

Strikingly, the results in Table 8.1 and in FIG. 21 show that His-CM18-TAT was able to increase GFP-NLS protein transduction efficiency by about 2-fold at 3 µM and 5 µM concentrations, as compared to CM18-TAT-Cys. These results suggest that adding a histidine-rich domain to a shuttle agent comprising an ELD and CPD, may significantly increase its polypeptide cargo transduction efficiency. Alternatively or in parallel, combining the shuttle agents with a further independent synthetic peptide containing a histidine-rich domain fused to a CPD (but lacking an ELD) may provide a similar advantage for protein transduction, with the added advantage of allowing the concentration of the histidine-rich domain to be varied or controlled independently from the concentration of the shuttle agent. Without being bound by theory, the histidine-rich domain may act as a proton sponge in the endosome, providing another mechanism of endosomal membrane destabilization.

Example 9

His-CM18-PTD4 Increases Transduction Efficiency and Nuclear Delivery of GFP-NLS, mCherry™-NLS and FITC-Labeled Anti-Tubulin Antibody 9.1 Protein Transduction Protocols Protocol A: Protein Transduction Assay for Delivery in Cell Culture Medium One day before the transduction assay was performed, cells in exponential growth phase were harvested and plated in a 96-well plate (20,000 cells per well). The cells were incubated overnight in appropriate growth media containing FBS (see Example 1). The next day, in separate sterile 1.5-mL tubes, cargo protein at the desired concentration was pre-mixed (pre-incubated) for 10 min at 37° C. with the desired concentration of shuttle agents in 50 µL of fresh serum-free medium (unless otherwise specified). The media in wells was removed and the cells were washed one to three times (depending on the type of cells used) with PBS previously warmed at 37° C. The cells were incubated with the cargo protein/shuttle agent mixture at 37° C. for the desired length of time. After the incubation, the cells were washed three times with PBS and/or heparin (0.5 mg/mL) previously warmed at 37° C. The washes with heparin were used for human THP-1 blood cells to avoid undesired cell membrane-bound protein background in subsequent analyses (microscopy and flow cytometry). The cells were finally incubated in 50 µL of fresh medium with serum at 37° C. before analysis.

Protocol B: Protein Transduction Assay for Adherent Cells in PBS

One day before the transduction assay was performed, cells in exponential growth phase were harvested and plated in a 96-well plate (20,000 cells per well). The cells were incubated overnight in appropriate growth media containing serum (see Example 1). The next day, in separate sterile 1.5-mL tubes, shuttle agents were diluted in sterile distilled water at room temperature (if the cargo is or comprised a nucleic acid, nuclease-free water was used). Cargo protein(s) were then added to the shuttle agents and, if necessary, sterile PBS was added to obtain the desired concentrations of shuttle agent and cargo in a sufficient final volume to cover the cells (e.g., 10 to 100 µL per well for a 96-well plate). The shuttle agent/cargo mixture was then immediately used for experiments. At least three controls were included for each experiment, including: (1) shuttle agent alone (e.g., at highest concentration tested); (2) cargo alone; and (3) without any cargo or shuttle agent. The media in wells was removed, cells were washed once with PBS previously warmed at 37° C., and the shuttle agent/cargo mixture was then added to cover all cells for the desired length of time. The shuttle agent/cargo mixture in wells was removed, the cells were washed once with PBS, and fresh complete medium was added. Before analysis, the cells were washed once with PBS and fresh complete medium was added.

Protocol C: Protein Transduction Assay for Suspension Cells in PBS

One day before the transduction assay was performed, suspension cells in exponential growth phase were harvested and plated in a 96-well plate (20,000 cells per well). The cells were incubated overnight in appropriate growth media containing serum (see Example 1). The next day, in separate sterile 1.5-mL tubes, shuttle agents were diluted in sterile distilled water at room temperature (if the cargo is or comprised a nucleic acid, nuclease-free water was used). Cargo protein(s) were then added to the shuttle agents and, if necessary, sterile PBS or cell culture medium (serum-free) was added to obtain the desired concentrations of shuttle agent and cargo in a sufficient final volume to resuspend the cells (e.g., 10 to 100 µL per well in a 96-well plate). The shuttle agent/cargo mixture was then immediately used for experiments. At least three controls were included for each experiment, including: (1) shuttle agent alone (e.g., at highest concentration tested); (2) cargo alone; and (3) without any cargo or shuttle agent. The cells were centrifuged for 2 minutes at 400 g, the medium was then removed and the cells were resuspended in PBS previously warmed at 37° C. The cells were centrifuged again 2 minutes at 400 g, the PBS removed, and the cells were resuspended in the shuttle agent/cargo mixture. After the desired incubation time, 100 µL of complete medium was added directly on the cells.

Cells were centrifuged for 2 minutes at 400 g and the medium was removed. The pellet was resuspended and washed in 200 μL of PBS previously warmed at 37° C. After another centrifugation, the PBS was removed and the cells were resuspended in 100 μL of complete medium. The last two steps were repeated one time before analysis.

Figure 22A:
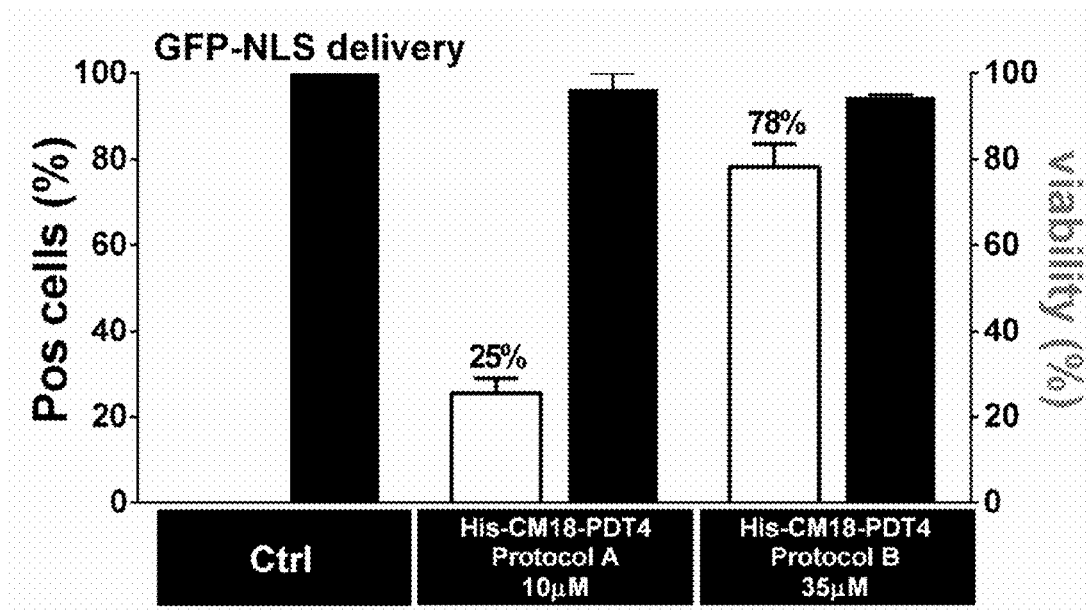
FIGS. 22A and 22B show the results of a transduction efficiency experiment in which GFP-NLS cargo protein was intracellularly delivered using the shuttle His-CM18-PTD4 in HeLa cells. GFP-NLS transduction efficiency was evaluated by flow cytometry and the percentage of GFP fluorescent cells ("Pos cells (%)"), as well as corresponding cell viability data ("viability (%)") are shown.

9.2 GFP-NLS Transduction by His-CM18-PTD4 in HeLa Cells Using Protocol A or B: Flow Cytometry To compare the effects of different protocols on shuttle agent transduction efficiency, HeLa cells were cultured and tested in the protein transduction assays using Protocol A or B as described in Example 9.1. Briefly, GFP-NLS recombinant protein (5 μM; see Example 5.1) was co-incubated with 10 μM of His-CM18-PTD4 and exposed to HeLa cells for 1 hour using Protocol A, or was co-incubated with 35 μM of His-CM18-PTD4 and exposed to HeLa cells for 10 seconds using Protocol B. The cells were subjected to flow cytometry analysis as described in Example 3.3. Results are shown in Table 9.1 and FIG. 22A. ("Pos cells (%)" is the percentage of cells emanating a GFP signal).

TABLE 9.1

Comparison of Protein Transduction Protocols A and B: Data from FIG. 22A

| Protocol | Shuttle | Cells | Conc. of shuttle (μM) | Conc. of GFP-NLS (μM) | Mean % cells with GFP signal (±St. Dev.; n = 3) | Cell viability (%) (±St. Dev.; n = 3) |
|---|---|---|---|---|---|---|
| B | None ("Ctrl") | HeLa | 0 | 5 | 0.53 ± 0.07 | 100 |
| A | His-CM18-PTD4 | HeLa | 10 | 5 | 25.4 ± 3.6 | 96.4 ± 2.7 |
| B | His-CM18-PTD4 | HeLa | 35 | 5 | 78.3 ± 5.3 | 94.6 ± 0.4 |

The above results show that higher protein transduction efficiency for the cargo GFP-NLS using the shuttle agent His-CM18-PTD4 was obtained using Protocol B, as compared to Protocol A.

Figure 22B:
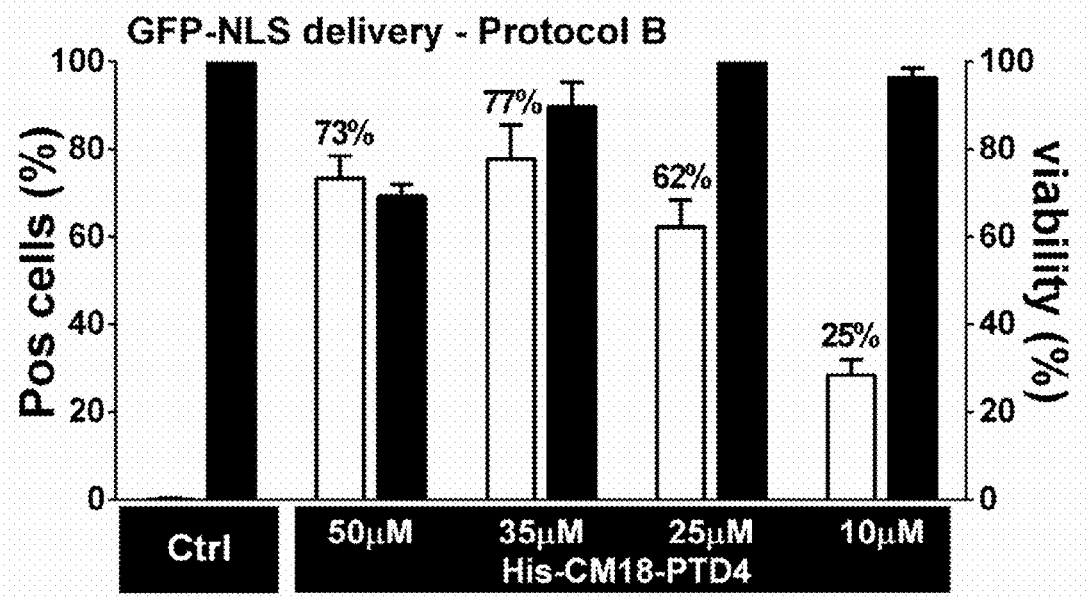

9.3 GFP-NLS Transduction by His-CM18-PTD4 in HeLa Cells Using Protocol B: Flow Cytometry A dose response experiment was performed to evaluate the effect of His-CM18-PTD4 concentration on protein transduction efficiency. HeLa cells were cultured and tested in the protein transduction assay described in Protocol B of Example 9.1. Briefly, GFP-NLS recombinant protein (5 μM; see Example 5.1) was co-incubated with 0, 50, 35, 25, or 10 μM of His-CM18-PTD4, and then exposed to HeLa cells for 10 seconds. The cells were subjected to flow cytometry analysis as described in Example 3.3. Results are shown in Table 9.2 and FIG. 22B.

The above results show that His-CM18-PTD4 is able to increase GFP-NLS transduction efficiency in HeLa cells in a dose-dependent manner.

9.4 GFP-NLS Transduction by His-CM18-PTD4 in HeLa Cells Using Protocol B: Visualization by Microscopy GFP-NLS recombinant protein (5 μM; see Example 5.1) was co-incubated with 35 μM of His-CM18-PTD4, and then exposed to HeLa cells for 10 seconds using Protocol B as described in Example 9.1. The cells were then subjected to fluorescence microscopy analysis as described in Examples 3.2 and 3.2a.

For the sample results shown in FIGS. 23 and 24, GFP fluorescence of the HeLa cells was immediately visualized by bright field and fluorescence microscopy at 4×, 20× and 40× magnifications after the final washing step.

In FIG. 23, the upper panels in FIGS. 23A, 23B and 23C show nuclei labelling (DAPI) at 4×, 20× and 40× magnifications, respectively, while the lower panels show corresponding GFP-NLS fluorescence. In FIG. 23C, white triangle windows indicate examples of areas of co-labelling between nuclei (DAPI) and GFP-NLS signals. In FIG. 23D, the upper and bottom panels show sample bright field images of the HeLa cells, and the middle panel shows the results of a corresponding FACS analysis (performed as described in Example 3.3), which indicates the percentage of cells in a 96-plate with a GFP signal. No significant GFP fluorescence was observed in negative control samples (i.e., cells exposed to GFP-NLS without any shuttle agent; data not shown).

FIG. 24 shows bright field (FIG. 24A) and fluorescent images (FIG. 24B). The inset in FIG. 24B shows the results of a corresponding FACS analysis (performed as described in Example 3.3), which indicates the percentage of cells in a 96-plate well with a GFP signal. No significant GFP

TABLE 9.2

Dose response of shuttle agent using Protocol B: Data from FIG. 22B

| Protocol | Shuttle | Cells | Conc. of shuttle (μM) | Conc. of GFP-NLS (μM) | Mean % cells with GFP signal (±St. Dev.; n = 3) | Cell viability (%) (±St. Dev.; n = 3) |
|---|---|---|---|---|---|---|
| B | None ("Ctrl") | HeLa | 0 | 5 | 0.13 ± 0.1 | 100 ± 0 |
|  | His-CM18-PTD4 |  | 50 | 5 | 73.2 ± 5.2 | 69.2 ± 2.7 |
|  |  |  | 35 | 5 | 77.7 ± 7.8 | 79.6 ± 5.9 |
|  |  |  | 25 | 5 | 62.1 ± 6.1 | 95.3 ± 3.7 |
|  |  |  | 10 | 5 | 25.3 ± 3.6 | 96.3 ± 2.3 | fluorescence was observed in negative control samples (i.e., cells exposed to GFP-NLS without any shuttle agent; data not shown).

For the sample results shown in FIG. 25, the HeLa cells were fixed, permeabilized and subjected to immuno-labelling as described in Example 3.2a before visualization by fluorescence microscopy as described in Example 3.2. GFP-NLS was labelled using a primary mouse monoclonal anti-GFP antibody (Feldan, #A017) and a secondary goat anti-mouse Alexa™-594 antibody (Abcam #150116). The upper panels in FIGS. 25A and 25B show nuclei labelling (DAPI), and the lower panels show corresponding labelling for GFP-NLS. FIGS. 25A and 25B show sample images at 20× and 40× magnifications, respectively. White triangle windows indicate examples of areas of co-labelling between nuclei and GFP-NLS. No significant GFP-NLS labelling was observed in negative control samples (i.e., cells exposed to GFP-NLS without any shuttle agent; data not shown).

FIG. 26 shows sample images captured with confocal microscopy at 63× magnification of living cells. FIG. 26A shows a bright field image, while FIG. 26B shows the corresponding fluorescent GFP-NLS. FIG. 26C is an overlay between the images in FIG. 26A and FIG. 26B. No significant GFP-NLS fluorescence was observed in negative control samples (i.e., cells exposed to GFP-NLS without any shuttle agent; data not shown).

Figure 24C:
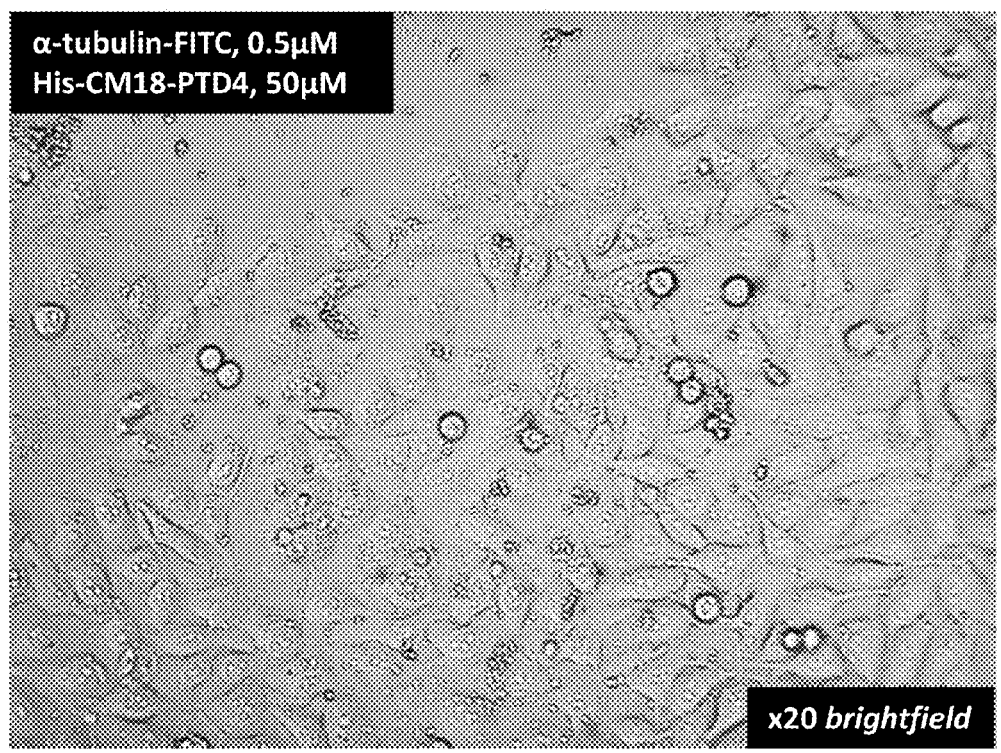
Figure 24D:
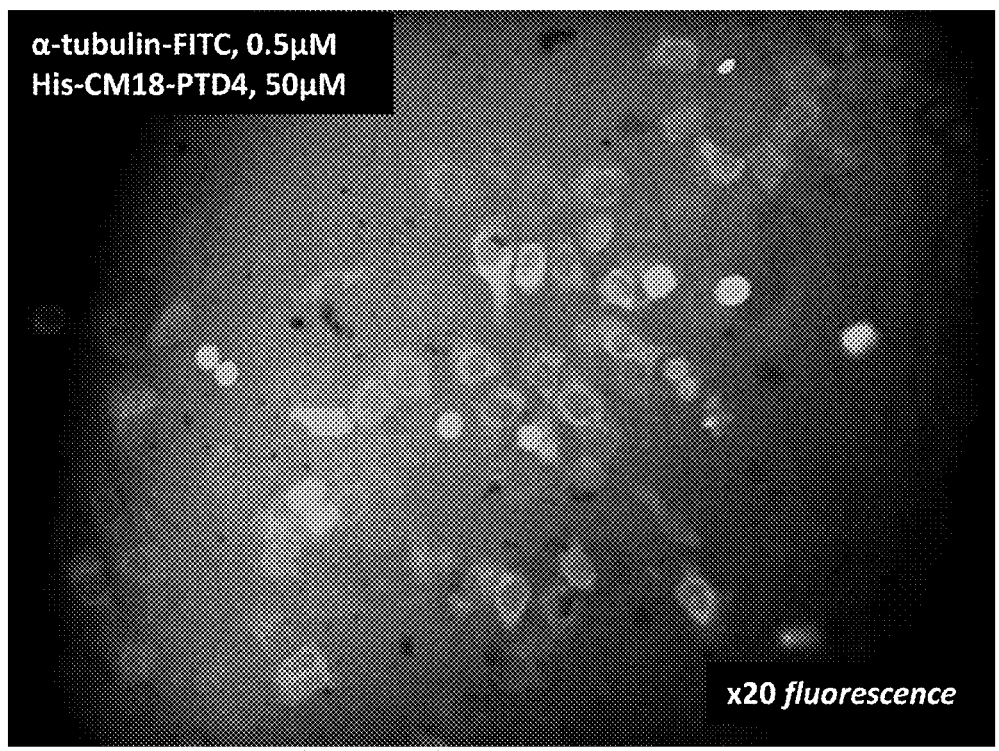

9.4a FTIC-Labeled Anti-Tubulin Antibody Transduction by His-CM18-PTD4 in HeLa Cells Using Protocol B: Visualization by Microscopy FITC-labeled anti-tubulin antibody (0.5 μM; Abcam, ab64503) was co-incubated with 50 μM of His-CM18-PTD4, and then exposed to HeLa cells for 10 seconds using Protocol B as described in Example 9.1. The cells were then subjected to fluorescence microscopy analysis as described in Examples 3.2 and 3.2a, wherein the FITC fluorescence of the anti-tubulin antibody in the HeLa cells was immediately visualized by bright field and fluorescence microscopy at 20× magnification after the final washing step. Sample results are shown in FIGS. 24C and 24D. No significant FITC fluorescence was observed in negative control samples (i.e., cells exposed to the FITC-labeled anti-tubulin antibody without any shuttle agent; data not shown).

Overall, the results in Examples 9.4 and 9.4a show that GFP-NLS and FITC-labeled anti-tubulin antibody cargos are successfully transduced and delivered to the nucleus and/or the cytosol of HeLa cells in the presence of the shuttle agent His-CM18-PTD4.

9.5 GFP-NLS Kinetic Transduction by His-CM18-PTD4 in HeLa Cells: Visualization by Microscopy GFP-NLS recombinant protein (5 μM; see Example 5.1) was co-incubated with 50 μM of His-CM18-PTD4, and then exposed to HeLa cells for 10 seconds using Protocol B as described in Example 9.1. After a washing step, the GFP fluorescence of the HeLa cells was immediately visualized by fluorescence microscopy (Example 3.2) at 20× magnification after different intervals of time. Typical results are shown in FIG. 27, in which fluorescence microscopy images were captured after 45, 75, 100, and 120 seconds (see FIGS. 27A, 27B, 27C and 27D, respectively).

Figure 27A:
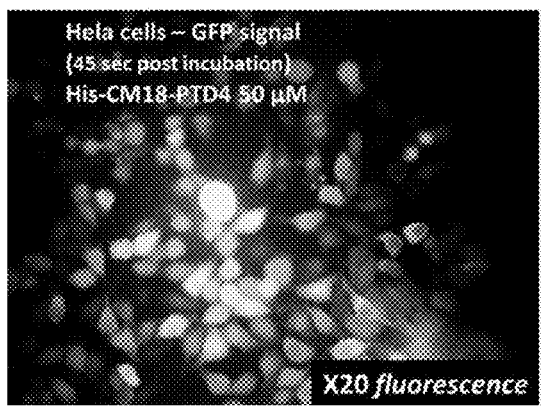
FIGS. 27A-27D show microscopy images of a kinetic (time-course) transduction experiment in HeLa cells, where the fluorescence of GFP-NLS cargo protein was tracked after 45 (FIG. 27A), 75 (FIG. 27B), 100 (FIG. 27C), and 120 (FIG. 27D) seconds following intracellular delivery with the shuttle His-CM18-PTD4. The diffuse cytoplasmic fluorescence pattern observed after 45 seconds (FIG. 27A) gradually becomes a more concentrated nuclear pattern at 120 seconds (FIG. 27D).
Figure 27B:
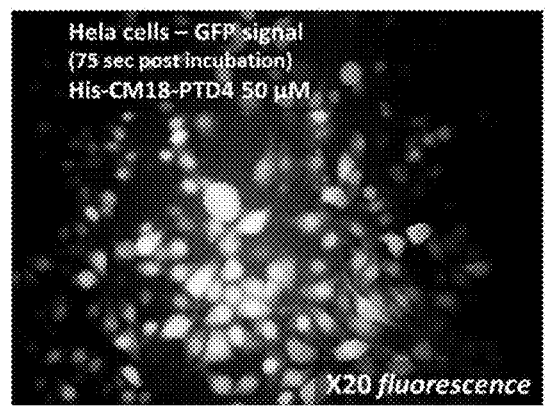
Figure 27C:
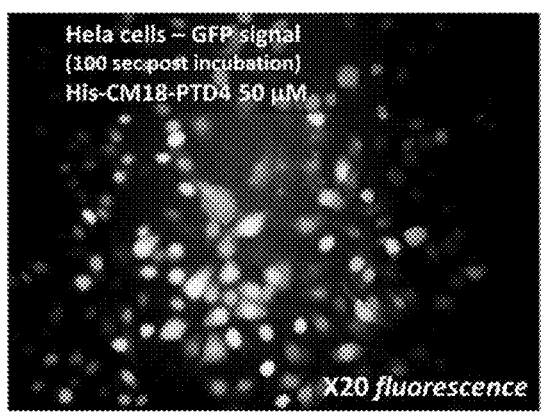
Figure 27D:
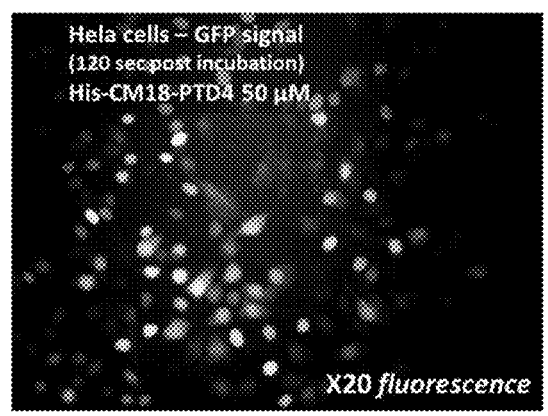
Figure 28A:
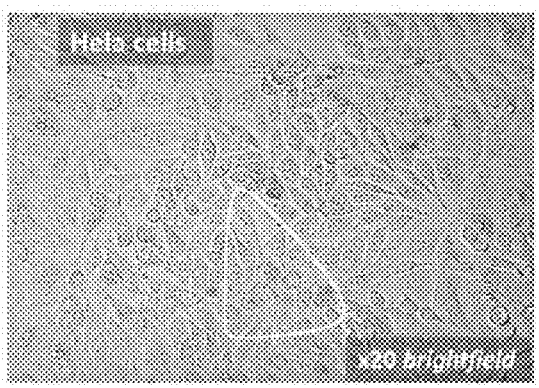
FIGS. 28A-28D show microscopy images of co-delivery transduction experiment in which two cargo proteins (GFP-NLS and mCherry™-NLS) are simultaneously delivered intracellularly by the shuttle His-CM18-PTD4 in HeLa cells. Cells and fluorescent signals were visualized by (FIG. 28A) bright field and (FIG. 28B-28D) fluorescence microscopy. White triangle windows indicate examples of areas of co-labelling between nuclei (DAPI) and GFP-NLS or mCherry™.
Figure 28B:
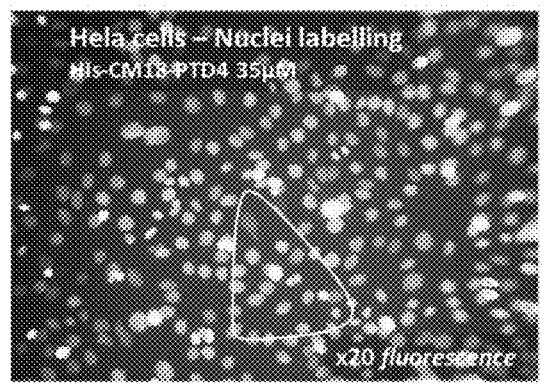
Figure 28C:
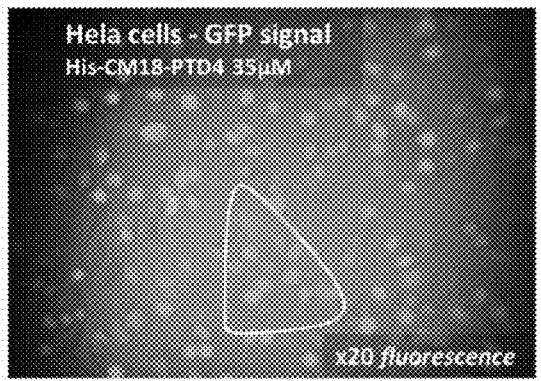
Figure 28D:
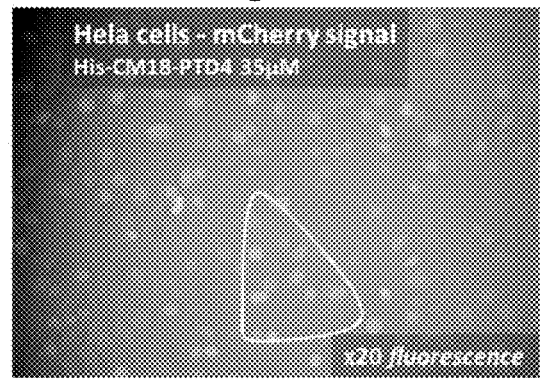

As shown in FIG. 27A, diffuse cellular GFP fluorescence was generally observed after 45 seconds, with areas of lower GFP fluorescence in the nucleus in many cells. These results suggest predominantly cytoplasmic and low nuclear distribution of the GPF-NLS delivered intracellularly via the shuttle agent after 45 seconds. FIGS. 27B-27D show the gradual redistribution of GFP fluorescence to the cell nuclei at 75 seconds (FIG. 27B), 100 seconds (FIG. 27 C), and 120 seconds (FIG. 27D) following exposure to the His-CM18-PTD4 shuttle agent and GFP-NLS cargo. No significant cellular GFP fluorescence was observed in negative control samples (i.e., cells exposed to GFP-NLS without any shuttle agent; data not shown).

The results in Example 9.5 show that GFP-NLS is successfully delivered to the nucleus of HeLa cells in the presence of the shuttle agent His-CM18-PTD4 by 2 minutes.

9.6 GFP-NLS and mCherry™-NLS Co-Transduction by His-CM18-PTD4 in HeLa Cells: Visualization by Microscopy mCherry™-NLS recombinant protein was constructed, expressed and purified from a bacterial expression system as described in Example 1.4. The sequence of the mCherry™-NLS recombinant protein was:

[SEQ ID NO: 73]
MHHHHHHGGGGSGGGGSGGASTGIRMVSKCEEDNMAIIKEFMRFKVHMEG

SVNGHEFEIEGEGEGRPYEGTQTAKLKVTKGGPLPFAWDILSPQFMYGSK

AYVKHPADIPDYLKLSFPEGFKWERVMNFEDGGVVTVTQDSSLQDGEFIY

KVKLRGTNFPSDGQVMQKKTMGWEASSERMYPEDGALKGEIKQRLKLKDG

GHYDAEVKTTYKAKKPVQLPGAYNVNIKLDITSHNEDYTIVEQYERAEGR

HSTGGMDELYKGGSGGGSGGGSGWIRASSGGR<u>SSDDEATADSQHAAPPKK</u>

<u>KRKV</u>GGSGGGSGGGSGGGRGTEIS
(MW = 34.71 kDa; pI = 6.68)
NLS sequence is underlined
Serine/glycine rich linkers are in bold GFP-NLS recombinant protein (5 μM; see Example 5.1) and mCherry™-NLS recombinant protein (5 μM) were co-incubated together with 35 μM of His-CM18-PTD4, and then exposed to HeLa cells for 10 seconds using Protocol B as described in Example 9.1. After washing steps, the cells were immediately visualized by bright field and fluorescence microscopy at 20× magnifications as described in Example 3.2. Sample results are shown in FIG. 28, in which corresponding images showing bright field (FIG. 28A), DAPI fluorescence (FIG. 28B), GFP-NLS fluorescence (FIG. 28C), and mCherry™-NLS fluorescence (FIG. 28D) are shown. White triangle windows indicate examples of areas of co-labelling between GFP-NLS and mCherry™ fluorescence signals in cell nuclei. No significant cellular GFP or mCherry™ fluorescence was observed in negative control samples (i.e., cells exposed to GFP-NLS or mCherry™ without any shuttle agent; data not shown).

These results show that GFP-NLS and mCherry™-NLS are successfully delivered together to the nucleus in HeLa cells in the presence of the shuttle agent His-CM18-PTD4.

9.7 GFP-NLS Transduction by His-CM18-PTD4 in THP-1 Suspension Cells: Flow Cytometry The ability of the His-CM18-PTD4 to deliver GFP-NLS in the nuclei of suspension cells was tested using THP-1 cells. THP-1 cells were cultured and tested in the protein transduction assays using Protocols A and C as described in Example 9.1. GFP-NLS (5 μM; see Example 5.1) was co-incubated with 1 μM of His-CM18-PTD4 and exposed to THP-1 cells for 1 hour (Protocol A), or was co-incubated with 5 μM of His-CM18-PTD4 and exposed to THP-1 cells for 15 seconds (Protocol C). The cells were subjected to flow cytometry analysis as described in Example 3.3. Results are shown in Table 9.3 and in FIG. 31.

TABLE 9.3

Figure 31:
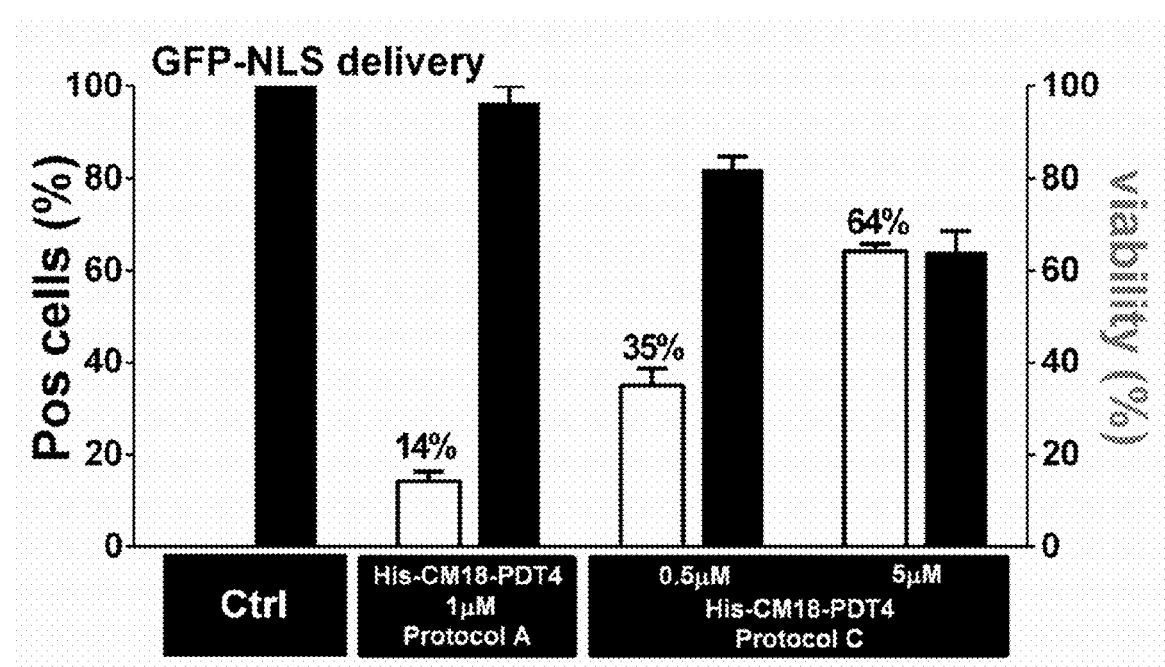
FIG. 31 shows the results of a transduction efficiency experiment in which GFP-NLS cargo protein was intracellularly delivered using the shuttle His-CM18-PTD4 in THP-1 cells using different Protocols (Protocol A vs C). GFP-NLS transduction efficiency was evaluated by flow cytometry and the percentage of GFP fluorescent cells ("Pos cells (%)"), as well as corresponding cell viability data ("viability (%)") are shown. "Ctrl" corresponds to THP-1 cells exposed to GFP-NLS cargo protein in the absence of a shuttle agent.

Data from FIG. 31

| Protocol | Shuttle | Cells | Conc. of shuttle (μM) | Conc. of GFP-NLS (μM) | Mean % cells with GFP signal (±St. Dev.; n = 3) | Cell viability (%) (±St. Dev.; n = 3) |
|---|---|---|---|---|---|---|
| C | No shuttle ("Ctrl") | THP-1 | 0 | 5 | 0.2 ± 0.03 | 99.1 ± 0.7 |
| A | His-CM18-PTD4 | | 1 | 5 | 14.2 ± 2.2 | 96.9 ± 3.6 |
| C | His-CM18-PTD4 | | 0.5 | 5 | 34.9 ± 3.8 | 82.1 ± 2.7 |
|   |   |   | 5 | 5 | 64.1 ± 1.6 | 64.0 ± 4.1 |

9.8 GFP-NLS Transduction by His-CM18-PTD4 in THP-1 Cells: Visualization by Microscopy GFP-NLS recombinant protein (5 μM; see Example 5.1) was co-incubated with 5 μM of His-CM18-PTD4, and then exposed to THP-1 cells for 15 seconds using Protocol C as described in Example 9.1. The cells were subjected to microscopy visualization as described in Example 3.2.

Figure 32D:
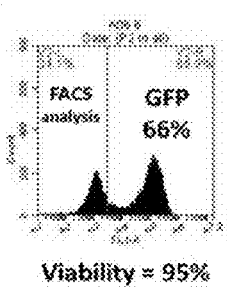

For the sample results shown in FIG. 32, GFP fluorescence of the HeLa cells was immediately visualized by bright field (upper panels) and fluorescence (lower panels) microscopy at 4×, 10× and 40× magnifications (FIG. 32A-32C, respectively) after the final washing step. White triangle windows in FIG. 32C indicate examples of areas of co-labelling between bright field and fluorescence images. FIG. 32D shows typical results of a corresponding FACS analysis (performed as described in Example 3.3), which indicates the percentage of cells in a 96-plate well with a GFP signal. Additional results are shown in FIG. 33, in which FIGS. 33A and 33B show bright field images, and FIGS. 33C and 33D show corresponding fluorescence images. White triangle windows indicate examples of areas of co-labelling between FIGS. 33A and 33C, as well as FIGS. 33B and 33D. The right-most panel shows typical results of a corresponding FACS analysis (performed as described in Example 3.3), which indicates the percentage of cells in a 96-plate well with a GFP signal.

No significant cellular GFP fluorescence was observed in negative control samples (i.e., cells exposed to GFP-NLS without any shuttle agent; data not shown).

The results in this example show that GFP-NLS is successfully delivered intracellularly in THP-1 cells in the presence of the shuttle agent His-CM18-PTD4.

Example 10

Different Multi-Domain Shuttle Agents, but not Single-Domain Peptides, Successfully Transduce GFP-NLS in HeLa and THP-1 Cells 10.1 GFP-NLS Transduction by Different Shuttle Agents in HeLa Cells: Flow Cytometry HeLa cells were cultured and tested in the protein transduction assays using Protocol B as described in Example 9.1. Briefly, GFP-NLS recombinant protein (5 μM; see Example 5.1) was co-incubated with 50 μM of different shuttle agents and exposed to the HeLa cells for 10 seconds. The cells were subjected to flow cytometry analysis as described in Example 3.3. Results are shown in Table 10.1 and FIG. 29A. "Pos cells (%)" is the mean percentages of all cells that emanate a GFP signal. The negative control ("Ctrl") corresponds to cells that were incubated with GFP-NLS recombinant protein (5 μM) without any shuttle agent.

TABLE 10.1

Data from FIG. 29A

| Protocol | Shuttle agent | Cells | Conc. of shuttle (μM) | Conc. of GFP-NLS (μM) | Mean % cells with GFP signal (±St. Dev.; n = 3) | Cell viability (%) (±St. Dev.; n = 3) |
|---|---|---|---|---|---|---|
| B | No shuttle ("ctrl") | HeLa | 0 | 5 | 0 | 100 |
|   | His-CM18-TAT | HeLa | 50 |   | 55.5 ± 3.6 | 35.2 ± 5.7 |
|   | His-CM18-Transportan (TPT) | HeLa |   |   | 33.2 ± 2.8 | 41.3 ± 3.3 |
|   | TAT-KALA | HeLa |   |   | 56.3 ± 3.6 | 95.6 ± 4.3 |
|   | His-CM18-PTD4 | HeLa |   |   | 68 ± 2.2 | 92 ± 3.6 |
|   | His-CM18-9Arg | HeLa |   |   | 57.2 ± 3.9 | 45.8 ± 5.4 |
|   | TAT-CM18 | HeLa |   |   | 39.4 ± 3.9 | 23.5 ± 1.1 |
|   | His-C(LLKK)$_3$C-PTD4 | HeLa |   |   | 76 ± 3.8 | 95 ± 2.7 |
|   | His-LAH4-PTD4 | HeLa |   |   | 63 ± 1.64 | 98 ± 1.5 |
|   | PTD4-KALA | HeLa |   |   | 73.4 ± 4.12 | 91.4 ± 3.67 |

* His-LAH4-PTD4: the intracellular GFP fluorescence pattern was observed by fluorescence microscopy as being punctate, suggesting that the GFP cargo remained trapped in endosomes.

10.2 GFP-NLS Transduction by Different Shuttle Agents with Varying Incubation Times in HeLa Cells: Flow Cytometry HeLa cells were cultured and tested in the protein transduction assays using Protocol B as described in Example 9.1. Briefly, GFP-NLS recombinant protein (5 μM; see Example 5.1) was co-incubated with 10 μM of TAT-KALA, His-CM18-PTD4, or His-C(LLKK)$_3$C-PTD4 for 1, 2, or 5 minutes. After the final washing step, the cells were subjected to flow cytometry analysis as described in Example 3.3. Results are shown in Table 10.2 and FIG. 29B. "Pos cells (%)" is the mean percentages of all cells that emanate a GFP signal. The negative control ("Ctrl") corresponds to cells that were incubated with GFP-NLS recombinant protein (5 μM) without any shuttle agent.

TABLE 10.2

Data from FIG. 29B

| Protocol | Shuttle agent | Cells | Conc. of shuttle (μM) | Incubation time | Mean % cells with GFP signal (±St. Dev.; n = 3) | Cell viability (%) (±St. Dev.; n = 3) |
|---|---|---|---|---|---|---|
| — | No shuttle ("Ctrl") | HeLa | 0 | 5 min. | 0 ± n/a | 97.5 ± 1.7 |
| B | TAT-KALA | HeLa | 10 | 1 min. | 83.7 ± 3.5 | 93.5 ± 2.7 |
|   |   |   |   | 2 min. | 86.2 ± 4.3 | 92.1 ± 3.1 |
|   |   |   |   | 5 min. | 68.1 ± 3.0 | 86 ± 4.4 |
|   | His-CM18-PTD4 | HeLa | 10 | 1 min. | 50.6 ± 3.5 | 97.6 ± 2.7 |
|   |   |   |   | 2 min. | 74 ± 3.3 | 80.9 ± 3.2 |
|   |   |   |   | 5 min. | 82.7 ± 5.0 | 66.2 ± 4.4 |
|   | His-C(LLKK)$_3$C-PTD4 | HeLa | 10 | 1 min. | 51.1 ± 3.5 | 99.5 ± 2.7 |
|   |   |   |   | 2 min. | 77.8 ± 4.3 | 94.3 ± 3.2 |
|   |   |   |   | 5 min. | 86.4 ± 4.0 | 80.8 ± 4.4 |

10.3 GFP-NLS Transduction by TAT-KALA, His-CM18-PTD4 and His-C(LLKK)$_3$C-PTD4 with Varying Incubation Times in HeLa Cells: Flow Cytometry HeLa cells were cultured and tested in the protein transduction assays using Protocol C as described in Example 9.1. Briefly, GFP-NLS recombinant protein (5 μM; see Example 5.1) was co-incubated with 5 μM of TAT-KALA, His-CM18-PTD4, or His-C(LLKK)$_3$C-PTD4 for 1, 2, or 5 minutes. After the final washing step, the cells were subjected to flow cytometry analysis as described in Example 3.3. Results are shown in Table 10.3 and FIG. 29C. The negative control ("Ctrl") corresponds to cells that were incubated with GFP-NLS recombinant protein (5 μM) without any shuttle agent.

TABLE 10.3

Figure 29C:
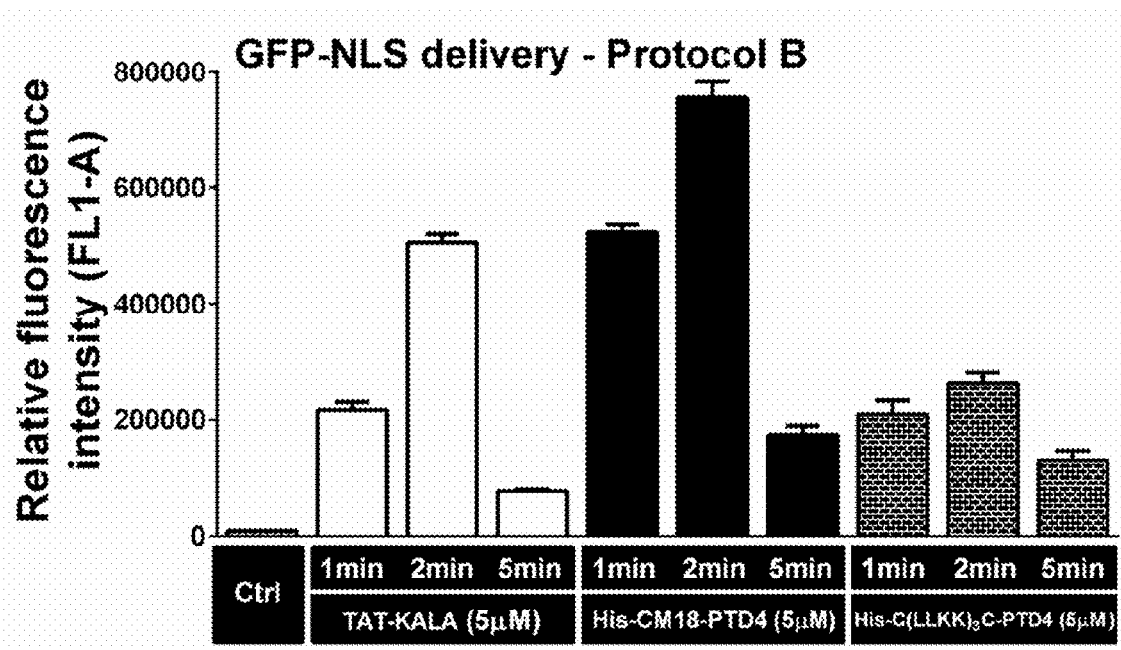

Data from FIG. 29C

| Protocol | Shuttle agent | Cells | Conc. of shuttle (μM) | Incubation time | Relative fluorescence intensity (FL1-A) (n = 3) | St. Dev. |
|---|---|---|---|---|---|---|
|   | No shuttle ("Ctrl") |   | 0 | 5 min. | 8903 | 501 |
| C | TAT-KALA | HeLa | 10 | 1 min. | 216 367 | 13 863.48 |
|   |   |   |   | 2 min. | 506 158 | 14 536.28 |
|   |   |   |   | 5 min. | 78 010 | 2 463.96 |
|   | His-CM18-PTD4 | HeLa | 10 | 1 min. | 524 151 | 12 366.48 |
|   |   |   |   | 2 min. | 755 624 | 26 933.16 |
|   |   |   |   | 5 min. | 173 930 | 15 567.33 |
|   | His-C(LLKK)$_3$C-PTD4 | HeLa | 10 | 1 min. | 208 968 | 23 669.19 |
|   |   |   |   | 2 min. | 262 411.5 | 19 836.84 |
|   |   |   |   | 5 min. | 129 890 | 16 693.29 |

10.4 GFP-NLS Transduction by Different Shuttle Agents in HeLa Cells: Flow Cytometry HeLa cells were cultured and tested in the protein transduction assays using Protocol B as described in Example 9.1. Briefly, GFP-NLS recombinant protein (5 μM; see Example 5.1) was co-incubated with 50 μM of different shuttle agents (see Table 1.3 for amino acid sequences and properties) and exposed to the HeLa cells for 10 seconds. The cells were subjected to flow cytometry analysis as described in Example 3.3. Results are shown in Tables 10.3a & 10.3b and FIGS. 29E & 29F. "Pos cells (%)" is the mean percentages of all cells that emanate a GFP signal. The negative control ("Ctrl") corresponds to cells that were incubated with GFP-NLS recombinant protein (5 μM) without any shuttle agent.

Example 5.1) was co-incubated with 10 μM of TAT-KALA, His-CM18-PTD4, or His-C(LLKK)$_3$C-PTD4 for 1, 2, or 5 minutes. After the final washing step, the cells were subjected to flow cytometry analysis as described in Example 3.3. Results are shown in Tables 10.3c & 10.3b and FIGS. 29G and 29H. "Pos cells (%)" is the mean percentages of all cells that emanate a GFP signal. The negative control TABLE 10.3a Data from FIG. 29E

| Domain structure | Shuttle agent | Conc. of shuttle (μM) | Conc. of GFP-NLS (μM) | Mean % cells with GFP signal (±St. Dev.; n = 3) | Cell viability (%) (±St. Dev.; n = 3) |
|---|---|---|---|---|---|
| — | No shuttle ("Ctrl") | 0 | 5 | 0 | 100 |
| ELD-CPD | VSVG-PTD4 | 50 | 5 | 3.5 ± 1.1 | 100 |
|  | EB1-PTD4 |  |  | 75.8 ± 8.26 | 39 ± 5.6 |
|  | JST-PTD4 |  |  | 0.84 ± 0.69 | 98.9 ± 0.57 |
| His-ELD-CPD | His-C(LLKK)$_3$C-PTD4 | 50 | 5 | 76 ± 3.8 | 95 ± 2.7 |
|  | His-LAH4-PTD4* |  |  | 63 ± 1.64 | 98 ± 1.5 |
|  | His-CM18-PTD4 |  |  | 68 ± 2.2 | 92 ± 3.6 |
|  | His-CM18-TAT |  |  | 55.5 ± 3.6 | 35.2 ± 5.7 |
|  | His-CM18-TAT-Cys** |  |  | 49.3 ± 4.1 | 41.4 ± 3.91 |
|  | His-CM18-9Arg |  |  | 57.2 ± 3.93 | 45.8 ± 3.53 |
|  | His-CM18-Transportan (TPT) |  |  | 33.2 ± 2.82 | 41.3 ± 3.29 |

Figure 29D:
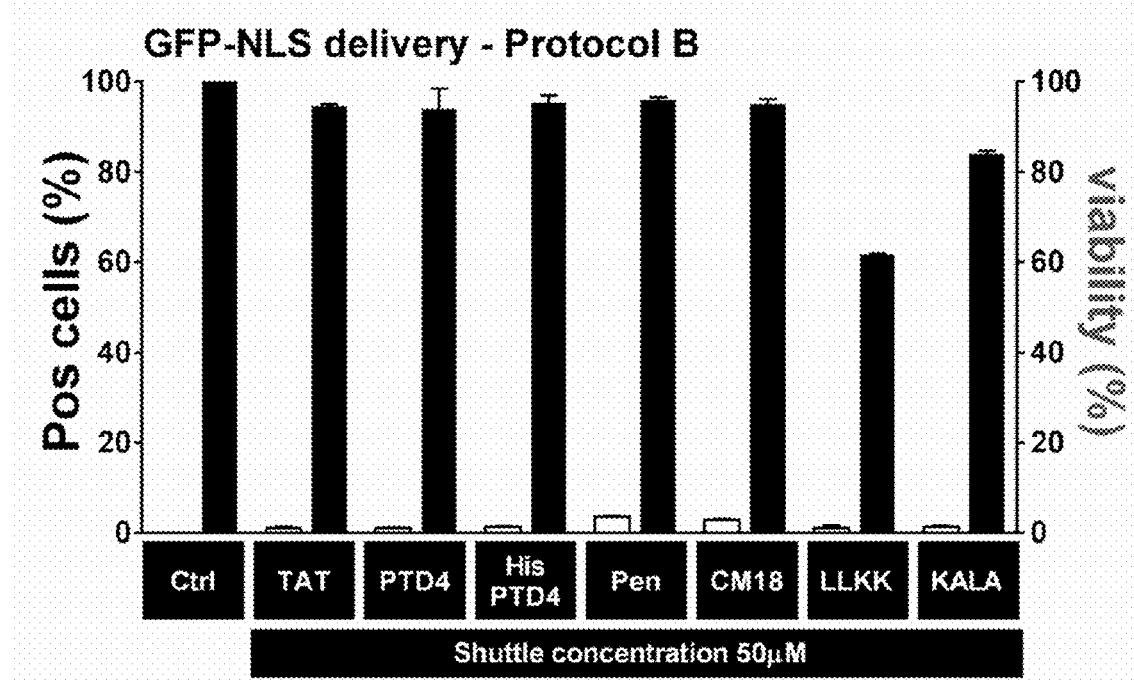
Figure 29E:
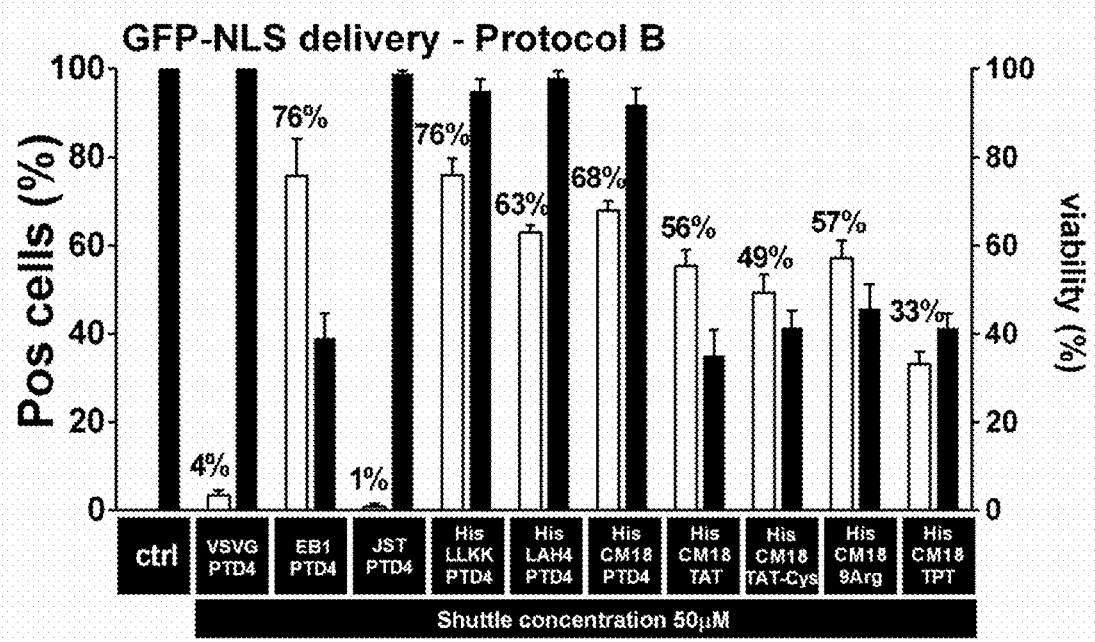

*His-LAH4-PTD4: the intracellular GFP fluorescence pattern was observed by fluorescence microscopy as being punctate, suggesting that the GFP cargo remained trapped in endosomes.
**Not shown in FIG. 29E.

TABLE 10.3b

Figure 29F:
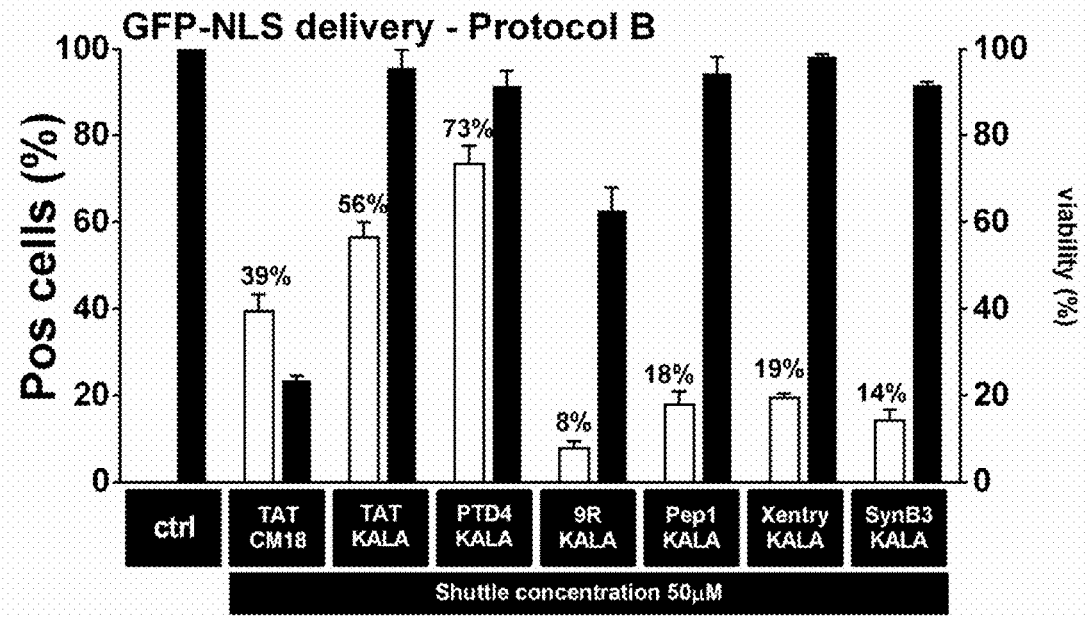

Data from FIG. 29F

| Domain structure | Shuttle agent | Conc. of shuttle (μM) | Conc. of GFP-NLS (μM) | Mean % cells with GFP signal (±St. Dev.; n = 3) | Cell viability (%) (±St. Dev.; n = 3) |
|---|---|---|---|---|---|
| — | No shuttle ("Ctrl") | 0 | 5 | 0 | 100 |
| CPD-ELD | TAT-CM18 | 50 | 5 | 39.4 ± 3.9 | 23.5 ± 1.1 |
|  | TAT-KALA |  |  | 56.3 ± 3.6 | 95.6 ± 4.3 |
|  | PTD4-KALA |  |  | 73.4 ± 4.12 | 91.4 ± 3.67 |
|  | 9Arg-KALA |  |  | 7.8 ± 1.53 | 62.8 ± 5.11 |
|  | Pep1-KALA |  |  | 17.2 ± 3.07 | 94.7 ± 3.77 |
|  | Xentry-KALA |  |  | 19.4 ± 1.01 | 98.3 ± 0.64 |
|  | SynB3-KALA |  |  | 14.3 ± 2.37 | 91.1 ± 0.82 |

HeLa cells were cultured and tested in the protein transduction assays using Protocol B as described in Example 9.1. Briefly, GFP-NLS recombinant protein (5 μM; see ("Ctrl") corresponds to cells that were incubated with GFP-NLS recombinant protein (5 μM) without any shuttle agent.

TABLE 10.3c

Figure 29G:
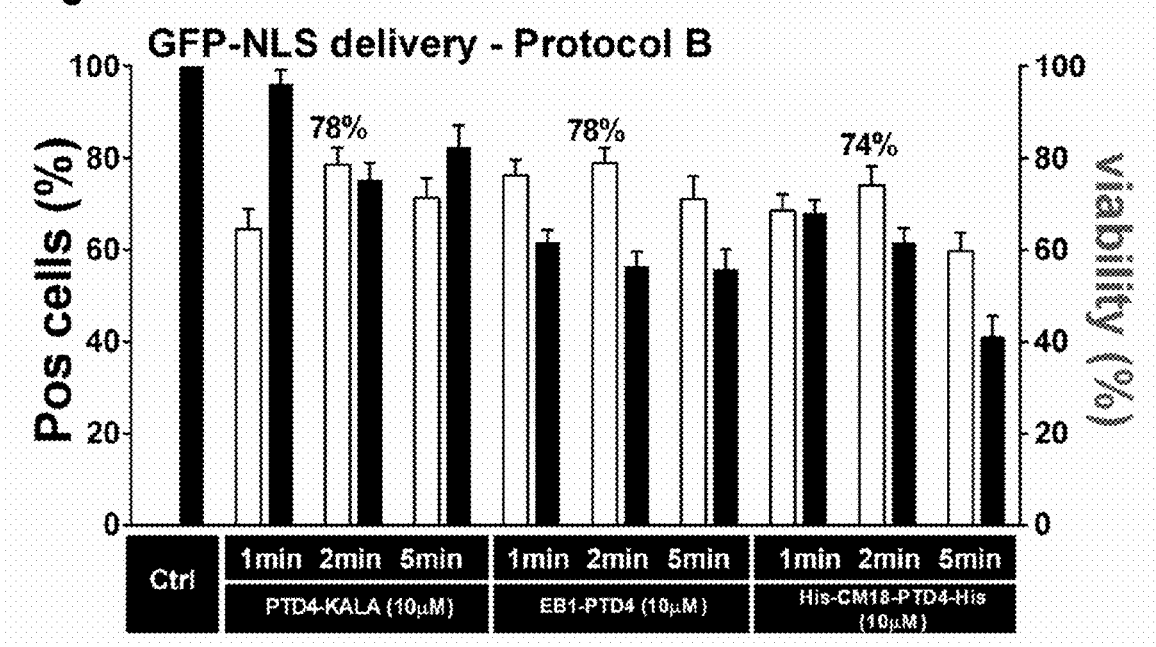

Data from FIG. 29G

| Domain structure | Shuttle agent | Conc. of shuttle (μM) | Conc. of GFP-NLS (μM) | Incubation time (min) | Mean % cells with GFP signal (±St. Dev.; n = 3) | Cell viability (%) (±St. Dev.; n = 3) |
|---|---|---|---|---|---|---|
| — | No shuttle ("Ctrl") | 0 | 5 | 5 | 0 ± n/a | 98.3 ± 0.9 |

TABLE 10.3c-continued

Data from FIG. 29G

| Domain structure | Shuttle agent | Conc. of shuttle (µM) | Conc. of GFP-NLS (µM) | Incubation time (min) | Mean % cells with GFP signal (±St. Dev.; n = 3) | Cell viability (%) (±St. Dev.; n = 3) |
|---|---|---|---|---|---|---|
| CPD-ELD | PTD4-KALA | 10 | 5 | 1 | 64.6 ± 4.3 | 96.2 ± 3.0 |
| | | | | 2 | 78.8 ± 3.6 | 75.3 ± 3.8 |
| | | | | 5 | 71.4 ± 4.2 | 82.4 ± 4.7 |
| ELD-CPD | EB1-PTD4 | 10 | 5 | 1 | 76.3 ± 3.5 | 61.7 ± 2.7 |
| | | | | 2 | 79.0 ± 3.3 | 56.6 ± 3.2 |
| | | | | 5 | 71.1 ± 5.0 | 55.8 ± 4.4 |
| His-ELD-CPD-His | His-CM18-PTD4-His | 10 | 5 | 1 | 68.6 ± 3.5 | 68.1 ± 2.7 |
| | | | | 2 | 74.1 ± 4.3 | 61.6 ± 3.2 |
| | | | | 5 | 59.8 ± 4.0 | 41.2 ± 4.4 |

TABLE 10.3d

Figure 29H:
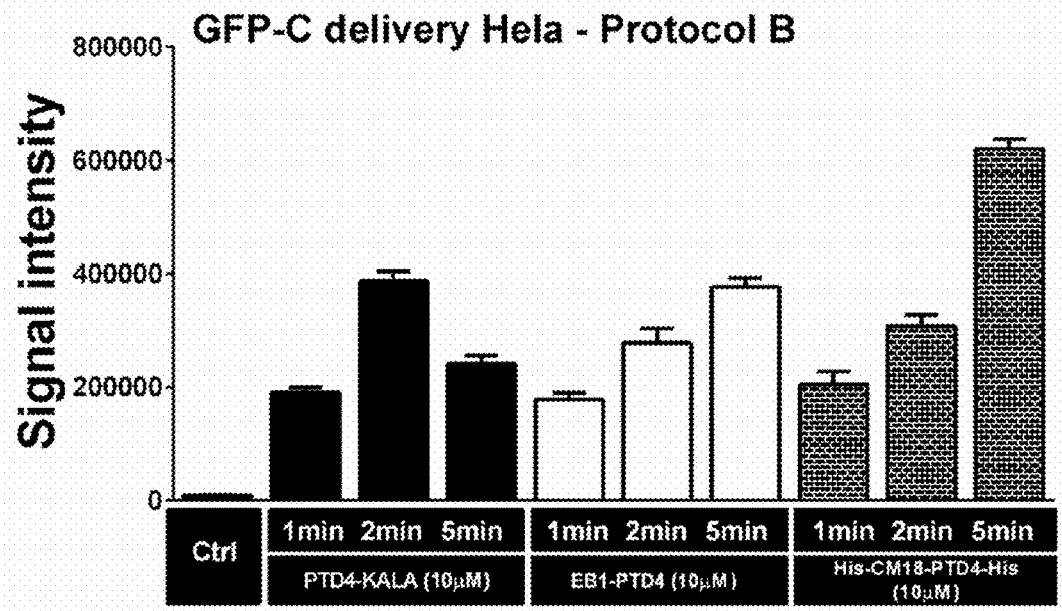

Data from FIG. 29H

| Domain structure | Shuttle agent | Conc. of shuttle (µM) | Conc. of GFP-NLS (µM) | Incubation time (min) | Relative Fluorescence Intensity (FL1-A) (±St. Dev.; n = 3) |
|---|---|---|---|---|---|
| — | No shuttle ("Ctrl") | 0 | 5 | 5 | 8903 ± 501.37 |
| CPD-ELD | PTD4-KALA | 10 | 5 | 1 | 190 287 ± 9445 |
| | | | | 2 | 386 480 ± 17 229 |
| | | | | 5 | 241 230 ± 14 229 |
| ELD-CPD | EB1-PTD4 | 10 | 5 | 1 | 178 000 ± 11 934 |
| | | | | 2 | 277 476 ± 25 319 |
| | | | | 5 | 376 555 ± 16 075 |
| His-ELD-CPD-His | His-CM18-PTD4-His | 10 | 5 | 1 | 204 338 ± 22 673 |
| | | | | 2 | 307 329 ± 19 618 |
| | | | | 5 | 619 964 ± 17 411 |

The shuttle agent CM18-PTD4 was used as a model to demonstrate the modular nature of the individual protein domains, as well as their ability to be modified. More particularly, the presence or absence of: an N-terminal cysteine residue ("Cys"); different flexible linkers between the ELD and CPD domains ("Li": GGS; "L2": GGSGGGS; and "L3": GGSGGGSGGGS) and different lengths, positions, and variants to histidine-rich domains; were studied.

HeLa cells were cultured and tested in the protein transduction assays using Protocol B as described in Example 9.1. Briefly, GFP-NLS recombinant protein (5 µM; see Example 5.1) was co-incubated with 20 µM of different shuttle peptide variants (see Table 1.3 for amino acid sequences and properties) of the shuttle agent His-CM18-PTD4 for 1 minute. After the final washing step, the cells were subjected to flow cytometry analysis as described in Example 3.3. Results are shown in Table 10.3e and FIG. 29I. "Pos cells (%)" is the mean percentages of all cells that emanate a GFP signal. The negative control ("Ctrl") corresponds to cells that were incubated with GFP-NLS recombinant protein (5 µM) without any shuttle agent.

TABLE 10.3e

Figure 29I:
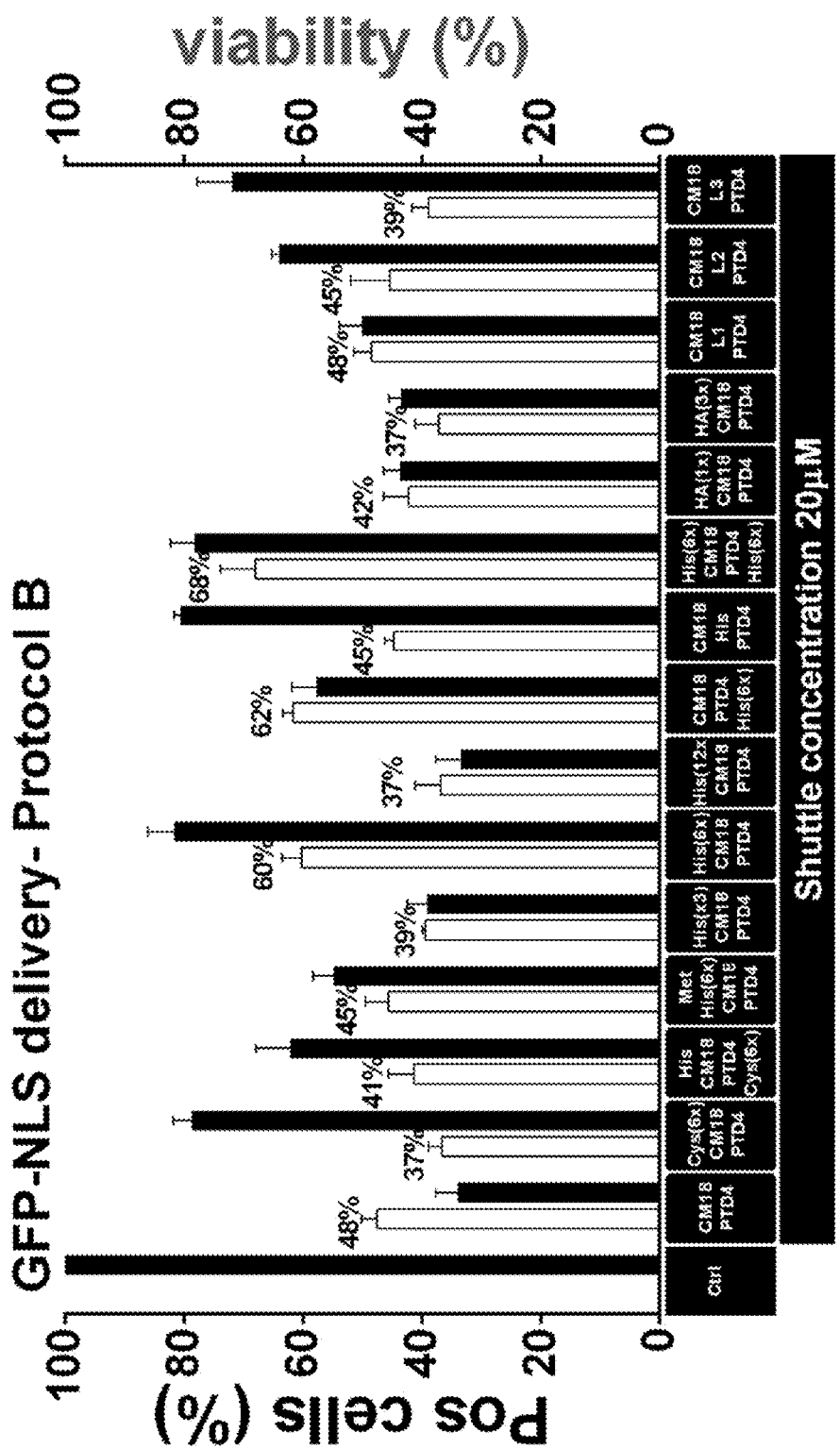
Figure 30A:
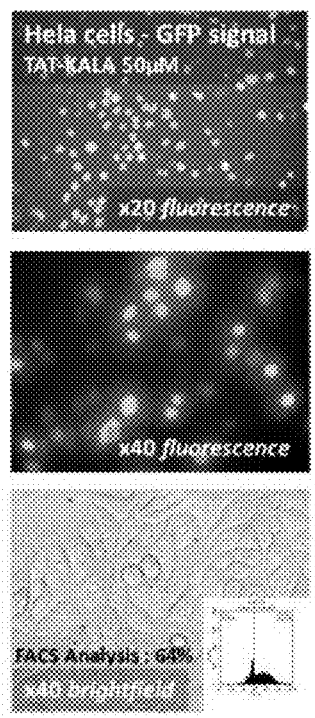
FIGS. 30A-30F show microscopy images of HeLa cells transduced with GFP-NLS using the shuttle agent
Figure 30B:
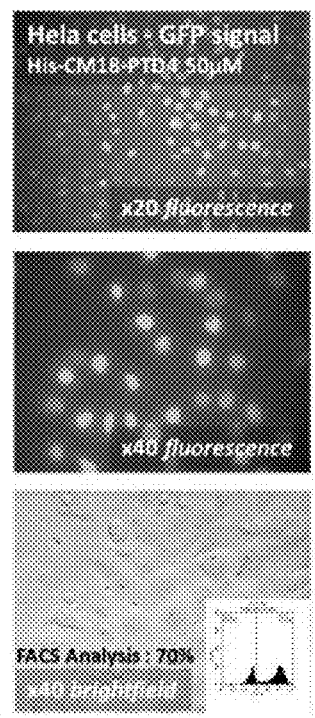
Figure 30C:
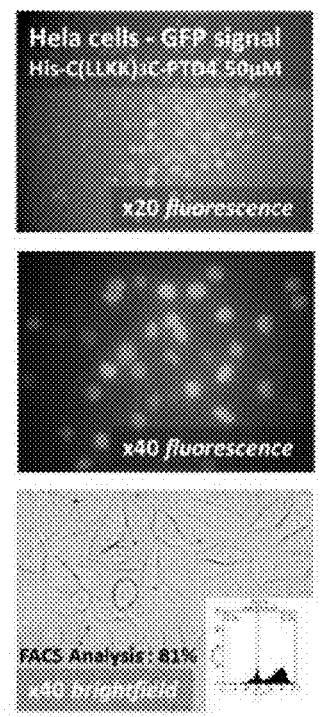
Figure 30D:
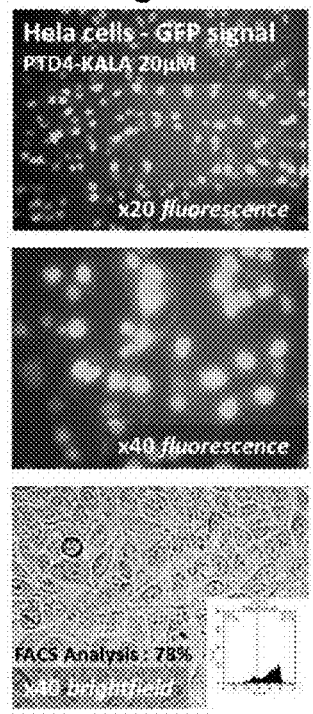
Figure 30E:
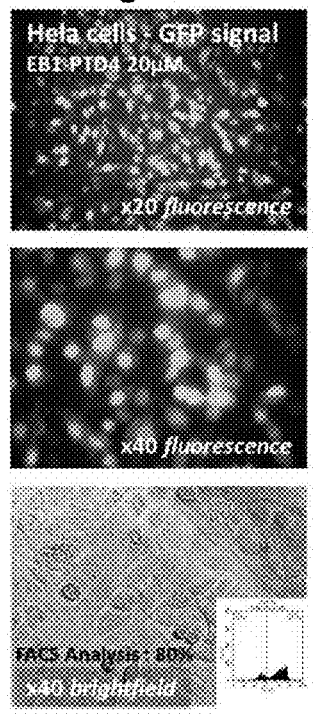
Figure 30F:
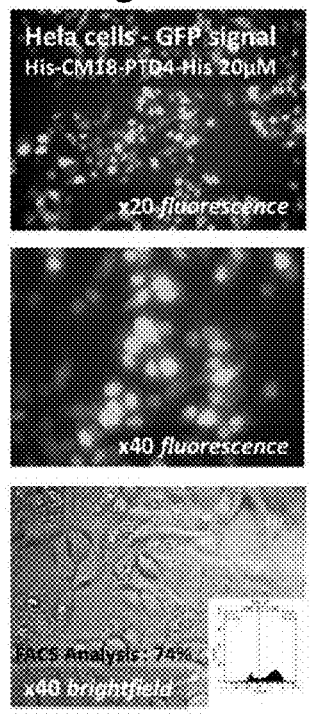

Data from FIG. 29I

| Domain structure | Shuttle agent | Conc. of shuttle (µM) | Conc. of GFP-NLS (µM) | Mean % cells with GFP signal (±St. Dev.; n = 3) | Cell viability (%) (±St. Dev.; n = 3) |
|---|---|---|---|---|---|
| — | No shuttle ("Ctrl") | 0 | 5 | 0 | 99.6 ± 0.12 |
| ELD-CPD | CM18-PTD4 | 20 | 5 | 47.6 ± 2.6 | 33.9 ± 3.7 |
| | Cys-CM18-PTD4 | | | 36.6 ± 2.3 | 78.7 ± 3.1 |
| | CM18-L1-PTD4 | | | 48.5 ± 3.0 | 50.1 ± 3.8 |
| | CM18-L2-PTD4 | | | 45.5 ± 6.5 | 64.0 ± 1.3 |
| | CM18-L3-PTD4 | | | 39.0 ± 2.7 | 71.9 ± 6.0 |
| His-ELD-CPD | His-CM18-PTD4 | 20 | 5 | 60.3 ± 3.2 | 81.6 ± 4.5 |
| | His-CM18-PTD4-6Cys | | | 41.3 ± 4.28 | 62 ± 5.76 |
| | Met-His-CM18-PTD4-Cys | | | 45.6 ± 3.88 | 54.9 ± 3.45 |

TABLE 10.3e-continued

Data from FIG. 29I

| Domain structure | Shuttle agent | Conc. of shuttle (µM) | Conc. of GFP-NLS (µM) | Mean % cells with GFP signal (±St. Dev.; n = 3) | Cell viability (%) (±St. Dev.; n = 3) |
|---|---|---|---|---|---|
| | 3His-CM18-PTD4 | | | 39.4 ± 0.5 | 39.2 ± 3.3 |
| | 12His-CM18-PTD4 | | | 36.9 ± 4.3 | 33.4 ± 4.3 |
| | HA-CM18-PTD4 | | | 42.3 ± 4.2 | 68.3 ± 4.1 |
| | 3HA-CM18-PTD4 | | | 37.2 ± 3.9 | 43.6 ± 2.8 |
| ELD-His-CPD | CM18-His-PTD4 | 20 | 5 | 61.7 ± 1.8 | 57.7 ± 4.2 |
| His-ELD-CPD-His | His-CM18-PTD4-His | 20 | 5 | 68.0 ± 6.0 | 78.6 ± 1.1 |

These results show that variations in a given shuttle (e.g., CM18-PTD4) may be used to modulate the degree of transduction efficiency and cell viability of the given shuttle. More particularly, the addition of an N-terminal cysteine residue to CM18-PTD4 (see Cys-CM18-PTD4), decreased GFP-NLS transduction efficiency by 11% (from 47.6% to 36.6%), but increased cell viability from 33.9% to 78.7%. Introduction of flexible linker domains (L1, L2, and L3) of different lengths between the CM18 and PTD4 domains did not result in a dramatic loss of transduction efficiency, but increased cell viability (see CM18-L1-PTD4, CM18-L2-PTD4, and CM18-L3-PTD4). Finally, variations to the amino acid sequences and/or positions of the histidine-rich domain(s) did not result in a complete loss of transduction efficiency and cell viability of His-CM18-PTD4 (see 3His-CM18-PTD4, 12His-CM18-PTD4, HA-CM18-PTD4, 3HA-CM18-PTD4, CM18-His-PTD4, and His-CM18-PTD4-His). Of note, adding a second histidine-rich domain at the C terminus of His-CM18-PTD4 (i.e., His-CM18-PTD4-His) increased transduction efficiency from 60% to 68% with similar cell viability.

10.5 Lack of GFP-NLS Transduction by Single-Domain Peptides or a His-CPD Peptide in HeLa Cells: Flow Cytometry HeLa cells were cultured and tested in the protein transduction assays using Protocol B as described in Example 9.1. Briefly, GFP-NLS recombinant protein (5 µM; see Example 5.1) was co-incubated with 50 µM of different single-domain peptides (TAT; PTD4; Penetratin; CM18; C(LLKK)$_3$C; KALA) or the two-domain peptide His-PTD4 (lacking an ELD), and exposed to the HeLa cells for 10 seconds. After the final washing step, the cells were subjected to flow cytometry analysis as described in Example 3.3. Results are shown in Table 10.4 and FIG. 29D. "Pos cells (%)" is the mean percentages of all cells that emanate a GFP signal. The negative control ("Ctrl") corresponds to cells that were incubated with GFP-NLS recombinant protein (5 µM) without any single-domain peptide or shuttle agent.

TABLE 10.4

Data from FIG. 29D

| Protocol | Domain | Single-domain peptide | Cells | Conc. of shuttle (µM) | Conc. of GFP-NLS (µM) | Mean % cells with GFP signal (±St. Dev.; n = 3) | Cell viability (%) (±St. Dev.; n = 3) |
|---|---|---|---|---|---|---|---|
| B | — | No peptide ("Ctrl") | HeLa | 0 | 5 | 0.1 ± 0.02 | 98.3 ± 0.59 |
| | CPD | TAT | HeLa | 50 | 5 | 1.1 ± 0.27 | 94.6 ± 0.44 |
| | | PTD4 | | | | 1.1 ± 0.06 | 94 ± 4.5 |
| | | Penetratin (Pen) | | | | 3.6 ± 0.1 | 96 ± 0.6 |
| | ELD | CM18 | HeLa | 50 | 5 | 2.9 ± 0.2 | 95 ± 1.2 |
| | | C(LLKK)$_3$C | | | | 1.1 ± 0.57 | 61.8 ± 0.1 |
| | | KALA | | | | 1.4 ± 0.13 | 84 ± 0.7 |
| | His-CPD | His-PTD4 | HeLa | 50 | 5 | 1.04 ± 0.12 | 96.5 ± 0.28 |

These results show that the single-domain peptides TAT, PTD4, Penetratin, CM18, C(LLKK)$_3$C, KALA, or the two-domain peptide His-PTD4 (lacking an ELD), are not able to successfully transduce GFP-NLS in HeLa cells.

10.6 GFP-NLS Transduction by TAT-KALA, His-CM18-PTD4, His-C(LLKK)$_3$C-PTD4, PTD4-KALA, EB1-PTD4, and His-CM18-PTD4-his in HeLa Cells: Visualization by Microscopy GFP-NLS recombinant protein (5 µM; see Example 5.1) was co-incubated with 50 µM of shuttle agent, and then exposed to HeLa cells for 10 seconds using Protocol B as described in Example 9.1. The cells were visualized by microscopy as described in Example 3.2, after an incubation time of 2 minutes.

For the sample results shown in FIG. 30, GFP fluorescence of the HeLa cells was immediately visualized by bright field (bottom row panels) and fluorescence (upper and middle row panels) microscopy at 20× or 40× magnifications after the final washing step. The results with the shuttle agents TAT-KALA, His-CM18-PTD4, and His- C(LLKK)₃C-PTD4 are shown in FIGS. 30A, 30B and 30C, respectively. The results with the shuttle agents PTD4-KALA, EB1-PTD4, and His-CM18-PTD4-His are shown in FIGS. 30D, 30E and 30F, respectively. The insets in the bottom row panels show the results of corresponding FACS analyses (performed as described in Example 3.3), which indicates the percentage of cells in a 96-plate well with a GFP signal. No significant cellular GFP fluorescence was observed in negative control samples (i.e., cells exposed to GFP-NLS without any shuttle agent; data not shown).

10.7 GFP-NLS Transduction by TAT-KALA, His-CM18-PTD4 and His-C(LLKK)₃C-PTD4 with Varying Incubation Times in THP-1 Cells: Flow Cytometry THP-1 cells were cultured and tested in the protein transduction assays using Protocol C as described in Example 9.1. Briefly, GFP-NLS recombinant protein (5 µM; see Example 5.1) was co-incubated with 1 µM of TAT-KALA, His-CM18-PTD4, or His-C(LLKK)₃C-PTD4 for 15, 30, 60, or 120 seconds. After the final washing step, the cells were subjected to flow cytometry analysis as described in Example 3.3. The mean percentages of cells emanating a GFP signal ("Pos cells (%)") are shown in Table 10.4a and in FIG. 34A. The mean fluorescence intensity is shown in Table 10.5 and FIG. 34B. The negative control ("Ctrl") corresponds to cells that were incubated with GFP-NLS recombinant protein (5 µM) without any shuttle agent.

Example 11

Repeated Daily Treatments with Low Concentrations of Shuttle Agent in the Presence of Serum Results in GFP-NLS Transduction in THP-1 Cells 11.1 GFP-NLS Transduction with His-CM18-PTD4 or His-C(LLKK)3C-PTD4 in THP-1 Cells: Flow Cytometry THP-1 cells were cultured and tested in the protein transduction assay using Protocol A as described in Example 9.1, but with the following modifications. GFP-NLS recombinant protein (5, 2.5, or 1 µM; see Example 5.1) was co-incubated with 0.5 or 0.8 µM of His-CM18-PTD4, or with 0.8 µM of His-C(LLKK)₃C-PTD4, and then exposed to THP-1 cells each day for 150 min in the presence of cell culture medium containing serum. Cells were washed and subjected to flow cytometry analysis as described in Example 3.3 after 1 or 3 days of repeated exposure to the shuttle agent/cargo. The results are shown in Table 11.1 and in FIGS. 35A, 35B, 35C and 35F. The negative control ("Ctrl") corresponds to cells that were incubated with GFP-NLS recombinant protein (5 µM) without any shuttle agent.

TABLE 10.4a

Figure 34A:
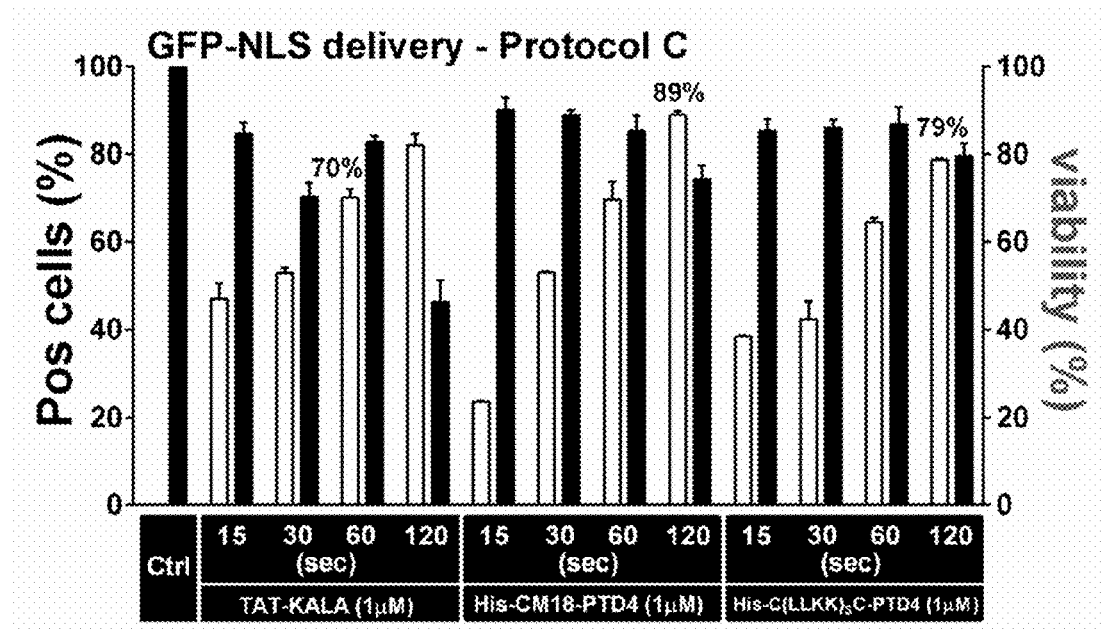
FIGS. 34A-34B show the results of GFP-NLS transduction efficiency experiments in THP-1 cells using the shuttle TAT-KALA, His-CM18-PTD4, or His-C(LLKK)$_3$C-PTD4. The cargo protein/shuttle agents were exposed to the THP-1 cells for 15, 30, 60 or 120 seconds. GFP-NLS transduction efficiency was evaluated by flow cytometry and the percentage of GFP fluorescent cells ("Pos cells (%)"), as well as corresponding cell viability data ("viability (%)") are shown in FIG. 34A.

Data from FIG. 34A

| Protocol | Shuttle agent | Cells | Conc. of shuttle (µM) | Conc. of GFP-NLS (µM) | Incubation time (sec.) | Mean % cells with GFP signal (±St. Dev.; n = 3) | Cell viability (%) (± St. Dev.; n = 3) |
|---|---|---|---|---|---|---|---|
| C | No shuttle ("Ctrl") | THP-1 | 0 | 5 | 120 | 1.12 ± 0.27 | 97.3 ± 1.55 |
|   | TAT-KALA | THP-1 | 1 | 5 | 15 | 47 ± 3.5 | 84.6 ± 2.7 |
|   |   |   |   |   | 30 | 52.9 ± 1.3 | 70.3 ± 3.2 |
|   |   |   |   |   | 60 | 70.1 ± 2.0 | 82.7 ± 1.4 |
|   |   |   |   |   | 120 | 82.1 ± 2.5 | 46.3 ± 4.9 |
|   | His-CM18-PTD4 | THP-1 | 1 | 5 | 15 | 23.7 ± 0.2 | 90 ± 3.0 |
|   |   |   |   |   | 30 | 53 ± 0.3 | 89 ± 1.1 |
|   |   |   |   |   | 60 | 69.6 ± 4.2 | 85.3 ± 3.6 |
|   |   |   |   |   | 120 | 89 ± 0.8 | 74.3 ± 3.2 |
|   | His-C(LLKK)₃C-PTD4 | THP-1 | 1 | 5 | 15 | 38.4 ± 0.3 | 85.2 ± 2.8 |
|   |   |   |   |   | 30 | 42.3 ± 4.2 | 86 ± 2.0 |
|   |   |   |   |   | 60 | 64.5 ± 1.0 | 86.9 ± 3.8 |
|   |   |   |   |   | 120 | 78.7 ± 0.3 | 79.6 ± 2.8 |

TABLE 10.5

Figure 34B:
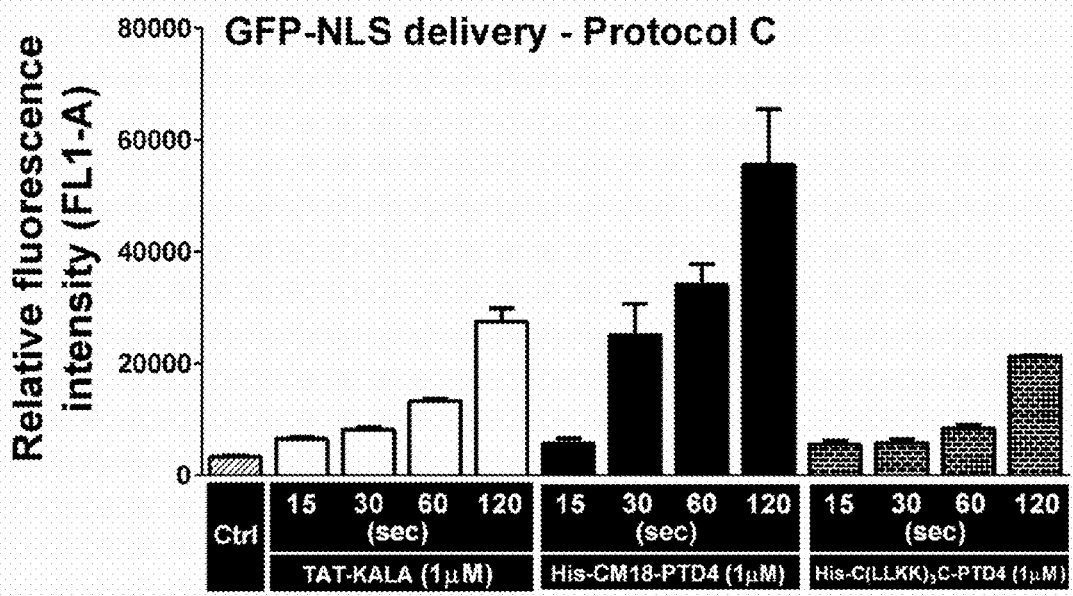

Data from FIG. 34B

| Protocol | Shuttle agent | Cells | Conc. of shuttle (µM) | Incubation time (sec.) | Relative fluorescence intensity (FL1-A) (n = 3) | Standard Deviation |
|---|---|---|---|---|---|---|
| C | No shuttle ("Ctrl") | THP-1 | 0 | 120 | 217 | 23.09 |
|   | TAT-KALA | THP-1 | 1 | 15 | 6 455.12 | 333.48 |
|   |   |   |   | 30 | 8 106.81 | 436.28 |
|   |   |   |   | 60 | 13 286.2 | 463.96 |
|   |   |   |   | 120 | 27 464.92 | 2 366.48 |
|   | His-CM18-PTD4 | THP-1 | 1 | 15 | 5 605.45 | 933.16 |
|   |   |   |   | 30 | 25 076.41 | 5 567.33 |
|   |   |   |   | 60 | 34 046.94 | 3 669.19 |
|   |   |   |   | 120 | 55 613.48 | 9 836.84 |
|   | His-C(LLKK)₃C-PTD4 | THP-1 | 1 | 15 | 5 475.12 | 693.29 |
|   |   |   |   | 30 | 5 755.8 | 635.18 |
|   |   |   |   | 60 | 8 267.38 | 733.29 |
|   |   |   |   | 120 | 21 165.06 | 209.37 |

TABLE 11.1

Data from FIG. 35A, 35B, 35C and 35F

| FIG. | Shuttle agent | Cells | Conc. of shuttle (µM) | Conc. of GFP-NLS (µM) | Exposure to shuttle/cargo (days) | Mean % cells with GFP signal (±St. Dev.; n = 3) | Cell viability (%) (±St. Dev.; n = 3) |
|---|---|---|---|---|---|---|---|
| 35A | No shuttle (Ctrl) | THP-1 | 0 | 5 | 0 | 0.15 ± 0.04 | 98.7 ± 0.1 |
|  | His-CM18-PTD4 |  | 0.5 | 5 | 1 | 12.1 ± 1 5 | 98.2 ± 2.4 |
|  |  |  |  |  | 3 | 73.4 ± 1.1 | 84.3 ± 3.8 |
| 35B | No shuttle (Ctrl) | THP-1 | 0 | 5 | 0 | 0.36 ± 0.09 | 97.1 ± 1.2 |
|  | His-CM18-PTD4 |  | 0.8 | 2.5 | 1 | 12.2 ± 0.9 | 92.3 ± 1.9 |
|  |  |  |  |  | 3 | 62.4 ± 3.5 | 68.5 ± 2.2 |
| 35C | No shuttle (Ctrl) | THP-1 | 0 | 5 | 0 | 0.28 ± 0.05 | 96.4 ± 2.0 |
|  | His-CM18-PTD4 |  | 0.8 | 1 | 1 | 1.6 ± 0.2 | 98.4 ± 6.4 |
|  |  |  |  |  | 3 | 6.5 ± 0.9 | 80.6 ± 4.6 |
| 35F | No shuttle (Ctrl) | THP-1 | 0 | 5 | 0 | 0.62 ± 0.11 | 96.3 ± 1.4 |
|  | His-C(LLKK)$_3$C-PTD4 |  | 0.8 | 1 | 1 | 1.8 ± 0.2 | 97.2 ± 2.2 |
|  |  |  |  |  | 3 | 6.6 ± 0.8 | 76.6 ± 3.4 |

Figure 35A:
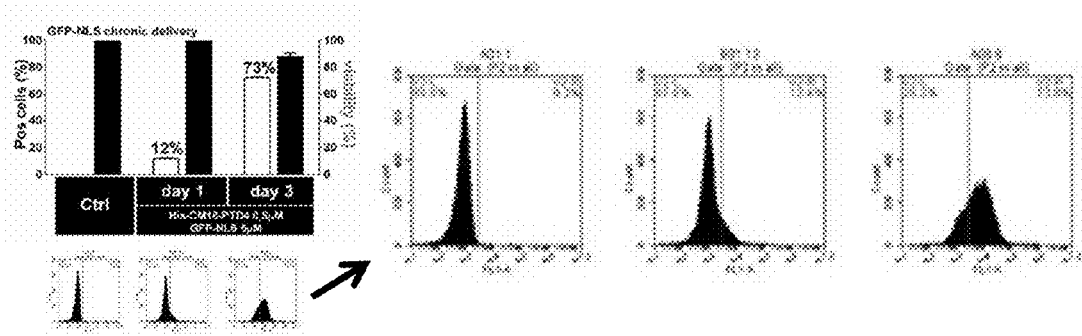
FIG. 35A-35F shows the results of transduction efficiency experiments in which THP-1 cells were exposed daily to GFP-NLS cargo in the presence of a shuttle agent for 2.5 hours. His-CM18-PTD4 was used in FIGS. 35A-35E, and His-C(LLKK)$_3$C-PTD4 was used in FIG. 35F. GFP-NLS transduction efficiency was determined by flow cytometry at Day 1 or Day 3, and the results are expressed as the percentage of GFP fluorescent cells ("Pos cells (%)"), as well as corresponding cell viability data ("viability (%)") in FIGS. 35A, 35B, 35C, and 35F.
Figure 35B:
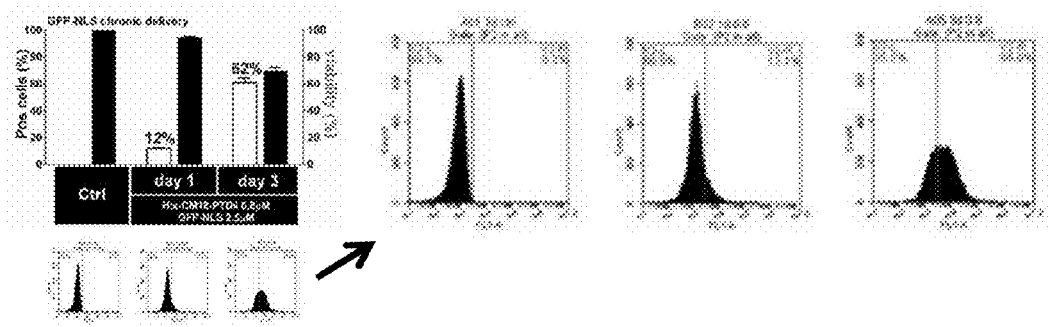
Figure 35C:
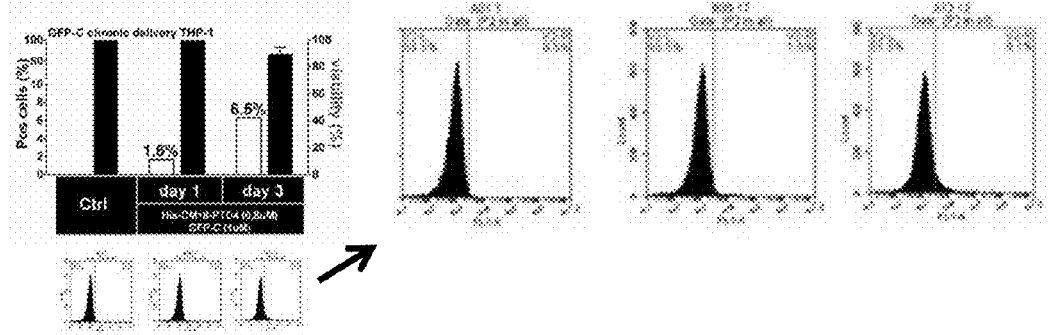
Figures 35D, 35E, 35F:
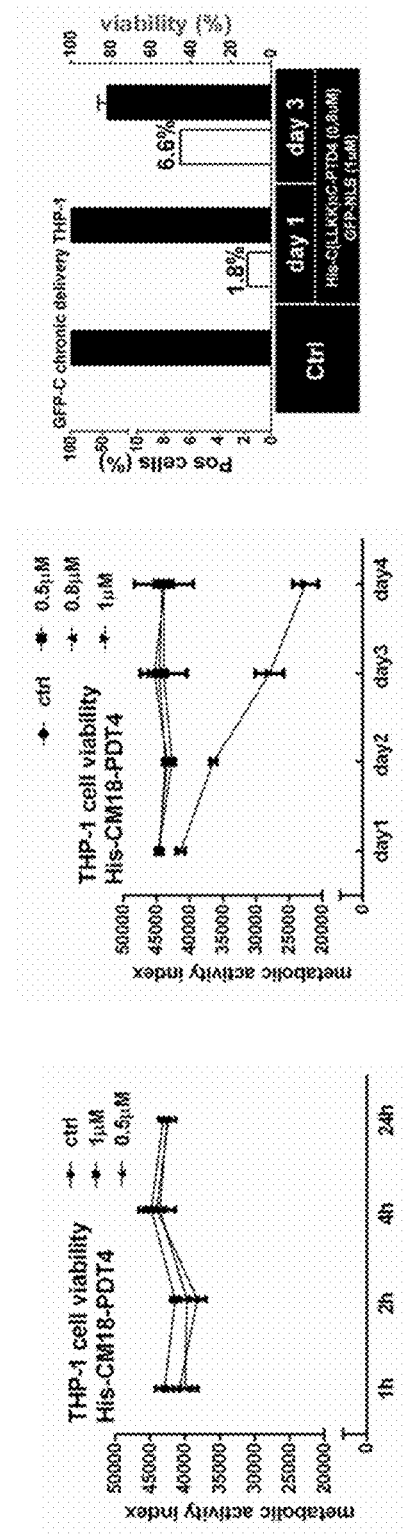

The viability of THP-1 cells repeatedly exposed to His-CM18-PTD4 and GFP-NLS was determined as described in Example 3.3a. The results are shown in Tables 11.2 and 11.3 and in FIGS. 35D and 35E. The results in Table 11.2 and FIG. 35D show the metabolic activity index of the THP-1 cells after 1, 2, 4, and 24 h, and the results in Table 11.3 and FIG. 35E show the metabolic activity index of the THP-1 cells after 1 to 4 days.

Example 12

His-CM18-PTD4 Increases Transduction Efficiency and Nuclear Delivery of GFP-NLS in a Plurality of Cell Lines 12.1 GFP-NLS Transduction with His-CM18-PTD4 in Different Adherent & Suspension Cells: Flow Cytometry The ability of the shuttle agent His-CM18-PTD4 to deliver GFP-NLS to the nuclei of different adherent and

TABLE 11.2

Data from FIG. 35D

| Shuttle agent | Cells | Conc. of shuttle (µM) | Conc. of GFP-NLS (µM) | Mean metabolic activity index (±St. Dev.; n = 3) (Exposure to shuttle/cargo) | | | |
|---|---|---|---|---|---|---|---|
|  |  |  |  | 1 h | 2 h | 4 h | 24 h |
| No shuttle (Ctrl) | THP-1 | 0 | 5 | 40810 ± 757.39 | 38223 ± 238.66 | 44058 ± 320.23 | 42362 ± 333.80 |
| His-CM18-PTD4 | THP-1 | 0.5 | 5 | 9974 ±1749.85 | 9707 ± 1259.82 | 3619 ± 2247.54 | 2559 ± 528.50 |
|  |  | 1 | 5 | 42915 ± 259.67 | 41386 ± 670.66 | 44806 ± 824.71 | 43112 ± 634.56 |

TABLE 11.3

Data from FIG. 35E

| Shuttle agent | Cells | Conc. of shuttle (µM) | Conc. of GFP-NLS (µM) | Mean metabolic activity index (±St. Dev.; n = 3) (Exposure to shuttle/cargo) | | | |
|---|---|---|---|---|---|---|---|
|  |  |  |  | 1 day | 2 days | 3 days | 4 days |
| No shuttle (Ctrl) | THP-1 | 0 | 5 | 44684 ± 283.27 | 43389 ± 642.47 | 45312 ± 963.40 | 43697 ± 1233 |
| His-CM18-PTD4 | THP-1 | 0.5 | 5 | 44665 ± 310.3 | 42664 ± 398.46 | 43927 ± 3511.54 | 43919 ± 4452.25 |
|  |  | 0.8 | 5 | 44531 ± 176.66 | 43667 ± 421.66 | 44586 ± 383.68 | 44122 ± 239.98 |
|  |  | 1 | 5 | 41386 ± 670.66 | 36422 ± 495.01 | 27965 ± 165.33 | 22564 ± 931.28 |

The results in Example 11 show that repeated daily (or chronic) treatments with relatively low concentrations of His-CM18-PTD4 or His-C(LLKK)$_3$C-PTD4 in the presence of serum result in intracellular delivery of GFP-NLS in THP-1 cells. The results also suggest that the dosages of the shuttle agents and the cargo can be independently adjusted to improve cargo transduction efficiency and/or cell viability.

suspension cells using Protocols B (adherent cells) or C (suspension cells) as described in Example 9.1 was examined. The cell lines tested included: HeLa, Balb3T3, HEK 293T, CHO, NIH3T3, Myoblasts, Jurkat, THP-1, CA46, and HT2 cells, which were cultured as described in Example 1. GFP-NLS (5 µM; see Example 5.1) was co-incubated with 35 µM of His-CM18-PTD4 and exposed to adherent cells for 10 seconds (Protocol B), or was co-incubated with 5 µM of His-CM18-PTD4 and exposed to suspension cells for 15 seconds (Protocol C). Cells were washed and subjected to flow cytometry analysis as described in Example 3.3. Results are shown in Table 12.1 and FIG. 36. "Pos cells (%)" is the mean percentages of all cells that emanate a GFP signal.

TABLE 12.1

Figure 36:
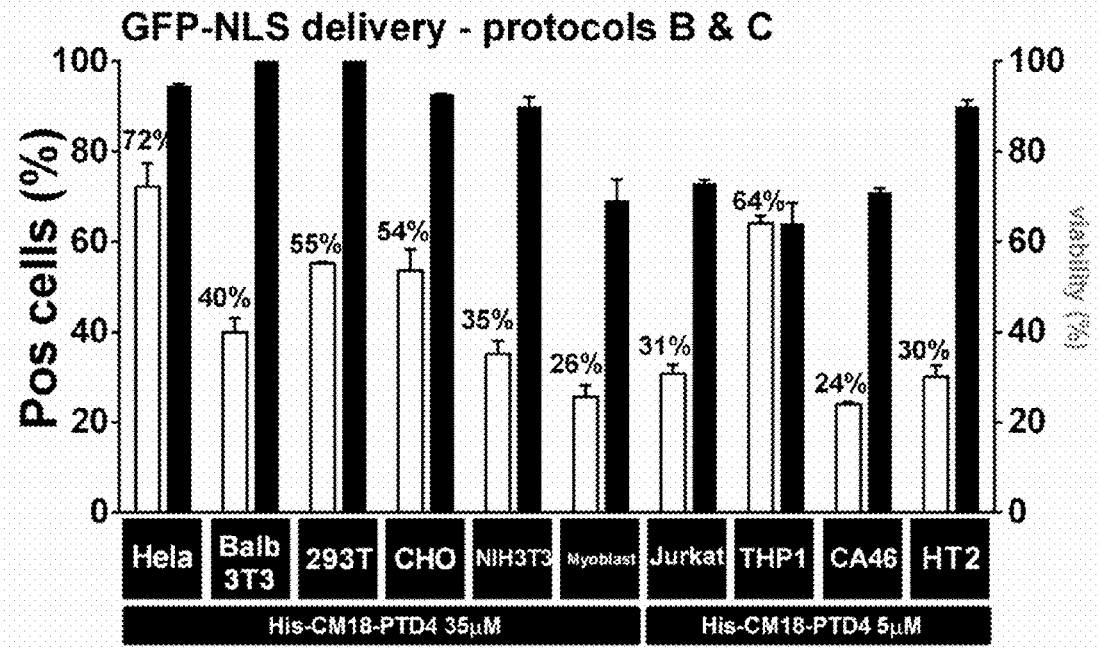
FIG. 36 shows a comparison of the GFP-NLS transduction efficiencies in a plurality of different types of cells (e.g., adherent and suspension, as well as cell lines and primary cells) using the shuttle His-CM18-PTD4, as measured by flow cytometry. The results are expressed as the percentage of GFP fluorescent cells ("Pos cells (%)"), as well as corresponding cell viability data ("viability (%)").

Data from FIG. 36

| Shuttle agent | Protocol | Conc. of shuttle (µM) | Conc. of GFP-NLS (µM) | Cells | Mean % cells with GFP signal (±St. Dev.; n = 3) | Cell viability (%) (±St. Dev.; n = 3) |
|---|---|---|---|---|---|---|
| His-CM18-PTD4 | B | 35 | 5 | HeLa | 72.3 ± 5.3 | 94.6 ± 0.4 |
| | | | | Balb3T3 | 40.2 ± 3.1 | 98.4 ± 0.6 |
| | | | | HEK293T | 55.3 ± 0.2 | 95.3 ± 1.2 |
| | | | | CHO | 53.7 ± 4.6 | 92.8 ± 0.1 |
| | | | | NIH3T3 | 35.4 ± 3.9 | 3.3 ± 5.4 |
| | | | | Myoblasts | 25.6 ± 2.6 | 23.5 ± 1.1 |
| | C | 5 | 5 | Jurkat | 30.7 ± 2.2 | 73.6 ± 0.7 |
| | | | | THP-1 | 64.1 ± 1.6 | 64.1 ± 4.5 |
| | | | | CA46 | 24.4 ± 0.6 | 71.6 ± 1.0 |
| | | | | HT2 | 30.5 ± 2.5 | 90.6 ± 1.5 |

Figure 37A:
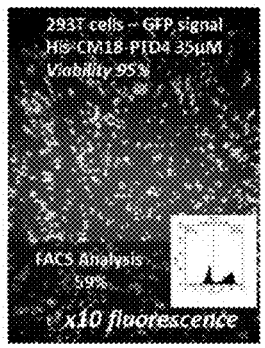
FIGS. 37A-37H show fluorescence microscopy images of different types of cells transduced with GFP-NLS cargo using the shuttle His-CM18-PTD4. GFP fluorescence was visualized by fluorescence microscopy at a 10× magnification. The results of parallel flow cytometry experiments are also provided in the insets (viability and percentage of GFP-fluorescing cells).
Figure 37B:
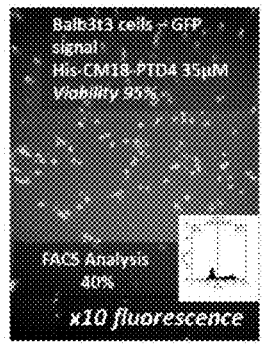
Figure 37C:
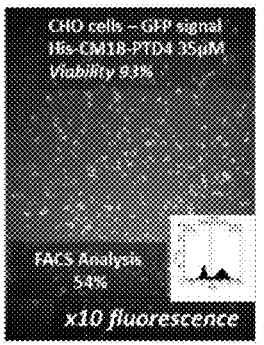
Figure 37D:
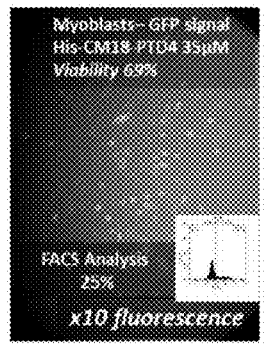
Figure 37E:
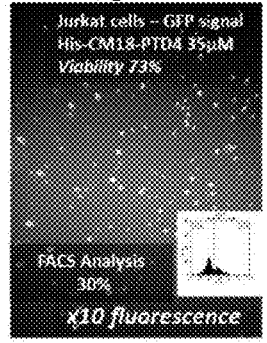
Figure 37F:
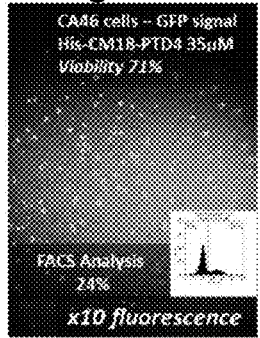
Figure 37G:
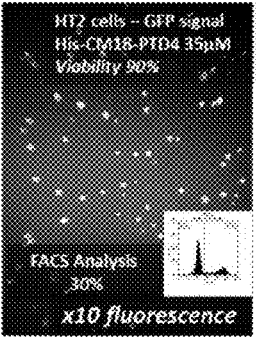
Figure 37H:
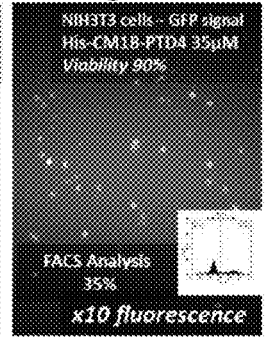

12.2 GFP-NLS Transduction with His-CM18-PTD4 in Several Adherent and Suspension Cells: Visualization by Microscopy GFP-NLS recombinant protein (5 µM; see Example 5.1) was co-incubated with 35 µM of His-CM18-PTD4 and exposed to adherent cells for 10 seconds using Protocol A, or was co-incubated with 5 µM of His-CM18-PTD4 and exposed to suspension cells for 15 seconds using Protocol B, as described in Example 9.1. After washing the cells, GFP fluorescence was visualized by bright field and fluorescence microscopy. Sample images captured at 10× magnifications showing GFP fluorescence are shown for 293T (FIG. 37A), Balb3T3 (FIG. 37B), CHO (FIG. 37C), Myoblasts (FIG. 37D), Jurkat (FIG. 37E), CA46 (FIG. 37F), HT2 (FIG. 37G), and NIH3T3 (FIG. 37H) cells. The insets show corresponding flow cytometry results performed as described in Example 3.3, indicating the percentage of GFP-NLS-positive cells. No significant cellular GFP fluorescence was observed in negative control samples (i.e., cells exposed to GFP-NLS without any shuttle agent; data not shown).

Nuclear localization of the GFP-NLS was further confirmed in fixed and permeabilized myoblasts using cell immuno-labelling as described in Example 3.2a. GFP-NLS was labeled using a primary mouse monoclonal anti-GFP antibody (Feldan, #A017) and a secondary goat anti-mouse Alexa™-594 antibody (Abcam #150116). Nuclei were labelled with DAPI. Sample results for primary human myoblast cells are shown in FIG. 38, in which GFP immuno-labelling is shown in FIG. 38A, and an overlay of the GFP immuno-labelling and DAPI labelling is shown in FIG. 38B. No significant cellular GFP labelling was observed in negative control samples (i.e., cells exposed to GFP-NLS without any shuttle agent; data not shown).

The microscopy results revealed that GFP-NLS is successfully delivered to the nucleus of all the tested cells using the shuttle agent His-CM18-PTD4.

Example 13

His-CM18-PTD4 Enables Transduction of a CRISPR/Cas9-NLS System and Genome Editing in Hela Cells

13.1 Cas9-NLS Recombinant Protein

Cas9-NLS recombinant protein was constructed, expressed and purified from a bacterial expression system as described in Example 1.4. The sequence of the Cas9-NLS recombinant protein produced was:

[SEQ ID NO: 74]
MDKKYSIGLDIGTNSVGWAVITDEYKVPSKKFKVLGNTDRHSIKKNLIGA

LLFDSGETAEATRLKRTARRRYTRRKNRICYLQEIFSNEMAKVDDSFFHR

-continued

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDHIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

-continued

```
DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGDGGRSSDDEATADSQHAAPPKKKRKVGGSGGGS

GGGSGGGRHHHHHH
(MW = 162.9 kDa; pI = 9.05)
NLS sequence is underlined
Serine/glycine rich linkers are in bold
```

13.2 Transfection Plasmid Surrogate Assay

This assay enables one to visually identify cells that have been successfully delivered an active CRISPR/Cas9 complex. As shown in FIG. 39A, the assay involves transfecting cells with an expression plasmid DNA encoding the fluorescent proteins mCherry™ and GFP, with a STOP codon separating their two open reading frames. Transfection of the cells with the expression plasmid results in mCherry™ expression, but no GFP expression (FIG. 39B). A CRISPR/Cas9 complex, which has been designed/programmed to cleave the plasmid DNA at the STOP codon, is then delivered intracellularly to the transfected cells expressing mCherry™ (FIG. 39D). Successful transduction of an active CRISPR/Cas9 complex results in the CRISPR/Cas9 complex cleaving the plasmid DNA at the STOP codon (FIG. 39C). In a fraction of the cells, random non-homologous DNA repair of the cleaved plasmid occurs and results in removal of the STOP codon, and thus GFP expression and fluorescence (FIG. 39E).

On Day 1 of the transfection plasmid surrogate assay, DNA plasmids for different experimental conditions (250 ng) are diluted in DMEM (50 μL) in separate sterile 1.5-mL tubes, vortexed and briefly centrifuged. In separate sterile 1.5-mL tubes, Fastfect™ transfection reagent was diluted in DMEM (50 μL) with no serum and no antibiotics at a ratio of 3:1 (3 μL of Fastfect™ transfection reagent for 1 μg of DNA) and then quickly vortexed and briefly centrifuged. The Fastfect™/DMEM mixture was then added to the DNA mix and quickly vortexed and briefly centrifuged. The Fastfect™/DMEM/DNA mixture is then incubated for 15-20 min at room temperature, before being added to the cells (100 μL per well). The cells are then incubated at 37° C. and 5% CO2 for 5 h. The media is then changed for complete medium (with serum) and further incubated at 37° C. and 5% CO2 for 24-48 h. The cells are then visualized under fluorescent microscopy to view the mCherry™ signal.

13.3 His-CM18-PTD4-Mediated CRISPR/Cas9-NLS System Delivery and Cleavage of Plasmid DNA RNAs (crRNA & tracrRNA) were designed to target a nucleotide sequence of the EMX1 gene, containing a STOP codon between the mCherry™ and GFP coding sequences in the plasmid of Example 13.2. The sequences of the crRNA and tracrRNA used were as follows:

```
crRNA [SEQ ID NO: 75]:
5'-GAGUCCGAGCAGAAGAAGAAGUUUUAGAGCUAUGCUGUUUUG-3' tracrRNA [SEQ ID NO: 76]:
5'-
AAACAGCAUAGCAAGUUAAAAUAAGGCUAGUCCGUUAUCAACUUGAAAAA

GUGGCACCGAGUCGGUGCU-3'
```

HeLa cells were cultured and subjected to the transfection plasmid surrogate assay as described in Example 13.2). On Day 1, the HeLa cells were transfected with a plasmid surrogate encoding the mCherry™ protein as shown in FIG. 39A. On Day 2, a mix of Cas9-NLS recombinant protein (2 μM; see Example 13.1) and RNAs (crRNA & tracrRNA; 2 μM; see above) were co-incubated with 50 μM of His-CM18-PTD4, and the mixture (CRISPR/Cas9 complex) was exposed to HeLa cells for 10 seconds using Protocol B as described in Example 9.1. Double-stranded plasmid DNA cleavage by the CRISPR/Cas9 complex at the STOP codon between the mCherry™ and GFP coding sequences (FIG. 39B), and subsequent non-homologous repair by the cell in some cases results in removal of the STOP codon (FIG. 39C), thereby allowing expression of both the mCherry™ and GFP fluorescent proteins in the same cell on Day 3 (FIG. 39D-39E). White triangle windows in FIGS. 39D and 39E indicate examples of areas of co-labelling between mCherry™ and GFP.

As a positive control for the CRISPR/Cas9-NLS system, HeLa cells were cultured and co-transfected with three plasmids: the plasmid surrogate (as described in Example 13.2) and other expression plasmids encoding the Cas9-NLS protein (Example 13.1) and the crRNA/tracrRNAs (Example 13.3). Typical fluorescence microscopy results are shown in FIG. 40A-D. Panels A and B show cells 24 hours post-transfection, while panels C and D show cells 72 hours post-transfection.

FIG. 40E-40H shows the results of a parallel transfection plasmid surrogate assay performed using 35 μM of the shuttle His-CM18-PTD4, as described for FIG. 39. FIGS. 40E and 40F show cells 24 hours post-transduction, while panels G and H show cells 48 hours post-transduction. FIGS. 40E and 40G show mCherry™ fluorescence, and FIGS. 40F and 40H show GFP fluorescence, the latter resulting from removal of the STOP codon by the transduced CRISPR/Cas9-NLS complex and subsequent non-homologous repair by the cell. No significant cellular GFP fluorescence was observed in negative control samples (i.e., cells exposed to CRISPR/Cas9-NLS complex without any shuttle agent; data not shown).

13.4 T7E1 Assay

The T7 endonuclease I (T7E1) can be used to detect on-target CRISPR/Cas genome editing events in cultured cells. As an overview, genomic DNA from target cells is amplified by PCR The PCR products are then denatured and reannealed to allow heteroduplex formation between wild-type DNA and CRISPR/Cas-mutated DNA. T7E1, which recognizes and cleaves mismatched DNA, is used to digest the heteroduplexes. The resulting cleaved and full-length PCR products are visualized by gel electrophoresis.

The T7E1 assay was performed with the Edit-R™ Synthetic crRNA Positive Controls (Dharmacon #U-007000-05) and the T7 Endonuclease I (NEB, Cat #M0302S). After the delivery of the CRISPR/Cas complex, cells were lysed in 100 μL of Phusion™ High-Fidelity DNA polymerase (NEB #M0530S) laboratory with additives. The cells were incubated for 15-30 minutes at 56° C., followed by deactivation for 5 minutes at 96° C. The plate was briefly centrifuged to collect the liquid at bottom of the wells. 50-μL PCR samples were set up for each sample to be analyzed. The PCR samples were heated to 95° C. for 10 minutes and then slowly (>15 minutes) cooled to room temperature. PCR product (~5 μL) was then separated on an agarose gel (2%) to confirm amplification. 15 μL of each reaction was incubated with T7E1 nuclease for 25 minutes at 37° C. Immediately, the entire reaction volume was run with the appropriate gel loading buffer on an agarose gel (2%).

13.5 His-CM18-PTD4 and His-C(LLKK)₃C-PTD4-Mediated CRISPR/Cas9-NLS System Delivery and Cleavage of Genomic PPIB Sequence A mix composed of a Cas9-NLS recombinant protein (25 nM; Example 13.1) and crRNA/tracrRNA (50 nM; see below) targeting a nucleotide sequence of the PPIB gene were co-incubated with 10 μM of His-CM18-PTD4 or His-C(LLKK)3C-PTD4, and incubated with HeLa cells for 16 h in medium without serum using Protocol A as described in Example 9.1.

The sequences of the crRNA and tracrRNAs constructed and their targets were:

```
Feldan tracrRNA [SEQ ID NO: 77]:
5'-
AAACAGCAUAGCAAGUUAAAAUAAGGCUAGUCCGUUAUCAACUUGAAAAA

GUGGCACCGAGUCGGUGCU-3'

PPIB crRNA [SEQ ID NO: 78]:
5'-GUGUAUUUUGACCUACGAAUGUUUUAGAGCUAUGCUGUUUUG-3'

Dharmacon tracrRNA [SEQ ID NO: 79]:
5'-
AACAGCAUAGCAAGUUAAAAUAAGGCUAGUCCGUUAUCAACUUGAAAAAG

UGGCACCGAGUCGGUGCUUUUUUU-3'
```

After 16 h, HeLa cells were washed with PBS and incubated in medium with serum for 48 h. HeLa cells were harvested to proceed with the T7E1 protocol assay as described in Example 13.4.

FIG. 41A shows an agarose gel with the PPIB DNA sequences after PCR amplification. Lane A shows the amplified PPIB DNA sequence in HeLa cells without any treatment (i.e., no shuttle or Cas9/RNAs complex). Lanes B: The two bands framed in white box #1 are the cleavage product of the PPIB DNA sequence by the CRIPR/Cas9 complex after the delivery of the complex with the shuttle His-C(LLKK)3C-PTD4. Lane C: These bands show the amplified PPIB DNA sequence after incubation of the HeLa cells with the Cas9/RNAs complex without shuttle (negative control). Lane D: The bands framed in white box #2 show the amplified PPIB DNA sequence after incubation of the HeLa cells with the Cas9/RNAs complex in presence of a lipidic transfection agent (DharmaFect™ transfection reagent # T-20XX-01) (positive control). Similar results were obtained using the shuttle His-CM18-PTD4 (data not shown).

Figure 41B:
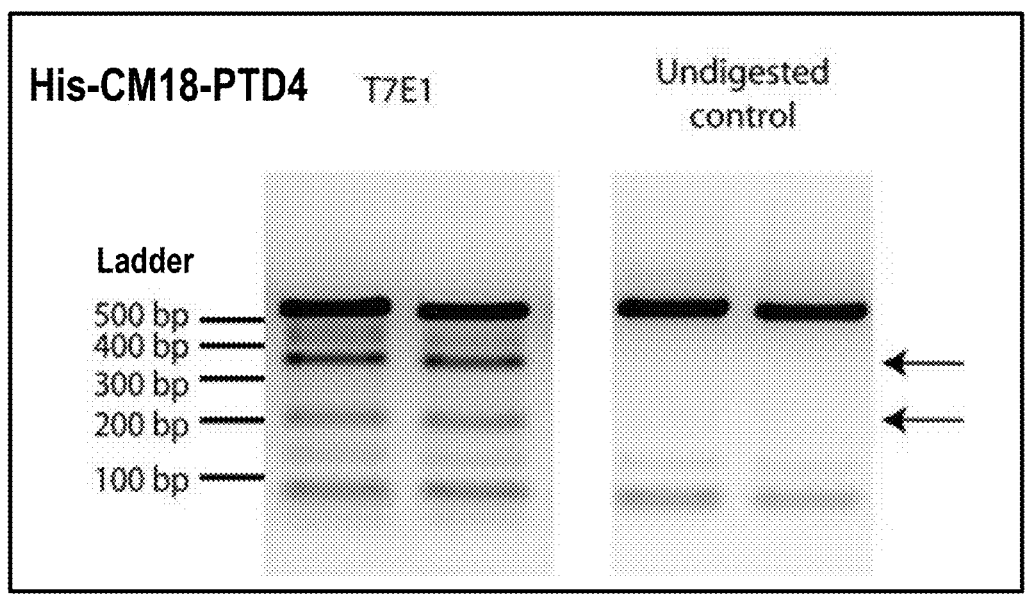
FIG. 41B shows the products of a DNA cleavage assay (T7E1 assay) separated by agarose gel electrophoresis, which is used to measure CRISPR/Cas9-mediated cleavage of cellular genomic DNA (PPIB DNA sequences). The left panel shows the cleavage product of the amplified PPIB DNA sequence by the CRIPR/Cas9 complex after the delivery of the complex with the shuttle agent His-CM18-PTD4 in HeLa cells. The right panel shows amplified DNA sequence before the T7E1 digestion procedure as a negative control.

FIG. 41B shows an agarose gel with the PPIB DNA sequences after PCR amplification. The left panel shows the cleavage product of the amplified PPIB DNA sequence by the CRIPR/Cas9 complex after the delivery of the complex with the shuttle agent His-CM18-PTD4 in HeLa cells. The right panel shows amplified DNA sequence before the T7E1 digestion procedure as a negative control.

Figure 41C:
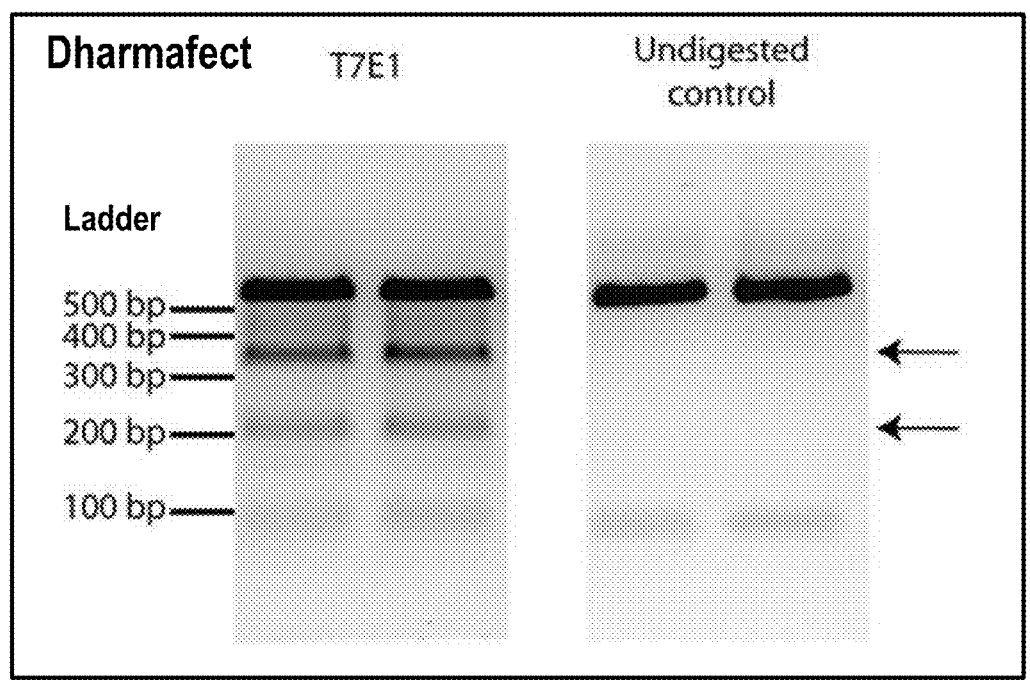
FIG. 41C shows the products of a DNA cleavage assay (T7E1 assay) separated by agarose gel electrophoresis, which is used to measure CRISPR/Cas9-mediated cleavage of cellular genomic DNA (PPIB DNA sequences). The left panel shows the amplified PPIB DNA sequence after incubation of the HeLa cells with the Cas9/RNAs complex in presence of a lipidic transfection agent (DharmaFect™ transfection reagent # T-20XX-01) (positive control). The right panel shows amplified DNA sequence before the T7E1 digestion procedure as a negative control.

FIG. 41C shows an agarose gel with the PPIB DNA sequences after PCR amplification. The left panel shows the amplified PPIB DNA sequence after incubation of the HeLa cells with the Cas9/RNAs complex in presence of a lipidic transfection agent (DharmaFect™ transfection reagent # T-20XX-01) (positive control). The right panel shows amplified DNA sequence before the T7E1 digestion procedure as a negative control.

These results show that the shuttle agents His-CM18-PTD4 and His-C(LLKK)3C-PTD4 successfully deliver a functional CRISPR/Cas9 complex to the nucleus of HeLa cells, and that this delivery results in CRISPR/Cas9-mediated cleavage of genomic DNA.

13.6 CRISPR/Cas9-NLS System Delivery by Different Shuttle Agents, and Cleavage of Genomic HPTR Sequence in HeLa and Jurkat Cells A mix composed of a Cas9-NLS recombinant protein (2.5 μM; Example 13.1) and crRNA/tracrRNA (2 μM; see below) targeting a nucleotide sequence of the HPTR gene were co-incubated with 35 μM of His-CM18-PTD4, His-CM18-PTD4-His, His-C(LLKK)3C-PTD4, or EB1-PTD4, and incubated with HeLa or Jurkat cells for 2 minutes in PBS using Protocol B as described in Example 9.1.

The sequences of the crRNA and tracrRNAs constructed and their targets were:

```
Feldan tracrRNA:
                                  [SEQ ID NO: 77]
5'-AAACAGCAUAGCAAGUUAAAAUAAGGCUAGUCCGUUAUCAACUU

GAAAAAGUGGCACCGAGUCGGUGCU-3'

HPRT crRNA:
                                 [SEQ ID NO: 103]
5'-AAUUAUGGGGAUUACUAGGAGUUUUAGAGCUAUGCU-3'
```

Figure 46A:
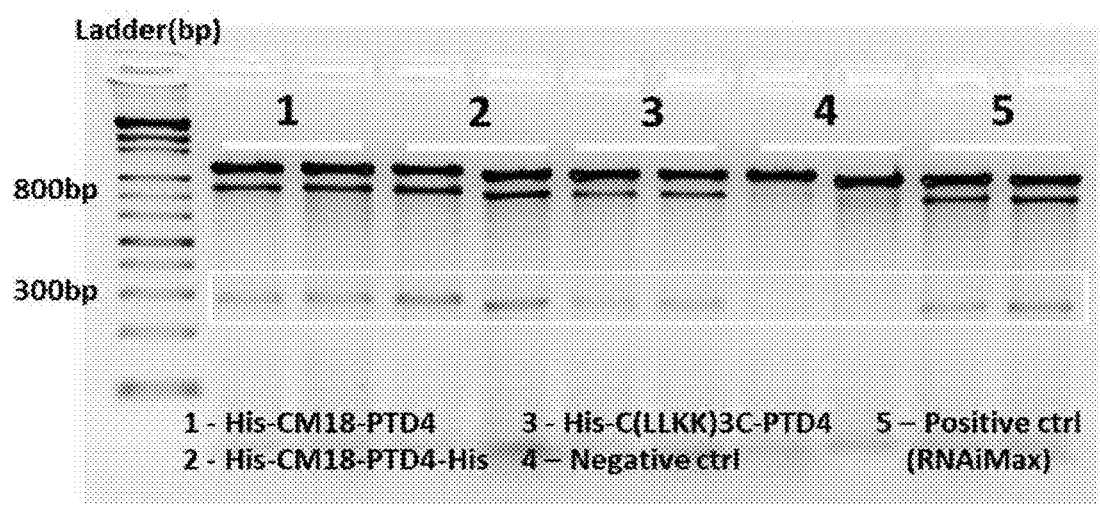
FIGS. 46A and 46B show the products of a DNA cleavage assay separated by agarose gel electrophoresis, which is used to measure CRISPR/Cas9-mediated cleavage of cellular genomic DNA (HPTR sequence) after intracellular delivery of the complex with different shuttle agents.
Figure 46B:
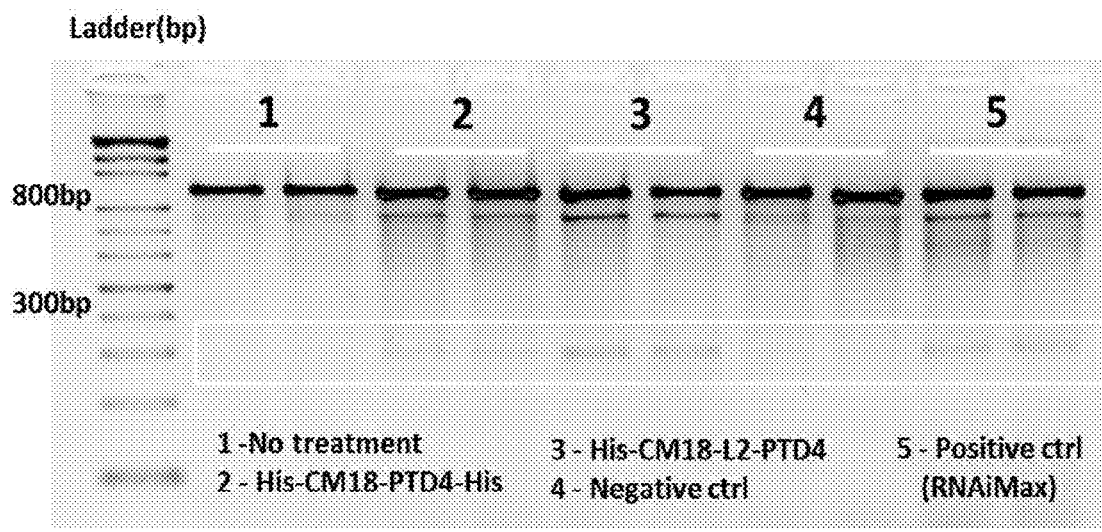

After 2 minutes, cells were washed with PBS and incubated in medium with serum for 48 h. Cells were harvested to proceed with the T7E1 protocol assay as described in Example 13.4. FIG. 46 shows an agarose gel with the HPTR DNA sequences after PCR amplification and the cleavage product of the amplified HPTR DNA sequence by the CRISPR/Cas9 complex after the delivery of the complex with the different shuttle agents. FIG. 46A shows the results with the shuttle agents: His-CM18-PTD4, His-CM18-PTD4-His, and His-C(LLKK)3C-PTD4 in HeLa cells. FIG. 46B shows the results with His-CM18-PTD4 and His-CM18-L2-PTD4 in Jurkat cells. Negative controls (lanes 4) show amplified HPTR DNA sequence after incubation of the cells with the CRISPR/Cas9 complex without the presence of the shuttle agent. Positive controls (lane 5 in FIGS. 46A and 46B) show the amplified HPTR DNA sequence after incubation of the cells with the Cas9/RNAs complex in presence of a lipidic transfection agent (Lipofectamine® RNAiMAX™ Transfection Reagent ThermoFisher Product No. 13778100).

These results show that different polypeptide shuttle agents of the present description may successfully deliver a functional CRISPR/Cas9 complex to the nucleus of HeLa and Jurkat cells, and that this delivery results in CRISPR/Cas9-mediated cleavage of genomic DNA.

Example 14

His-CM18-PTD4 Enables Transduction of the Transcription Factor HOXB4 in THP-1 Cells

14.1 HOXB4-WT Recombinant Protein

Human HOXB4 recombinant protein was constructed, expressed and purified from a bacterial expression system as described in Example 1.4. The sequence of the HOXB4-WT recombinant protein produced was:

```
                                  [SEQ ID NO: 80]
MHHHHHHMAMSSFLINSNYVDPKFPPCEEYSQSDYLPSDHSPGYYAGGQ

RRESSFQPEAGFGRRAACTVQRYPPPPPPPPPPGLSPRAPAPPPAGAL

LPEPGQRCEAVSSSPPPPPCAQNPLHPSPSHSACKEPVVYPWMRKV
```

-continued

```
HVSTVNPNYAGGEPKRSRTAYTRQQVLELEKEFHYNRYLTRRRRVEIAH

ALCLSERQIKIWFQNRRMKWKKDEIKLPNTKIRSGGAAGSAGGPPGRP

NGGPRAL
(MW = 28.54 kDa; pI = 9.89)
The initiator methionine and the 6x Histidine tag are shown in
bold.
``` different concentrations of His-CM18-PTD4 (0, 0.5, 7.5, 0.8 or 1 µM) and then exposed to THP-1 cells for 2.5 hours in the presence of serum. The cells were subjected to real time-PCR analysis as described in Example 14.2 to measure the mRNA levels of a target gene as a marker for HOXB4 activity, which was then normalized to the target gene mRNA levels detected in the negative control cells (no treatment), to obtain a "Fold over control" value. Total RNA levels (ng/µL) were also measured as a marker for cell viability. Results are shown in Table 14.1 and FIG. 42.

TABLE 14.1

Figure 42:
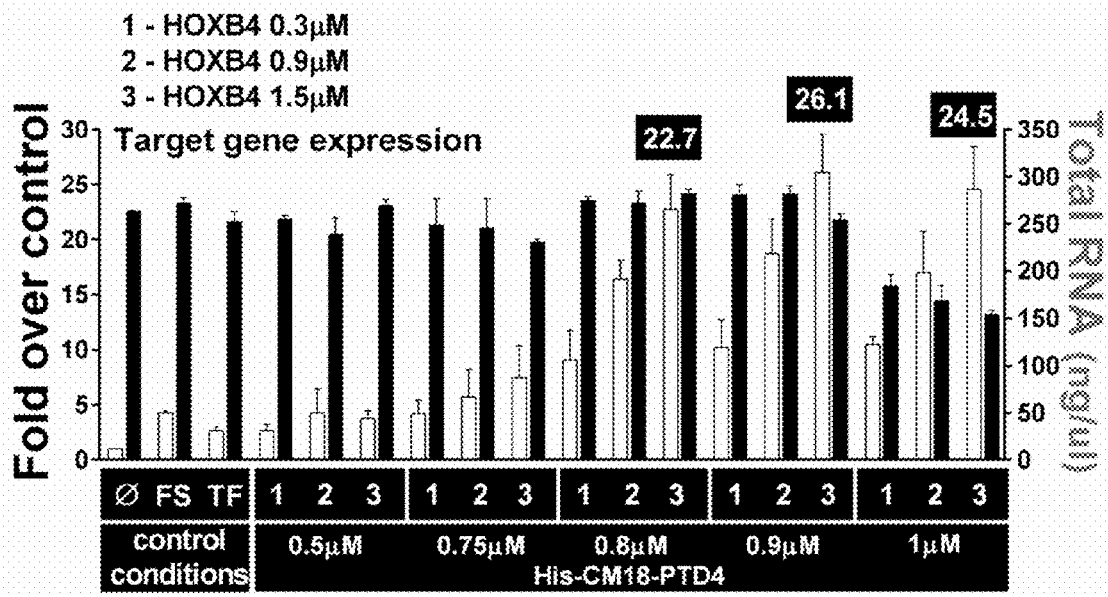
FIGS. 42-44 show the transcriptional activity of THP-1 cells that have been transduced with the transcription factor HOXB4 using different concentrations of the shuttle His-CM18-PTD4 and different cargo/shuttle exposure times. Successful intra-nuclear delivery of HOXB4 was determined by monitoring mRNA levels of a target gene by real-time PCR, and the results are normalized against those in the negative control (HOXB4 without shuttle agent) and expressed as "Fold over control" (left bars). Total cellular RNA (ng/µL) was quantified and used a marker for cell viability (right bars). "Ø" or "Ctrl" means "no treatment"; "TF" means "Transcription Factor alone"; "FS" means "shuttle alone".

Data from FIG. 42

| Cargo/shuttle agent (FIG. 41) | Cells | Conc. of shuttle (µM) | Conc. of HOXB4-WT (µM) | Fold over control (mean ± St. Dev) | Total RNA in ng/µL (mean ± St. Dev) |
|---|---|---|---|---|---|
| No treatment ("Ø") | THP-1 | 0 | 0 | 1 ± 0.1 | 263 ± 0.4 |
| HOXB4-WT alone ("TF") | THP-1 | 0 | 1.5 | 4.3 ± 0.1 | 271 ± 6.0 |
| His-CM18-PTD4 alone ("FS") | THP-1 | 1 | 0 | 2.7 ± 0.3 | 252 ± 10.7 |
| His-CM18-PTD4 + HOXB4-WT | THP-1 | 0.5 | 0.3 | 2.7 ± 0.6 | 255 ± 3.9 |
| | | | 0.9 | 4.3 ± 2.1 | 239 ± 17.5 |
| | | | 1.5 | 3.8 ± 0.7 | 269 ± 6.4 |
| His-CM18-PTD4 + HOXB4-WT | THP-1 | 0.75 | 0.3 | 4.2 ± 1.2 | 248 ± 28 |
| | | | 0.9 | 5.7 ± 2.5 | 245 ± 31 |
| | | | 1.5 | 7.5 ± 2.8 | 230 ± 3.3 |
| His-CM18-PTD4 + HOXB4-WT | THP-1 | 0.8 | 0.3 | 9.1 ± 2.7 | 274 ± 4.4 |
| | | | 0.9 | 16.4 ± 1.7 | 272 ± 12.5 |
| | | | 1.5 | 22.7 ± 3.2 | 282 ± 4.7 |
| His-CM18-PTD4 + HOXB4-WT | THP-1 | 0.9 | 0.3 | 10.2 ± 2.5 | 280 ± 11.3 |
| | | | 0.9 | 18.7 ± 3.1 | 281 ± 9.2 |
| | | | 1.5 | 26.1 ± 3.5 | 253 ± 7.1 |
| His-CM18-PTD4 + HOXB4-WT | THP-1 | 1 | 0.3 | 10.5 ± 0.7 | 184 ± 12.3 |
| | | | 0.9 | 17 ± 3.7 | 168 ± 16.2 |
| | | | 1.5 | 24.5 ± 3.9 | 154 ± 4.7 |

14.2 Real-Time Polymerase Chain Reaction (Rt-PCR)

Control and treated cells are transferred to separate sterile 1.5-mL tubes and centrifuged for 5 minutes at 300 g. The cell pellets are resuspended in appropriate buffer to lyse the cells. RNAase-free 70% ethanol is then added followed by mixing by pipetting. The lysates are transferred to an RNeasy™ Mini spin column and centrifuged 30 seconds at 13000 RPM. After several washes with appropriate buffers and centrifugation steps, the eluates are collected in sterile 1.5-mL tubes on ice, and the RNA quantity in each tube is then quantified with a spectrophotometer. For DNase treatment, 2 µg of RNA is diluted in 15 µL of RNase-free water. 1.75 µL of 10× DNase buffer and 0.75 µL of DNase is then added, followed by incubation at 37° C. for 15 minutes. For reverse transcriptase treatment, 0.88 µL of EDTA (50 nM) is added, followed by incubation at 75° C. for 5 minutes. In a PCR tube, 0.5 µg of DNase-treated RNA is mixed with 4 µL of iScript™ Reverse transcription Supermix (5×) and 20 µL of nuclease-free water. The mix is incubated in a PCR machine with the following program: 5 min at 25° C., 30 min at 42° C. and 5 min at 85° C. Newly synthesized cDNA is transferred in sterile 1.5-mL tubes and diluted in 2 µL of nuclease-free water. 18 µL per well of a qPCR machine (CFX-96TM) mix is then added in a PCR plate for analysis.

14.3 HOXB4-WT Transduction by His-CM18-PTD4 in THP-1 Cells: Dose Responses and Viability THP-1 cells were cultured and tested in the protein transduction assay using Protocol A as described in Example 9.1. Briefly, THP-1 cells were plated at 30000 cells/well one day before transduction. HOXB4-WT recombinant protein (0.3, 0.9, or 1.5 µM; Example 14.1) was co-incubated with These results show that exposing THP-1 cells to a mixture of the shuttle agent His-CM18-PTD4 and the transcription factor HOXB4-WT for 2.5 hours in the presence of serum results in a dose-dependent increase in mRNA transcription of the target gene. These results suggest that HOXB4-WT is successfully delivered in an active form to the nucleus of THP-1 cells, where it can mediate transcriptional activation.

14.4 HOXB4-WT Transduction by His-CM18-PTD4 in THP-1 Cells: Time Course and Viability (0 to 48 Hours)

THP-1 cells were cultured and tested in the protein transduction assay using Protocol A as described in Example 9.1. Briefly, THP-1 cells were plated at 30000 cells/well one day before the first time course experiment. HOXB4-WT recombinant protein (1.5 µM; Example 14.1) was co-incubated with His-CM18-PTD4 (0.8 µM) and then exposed to THP-1 cells for 0, 2.5, 4, 24 or 48 hours in presence of serum. The cells were subjected to real time-PCR analysis as described in Example 14.2 to measure mRNA levels of a target gene as a marker for HOXB4 activity, which was then normalized to the target gene mRNA levels detected in the negative control cells (no treatment), to obtain a "Fold over control" value. Total RNA levels (ng/µL) were also measured as a marker for cell viability. Results are shown in Table 14.2 and FIG. 43.

TABLE 14.2

Figure 43:
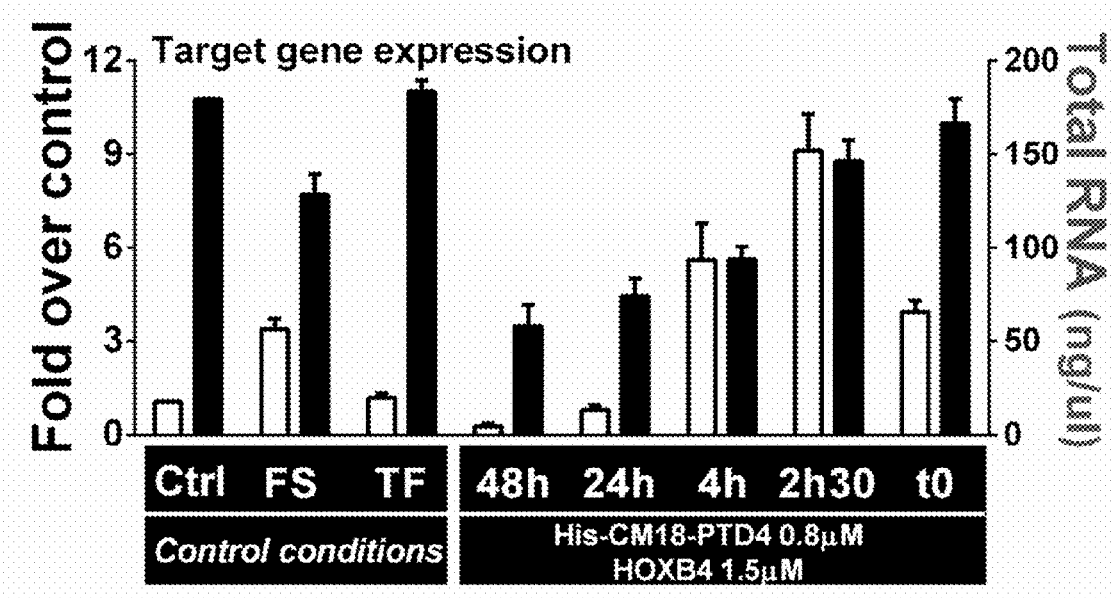

Data from FIG. 43

| Cargo/shuttle agent (FIG. 43) | Cells | Conc. of shuttle (μM) | Conc. of HOXB4-WT (μM) | Exposure time (hours) | Fold over control (mean ± St. Dev) | Total RNA in ng/μL (mean ± St. Dev) |
|---|---|---|---|---|---|---|
| No treatment ("Ctrl") | THP-1 | 0 | 0 | — | 1 ± 0.1 | 180 ± 0.4 |
| HOXB4-WT alone ("TF") | THP-1 | 0 | 1.5 | 2.5 h | 3.4 ± 0.3 | 129 ± 10.7 |
| His-CM18-PTD4 alone ("FS") | THP-1 | 0.8 | 0 | 2.5 h | 1.2 ± 0.14 | 184 ± 6.0 |
| His-CM18-PTD4 + HOXB4-WT | THP-1 | 0.8 | 1.5 | 48 h | 0.27 ± 0.1 | 58 ± 11.2 |
| | | | | 24 h | 0.8 ± 0.14 | 74 ± 9.2 |
| | | | | 4 h | 5.6 ± 1.2 | 94 ± 7.1 |
| | | | | 2.5 h | 9.1 ± 1.2 | 146 ± 11.6 |
| | | | | 0 | 3.9 ± 0.4 | 167 ± 13 |

14.5 HOXB4-WT Transduction by His-CM18-PTD4 in THP-1 Cells: Time Course and Viability (0 to 4 Hours)

THP-1 cells were cultured and tested in the protein transduction assay using Protocol A as described in Example 9.1. Briefly, THP-1 cells were plated at 30000 cells/well one day before the first time course experiment. HOXB4-WT recombinant protein (0.3 μM; Example 14.1) was co-incubated with His-CM18-PTD4 (0.8 μM) and then exposed to THP-1 cells for 0, 0.5, 1, 2, 2.5, 3 or 4 hours in presence of serum. The cells were subjected to real time-PCR analysis as described in Example 14.2 to measure mRNA levels of a target gene as a marker for HOXB4 activity, which was then normalized to target gene mRNA levels detected in the negative control cells (no treatment), to obtain a "Fold over control" value. Total RNA levels (ng/μL) were also measured as a marker for cell viability. Results are shown in Table 14.3 and FIG. 44.

1/500, and a secondary anti-mouse antibody Alexa™-594 (Abcam #150116) diluted 1/1000. Nuclei were labelled with DAPI. The cells were visualized by bright field and fluorescence microscopy at 20× and 40× magnifications as described in Example 3.2, and sample results are shown in FIG. 45. Co-localization was observed between nuclei labelling (FIGS. 45A and 45C) and HOXB4-WT labelling (FIGS. 45B and 45D), indicating that HOXB4-WT was successfully delivered to the nucleus after 30 min in the presence of the shuttle agent His-CM18-PTD4. White triangle windows show examples of areas of co-localization between the nuclei (DAPI) and HOXB4-WT immuno-labels.

14.7 HOXB4-WT Transduction by Different Shuttle Agents in THP-1 Cells: Dose Responses and Viability THP-1 cells were cultured and tested in the protein transduction assay using Protocol A as described in Example 9.1. Briefly, THP-1 cells were plated at 30000 cells/well one

TABLE 14.3

Figure 44:
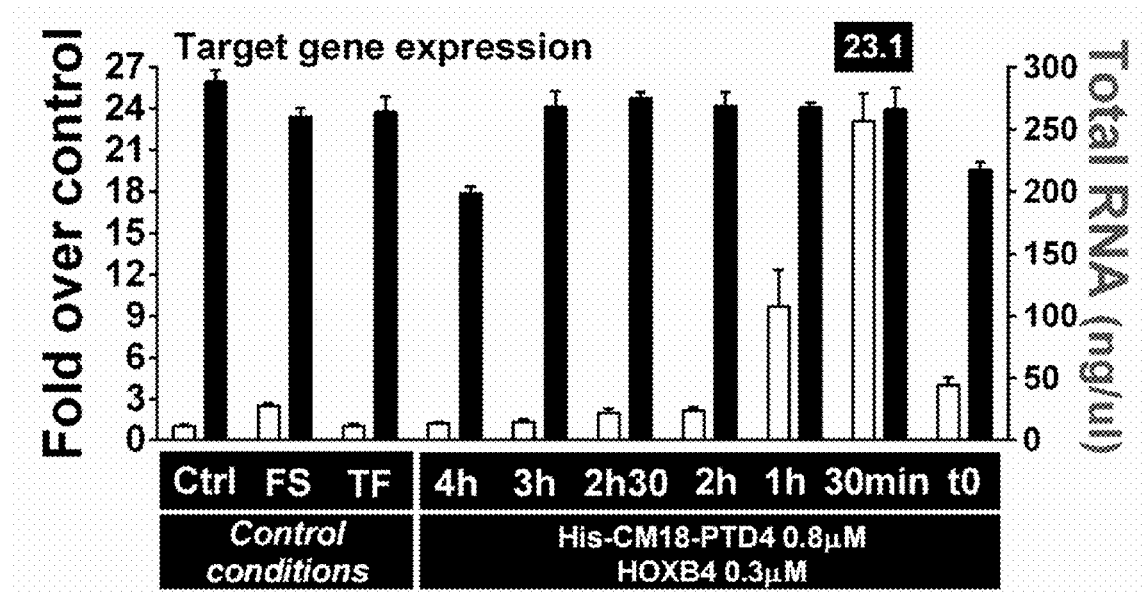
Figure 45A:
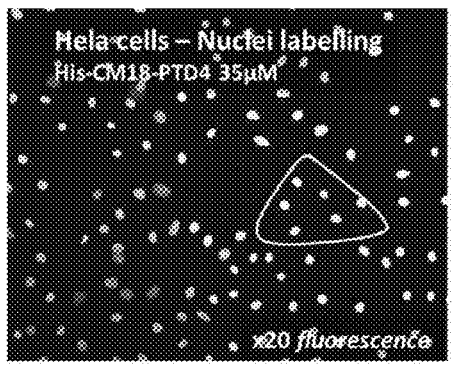
FIGS. 45A-45D show fluorescence microscopy images of HeLa cells transduced with wild-type HOXB4 cargo using the shuttle His-CM18-PTD4. After a 30-minute incubation to allow transduced HOXB4-WT to accumulate in the nucleus, the cells were fixed, permeabilized and HOXB4-WT was labelled using a primary anti-HOXB4 monoclonal antibody and a fluorescent secondary antibody (FIGS. 45B and 45D). Nuclei were labelled with DAPI (FIGS. 45A and 45C). White triangle windows indicate examples of areas of co-labelling between nuclei and HOXB4—compare FIG. 45A vs 45B (×20 magnification), and FIG. 45C vs 45D (×40 magnification).
Figure 45B:
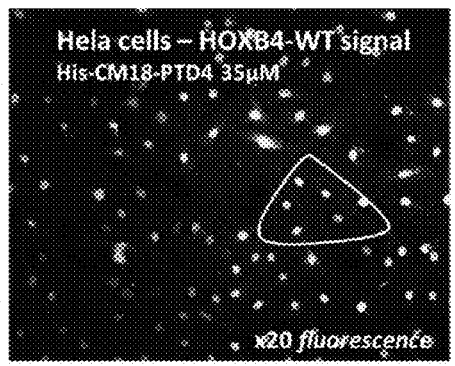
Figure 45C:
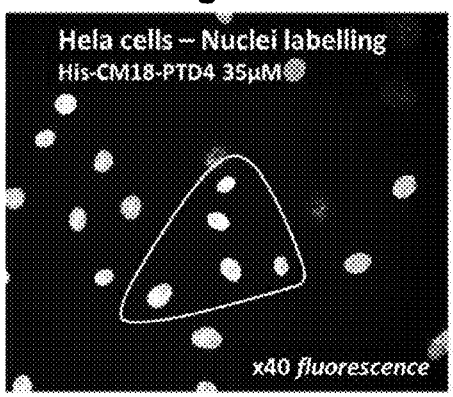
Figure 45D:
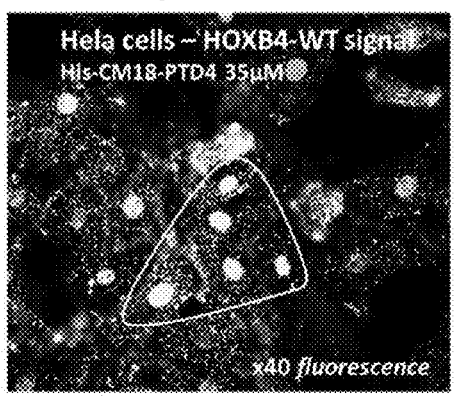

Data from FIG. 44

| Cargo/shuttle agent (FIG. 42) | Cells | Conc. of shuttle (μM) | Conc. of HOXB4-WT (μM) | Exposure time (hours) | Fold over control (mean ± St. Dev) | Total RNA in ng/μL (mean ± St. Dev) |
|---|---|---|---|---|---|---|
| No treatment ("Ctrl") | THP-1 | 0 | 0 | — | 1 ± 0.1 | 289 ± 9.2 |
| His-CM18-PTD4 alone ("FS") | THP-1 | 0 | 0.3 | 2.5 h | 2.5 ± 0.2 | 260 ± 7.1 |
| HOXB4-WT alone ("TF") | THP-1 | 0.8 | 0 | 2.5 h | 1 ± 0.14 | 264 ± 12.3 |
| His-CM18-PTD4 + HOXB4-WT | THP-1 | 0.8 | 0.3 | 4 h | 1.2 ± 0.1 | 198 ± 6.0 |
| | | | | 3 h | 1.3 ± 0.21 | 268 ± 12.5 |
| | | | | 2.5 h | 2 ± 0.3 | 275 ± 4.7 |
| | | | | 2 h | 2.2 ± 0.2 | 269 ± 12.5 |
| | | | | 1 | 9.7 ± 2.6 | 268 ± 3.9 |
| | | | | 0.5 | 23.1 ± 2.0 | 266 ± 17.5 |
| | | | | 0 | 4 ± 0.5 | 217 ± 6.4 |

14.6 HOXB4-WT Transduction by His-CM18-PTD4 in HeLa Cells: Immuno-Labelling and Visualization by Microscopy Recombinant HOXB4-WT transcription factor (25 μM; Example 14.1) was co-incubated with 35 μM of His-CM18-PTD4 and exposed to HeLa cells for 10 seconds using Protocol B as described in Example 9.1. After a 30-minute incubation to allow transduced HOXB4-WT to accumulate in the nucleus, the cells were fixed, permeabilized and immuno-labelled as described in Example 3.2a. HOXB4-WT was labelled using a primary mouse anti-HOXB4 monoclonal antibody (Novus Bio #NBP2-37257) diluted day before the first time course experiment. HOXB4-WT recombinant protein (1.5 μM; Example 14.1) co-incubated with the shuttle agents His-CM18-PTD4, TAT-KALA, EB1-PTD4, His-C(LLKK)3C-PTD4 and His-CM18-PTD4-His at 0.8 μM, and then exposed to THP-1 cells for 2.5 hours in presence of serum. The cells were subjected to real time-PCR analysis as described in Example 14.2 to measure mRNA levels of a target gene as a marker for HOXB4 activity, which was then normalized to target gene mRNA levels detected in the negative control cells (no treatment), to obtain a "Fold over control" value. Total RNA levels (ng/µL) were also measured as a marker for cell viability. Results are shown in Table 14.4 and FIG. 47.

TABLE 14.4

Figure 47:
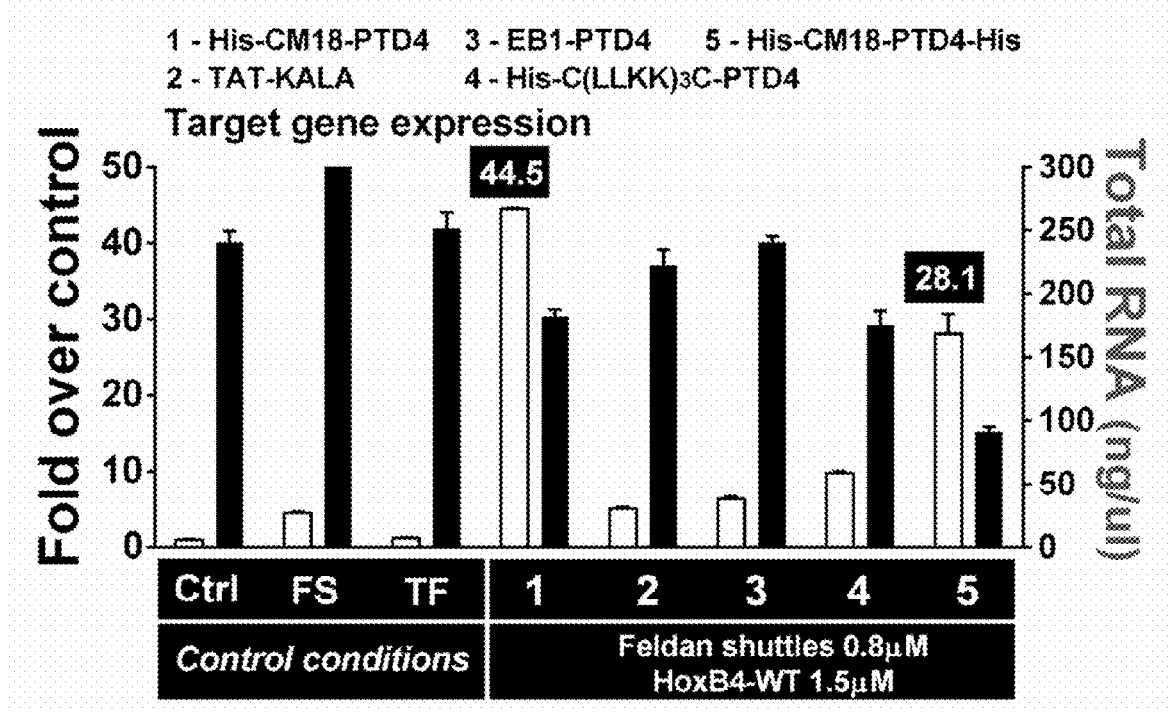
FIG. 47 shows the transcriptional activity of THP-1 cells that have been transduced with the transcription factor HOXB4 using the shuttle agents His-CM18-PTD4, TAT-KALA, EB1-PTD4, His-C(LLKK)3C-PTD4 and His-CM18-PTD4-His. Successful intra-nuclear delivery of HOXB4 was determined by monitoring mRNA levels of a target gene by real-time PCR, and the results were normalized against those in the negative control (HOXB4 without shuttle agent) and expressed as "Fold over control" (left bars). Total cellular RNA (ng/µL) was quantified and used a marker for cell viability (right bars). "Ø" or "Ctrl" means "no treatment"; "TF" means "Transcription Factor alone"; "FS" means "shuttle alone".

Data from FIG. 47

| Cargo/shuttle agent | Shuttle conc. (µM) | HOXB4-WT Conc. (µM) | Exposure time | Fold over control (mean ± St. Dev) | Total RNA in ng/µL (mean ± St. Dev) |
|---|---|---|---|---|---|
| No treatment ("Ctrl") | 0 | 0 | — | 1 ± 0.09 | 240.3 ± 8.9 |
| His-CM18-PTD4 alone ("FS") | 0 | 1.5 | 2.5 h | 2.5 ± 0.3 | 303.9 ± 7.6 |
| HOXB4-WT alone ("TF") | 0.8 | 0 | 2.5 h | 1 ± 0.11 | 251.9 ± 11.9 |
| His-CM18-PTD4 + HOXB4-WT | 0.8 | 1.5 | 2.5 h | 44.5 ± 0.09 | 182 ± 5.97 |
| TAT-KALA + HOXB4-WT | | | | 5.1 ± 0.21 | 222.4 ± 12.5 |
| EB1-PTD4 + HOXB4-WT | | | | 6.4 ± 0.3 | 240.4 ± 4.71 |
| His-C(LLKK)3C-PTD4 + HOXB4-WT | | | | 9.8 ± 0.19 | 175.3 ± 11.25 |
| His-CM18-PTD4-His + HOXB4-WT | | | | 28.1 ± 2.61 | 91.4 ± 3.92 |

Example 15

In Vivo GFP-NLS Delivery in Rat Parietal Cortex by His-CM18-PTD4

The ability of the shuttle agent His-CM18-PTD4 to deliver GFP-NLS in vivo in the nuclei of rat brain cells was tested.

In separate sterile 1.5-mL tubes, shuttle agent His-CM18-PTD4 was diluted in sterile distilled water at room temperature. GFP-NLS, used as cargo protein, was then added to the shuttle agent and, if necessary, sterile PBS was added to obtain the desired concentrations of shuttle agent and cargo in a sufficient final volume for injection in rat brain (e.g., 5 µL per each injection brain site). The shuttle agent/cargo mixture was then immediately used for experiments. One negative control was included for the experiment, which corresponds to the injection of the GFP-NLS alone.

Bilateral injections were performed in the parietal cortex of three rats. In the left parietal cortex (ipsilateral), a mix composed of the shuttle agent (20 µM) and the GFP-NLS (20 µM) was injected, and in the right parietal cortex (contralateral), only the GFP-NLS (20 µM) was injected as a negative control. For surgical procedures, mice were anesthetized with isoflurane. Then the animal was placed in a stereotaxic frame, and the skull surface was exposed. Two holes were drilled at the appropriate sites to allow bilateral infusion of the shuttle/cargo mix or GFP-NLS alone (20 µM) with 5-µL Hamilton syringe. Antero-posterior (AP), lateral (L), and dorso-ventral (DV) coordinates were taken relative to the bregma: (a) AP +0.48 mm, L ±3 mm, V −5 mm; (b) AP −2 mm, L ±1.3 mm, V −1.5 mm; (c) AP −2.6 mm, L ±1.5 mm, V −1.5 mm. The infused volume of the shuttle/cargo mix or cargo alone was 5 µL per injection site and the injection was performed for 10 minutes. After that, experimenter waited 1 min before removing the needle from the brain. All measures were taken before, during, and after surgery to minimize animal pain and discomfort. Animals were sacrificed by perfusion with paraformaldehyde (4%) 2 h after surgery, and brain were collected and prepared for microcopy analysis. Experimental procedures were approved by the Animal Care Committee in line with guidelines from the Canadian Council on Animal Care.

Figure 48B:
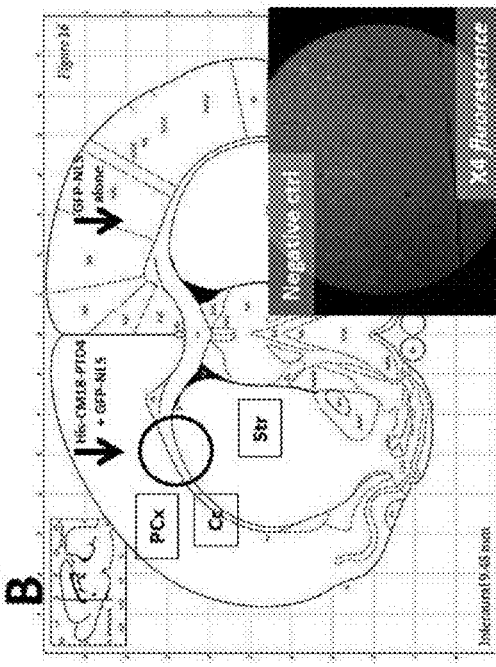
FIGS. 48A-48D show in vivo GFP-NLS delivery in rat parietal cortex by His-CM18-PTD4. Briefly, GFP-NLS (20 µM) was injected in the parietal cortex of rat in presence of the shuttle agent His-CM18-PTD4 (20 µM) for 10 min. Dorso-ventral rat brain slices were collected and analyzed by fluorescence microscopy at 4× (FIG. 48A), 10× (FIG. 48C) and 20× magnifications (FIG. 48D). The injection site is located in the deepest layers of the parietal cortex (PCx). In presence of the His-CM18-PTD4 shuttle agent, the GFP-NLS diffused in cell nuclei of the PCx, of the Corpus Callus (Cc) and of the striatum (Str) (white curves mark limitations between brains structures).
Figure 48D:
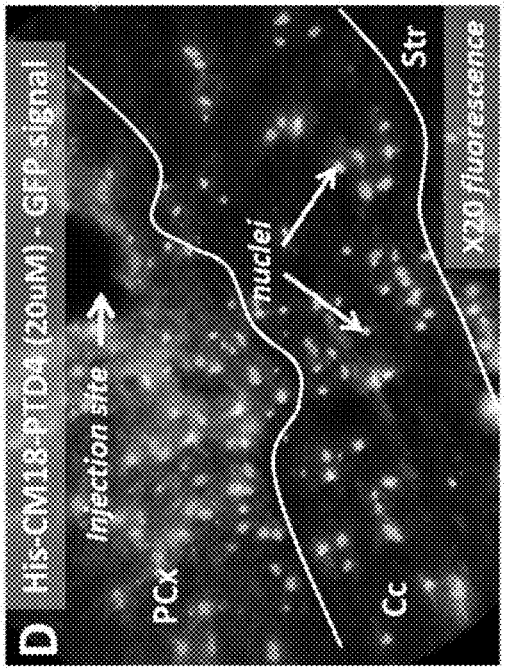
Figure 48A:
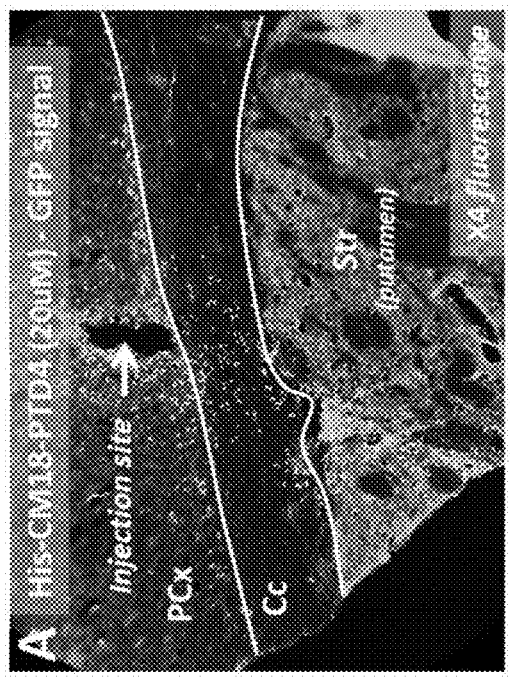
Figure 48C:
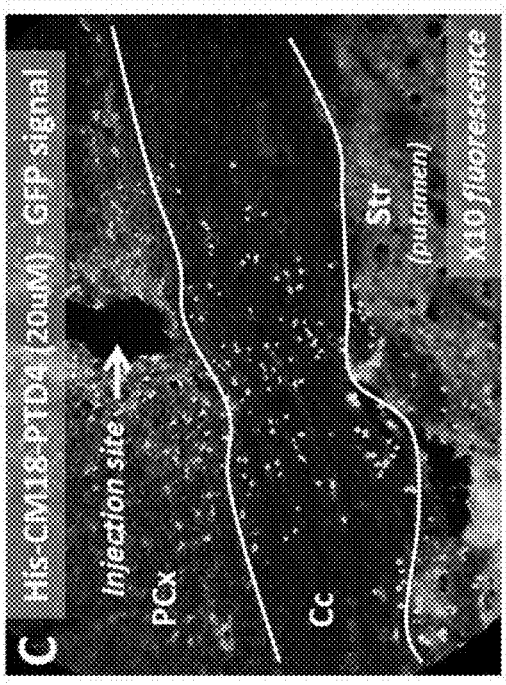

Dorso-ventral rat brain slices were collected and analysed by fluorescence microscopy and results are shown in at 4× (FIG. 48A), 10× (FIG. 48C) and 20× (FIG. 48D) magnifications. The injection site is located in the deepest layers of the parietal cortex (PCx). In the presence of the His-CM18-PTD4 shuttle, the GFP-NLS diffused in cell nuclei of the PCx, of the Corpus Callus (Cc) and of the striatum (Str) (White curves mean limitations between brains structures). FIG. 48B shows the stereotaxic coordinates of the injection site (black arrows) from the rat brain atlas of Franklin and Paxinos. The injection of GFP-NLS in presence of His-CM18-PTD4 was performed on the left part of the brain, and the negative control (an injection of GFP-NLS alone), was done on the contralateral site. The black circle and connected black lines in FIG. 48B show the areas observed in the fluorescent pictures (FIGS. 48A, 48C and 48D).

This experiment demonstrated the cell delivery of the cargo GFP-NLS after its stereotaxic injection in the rat parietal cortex in the presence of the shuttle agent His-CM18-PTD4. Results show the delivery of the GFP-NLS in the nucleus of cells from the deeper layers of the parietal cortex (injection site) to the corpus callus and the dorsal level of the striatum (putamen). In contrast, the negative control in which GFP-NLS is only detectable locally around the injection site. This experiment shows that shuttle agent induced nuclear delivery of the cargo in the injection site (parietal cortex) and its diffusion through both neighboring brain areas (corpus callus and striatum rat brain).

Example A

Physiochemical Properties of Domain-Based Peptide Shuttle Agents

A plurality of different peptides was initially screened with the goal of identifying polypeptide-based shuttle agents that can deliver independent polypeptide cargos intracellularly to the cytosol/nucleus of eukaryotic cells. On one hand, these large-scale screening efforts led to the discovery that domain-based peptide shuttle agents (see Examples 1-15), comprising an endosome leakage domain (ELD) operably linked to a cell penetrating domain (CPD), and optionally one or more histidine-rich domains, can increase the transduction efficiency of an independent polypeptide cargo in eukaryotic cells, such that the cargo gains access to the cytosol/nuclear compartment. Conversely, these screening efforts revealed some peptides having no or low polypeptide cargo transduction power, excessive toxicity, and/or other undesirable properties (e.g., poor solubility and/or stability).

Based on these empirical data, the physiochemical properties of successful, less successful, and failed peptides were compared in order to better understand properties common to the more successful shuttle agents. This approach involved manually stratifying the different peptides according to transduction performance with due consideration to, for example: (1) their solubility/stability/ease of synthesis; (2) their ability to facilitate endosomal escape of calcein (e.g., see Example 2); (3) their ability to deliver one or more types of independent polypeptide cargo intracellularly, as evaluated by flow cytometry (e.g., see Examples 3-6 and 8-15) in different types of cells and cell lines (e.g., primary, immortalized, adherent, suspension, etc.) as well as under different transduction protocols; and (4) their ability to deliver polypeptide cargos to the cytosol and/or nucleus, as evaluated by fluorescence microscopy (e.g., for fluorescently labelled cargos), increased transcriptional activity (e.g., for transcription factor cargos), or genome editing capabilities (e.g., for nuclease cargos such as CRISPR/Cas9 or CRISPR/Cpf1) (e.g., see Examples 3-6 and 8-15), and toxicity towards different types of cells and cell lines (e.g., primary, immortalized, adherent, suspension, etc.), under different transduction protocols.

In parallel to the above-mentioned manual curation, the transduction power and cellular toxicity of each peptide for a given fluorescently-labelled cargo (GFP, GFP-NLS, or fluorescently-labelled antibodies) and cell line were combined into a single "transduction score" as a further screening tool, which was calculated as follows: [(Highest percentage transduction efficiency observed by flow cytometry for a given peptide in a cell type)×(Percentage viability for the peptide in the tested cell line)]/1000, giving an overall transduction score between 0 and 10 for a given cell type and polypeptide cargo. These analyses identified domain-based peptides having transduction scores ranging from about 8 (e.g., for successful domain-based peptide shuttle agents) to as low as 0.067 (e.g., for single-domain negative control peptides).

The above-mentioned manual curation and "transduction score"-based analyses revealed a number of parameters that are common to many successful domain-based shuttle agents. Some of these parameters are listed in the Table A1. An example of a "transduction score"-based analyses in HeLa cells using GFP as a polypeptide cargo is shown in Table A2. Other transduction score-based analyses using cell lines other than HeLa and polypeptides cargos other than GFP, were also performed but are not shown here for brevity.

No successful shuttle agents were found having less than 20 amino acid residues in length (see parameter 1 in Tables A1 and A2). The four amino acids alanine, leucine, lysine and arginine, were the principal and most recurrent residues in most of the successful shuttle agents (35-85% of residues of the peptide; see parameter 10). These residues dictate the alpha-helical structure and amphiphilic nature of these peptide sequences (parameters 2-5). There was often a balance between the percentages of A/L residues (15-45%) and K/R residues (20-45%) in the shuttle agents (parameters 11, 12 and 14), and the percentages of negatively charged residues was often found to be not greater than 10% (parameter 14). Conversely, the sixteen other amino acid residues (other than A, L, K, and R) represented generally between 10-45% of the shuttle agents (parameter 15). Successful shuttle agents generally had a predicted isoelectric point (pI) of between 8-13 (parameter 7), and a predicted net charge greater than or equal to +4 (parameter 6), with dCM18-TAT-Cys having a predicted net charge of as high as +26. Hydrophobic residues (A, C, G, I, L, M, F, P, W, Y, V) composed generally between 35-65% of the shuttle agents, and neutral hydrophilic residues (N, Q, S, T) represented generally from 0-30% (parameters 8 and 9).

As shown in Table A2, the most successful shuttle agents (e.g., transduction scores above 5.0) generally had few parameters outside the ranges set forth in Table A1. However, significant increases in transduction efficiency were also observed for shuttle agents in which several parameters were not satisfied, depending for example on the extent to which the unsatisfied parameters fall outside the recommended range, and/or on whether other parameters fall closer to the middle of a recommended range. Thus, shuttle agents having several parameters which fall within "optimal" ranges may compensate for other parameters falling outside of the recommended ranges. As mentioned above, peptides shorter than 20 amino acids did not show any significant transduction ability (e.g. transduction scores less than 0.4), regardless of how many other parameters were satisfied. Among the peptides greater than 20 amino acids in length and having transduction scores lower than 0.4, VSVG-PTD4 (score of 0.35) failed to satisfy six parameters, while JST-PTD4 (score of 0.083) failed to satisfy ten parameters. KALA (score of 0.12) failed to satisfy four parameters, with parameters 11 and 14 far exceeding the recommended ranges, reflecting an overabundance of A/L residues and a large imbalance between the percentages of A/L and L/R residues. It is to be understood that the transduction score ranges appearing the Table A2 are arbitrarily selected, and that other ranges can be selected and are within the scope of the present description.

TABLE A1

General physicochemical properties of successful domain-based peptide shuttle agents

| | Parameter | Description | Result |
|---|---|---|---|
| 1 | Minimum length | The minimum length of peptide shuttle agent. | 20 amino acids |
| 2 | Amphipathic alpha-helix | Peptide shuttle agent comprises a predicted amphipathic alpha-helix conformation. (Based on 3D modeling using PEP-FOLD, an online resource for de novo peptide structure prediction: http://bioserv.rpbs.univ-paris-diderot.fr/services/PEP-FOLD/). | Yes |

TABLE A1-continued

General physicochemical properties of successful domain-based peptide shuttle agents

| | Parameter | Description | Result |
|---|---|---|---|
| 3 | Positively-charged surface | Predicted amphipathic alpha-helix conformation comprises a positively-charged hydrophilic face rich in R and/or K residues. (Based on observation of at least 3 K/R residues clustered to one side of a helical wheel modeling, using the online helical wheel projection tool available at: http://rzlab.ucr.edu/scripts/wheel/wheel.cgi). | Yes |
| 4 | % Highly hydrophobic core | Predicted amphipathic alpha-helix conformation comprises a highly hydrophobic core composed of spatially adjacent L, I, F, V, W, and/or M residues representing a percentage of the overall peptide sequence (calculated excluding histidine-rich domains). This parameter was calculated by first arranging the amino acids of the peptide in an opened cylindrical representation, then delineating an area of contiguous highly hydrophobic residues (L, I, F, V, W, M), as shown in FIG. 49A, right panel. The number of highly hydrophobic residues comprised in this delineated highly hydrophobic core was then divided by the total amino acid length of the peptide, excluding N- and/or C-terminal histidine-rich domains. For example, for the peptide shown in FIG. 49A, there are 8 residues in the delineated highly hydrophobic core, and 25 total residues in the peptide (excluding the terminal 12 histidines). Thus, the highly hydrophobic core is 32% (8/25). | 12-50% |
| 5 | Hydrophobic moment | Calculated hydrophobic moment (μ; calculated while excluding histidine-rich domains), using the online helical wheel projection program available from: http://rzlab.ucr.edu/scripts/wheel/wheel.cgi. | 3.5-11 |
| 6 | Net charge | Predicted net charge at physiological pH (calculated from the side chains of K, R, D, and E residues). | ≥+4 |
| 7 | pI | Predicted isoelectric point (pI). (Calculated with the Prot Param software available at: http://web.expasy.org/protparam/). | 8-13 |
| 8 | % hydrophobic residues | Overall percentage of hydrophobic residues (A, C, G, I, L, M, F, P, W, Y, V) in the peptide shuttle agent. | 35-65% |
| 9 | % neutral hydrophilic residues | Overall percentage of neutral hydrophilic residues (N, Q, S, T) in the peptide shuttle agent. | 0-30% |
| 10 | % A, L, K, R | Overall percentage of residues in the peptide shuttle agent which are A, L, K, or R. | 35-85% |
| 11 | % A or L | Overall percentage of residues in the peptide shuttle agent which are A or L. (Number of A + L residues)/(Total number of residues), with there being at least 5% of L in the peptide. | 15-45% |
| 12 | % Positive residues | Overall percentage of residues in the peptide shuttle agent which are K or R. (Number of K + R residues)/(Total number of residues). | 20-45% |
| 13 | % Negative residues | Overall percentage of residues in the peptide shuttle agent which are D or E. (Number of D + E residues)/(Total number of residues). | 0-10% |
| 14 | Difference between % of A/L and K/R | Overall difference (absolute value) between the percentage of A or L (parameter 11) and the percentage of K or R (parameter 12) in the peptide shuttle agent. (Parameter 11)-(Parameter 12). | ≤10% |
| 15 | % infrequent amino acid residues | Overall percentage of residues which are Q, Y, W, P, I, S, G, V, F, E, D, C, M, N, T, or H (i.e., not A, L, K, or R). (Number of Q + Y + W + P + I + S + G + V + F + E + D + C + M + N + P + H residues)/(Total number of residues). | 10-45% |

TABLE A2

Physiochemical properties of domain-based peptides stratified by transduction score (in HeLa cells using GFP or GFP-NLS as cargo)

| Peptide name | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| Transduction scores between 3.1-8.0 | | | | | | | | | | | | | | | |
| TAT-KALA | 42 | Y | Y | 12.1 | 3.6 | 13 | 11.5 | 54.5 | 7.5 | 81 | 43.9 | 36.5 | 4.9 | 7.3 | 11.9 |
| His-CM18-PTD4-His | 41 | Y | Y | 24.1 | 6.7 | 8 | 11.8 | 51.6 | 8.1 | 52 | 22.6 | 23 | 0 | −5.7 | 26.8 |
| His-CM18-PTD4 | 35 | Y | Y | 26 | 6.7 | 8 | 11.8 | 51.6 | 8.1 | 52 | 22.6 | 23 | 0 | −5.7 | 31.4 |
| His-C(LLKK)₃C-PTD4 | 31 | Y | Y | 24 | 3.6 | 9 | 11.2 | 45.8 | 2.7 | 43 | 20 | 22.9 | 2.9 | −2.9 | 35.5 |
| CM18-L2-PTD4 | 36 | Y | Y | 22.2 | 6.9 | 8 | 11.8 | 63.9 | 14 | 50 | 27.7 | 22.2 | 0 | 5.5 | 50 |

TABLE A2-continued

Physiochemical properties of domain-based peptides stratified by
transduction score (in HeLa cells using GFP or GFP-NLS as cargo)

| Peptide name | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| CM18-His-PTD4 | 35 | Y | Y | 22.8 | 6.7 | 8 | 11.8 | 51.6 | 8.1 | 52 | 22.6 | 23 | 0 | -5.7 | 31.4 |
| CM18-PTD4-His | 35 | Y | Y | 22.8 | 6.7 | 8 | 11.8 | 51.6 | 8.1 | 52 | 22.6 | 23 | 0 | -5.7 | 31.4 |
| His-CM18-TAT | 35 | Y | Y | 24.1 | 6 | 13 | 12.3 | 37.4 | 8.6 | 49 | *__11.5__* | 37.1 | 0 | *__-2.5__* | 34.4 |
| EB1-PTD4 | 34 | Y | Y | 26.5 | 6.3 | 10 | 12.3 | 52.8 | 14.6 | 59 | 29.4 | 29 | 0 | 0 | 35.3 |
| Transduction scores between 0.5-3.0 ||||||||||||||||
| HA-CM18-PTD4 | 36 | Y | Y | 26.6 | 6.7 | 8 | 11.8 | 52.4 | 8.9 | 53 | 30.5 | 22.2 | 0 | 8.3 | 30.6 |
| 6Cys-CM18-PTD4 | 35 | Y | Y | 22.6 | 6.5 | 8 | 9.7 | *__68.7__* | 8.6 | 52 | 28.6 | 22.9 | 0 | 3.7 | 48.8 |
| CM18-L3-PTD4 | 41 | Y | Y | 19.5 | 3.9 | 8 | 11.8 | 64 | 16.3 | 44 | 24.4 | *__19.5__* | 0 | 4.9 | *__51.3__* |
| His-CM18-PTD4-6Cys | 41 | Y | Y | 32 | 6.8 | 8 | 9.7 | 58.4 | 2.4 | 44 | 24.4 | *__19.5__* | 0 | 4.9 | 41.5 |
| Met-His-CM18-TAT-Cys | 37 | Y | Y | 20 | 6.2 | 13 | 12 | 54 | 8.1 | 49 | *__10.8__* | 21.6 | 0 | 5.4 | 35.2 |
| CM18-L1-PTD4 | 32 | Y | Y | 25.8 | 6.1 | 8 | 11.8 | 59.1 | 14.9 | 56 | 31.3 | 25 | 0 | *__-11__* | 43.8 |
| Xentry-KALA | 37 | Y | Y | 25 | 5.2 | 6 | 9.9 | *__67.3__* | 0.7 | 76 | *__54__* | 21.6 | 5.4 | *__32__* | 16.2 |
| CM18-TAT-Cys | 30 | *__N__* | *__N__* | *__10.8__* | 6.2 | 13 | 12 | 46.3 | 10 | 57 | *__13.3__* | 43.3 | 0 | *__-30__* | 43.5 |
| Pep1-KALA | 51 | Y | Y | 26.6 | 9.1 | 8 | 10 | 51.1 | *__58.9__* | 61 | 35.3 | 25.5 | 9.8 | 9.8 | 27.5 |
| 3HA-CM18-PTD4 | 38 | Y | Y | 15.9 | 6.7 | 8 | 11.8 | 57.9 | 7.9 | 55 | 34.2 | 21.1 | 0 | *__13.1__* | 29 |
| CM18-PTD4 | 29 | Y | Y | 24.2 | 6.7 | 8 | 11.8 | 60.8 | 10.3 | 62 | 34.4 | 27.5 | 0 | 6.9 | 38 |
| 3His-CM18-PTD4 | 32 | Y | Y | 27.6 | 6.7 | 8 | 11.8 | 56.1 | 9.3 | 56 | 29.4 | 25 | 0 | 0 | 34.5 |
| His-CM18-Transportan | 50 | Y | Y | 25 | *__2.6__* | 9 | 10.6 | 58 | 14 | 51 | 32 | *__18__* | 0 | *__13__* | 38 |
| SynB3-KALA | 40 | Y | Y | 22.8 | 3.7 | 10 | 11.1 | 57.5 | 5 | 78 | *__47.5__* | 30 | 5 | *__17.5__* | 15 |
| 12His-CM18-PTD4 | 41 | Y | Y | 15 | 6.7 | 8 | 11.8 | 46.4 | 8.8 | 44 | 24.4 | 21.2 | 0 | 4.9 | 26.9 |
| TAT-CM18 | 30 | Y | Y | 27.6 | 4 | 13 | 12 | 46.6 | 10 | 57 | *__13.3__* | 43.3 | 0 | *__-30__* | 43.5 |
| 9Arg-KALA | 39 | Y | Y | 23.5 | 4.5 | 14 | 12.1 | 51.4 | 0 | *__87__* | *__46.2__* | 41 | 5.1 | 5.2 | *__5.1__* |
| Transduction scores between 0.07-0.4 ||||||||||||||||
| VSVG-PTD4 | 36 | *__N__* | *__N__* | | 4.1 | 6 | 10.3 | 47.4 | 14 | *__33__* | *__16.7__* | *__16.6__* | 0 | 0.1 | *__61.3__* |
| Penetratin-cys | *__17__* | *__N__* | *__N__* | 23.5 | 5.5 | 7 | 11.8 | 41.3 | 17.7 | 41 | *__0__* | 41.1 | 0 | *__-41__* | *__58.8__* |
| CM18 | *__18__* | *__N__* | *__N__* | 47 | 4.3 | 5 | 10.6 | 61.3 | 11.1 | 50 | 22.3 | 27.8 | 0 | -5.5 | 50 |
| KALA | 30 | Y | Y | 20 | 4.5 | 5 | 9.9 | *__66.6__* | 0 | 83 | *__60__* | 23.3 | 6.7 | *__36.7__* | *__6.7__* |
| TAT-cys | *__12__* | *__N__* | *__N__* | *__0__* | *__1.9__* | 8 | 12 | *__24.9__* | 8.3 | 57 | *__0__* | | 0 | *__17.6__* | 33.3 |
| PTD4 | *__11__* | Y | Y | *__0__* | *__2.4__* | *__3__* | 11.7 | 64.6 | 9.1 | 82 | *__54.5__* | 27.3 | 0 | *__27.2__* | 18.2 |
| His-PTD4 | *__17__* | Y | Y | *__0__* | *__2.4__* | *__3__* | 11.7 | 41.2 | 5.9 | 53 | *__35.3__* | *__17.6__* | 0 | *__17.7__* | 11.8 |
| JST-PTD4 | 31 | *__N__* | *__N__* | 35.6 | *__13.8__* | *__2__* | *__4.7__* | *__67.6__* | 9.6 | 65 | *__54.8__* | *__9.7__* | *__16.1__* | *__45.1__* | 19.4 |
| C(LLKK)₃C | *__14__* | Y | Y | 42.9 | 5 | 6 | 10.1 | 57.2 | 0 | *__86__* | 42.9 | 42.9 | 0 | 0 | 14.3 |

Y = Yes; N = No; Cells with plain text = value falls within parameter range set forth in Table A1; Cells with bolded, underlined, and italics text = value falls outside parameter range set forth in Table A1. His-LAH4-PTD4 yielded a transduction score of above 5.0, but was excluded from this analysis because the intracellular GFP fluorescence pattern was observed by fluorescence microscopy as being punctate, suggesting that the GFP cargo remained trapped in endosomes. Nevertheless, it is worth noting that His-LAH4-PTD4 had several parameters falling outside the ranges set forth in Table A1 with respect to parameters 2, 3, 11, 12, 14 and 15.

Example B

Rational Design of Synthetic Peptide Shuttle Agents

The parameters set forth in Table A1, and empirical knowledge gained (e.g., from Examples 1-15), were used to manually design the peptides listed in Table B1 in order to evaluate whether the parameters can be used for designing successful peptide shuttle agents.

The peptides listed in Table B1 were tested for their ability to transduce GFP-NLS cargo (see Example 3.4) in HeLa cells, using the protein transduction assay as generally described in Example 3.1a. GFP-NLS recombinant protein (10 μM) was co-incubated with 10 μM of the peptides and then exposed to HeLa cells for 1 min. The cells were subjected to flow cytometry analysis as described in Example 3.3. Results are shown in Tables B2 and B3. A "transduction score"-based analysis was also performed as discussed is Example A, and the results are shown in Table B4. Successful nuclear delivery of the transduced GFP-NLS (generally after only 1 minute of exposure to the peptide) was confirmed by fluorescence microscopy as described in Example 3.2 (data not shown).

Peptides FSD1-FSD5 were initially designed based on the successful domain-based shuttle agent His-CM18-PTD4-His, with peptides FSD1-FSD4 being designed to intentionally unrespect one or more parameters set forth in Table A1, and FSD5 being designed to respect all fifteen parameters. As can be seen from Table B2, peptides FSD1-FSD4 displayed transduction efficiencies ranging from 2.45% to 37.6%. In contrast, the peptide FSD5 displayed high transduction efficiency (70.5%) and low toxicity (cell viability of 86%).

Figure 49C:
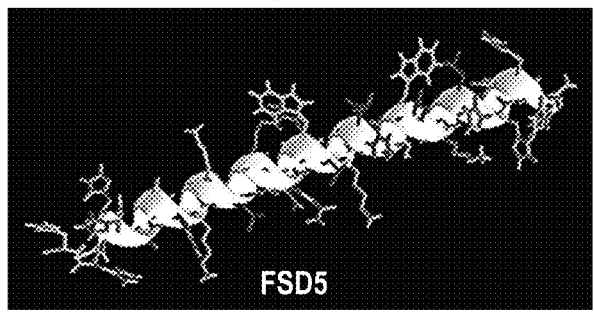
FIGS. 49C-49F show predicted 3-dimensional models of the structures of the peptides FSD5, FSD18, VSVG-PTD4, and FSD44, respectively.
Figure 49D:
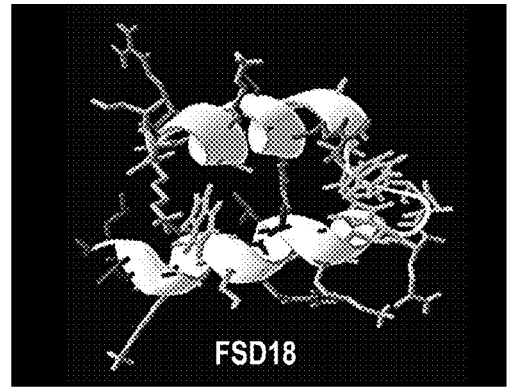
Figure 49E:
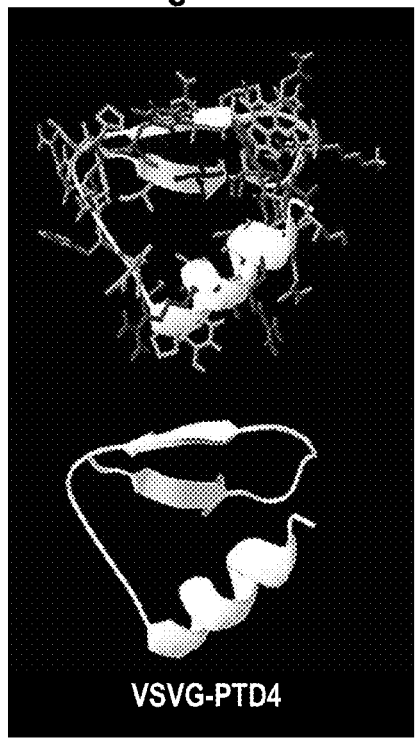
Figure 49F:
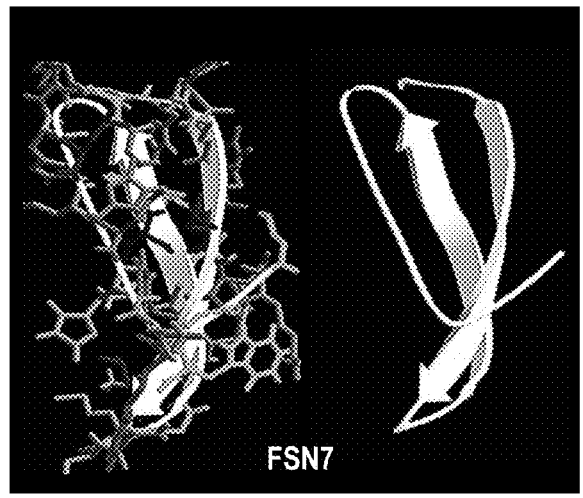

3-dimensional modeling using PEP-FOLD, an online resource for de novo peptide structure prediction, predicted an alpha-helical conformation for FSD5 (see FIG. 49C; http://bioserv.rpbs.univ-paris-diderot.fr/services/PEP-FOLD/). In contrast, the peptide VSVG-PTD4, which showed only 3.5% transduction efficiency (see Table 10.3a), was predicted to adopt a different structure which included a shorter alpha helix, short beta-sheets (white arrows), and random coils (white shapeless lines).

Helical wheel projections and side opened cylindrical representations of FSD5 and VSVG-PTD4 shown in FIGS. 49A and 49B (adapted from: http://rzlab.ucr.edu/scripts/wheel/wheel.cgi) illustrate the amphipathic nature of FSD5, as compared to VSVG-PTD4. The geometrical shape of each amino acid residue corresponds to its biochemical property based on the side chain of the residue (i.e., hydrophobicity, charge, or hydrophilicity). One of the main differences between the two opened cylindrical representations of FSD5 and VSVG-PTD4 is the presence of a highly hydrophobic core in FSD5 (outlined in FIG. 49A, left and right panels), which is not present in VSVG-PTD4. The cylinder in the lower middle panels of FIGS. 49A and 49B represent simplified versions of the opened cylindrical representations in the right panels, in which: "H" represents the high hydrophobic surface area; "h" represents low hydrophobic surface area; "+" represents positively charged residues; and "h" represent hydrophilic residues.

In light of the high transduction efficiency of FSD5, we used this shuttle agent as model to design peptides FSD6-FSD26. As shown in Table B2, a relatively high degree of amino acid substitutions was possible without completely losing transduction power, provided that most of the design parameters set forth in Table A1 were respected. The only peptide that displayed nearly a complete loss transduction efficiency among FSD6-FSD26 was FSD6, which is not predicted to adopt an amphipathic alpha-helix structure. Interestingly, peptide FSD18 showed high toxicity in HeLa cells when used at 10 µM, but showed high transduction efficiency and relatively low toxicity when used in other types of cells (see Examples E and G), suggesting that peptide toxicity may vary depending on the type of cells. 3-dimensional modeling using PEP-FOLD predicted two separate alpha-helices for FSD18 (see FIG. 49D).

Peptides FSN1-FSN8 were designed to explore the effects on transduction efficiency when one or more of the design parameters set forth in Table A1 are not respected. For example, FSN7 displayed only 3.56% transduction efficiency and is predicted by PEP-FOLD to form two beta-sheets and no alpha-helices (FIG. 49F).

TABLE B1

Manually-designed synthetic peptides and shuttle agents tested

| Peptide | SEQ ID NO: | Amino acid sequence | Length (a.a) | MW (kDa) | pI | Charge |
|---|---|---|---|---|---|---|
| FSD1 | 104 | HHHHHHKWKLLRRAAKKAARRYLKLLLKQLKLHHHHHH | 38 | 4.85 | 12.03 | 11+/0- |
| FSD2 | 105 | HHHHHHWLKLLRRAAKKAARLYRKLLRKARKLHHHHHH | 38 | 4.86 | 12.31 | 12+/0- |
| FSD3 | 106 | HHHHHHKRKKKRRAKKKRAWLYLALLLWALALHHHHHH | 38 | 4.87 | 12.03 | 11+/0- |
| FSD4 | 107 | HHHHHHKRQLKRKLRKWKRLLRLLRLLARLWLHHHHHH | 38 | 5.1 | 12.78 | 12+/0- |
| FSD5 | 108 | HHHHHHLLKLWSRLLKLWTQGRRLKAKRAKAHHHHHH | 37 | 4.68 | 12.49 | 9+/0- |
| FSD6 | 109 | HHHHHHWYLALLALYWQRAKAKTRQRRRHHHHHH | 34 | 4.49 | 11.84 | 7+/0- |
| FSD7 | 110 | HHHHHHWARLARAFARAIKKLYARALRRQARTG | 33 | 3.99 | 12.4 | 9+/0- |
| FSD8 | 111 | HHHHHHKWKLARAFARAIKKLYARALRRQARTG | 33 | 4.02 | 12.31 | 10+/0- |
| FSD9 | 112 | HHHHHHKWKLARAFARAIKKLYARALRRQARTGHHHHHH | 39 | 4.85 | 12.31 | 10+/0- |
| FSD10 | 113 | KWKLARAFARAIKKLGGSGGGSYARALRRQARTG | 34 | 3.66 | 12.31 | 10+/0- |
| FSD11 | 114 | HHHHHHKWKLARAFARALRAIKKLYARALRRQARTG | 36 | 4.36 | 12.4 | 11+/0- |
| FSD12 | 115 | KWKLARAFARAIKKLYARALRRQARTG | 27 | 3.2 | 12.31 | 10+/0- |
| FSD13 | 116 | HHHHHHKWAKLLRAFAKAIKKLYARLARRQARTGHHHHHH | 40 | 4.93 | 12.19 | 10+/0- |
| FSD14 | 117 | HHHHHHLALARWARYFRILAKLKRTKRGQAKAHHHHHH | 38 | 4.73 | 12.19 | 9+/0- |

TABLE B1-continued

Manually-designed synthetic peptides and shuttle agents tested

| Peptide | SEQ ID NO: | Amino acid sequence | Length (a.a) | MW (kDa) | pI | Charge |
|---|---|---|---|---|---|---|
| FSD15 | 118 | HHHHHHKWKIARAFARSLKKLYARLLARQAKTGHHHHHH | 39 | 4.79 | 12.02 | 9+/0− |
| FSD16 | 119 | HHHHHHLLKLWSRLLKLWTQGRRLKAKRAKA | 31 | 3.86 | 12.49 | 9+/0− |
| FSD17 | 120 | HHHHHHLAKLFKWLRALIRQGAKRKTKRASAHHHHHH | 37 | 4.56 | 12.49 | 9+/0− |
| FSD18 | 121 | LLKLWSRLLKLWTQGGSGGGSGRRLKAKRAKA | 32 | 3.49 | 12.49 | 9+/0− |
| FSD19 | 122 | HHHHHHLLKLWSRLLKTWTQGRRLKAKSAQASTRQAHHHHHH | 36 | 4.32 | 12.48 | 8+/0− |
| FSD20 | 123 | HHHHAAVLKLWKRLLKLFRKGRRLKAKRAKAKR | 33 | 4.12 | 12.71 | 14+/0− |
| FSD21 | 124 | HHHHHHFLKIWSRLIKIWTQGRRKGAQAAFR | 31 | 3.85 | 12.48 | 7+/0− |
| FSD22 | 125 | HHHHHHVLKLWSRILKAFTQGRRMAAKRAKCNHHHHHH | 32 | 3.87 | 12.02 | 8+/0− |
| FSD23 | 126 | HHHHHHLLKLWSRLLKEWTQGRRLEAKRAEAHHHHHH | 31 | 3.88 | 10.93 | 7+/3− |
| FSD24 | 127 | HHHHHHLLCLWSRLLKLWTQGERLKAKCAKACER | 34 | 4.14 | 9.75 | 7+/2− |
| FSD25 | 128 | HHHHHHVWKLFWTLLAAIYGRGKARQKRAKRQARG | 35 | 4.25 | 12.19 | 9+/0− |
| FSD26 | 129 | ALLGLFIKWVKKVGTLFRKAKAGAQNRRAKAQKGK | 35 | 3.88 | 12.33 | 11+/0− |
| FSN1 | 130 | HHHHHHKRKRRSKKRKLWTQGWLLLALLALAHHHHHH | 31 | 3.86 | 12.49 | 9+/0− |
| FSN2 | 131 | HHHHHHKLKLRSRLKWGRTQLWRALAKKALLHHHHHH | 31 | 3.86 | 12.49 | 9+/0− |
| FSN3 | 132 | HHHHHHQFLCFWLNKMGKHNTVWHGRHLKCHKRGKG | 31 | 3.82 | 11.75 | 7+/0− |
| FSN4 | 133 | HHHHHHLLYLWRRLLKFWCAGRRVYAKCAKAYGCF | 35 | 4.23 | 10.06 | 7+/0− |
| FSN5 | 134 | HHHHHHLLKLWRRLLKLFRKALRALAKRAKSALKRAQAA | 39 | 4.68 | 12.71 | 12+/0− |
| FSN6 | 135 | HHHHHHLLKLWSRLLKLWTQALRALAKRAKALAHHHHHH | 33 | 3.96 | 12.31 | 7+/0− |
| FSN7 | 136 | LIKLWSRFIKFWTQGRRIKAKLARAGQSWFG | 31 | 3.75 | 12.48 | 8+/0− |
| FSN8 | 137 | HHHHHHFRKLWLAIVRAKK | 19 | 2.4 | 12.02 | 5+/0− |

Results computed using ProtParam™ online tool available from ExPASy™ Bioinformatics Resource Portal (http://web.expasy.org/protparam/);
pI: Isoelectric point;
Charge: Total number of positively (+) and negatively (−) charged residues

TABLE B2

Transduction of GFP-NLS in HeLa cells

| Cells | Peptide | Mean % cells with GFP signal (±St. Dev.; n = 3) | Cell viability (%) (±St. Dev.; n = 3) | Design comments |
|---|---|---|---|---|
| HeLa | No peptide | 0.41 ± 0.015 | 100 | n/a |
| | FSD1 | 37.6 ± 3.44 | 60.3 ± 6.18 | Low % of infrequent amino acids (Q, Y, W, P, I, S, G, V, F, E, D, C, M, N, T, H) |
| | FSD2 | 11.9 ± 1.69 | 76.3 ± 5.99 | High hydrophobic moment |
| | FSD3 | 2.45 ± 0.32 | 91.1 ± 6.37 | No predicted amphipathic alpha helix |
| | FSD4 | 6.60 ± 0.84 | 86.1 ± 8.15 | Low % of hydrophobic amino acids; Low % of infrequent amino acids (Q, Y, W, P, I, S, G, V, F, E, D, C, M, N, T, H) |
| | FSD5 | 70.5 ± 6.44 | 86 ± 7.45 | — |
| | FSD6 | 1 ± 0.12 | 88.1 ± 7.66 | No predicted amphipathic alpha helix |
| | FSD7 | 78.30 ± 5.11 | 38.5 ± 3.48 | — |
| | FSD8 | 62.30 ± 5.61 | 64.8 ± 7.59 | — |

TABLE B2-continued

Transduction of GFP-NLS in HeLa cells

| Cells | Peptide | Mean % cells with GFP signal (±St. Dev.; n = 3) | Cell viability (%) (±St. Dev.; n = 3) | Design comments |
|---|---|---|---|---|
| | FSD9 | 68.21 ± 6.35 | 67.3 ± 5.19 | — |
| | FSD10 | 73.23 ± 4.94 | 79.8 ± 4.73 | — |
| | FSD11 | 68.29 ± 3.11 | 60.9 ± 7.59 | — |
| | FSD12 | 61.58 ± 5.33 | 67.8 ± 4.83 | — |
| | FSD13 | 75.94 ± 7.48 | 49.5 ± 5.13 | High hydrophobic moment |
| | FSD14 | 43.25 ± 5.35 | 92.8 ± 7.42 | — |
| | FSD15 | 54.97 ± 4.28 | 96.1 ± 2.61 | — |
| | FSD16 | 57.34 ± 4.11 | 88.2 ± 2.66 | — |
| | FSD17 | 52.83 ± 6.69 | 99.1 ± 2.09 | — |
| | FSD18 | 77.11 ± 3.25 | 82.4 +/− 4.71 | — |
| | FSD19 | 55.17 ± 4.62 | 80.6 ± 5.36 | — |
| | FSD20 | 75.23 ± 5.91 | 65.4 ± 6.18 | — |
| | FSD21 | 46.74 ± 4.03 | 75.6 ± 5.99 | — |
| | FSD22 | 45.09 ± 3.95 | 80.2 ± 7.21 | — |
| | FSD23 | 50.34 ± 4.29 | 65.3 ± 5.44 | — |
| | FSD24 | 37.48 ± 4.08 | 75.3 ± 3.93 | — |
| | FSD25 | 32.67 ± 3.17 | 71.7 ± 5.08 | — |
| | FSD26 | 47.63 ± 4.19 | 59.26 ± 1.27 | — |

"—" = No parameters outside the limits set forth in Table A1.

TABLE B3

Transduction of GFP-NLS in HeLa cells

| Cells | Peptide | Mean % cells with GFP signal (±St. Dev.; n = 3) | Cell viability (%) (±St. Dev.; n = 3) | Design comments |
|---|---|---|---|---|
| HeLa | No peptide | 0.38 ± 0.02 | 100 | |
| | FSN1 | 9.14 ± 0.93 | 94.3 ± 3.07 | Low hydrophobic moment; weak amphiphilic structure |
| | FSN2 | 12.13 ± 2.06 | 91.3 ± 4.66 | Weak hydrophobic surface |
| | FSN3 | 1.86 ± 97.15 | 97.2 ± 2.03 | No predicted alpha-helical structure |
| | FSN4 | 5.84 ± 0.49 | 90.5 ± 4.18 | >65% hydrophobic amino acids |
| | FSN5 | 13.29 ± 1.24 | 85.36 ± 6.16 | Alanine + Leucine >40% |
| | FSN6 | 15.74 ± 1.63 | 32.63 ± 4.26 | High hydrophobic moment; difference between A/L and K/R residues is >20% |
| | FSN7 | 3.56 ± 0.36 | 93.45 ± 3.61 | No predicted alpha-helical structure; high hydrophobic moment; 55% of infrequent residues (other than A, L, K, R) |
| | FSN8 | 3.52 ± 0.41 | 94.53 ± 3.72 | Peptide length is less than 20 |

TABLE B4

Physiochemical properties of peptides stratified by transduction score (in HeLa cells using GFP-NLS as cargo)

| Peptide name | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| | | | | | | Transduction scores above 4.0 | | | | | | | | | |
| FSD5 | 37 | Y | Y | 32 | 8.3 | 9 | 12.5 | 42 | 9.6 | 51 | 27 | 29 | 0 | 2.7 | 16.2 |
| FSD10 | 34 | Y | Y | 14.7 | 7 | 10 | 12.3 | 58.6 | 11.7 | 59 | 29.4 | 29.4 | 0 | 0 | 41.3 |
| FSD15 | 39 | Y | Y | 22.2 | 6.7 | 9 | 12 | 45.3 | 9 | 58 | 30.3 | 27.3 | 0 | 8 | 20.5 |
| FSD17 | 37 | Y | Y | 29.2 | 5.5 | 9 | 12.5 | 41.8 | 9.6 | 58 | 29 | 29 | 0 | 0 | 18.9 |
| FSD16 | 31 | Y | Y | 32 | 8.3 | 9 | 12.5 | 42 | 9.6 | 61 | 27 | 29 | 0 | 2.7 | 19.4 |
| FSD20 | 33 | Y | Y | 27.2 | 7.2 | 14 | 12.7 | 45.4 | 0 | 76 | 33.4 | 42.4 | 0 | −9 | 12 |
| FSD9 | 39 | Y | Y | 18.5 | 6.3 | 10 | 12.3 | 38.6 | 5.2 | 51 | 25.6 | 25.7 | 0 | −0.1 | 17.9 |

TABLE B4-continued

Physiochemical properties of peptides stratified by transduction score (in HeLa cells using GFP-NLS as cargo)

| Peptide name | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| FSD19 | 36 | Y | Y | 19.1 | 8.7 | 8 | 12.5 | 36.2 | 24.9 | 43 | 23.8 | 22.2 | 0 | 4.8 | 28.5 |
| FSD12 | 27 | Y | Y | 18.5 | 6.3 | 10 | 12.3 | 44.4 | 7.4 | 74 | 37 | 37 | 0 | 0 | 25.9 |
| FSD11 | 36 | Y | Y | 17.6 | 7.3 | 11 | 12.4 | 47.3 | 5.6 | 64 | 33.4 | 30.5 | 0 | 2.9 | 19.4 |
| FSD8 | 33 | Y | Y | 18.5 | 6.3 | 10 | 12.3 | 45.3 | 6 | 61 | 33.3 | 30.3 | 0 | 3 | 21.2 |
| FSD14 | 38 | Y | Y | 26.9 | 5.2 | 9 | 12.2 | 46.8 | 6.2 | 59 | 31.3 | 28.1 | 0 | 3.2 | 18.5 |
| Transduction scores between 1.0-4.0 | | | | | | | | | | | | | | | |
| FSD13 | 40 | Y | Y | 25 | *10.3* | 10 | 12.2 | 35.1 | 8.1 | 46 | 21.6 | 24.3 | 0 | -2.7 | 20 |
| FSD22 | 32 | Y | Y | 20.9 | 7.1 | 8 | 12 | 43.6 | 9.3 | 39 | 18.4 | 25 | 0 | -2.6 | 28.6 |
| FSD21 | 31 | Y | Y | 35.7 | 9.5 | 7 | 12.5 | 45.3 | 12.9 | 39 | 16.2 | 22.6 | 0 | -6.4 | 42.1 |
| FSD23 | 31 | Y | Y | 21.6 | 8.2 | 4 | 10.9 | 38.8 | 9.6 | 43 | 24.3 | 22.6 | 0 | 5.4 | 24.3 |
| FSD7 | 33 | Y | Y | 17.2 | 8.3 | 9 | 12.4 | 48.3 | 5 | 61 | 33.3 | 27.3 | 0 | 10 | 21.2 |
| FSD24 | 34 | Y | Y | 26.5 | 8 | 5 | 9.75 | 47 | 8.7 | 50 | 29.4 | 20.6 | 5.9 | 8.8 | 32.3 |
| FSD26 | 35 | Y | Y | 28.6 | 7 | 11 | 12.3 | 60 | 11.5 | 60 | 28.5 | 31.5 | 0 | -3 | 40.1 |
| FSD25 | 35 | Y | Y | 14.3 | 7.1 | 8 | 12.2 | 48.8 | 8.6 | 63 | 37.1 | 25.7 | 2.9 | 9.7 | 20.1 |
| FSD1 | 38 | Y | Y | 23 | 7.9 | 11 | 12 | 36.8 | 2.6 | 61 | 31.6 | 28.9 | 0 | 2.7 | *7.9* |
| FSD18 | 32 | Y | Y | 25 | 8 | 9 | 12.5 | 59 | 12.6 | 52 | 28.6 | 21.9 | 0 | 5.7 | 43.8 |
| FSN5 | 39 | Y | Y | 28.3 | *12.3* | 12 | 12.7 | 48.8 | 5.2 | 74 | 43.6 | 30.8 | 0 | *12.8* | 10.4 |
| FSN2 | 31 | Y | Y | 24.3 | *1.4* | 9 | 12.5 | 35.1 | 9.6 | 51 | 27 | 29 | 0 | 2.7 | 16.2 |
| Transduction scores between 0.5-1.0 | | | | | | | | | | | | | | | |
| FSD2 | 38 | Y | Y | 15.4 | *10.9* | 12 | 12.3 | 43.7 | 0 | 63 | 31.6 | 28.9 | 0 | 0 | 19 |
| FSN1 | 31 | *N* | *N* | 24.3 | *2.4* | 9 | 12.5 | 35.1 | 9.6 | 51 | 27 | 29 | 0 | 2.7 | 16.2 |
| FSD4 | 38 | Y | Y | 30.8 | 8.8 | 12 | 12.8 | *33.2* | 2.6 | 61 | 28.9 | 31.6 | 0 | -2.7 | *7.9* |
| FSN4 | 35 | Y | Y | 28.6 | *9.9* | 7 | 10.1 | *68.7* | 0 | 46 | 25.7 | 20 | 0 | 5.7 | 37.2 |
| FSN6 | 33 | Y | Y | 28.2 | *11.3* | 7 | 12.3 | 51.6 | 9 | 57 | 38.5 | 21.2 | 0 | *20.5* | 12.9 |
| Transduction scores below 0.5 | | | | | | | | | | | | | | | |
| FSN7 | 31 | Y | Y | *11.1* | *11* | 8 | 12.5 | 58.2 | 16.2 | 45 | 19.4 | 25.8 | 0 | -6.4 | *55* |
| FSN8 | *19* | Y | Y | 38.8 | 4.2 | 5 | 12 | 36.9 | 0 | 47 | 21 | 26.3 | 0 | -5.3 | 26.5 |
| FSD3 | 38 | *N* | *N* | 31.7 | *1.9* | 11 | 12 | 39.5 | 0 | 61 | 31.6 | 28.9 | 0 | 2.7 | *7.8* |
| FSN3 | 31 | *N* | Y | 29.6 | 5.4 | 7 | 11.8 | 35.5 | 19.3 | *28* | *8.3* | 22.6 | 0 | *-11.2* | 44.7 |
| FSD6 | 34 | *N* | *N* | 25.1 | 3.5 | 7 | 11.8 | 42.8 | 10.7 | 44 | 23.6 | 25 | 0 | 3 | 17.7 |

Y = Yes; N = No; Cells with plain text = value falls within parameter range set forth in Table A1; Cells with bolded, underlined, and italicized text = value falls outside parameter range set forth in Table A1

The primary amino acid sequences of peptides FSD5, FSD16, FSD18, FSD19, FSD20, FSD22, and FSD23 are related, as shown in the alignment below.

```
FSD23    -----LLKLWSRLLKEWTQG-------RRLEAKRAEA-----

FSD19    -----LLKLWSRLLKTWTQG-------RRLKAKSAQASTRQA

FSD5     -----LLKLWSRLLKLWTQG-------RRLKAKRAKA-----

FSD18    -----LLKLWSRLLKLWTQGGSGGGSGRRLKAKRAKA--

FSD16    -----LLKLWSRLLKLWTQG-------RRLKAKRAKAKR--

FSD20    AAVLKLWKRLLKLFRKG----------RRLKAKRAKAKR---

FSD22    ----VLKLWSRILKAFTQG--------RRMAAKRAKCN----

LKLW-R-LK----G           RR--AK-A (SEQ ID NO: 158)         (SEQ ID NO: 159)
```

Example C

Machine Learning-Assisted Design of Synthetic Peptide Shuttle Agents

The peptides listed in Table C1 were designed using an algorithm described in an article by Sebastien Giguère et al. entitled "Machine Learning Assisted Design of Highly Active Peptides for Drug Discovery" (Giguère et al., 2014). This computational prediction method is founded on the use of algorithms based on the Kernel and machine learning methods (Shawe-Taylor J. and Cristianini N., 2004). These algorithms aim to sort peptides with maximal bioactivity depending on a biological effect of interest. Here, we considered all the peptides that we tested to date in protein transduction assays, and separated them into three distinct groups. The composition of the groups was based on a "transduction score" calculated as described in Example A. Group 1 was composed of peptides demonstrating efficient cell delivery with low toxicity; Group 2 was composed of peptides demonstrating efficient cell delivery but with elevated toxicity; and Group 3 was composed of peptides that did not demonstrate any significant polypeptide cargo transduction ability.

The scores of the peptides in each group were used as starting data points for the generation of further peptide variants. The algorithm was programmed to use the peptide sequences and the scores of the peptides of Group 1 as the positive references for the prediction of peptide variants with efficient transduction ability. The sequences and the scores of Groups 2 and 3 were included as negative controls in the algorithm to delineate the search field. The peptide variants generated by the algorithm were limited to those having a length of 35 amino acids. After running, the prediction method generated sixteen sequences (FSD27 to FSD42). After analyzing the sequences of these sixteen sequences with respect to the design parameters set forth in Table A1, only peptides FSD27, FSD34 and FSD40 satisfied all of the design parameters (see Table C2). The other peptide variants had one or more parameters outside those set forth in Table A1.

TABLE C1

Machine-designed synthetic peptides and shuttle agents tested

| Peptide | SEQ ID NO: | Amino acid sequence | Length (a.a.) | MW (kDa) | pI | Charge |
|---|---|---|---|---|---|---|
| FSD27 | 138 | HHHHHHKWKLFWEAKLAKYARAAARQARAARQARA | 35 | 4.21 | 11.85 | 9+/1− |
| FSD28 | 139 | HHHHHHMAHLWESNARKFWKKAFAQHAAAHIAEA | 35 | 4.18 | 9.7 | 4+/2− |
| FSD29 | 140 | LHHHSHHLIHIWLLFKLKLKKKKAARRARRARRHH | 35 | 4.43 | 12.71 | 12+/0− |
| FSD30 | 141 | HHHHHHCLLKKWEAKLAKKIGGGGRQARAKALAKA | 35 | 3.88 | 10.74 | 9+/1− |
| FSD31 | 142 | YHHHHHKWKKRWEAKLAKALRAAGRQARAKALAKA | 35 | 4.12 | 11.62 | 11+/1− |
| FSD32 | 143 | IVRHEHCMIHLWYKNLAKYCSTSHARRLARRRAHH | 35 | 4.35 | 10.92 | 8+/1− |
| FSD33 | 144 | HHHHHHHHRQRRRWEARGGFLGGGGYARAARQARA | 35 | 4.12 | 12.22 | 8+/1− |
| FSD34 | 145 | HHHHHHKLIHIWEAKLFKKIRAAARQARARRAAKA | 35 | 4.19 | 12.19 | 10+/1− |
| FSD35 | 146 | HHHHHHKLLKRWEAKLAKALAKALAKHLAKALAKA | 35 | 3.97 | 10.82 | 9+/1− |
| FSD36 | 147 | HHHHHHCLIHIWEAKLAKKCGGGGYARAAARQARA | 35 | 3.89 | 10.06 | 6+/1− |
| FSD37 | 148 | RLHHSHHLIHIWLLFKLKLKKKKRAARRARRHHHL | 35 | 4.47 | 12.71 | 12+/0− |
| FSD38 | 149 | GHHHHHHHLIHIWEAKLAKLAKALARAAARQARAK | 35 | 3.99 | 11.74 | 7+/1− |
| FSD39 | 150 | HHHHHHHHRQRRRWEARGFLGGGGYARAARQARAA | 35 | 4.14 | 12.22 | 8+/1− |
| FSD40 | 151 | YGRKKRYMLRLWYQNLRMYCKKAYAQHRARQHAKL | 35 | 4.53 | 10.81 | 11+/0− |
| FSD41 | 152 | LHHHHHKLIHIWEAKLAKALAKALARRAAARQARA | 35 | 3.99 | 12.02 | 8+/1− |
| FSD42 | 153 | HHHHHHCMKVVWEIVLAKYKGGGGRARAASRRARA | 35 | 3.98 | 11.47 | 8+/1− |

Results computed using ProtParam ™ online tool available from ExPASy ™ Bioinformatics Resource Portal (http://web.expasy.org/protparam/);
pI: Isoelectric point;
Charge: Total number of positively (+) and negatively (−) charged residues

TABLE C2

FSD27 to FSD42 sequences and properties

| Peptide | Comments concerning out of limit parameter(s) with respect to Table A1 |
|---|---|
| FSD27 | No out of limit parameters. |
| FSD28 | No predicted amphiphilic alpha-helical structure<br>Highly hydrophobic core <12% of the total surface |
| FSD29 | No predicted amphiphilic alpha-helical structure<br>Highly hydrophobic core <12% of the total surface<br>Low hydrophobic moment (3.3) |
| FSD30 | Highly hydrophobic core <12% of the total surface<br>Low hydrophobic moment (2.6) |
| | Net charge below +4 (+2)<br>Low percentage K/R residues (11.5%)<br>Difference between % A/L and % K/R greater than 10% (17.1%) |

TABLE C2-continued

FSD27 to FSD42 sequences and properties

| Peptide | Comments concerning out of limit parameter(s) with respect to Table A1 |
|---|---|
| FSD31 | Highly hydrophobic core <12% of the total surface |
| FSD32 | No predicted amphiphilic alpha-helical structure<br>Highly hydrophobic core <12% of the total surface |
| FSD33 | Highly hydrophobic core <12% of the total surface<br>Low hydrophobic moment (2.1)<br>Less than 5% leucines (2.9%)<br>Difference between % A/L and % K/R greater than 10% (22.9%) |
| FSD34 | No out of limit parameters. |
| FSD35 | Highly hydrophobic core <12% of the total surface<br>Low hydrophobic moment (2.8)<br>High % of A/L (48.6%)<br>Difference between % A/L and % K/R greater than 10% (22.8%)<br>Low % of total non-A/L/K/R residues (2.85%) |
| FSD36 | No predicted amphiphilic alpha-helical structure<br>Low hydrophobic moment (3.3)<br>Highly hydrophobic core <12% of the total surface<br>Difference between % A/L and % K/R greater than 10% (11.4%) |
| FSD37 | No predicted amphiphilic alpha-helical structure |
| FSD38 | Difference between % A/L and % K/R greater than 10% (20%) |
| FSD39 | Highly hydrophobic core <12% of the total surface |
| FSD40 | No out of limit parameters. |
| FSD41 | High % of A/L (46%)<br>Difference between % A/L and % K/R greater than 10% (23%) |
| FSD42 | Less than 5% leucines (2.9%) |

HeLa cells were cultured and tested in the protein transduction assay described in Example 3.1a. GFP-NLS recombinant protein (10 μM) was co-incubated with 10 μM of the peptide and then exposed to HeLa cells for 1 min. The cells were subjected to flow cytometry analysis as described in Example 3.3. Results are shown in Table C3.

TABLE C3

Transduction of GFP-NLS in HeLa cells by machine-designed synthetic peptides

| Cells | Peptide | Mean % cells with GFP signal (±St. Dev.; n = 3) | Cell viability (%) (±St. Dev.; n = 3) |
|---|---|---|---|
| HeLa | No peptide | 0.22 ± 0.03 | 100 |
| | FSD27* | 25.49 ± 6.52 | 96.6 ± 4.94 |
| | FSD28 | 0.83 ± 0.29 | 99.4 ± 4.04 |
| | FSD29 | 6.43 ± 2.6 | 89.8 ± 8.48 |
| | FSD30 | 1.75 ± 1.14 | 99.1 ± 0.52 |
| | FSD31 | 6.90 ± 1.27 | 97.8 ± 4.22 |
| | FSD32 | 3.12 ± 1.03 | 99.2 ± 3.37 |
| | FSD33 | 0.68 ± 0.45 | 98.1 ± 1.73 |
| | FSD34* | 32.89 ± 8.9 | 97.9 ± 8.18 |
| | FSD35 | 2.08 ± 0.92 | 81.7 ± 3.45 |
| | FSD36 | 0.35 ± 0.2 | 98.9 ± 0.38 |
| | FSD37* | 11.57 ± 2.99 | 73.9 ± 2.62 |
| | FSD38 | 4.61 ± 1.33 | 98.1 ± 7.35 |
| | FSD39 | 0.23 ± 0.09 | 97.3 ± 2.07 |
| | FSD40* | 32.66 ± 0.77 | 83.9 ± 4.16 |
| | FSD41* | 36.99 ± 0.88 | 79.5 ± 0.33 |
| | FSD42 | 1.59 ± 0.39 | 97.3 ± 1.07 |

*Peptides demonstrating transduction efficiencies above 10% appear in bold.

Interestingly, the three peptides generated using the algorithm that respected all of the design parameters set forth in Table A1 (i.e., FSD27, FSD34 and FSD40) each demonstrated 25-33% transduction efficiency, with cell viabilities ranging from 83.9%-98%. The other peptides generally demonstrated transduction efficiencies below 12%, except for FSD41, which demonstrated a transduction efficiency of 37% (albeit with higher toxicity than FSD27, FSD34, and FSD40). Although only a single parameter (i.e., efficiency score) was used to program the algorithm, the results with FSD27, FSD34 and FSD40 validate the usefulness of the design parameters set forth in Table A1.

Example D

Rationally-Designed Peptides Facilitate Escape of Endosomally-Trapped Calcein

Calcein endosomal escape assays were performed as generally described in Example 2 and characterized fluorescence microscopy (data not shown) and by flow cytometry (results for FSD5 are shown below). FSD18 displayed similar results to FSD5 (data not shown).

TABLE D1

Calcein endosome escape assays

| Cells | Peptide | Peptide exposure time (min) | Peptide conc. (μM) | Mean Counts (±St. Dev.; n = 3) | Mean Factor |
|---|---|---|---|---|---|
| HeLa | No peptide | 0 | 0 | 4.94 ± 0.39 | 1.0 |
| | FSD5 | 1 | 10 | 76.31 ± 5.18 | 15.4 |
| | | | 7.5 | 56.41 ± 5.33 | 11.3 |
| | | | 5 | 16.27 ± 1.27 | 3.0 |
| | | | 2.5 | 12.41 ± 0.92 | 1.5 |

The result from fluorescence microscopy and flow cytometry experiments showed that rationally-designed peptide shuttle agents facilitate the escape of endosomally-trapped calcein in a dose-dependent fashion, similar to the domain-based peptide shuttle agents.

Example E

Rationally-Designed Peptides Increase Transduction Efficiency in Different Cell Types Protein transduction assays in different cell types were conducted as generally described in Example 3.1a (adherent cells) or Example 3.1b (suspension cells), using rationally-designed peptides at the indicated concentrations, 10 μM GFP-NLS as cargo, and at the indicated times, before being characterized by flow cytometry (Example 3.3) and fluorescence microscopy (Example 3.2). The results from the flow cytometry are shown in the tables below. Successful delivery of GFP-NLS to the nucleus of cells was verified by fluorescence microscopy (data not shown).

TABLE E1

GFP-NLS transduction in HeLa cells

| Cells | Peptide | Peptide conc. (µM) | Conc. of GFP-NLS (µM) | Incubation time (min) | Mean % cells with GFP signal (±St. Dev.; n = 3) | Cell viability (%) (±St. Dev.; n = 3) |
|---|---|---|---|---|---|---|
| HeLa | No peptide | 0 | 10 | 2 | 0.38 ± 0.05 | 100 |
| | FSD5 | 10 | | 1 | 70.5 ± 6.44 | 76 ± 7.45 |
| | | 8 | | 1 | 68.5 ± 5.27 | 85 ± 6.27 |
| | | 5 | | 2 | 63.1 ± 4.19 | 35.5 ± 4.82 |
| | FSD9 | 10 | | 1 | 73.5 ± 5.51 | 79.5 ± 6.33 |
| | | 8 | | 1 | 70.2 ± 6.83 | 82.3 ± 7.16 |
| | | 5 | | 2 | 58.4 ± 4.93 | 45.6 ± 3.64 |
| | FSD10 | 10 | | 1 | 73.1 ± 5.24 | 79.75 ± 6.37 |
| | | 8 | | 1 | 55.9 ± 5.22 | 83.42 ± 6.38 |
| | | 5 | | 2 | 45.8 ± 4.16 | 55.61 ± 4.28 |

TABLE E2

GFP-NLS transduction in HCC-78 cells (human non-small cell lung carcinoma)

| Cells | Peptide | Peptide conc. (µM) | Conc. of GFP-NLS (µM) | Incubation time (min) | Mean % cells with GFP signal (±St. Dev.; n = 3) | Cell viability (%) (±St. Dev.; n = 3) |
|---|---|---|---|---|---|---|
| HCC-78 | No peptide | 0 | 10 | 2 | 0.21 ± 0.03 | 100 |
| | FSD5 | 10 | | 1 | 41.9 ± 3.61 | 15.9 ± 0.83 |
| | | 8 | | 1 | 69.3 ± 5.27 | 87.7 ± 6.52 |
| | | 5 | | 2 | 34.1 ± 3.57 | 75.3 ± 6.18 |
| | FSD10 | 10 | | 1 | 45.0 ± 4.23 | 63.1 ± 5.27 |
| | | 8 | | 1 | 15.7 ± 2.67 | 76.1 ± 6.19 |
| | | 5 | | 2 | 22.8 ± 3.06 | 83.1 ± 5.99 |
| | FSD12 | 10 | | 1 | 35.9 ± 3.18 | 46.5 ± 4.18 |
| | | 8 | | 1 | 39.7 ± 4.08 | 66.3 ± 6.03 |
| | | 5 | | 2 | 21.4 ± 2.53 | 75.1 ± 6.31 |

TABLE E3

GFP-NLS transduction in NCI-H196 cells (human small cell lung cancer)

| Cells | Peptide | Peptide conc. (µM) | Conc. of GFP-NLS (µM) | Incubation time (min) | Mean % cells with GFP signal (±St. Dev.; n = 3) | Cell viability (%) (±St. Dev.; n = 3) |
|---|---|---|---|---|---|---|
| NCI-H196 | No peptide | 0 | 10 | 2 | 0.1 ± 0.02 | 100 |
| | FSD5 | 10 | | 1 | 16 ± 1.27 | 47.19 ± 3.54 |
| | | 8 | | 1 | 9.1 ± 0.99 | 69.94 ± 6.38 |
| | | 5 | | 2 | 7.3 ± 0.82 | 77.19 ± 6.17 |
| | FSD10 | 10 | | 1 | 8.3 ± 0.76 | 85.44 ± 7.66 |
| | | 8 | | 1 | 7.4 ± 0.83 | 80.97 ± 8.02 |
| | | 5 | | 2 | 6.4 ± 0.71 | 83.22 ± 7.51 |
| | FSD12 | 10 | | 1 | 6.3 ± 0.68 | 72.52 ± 6.29 |
| | | 8 | | 1 | 4.5 ± 0.38 | 71.86 ± 6.44 |
| | | 5 | | 2 | 5.1 ± 0.42 | 76.51 ± 6.37 |

TABLE E4

GFP-NLS transduction in THP-1 cells

| Cells | Peptide | Peptide conc. (µM) | Conc. of GFP-NLS (µM) | Incubation time (min) | Mean % cells with GFP signal (±St. Dev.; n = 3) | Cell viability (%) (±St. Dev.; n = 3) |
|---|---|---|---|---|---|---|
| THP-1 | No peptide | 0 | 10 | 1.5 | 0.27 ± 0.01 | 100 |
| | FSD10 | 1 | | 1 | 42.6 ± 4.29 | 93.5 ± 5.64 |
| | | 1 | | 1.5 | 59.4 ± 3.61 | 78.4 ± 6.15 |
| | | 2 | | 0.5 | 60.5 ± 5.27 | 96.3 ± 2.16 |
| | | 2 | | 1 | 71.9 ± 5.63 | 85.6 ± 5.22 |

TABLE E4-continued

GFP-NLS transduction in THP-1 cells

| Cells | Peptide | Peptide conc. (µM) | Conc. of GFP-NLS (µM) | Incubation time (min) | Mean % cells with GFP signal (±St. Dev.; n = 3) | Cell viability (%) (±St. Dev.; n = 3) |
|---|---|---|---|---|---|---|
| | FSD18 | 1 | | 1 | 43.6 ± 3.55 | 95.3 ± 3.11 |
| | | 1 | | 1.5 | 41.7 ± 2.82 | 86.5 ± 6.27 |
| | | 2 | | 0.5 | 53.4 ± 4.29 | 97.9 ± 1.73 |
| | | 2 | | 1 | 78.3 ± 5.48 | 98.6 ± 0.37 |
| | FSD19 | 2 | | 0.5 | 55.4 ± 4.63 | 68.7 ± 4.29 |
| | | 5 | | 0.25 | 61.5 ± 6.07 | 60.5 ± 5.71 |
| | FSD21 | 2 | | 0.5 | 47.1 ± 3.83 | 75.6 ± 6.38 |
| | | 5 | | 0.25 | 57.3 ± 4.52 | 62.5 ± 5.16 |
| | FSD25 | 2 | | 0.5 | 51.9 ± 6.39 | 79.7 ± 6.52 |
| | | 5 | | 0.25 | 51.5 ± 4.17 | 66.9 ± 5.17 |

TABLE E5

GFP-NLS transduction in various suspension cells

| Peptide | Cells | Peptide conc. (µM) | Conc. of GFP-NLS (µM) | Incubation time (min) | Mean % cells with GFP signal (±St. Dev.; n = 3) | Cell viability (%) (±St. Dev.; n = 3) |
|---|---|---|---|---|---|---|
| No peptide | [All] | 0 | 10 | 90 | 0.36 ± 0.03* | 100* |
| FSD18 | DOHH2 | 1 | | 90 | 2.4 ± 0.42 | 62.5 ± 6.17 |
| | | 2 | | 30 | 26.8 ± 2.19 | 79.8 ± 6.18 |
| | | 10 | | | 27.2 ± 2.46 | 25.0 ± 2.66 |
| | HT2 | 1 | | 90 | 12.3 ± 0.96 | 88.3 ± 7.91 |
| | | 2 | | 30 | 31.0 ± 2.55 | 80.7 ± 7.10 |
| | | 10 | | | 82.5 ± 4.07 | 63.9 ± 5.35 |
| | Jurkat | 1 | | 90 | 10.1 ± 1.11 | 98.6 ± 0.39 |
| | | 2 | | 30 | 11.0 ± 1.29 | 97.4 ± 1.09 |
| | | 10 | | | 9.9 ± 1.06 | 96.6 ± 2.46 |
| | KMS-12BM | 1 | | 90 | 13.6 ± 2.17 | 97.6 ± 1.05 |
| | | 2 | | 30 | 26.2 ± 3.93 | 95.1 ± 3.56 |
| | | 10 | | | 21.0 ± 1.76 | 92.7 ± 4.11 |
| | REC-1 | 1 | | 90 | 1.80 ± 0.88 | 96.2 ± 2.53 |
| | | 2 | | 30 | 10.9 ± 1.34 | 99.0 ± 0.39 |
| | | 10 | | | 25.0 ± 1.89 | 25.0 ± 3.17 |
| | NK | 1 | | 90 | 2.80 ± 0.33 | 99.1 ± 0.08 |
| | | 2 | | 30 | 6.41 ± 1.12 | 98.3 ± 1.00 |
| | | 5 | | 15 | 65.7 ± 5.27 | 94.9 ± 1.63 |

*Quantification of the negative control ("no peptide") was similar for all cell lines tested. Thus, the data (*) represents an average from the "no peptide" controls for all cell lines tested.

Example F

Rationally-Designed Peptide Shuttle Agents Enable Transduction of Antibodies

F.1 Transduction of Fluorescently Labeled Antibodies by FSD5 in HeLa Cells

Protein transduction assays were conducted as generally described in Example 3.1, using the peptide FSD5 and an antibody as cargo after 1 min incubation time, before being characterized by fluorescence microscopy (Example 3.2). FIG. 50 shows the results of the cytoplasmic transduction of Goat Anti-Mouse IgG H&L (Alexa Fluor® 488) and Goat Anti-Rabbit IgG H&L (Alexa Fluor® 594) antibodies delivered in HeLa cells by the peptide FSD5 (8 µM) for 1 min and visualized by fluorescence microscopy at 20× magnification for the Alexa Fluor 594 Ab (FIG. 50A); and at 10× and 20× magnification for the Alexa Fluor 488 Ab (FIGS. 50B and 50C, respectively). The bright field and fluorescence images of living cells are shown in upper and lower panels, respectively.

The following experiments show that other FSD peptides can also deliver functional antibodies: an anti-NUP98 antibody which labels the nuclear membrane, and two anti-Active Caspase3 antibodies that bind and inactivate the pro-apoptotic Caspase 3 protein. The delivery, microscopy and cell immune-labelling protocols are described in Example 3.

F.2 Transduction of Anti-NUP98 Antibody by FSD19 in HeLa Cells

Figure 50D:
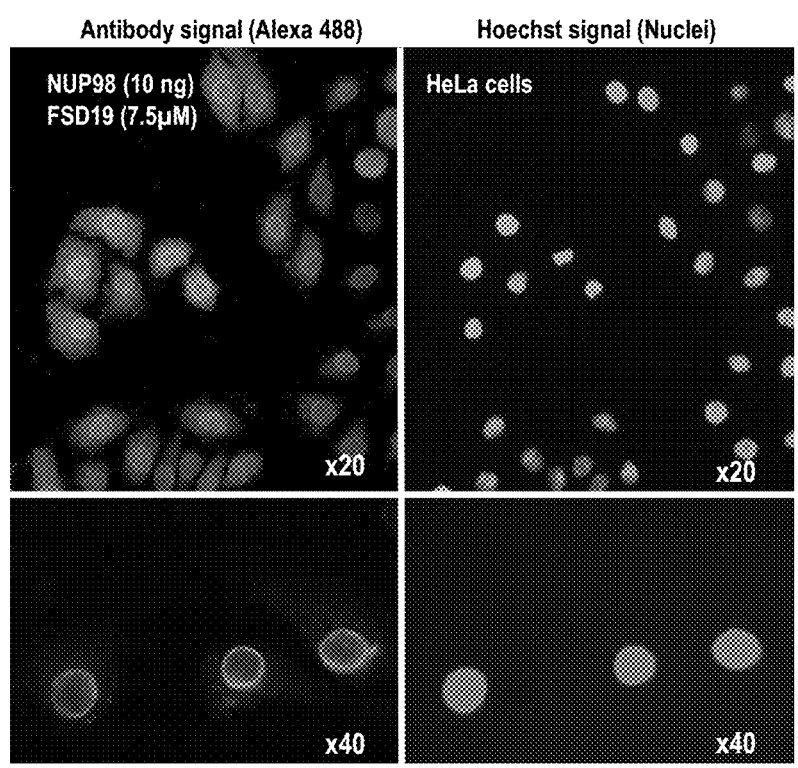
FIG. 50D shows the results of a transduction experiment in which an anti-NUP98 antibody, which recognizes an antigen in the perinuclear membrane, was transduced into HeLa cells using the shuttle agent FSD19. Following transduction, HeLa cells were fixed, permeabilized and labelled with a fluorescent (Alexa™ 488) secondary antibody recognizing the anti-NUP98 antibody (left panels) and Hoechst nuclear staining (right panels). Upper and lower panels indicate images taken under 20× and 40× magnification, respectively.

Anti-NUP98 antibody (10 µg) was co-incubated with 7.5 µM of FSD19 and exposed to HeLa cells for 4 hours. Cells are washed, fixed with paraformaldehyde 4%, permeabilized with 0.1% Triton™ and labeled with a fluorescently labeled (Alexa™ Fluor 488) goat anti-rat antibody. Antibody bound to the perinuclear membrane and cell nuclei were visualized by fluorescence microscopy at 20× (upper panels) and 40× (lower panels). As shown in FIG. 50D, green fluorescent signal emanated from the nuclear membrane (left panels) and overlapped with Hoechst staining (right panels), demonstrating that the anti-NUP98 antibody retained its functionality inside the cell following its transduction.

F.3 Transduction of Two Functional Anti-Active Caspase 3 Antibodies by FSD23 in THP-1 and Jurkat Cells: Quantification by ELISA Cleaved PARP Assay A monoclonal (mAb) and a polyclonal (pAb) anti-Active Caspase 3 antibodies (2 µg) were independently co-incubated with THP-1 and Jurkat cells for 5 min in the presence of FSD23 at 7.5 µM. The anti-apoptotic effect of each antibody was assessed via the level of Caspase 3-activated apoptosis with an ELISA cleaved PARP assay and quantified by spectrometry as described below.

The day of the experiment, cells in exponential growth phase were harvested, centrifugated (400 g for 3 min) and resuspended in serum-free RPMI in a 96-well plate (500,000 cells in 150 µL per well). Cells were centrifugated and incubated for 5 min with a mix composed by the peptide to be tested (7.5 µM) and 2 µg of the antibody to be transduced. Cells were centrifuged and resuspended in RPMI with serum in a 24-well plate for 1 h at 37° C. Actinomycin D (2 µg/mL), a cytotoxic inducer of apoptosis, was incubated with the cells for 4 h. Cells were washed with cold PBS and tested using the PARP (Cleaved) [214/215] Human ELISA Kit (ThermoFisher) according to the manufacturer's instructions followed by spectroscopy analysis. Results are shown in Table FI.

TABLE F1

Cleaved PARP ELISA assay after transduction of anti-TNF or anti-Active Caspase 3 antibody by FSD23 in THP-1 and Jurkat cells

| Cell type | Antibody | Actinomycin D | Optical Density (O.D.) PARP cleavage assay |
|---|---|---|---|
| THP-1 | anti-TNF (control) | − | 0.334 |
|  |  | + | 1.162 |
|  | anti-Active Caspase 3 mAb | − | 0.207 |
|  |  | + | 0.856 |
|  | anti-Active Caspase 3 pAb | − | 0.192 |
|  |  | + | 0.653 |
| Jurkat | anti-TNF (control) | − | 0.281 |
|  |  | + | 0.486 |
|  | anti-Active Caspase 3 mAb | − | 0.174 |
|  |  | + | 0.301 |
|  | anti-Active Caspase 3 pAb | − | 0.149 |
|  |  | + | 0.333 |

Results in THP-1 and in Jurkat cells show that FSD23 successfully transduced functional anti-Active Caspase 3 antibodies. Anti-TNF antibody was used as a non-specific negative control and actinomycin D as a cytotoxic inducer of apoptosis. In the absence of actinomycin D ("−"), the delivery of each anti-Active Caspase 3 mAb and pAb resulted in the reduction of the basal level of apoptosis compared to the "anti-TNF" control, in which the delivery of the anti-TNF antibody had no discernable impact on cell viability. In presence of actinomycin D ("+"), the resulting apoptosis was reduced after the delivery of both anti-Active Caspase 3 antibodies with FSD23 compared to the "anti-TNF" control.

Example G

Rationally-Designed Peptide Shuttle Agents Enable Transduction of CRISPR-Based Genome Editing Complexes We tested the ability of rationally-designed peptide shuttle agents to deliver functional CRISPR-based genome editing complexes to the nucleus of eukaryotic cells using standard DNA cleavage assays. These assays were used to measure CRISPR/Cas9 and CRISPR/Cpf1-mediated cleavage of cellular genomic DNA sequences HPRT (Hypoxanthine Phosphoribosyltransferase 1) and DNMT1 (DNA (Cytosine-5-)-Methyltransferase 1), respectively. Homologous-directed recombination (HDR) of short (72 bp) and long (1631 bp) DNA templates were performed at the HPRT genomic cut site, and measured after intracellular delivery of the genome editing complexes with different shuttle agents.

G.1 CRISPR/Cas9-NLS Complex Transduction by Rationally-Designed Peptide Shuttle Agents, Cleavage of Genomic Target Sequence, and Homologous-Directed Recombination in Different Cell Lines G.1.1 Transduction of Functional CRISPR/Cas9-NLS Complexes Cas9-NLS recombinant protein was prepared as described in Example 13.1. A mix composed of a Cas9-NLS recombinant protein and crRNA/tracrRNA (see below) targeting a nucleotide sequence of the HPTR genes were co-incubated with different concentrations of FSD5, FSD8, FSD10 or FSD18 and incubated with HeLa, HCC-78, NIC-H196 or REC-1 cells for 2 min in PBS, or 48 h in medium with serum, using the transduction protocols as generally described in Example 3.1a. Cells were then washed with PBS and harvested to proceed with the T7E1 protocol assay as described in Example 13.4.

The sequences of the crRNA and tracrRNAs constructed and their targets were:

Feldan tracrRNA:
[SEQ ID NO: 77]
5'-AAACAGCAUAGCAAGUUAAAAUAAGGCUAGUCCGUUAUCAACUUG

AAAAAGUGGCACCGAGUCGGUGCU-3'

HPRT crRNA:
[SEQ ID NO: 103]
5'-AAUUAUGGGGAUUACUAGGAGUUUUAGAGCUAUGCU-3'

FIGS. 51A-51F show the results of the cleavage of the targeted genomic HPRT DNA sequence with the CRISPR/Cas9 (2.5 µM) and the crRNA/tracrRNA (2 µM) in the absence ("−ctrl") or presence of the shuttle agents FSD5, FSD8, FSD10 or FSD18 used at different concentrations, exposure times, and in different types of cells: HeLa (FIGS. 51A and 51B); NK (FIG. 51C); NIC-196H (FIG. 51D); HCC-78 (FIG. 51E) and REC-1 cells (FIG. 51F), after separation by agarose gel electrophoresis. In some cases, gel lanes were loaded in duplicate. Thin dashed arrows indicate the bands corresponding to the target gene, and thicker solid arrows indicate the bands corresponding to the cleavage products of this target gene, which indicate the successful transduction of functional CRISPR/Cas9-NLS genome editing complexes. We used a Bio-Rad ImageLab™ software (Version 5.2.1, Bio-Rad, http://www.bio-rad.com/en-ca/product/image-lab-software?tab=Download) to quantify the relative signal intensities of each of the different bands directly on gels. The sum of all the bands in a given lane corresponds to 100% of the signal, and the numerical value in italics at the bottom of each lane is the sum of the relative signals (%) of only the two cleavage product bands (thicker solid arrows). No cleave product bands were found in the negative controls ("−ctrl", i.e., to cells that were exposed to CRISPR/Cas9-NLS complex in the absence of shuttle agent). These results indicate the successful delivery of the CRISPR genome-editing complexes to the nucleus, resulting in cleave of the target gene.

G.1.2 Transduction of CRISPR/Cas9-NLS Complexes with Short Linear DNA Template, Resulting in Homologous-Directed Recombination A mix was prepared containing: a Cas9-NLS recombinant protein (2.5 µM) (see Example 13.1); the crRNA/tracrRNA (2 µM) targeting a nucleotide sequence of the HPTR genes (see above); the peptide shuttle agent FSD5 (15 μM); and either 0 ng or 500 ng of a short linear template DNA (72 bp; see below).

Short DNA template:
[SEQ ID NO: 154]
5'-TGAAATGGAGAGCTAAATTATGGGGATTACAAGCTTGATAGCGA

AGGGGCAGCAATGAGTTGACACTACAGA-3'

This mixture was exposed to HeLa cells for 48 h in culture media containing serum. Cells were then washed and subjected to the T7E1 assay as described in Example 13.4.

Figure 51G:
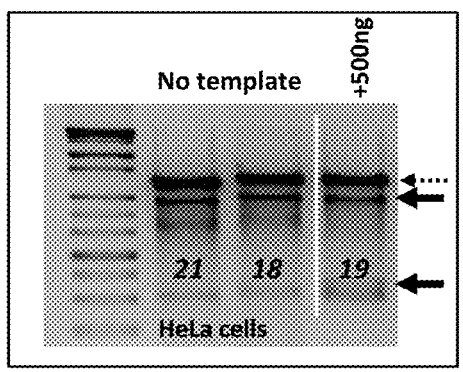
FIG. 51G shows the cleavage of the targeted HPRT genomic sequence by the CRISPR/Cas9-NLS complex transduced by FSD5, in the absence ("No template") or presence ("+500 ng") of a short DNA template (72 bp). Thin dashed arrows indicate the bands corresponding to the target gene, and thick solid arrows indicate the bands corresponding to the CRISPR/Cas9-NLS-mediated cleavage products of this target gene, which indicate the successful transduction of fully functional genome editing complexes in the presence and absence of the DNA template. The numerical value in italics at the bottom of each lane is the sum of the relative signals (%) of only the two cleavage product bands (thick solid arrows).

FIG. 51G shows the cleavage of the targeted HPRT genomic sequence by the CRISPR/Cas9 complex transduced by FSD5 (15 μM), in the absence ("No template") or presence (+500 ng) of the short DNA template. Thin dashed arrows indicate the bands corresponding to the target gene, and thicker solid arrows indicate the bands corresponding to the cleavage products of this target gene, which indicate the successful transduction of fully functional genome editing complexes. The numerical value in italics at the bottom of each lane is the sum of the relative signals (%) of only the two cleavage product bands (thicker solid arrows). These results show that FSD5 can transduce a functional CRISPR/Cas9 complex in the presence or absence of template DNA.

Figure 51H:
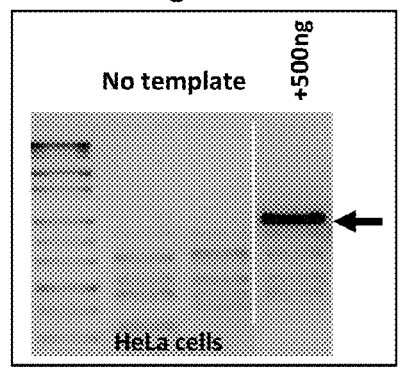
FIG. 51H shows the results of a PCR-amplification of the samples of FIG. 51G, using primers specific for the short DNA template, indicating genomic insertion of the DNA template sequence (see arrow in FIG. 51H).

To verify whether homologous-directed recombination occurred, we used the genomic DNA extracted from FSD5/CRISPR/short DNA template-treated cells to amplify the short DNA template sequence with specifically designed oligonucleotide primers targeting this sequence. The amplification of the short DNA template sequence confirmed the insertion of this template in the genome after the cutting of the HPRT gene by the CRISPR/Cas9-NLS genome editing complex. The PCR products were resolved by agarose gel electrophoresis and the results are shown in FIG. 51H. No amplification was detected in the "no template" sample, in which the genomic DNA was cut but no DNA template was provided (FIG. 51H). In contrast, an amplicon of appropriate size (FIG. 51H, thick solid line) was detected for the "+500 ng" sample, in which the genomic DNA was cut and a DNA template was provided. Detection of the amplicon indicates successful insertion of the short DNA template sequence into the genome. These results show that FSD5 can transduce CRISPR/Cas9 complex in the presence of a short DNA template, resulting in homologous-directed recombination.

G.1.3 Transduction of CRISPR/Cas9-NLS Complexes with Long Linear DNA Template, Resulting in Homologous-Directed Recombination A mix was prepared containing: a Cas9-NLS recombinant protein (2.5 μM) (see Example 13.1); the crRNA/tracrRNA (2 μM) targeting a nucleotide sequence of the HPTR genes (see above); the peptide shuttle agent FSD5 (15 μM); and either 0 ng or 500 ng of a long linear template DNA encoding GFP (1631 bp; see below).

GFP coding DNA template:
[SEQ ID NO: 156]
5'AAGTAATCAATTACGGGGTCATTAGTTCATAGCCCATATATGGAGTT

CCGCGTTACATAACTTACGGTAAATGGCCCGCCTGGCTGACCGCCCAA

CGACCCCCGCCCATTGACGTCAATAATGACGTATGTTCCCATAGTAAC

GCCAATAGGGACTTTCCATTGACGTCAATGGGTGGAGTATTTACGGTAA

ACTGCCCACTTGGCAGTACATCAAGTGTATCATATGCCAAGTACGCCC

-continued

CCTATTGACGTCAATGACGGTAAATGGCCCGCCTGGCATTATGCCCAG

TACATGACCTTATGGGACTTTCCTACTTGGCAGTACATCTACGTATTAGT

CATCGCTATTACCATGGTGATGCGGTTTTGGCAGTACATCAATGGGCGT

GGATAGCGGTTTGACTCACGGGGATTTCCAAGTCTCCACCCCATTGAC

GTCAATGGGAGTTTGTTTTGGCACCAAAATCAACGGGACTTTCCAAAAT

GTCGTAACAACTCCGCCCCATTGACGCAAATGGGCGGTAGGCGTGTA

CGGTGGGAGGTCTATATAAGCAGAGCTGGTTTAGTGAACCGTCAGATC

CGCTAGCGCTACCGGTCGCCACCATGGTGAGCAAGGGCGAGGAGCT

GTTCACCGGGGTGGTGCCCATCCTGGTCGAGCTGGACGGCGACGTAA

ACGGCCACAAGTTCAGCGTGTCCGGCGAGGGCGAGGGCGATGCCAC

CTACGGCAAGCTGACCCTGAAGTTCATCTGCACCACCGGCAAGCTGC

CCGTGCCCTGGCCCACCCTCGTGACCACCCTGACCTACGGCGTGCA

GTGCTTCAGCCGCTACCCCGACCACATGAAGCAGCACGACTTCTTCA

AGTCCGCCATGCCCGAAGGCTACGTCCAGGAGCGCACCATCTTCTT

CAAGGACGACGGCAACTACAAGACCCGCGCCGAGGTGAAGTTCGAG

GGCGACACCCTGGTGAACCGCATCGAGCTGAAGGGCATCGACTTCAA

GGAGGACGGCAACATCCTGGGGCACAAGCTGGAGTACAACTACAACA

GCCACAACGTCTATATCATGGCCGACAAGCAGAAGAACGGCATCAAGG

TGAACTTCAAGATCCGCCACAACATCGAGGACGGCAGCGTGCAGCTC

GCCGACCACTACCAGCAGAACACCCCCATCGGCGACGGCCCCGTGC

TGCTGCCCGACAACCACTACCTGAGCACCCAGTCCGCCCTGAGCAAA

GACCCCAACGAGAAGCGCGATCACATGGTCCTGCTGGAGTTCGTGAC

CGCCGCCGGGATCACTCTCGGCATGGACGAGCTGTACAAGTCCGGAC

TCAGATCTCGAGCTCAAGCTTCGAATTCTGCAGTCGACGGTACCGCGG

GCCCGGGATCCACCGGATCTAGATAACTGATCATAATCAGCCATACCA

CATTTGTAGAGGTTTTACTTGCTTTAAAAAACCTCCCACACCTCCCCCT

GAACCTGAAACATAAAATGAATGCAATTGTTGTTGTTAACTTGTTTATTG

CAGCTTATAATGGTTACAAATAAAGCAATAGCATCACAAATTTCACAAA

TAAAGCATTTTTTTCACTGCATTCTAGTTGTGGTTTGTCCAAACTCATCA

ATGTATCTTAA-3'

This mixture was exposed to HeLa cells for 48 h in culture media containing serum. Cells were then washed with PBS and harvested to proceed with the T7E1 protocol assay as described in Example 13.4.

Figure 51I:
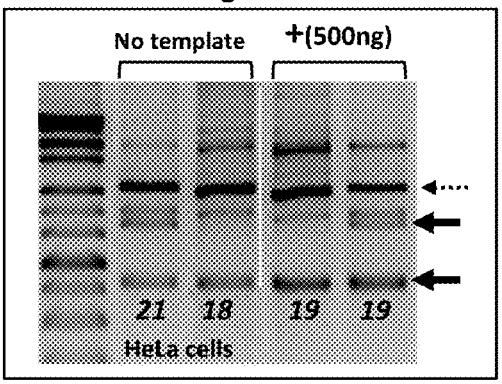
FIG. 51I shows the cleavage of the targeted HPRT genomic sequence by the CRISPR/Cas9-NLS complex transduced by FSD5, in the absence ("No template") or presence ("+500 ng") of a long linear DNA template (1631 bp). Thin dashed arrows indicate the bands corresponding to the target gene, and thick solid arrows indicate the bands corresponding to the CRISPR/Cas9-NLS-mediated cleavage products of this target gene, which indicate the successful transduction of fully functional genome editing complexes in the presence and absence of the DNA template. The numerical value in italics at the bottom of each lane is the sum of the relative signals (%) of only the two cleavage product bands (thick solid arrows).

FIG. 51I shows the cleavage of the targeted genomic HPRT genomic sequence by the CRISPR/Cas9 complex transduced by FSD5 (15 μM), in the absence ("No template") or presence ("+500 ng") of the long DNA template. The cleavage products are indicated with thick solid arrows. These results show that FSD5 can transduce a functional CRISPR/Cas9 complex in the presence or absence of a long template DNA.

Figure 51J:
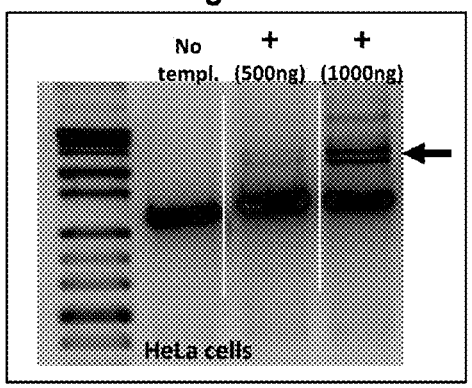
FIG. 51J shows the results of a PCR-amplification of the samples of FIG. 51I, using primers designed to amplify across the genomic cleavage site. Genomic insertion of the long DNA template sequence is visible by the presence of a larger band in the "+500 ng" (faint) and "+1000 ng" (darker) lanes—see arrow in FIG. 51J.

To verify whether homologous-directed recombination occurred, we used the genomic DNA extracted from FSD5/CRISPR/long DNA template-treated cells to amplify the long DNA template sequence with specifically designed oligonucleotide primers flanking this sequence. The amplification of the long DNA template sequence confirmed the insertion of this template in the genome after the cutting of the HPRT gene by the CRISPR/Cas9-NLS genome editing complex. The PCR products were resolved by agarose gel electrophoresis and the results are shown in FIG. 51J. In the "No template" sample, a single band corresponding to the amplicon lacking the long DNA template insertion was detected. In contrast, additional larger bands (indicated with an arrow) were detected for the "+500 ng" (faint) and "+1000 ng" (darker) samples, indicating some insertion of the long DNA template into the genomic DNA had occurred. These results show that FSD5 can transduce CRISPR/Cas9 complex in the presence of a long DNA template, resulting in homologous-directed recombination.

G.2 CRISPR/Cpf1-NLS Complex Transduction by Rationally-Designed Shuttle Agents, Cleavage of Genomic Target Sequence in HeLa and NK Cells A mix composed of a Cpf1-NLS recombinant protein (2.5 µM) and crRNA (2 µM; see below) targeting a nucleotide sequence of the DNMT1 gene was co-incubated with different concentrations of FSD18 and incubated with HeLa or NK cells for 2 min in HeLa cells, or 90 sec in NK cells in PBS or in medium without serum using transduction protocols as described in Example 3.1a.

The sequence of the Cpf1-NLS recombinant protein produced was:

[SEQ ID NO: 155]
MTQFEGFTNLYQVSKTLRFELIPQGKTLKHIQEQGFIEEDKARNDHYKE

LKPIIDRIYKTYADQCLQLVQLDWENLSAAIDSYRKEKTEETRNALIEE

QATYRNAIHDYFIGRTDNLTDAINKRHAEIYKGLFKAELFNGKVLKQLG

TVTTTEHENALLRSFDKFTTYFSGFYENRKNVFSAEDISTAIPHRIVQD

NFPKFKENCHIFTRLITAVPSLREHFENVKKAIGIFVSTSIEEVFSFPF

YNQLLTQTQIDLYNQLLGGISREAGTEKIKGLNEVLNLAIQKNDETAIR

IASLPHRFIPLFKQILSDRNTLSFILEEFKSDEEVIQSFCKYKTLLRNE

NVLETAEALFNELNSIDLTHIFISEIKKLETISSALCDHWDTLRNALYE

RRISELTGKITKSAKEKVQRSLKHEDINLQEIISAAGKELSEAFKQKTS

EILSHAHAALDQPLPTTLKKQEEKEILKSQLDSLLGLYEILLDWFAVDE

SNEVDPEFSARLTGIKLEMEPSLSFYNKARNYATKKPYSVEKFKLNFQM

PTLASGWDVNKEKNNGAILFVKNGLYYLGIMPKQKGRYKALSFEPTEKT

SEGFDKMYYDYFPDAAKMIPKCSTQLKAVTAHFQTHTTPILLSNNFIEP

LEITKEIYDLNNPEKEPKKFQTAYAKKTGDQKGYREALCKWIDFTRDFL

SKYTKTTSIDLSSLRPSSQYKDLGEYYAELNPLLYHISFQRIAEKEIMD

AVETGKLYLFQIYNKDFAKGEIHGKPNLHTLYWTGLFSPENLAKTSIKL

NGQAELFYRPKSRMKRMAHRLGEKMLNKKLKDQKTPIPDTLYQELYDYV

NHRLSHDLSDEARALLPNVITKEVSHEIIKDRRFTSDKFFFHVPITLNY

QAANSPSKFNQRVNAYLKEHPETPIIGIDRGERNLIYITVIDSTGKILE

QRSLNTIQQFDYQKKLDNREKERVAARQAWSVVGTIKDLKQGYLSQVIH

EIVDLMIHYQAVVVLENLNFGFKSKRTGIAEKAVYQQFEKMLIDKLNCL

VLKDYPAEKVGGVLNPYQLTDQFTSFAKMGTQSGFLFYVPAPYTSKIDP

LTGFVDPFVWKTIKNHESRKHFLEGFDFLHYDVKTGDFILHFKMNRNLS

FQRGLPGFMPAWDIVFEKNETQFDAKGTPFIAGKRIVPVIENHRFTGRY

RDLYPANELIALLEEKGIVFRDGSNILPKLLENDDSHAIDTMVALIRSV

LQMRNSNAATGEDYINSPVRDLNGVCFDSRFQNPEWPMDADANGAYHIA

LKGQLLLNEILKESKDLKLQNGISNQDWLAYIQELRNGG<u>RSSDDEATAD</u>

<u>SQHAAPPKKKRKV</u>GGSGGGSGGGSGGGRHHHHHH
(MW = 155.7 kDa; pI = 8.34)
NLS sequence is underlined
Serine/glycine rich linkers are in bold The sequences of the crRNA used was as follows:

DNMT1 crRNA:
[SEQ ID NO: 157]
5'-AAUUUCUACUGUUGUAGAUCUGAUGGUCCAUGUCUGUUACUC-3'

Figure 51K:
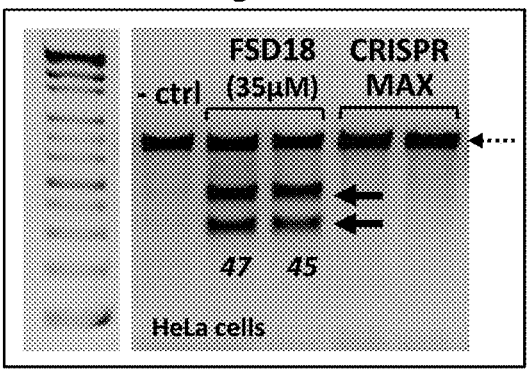
FIGS. 51K and 51L show the results of the cleavage of the targeted genomic DNMT1 DNA sequence with a CRISPR/Cpf1-NLS genome editing complex in the absence ("−ctrl") or presence of the shuttle agent FSD18 in HeLa (FIG. 51K) and NK cells (FIG. 51L), after PCR-amplification and separation by agarose gel electrophoresis. Thin dashed arrows indicate the bands corresponding to the target gene, and thick solid arrows indicate the bands corresponding to the CRISPR/Cpf1-NLS-mediated cleavage products of this target gene, which indicate the successful transduction of fully functional genome editing complexes. An imaging software was used to quantify the relative signal intensities of each of the different bands directly on gels. The sum of all the bands in a given lane corresponds to 100% of the signal, and the numerical value in italics at the bottom of each lane is the sum of the relative signals (%) of only the two cleavage product bands (thick solid arrows). No genomic DNA cleavage was observed using the lipofectamine-based transfection reagent CRISPRMAX™ to transduce the CRISPR/Cpf1-NLS genome editing complex.
Figure 51L:
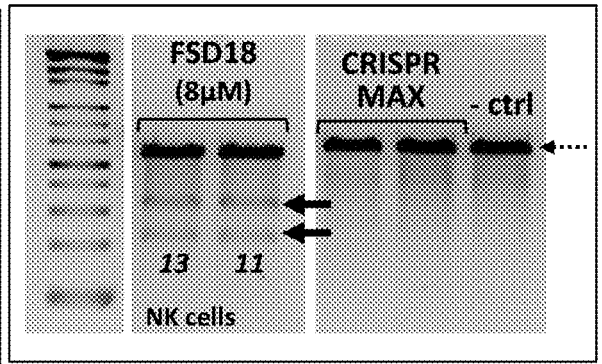

After 2 min (HeLa) or 90 sec (NK), cells were washed with PBS and harvested to proceed with the T7E1 protocol assay as described in Example 13.4. The PCR-amplified DNMT1 DNA sequence and the PCR-amplified cleavage product of this sequence were resolved on agarose gels and the results are shown in FIGS. 51K (HeLa cells) and 51L (NK cells). The negative control ("–ctrl") corresponds to cells that were exposed to CRISPR/Cpf1-NLS complex in the absence of the shuttle agent. Thin dashed arrows indicate the bands corresponding to the target gene, and thick solid arrows indicate the bands corresponding to the cleavage products of this target gene, which indicate the successful transduction of fully functional CRISPR/Cpf1-NLS genome editing complexes. The numerical value in italics at the bottom of each lane is the sum of the relative signals (%) of only the two cleavage product bands (thick solid arrows). These results show that FSD18 can transduce a functional CRISPR/Cpf1-NLS complex into the nucleus of these cells to effect cleavage of the target gene.

The CRISPRMAX™ technology is a commercially available lipofectamine-based transfection reagent optimized for CRISPR-Cas9 protein delivery. However, an equivalent reagent does not presently exist for the transduction of CRISPR-Cpf1. Interestingly, when we used the CRISPRMAX™ reagent, it was unable to deliver the CRISPR/Cpf1-NLS complex in adherent and suspension cells. In contrast, FSD18 enabled a robust cleavage of the DNMT1 target in HeLa cells, and a lower but observable cleavage in NK cells.

These results show that the shuttle agent FSD18 successfully delivered a functional CRISPR/Cpf1-NLS complex to the nucleus of HeLa and NK cells, and that this delivery resulted in a CRISPR/Cpf1-NLS-mediated cleavage of genomic DNA.

Examples G.3-G.9

Rationally-Designed Peptide Shuttle Agents Enable Single or Multiple Gene Targeting, and/or Co-Delivery of Different CRISPR-Based Genome Editing Complexes These examples support the ability of rationally-designed peptide shuttle agents to enable the delivery and edition of multiple gene targets simultaneously. Functional CRISPR-based genome editing complexes were delivered to the nucleus of eukaryotic cells, and successful genome editing was evaluated using standard DNA cleavage assays. These assays were used to measure CRISPR/Cas9-mediated cleavage of cellular genomic DNA sequences HPRT (Hypoxanthine Phosphoribosyltransferase 1) and B2M (02 microglobulin HLA subunit), and to measure CRISPR/Cpf1-mediated cleavage of cellular genomic DNA sequences NKG2A (Inhibitory NK cell receptor 2A), GSK3 (Glycogen Synthase Kinase 3), CBLB (E3 Ubiquitin-protein Ligase), DNMT1 (DNA (Cytosine-5-)-Methyltransferase 1) and B2M (02 microglobulin HLA subunit). We also performed more complex genome editing approaches with the delivery of multiple CRISPR systems targeting one or two genes in the same cells. CRISPR/Cas9 and CRISPR/Cpf1 complexes were delivered together in HeLa cells to edit the HPRT and DNMT1 genes, respectively, or to edit the B2M gene in two different loci of exon 2. Finally, we co-delivered two CRISPR/Cpf1 complexes, each carrying a specific crRNA, to edit two exons in the B2M gene in NK cells.

G3 Different Rationally-Designed Peptide Shuttle Agents Deliver CRISPR/Cas9-NLS and CRISPR/Cpf1 Complexes for B2M Gene Editing in HeLa, THP-1 and NK Cells Cas9-NLS recombinant protein was prepared as described in Example 13.1. Cpf1-NLS recombinant protein was prepared as described in Example G.2. A mix composed of a Cas9-NLS recombinant protein with its respective crRNA/tracrRNA, or a Cpf1-NLS recombinant protein with its respective single guide crRNA(s) (see below) targeting a nucleotide sequence of the B2M gene, was co-incubated with different concentrations of the peptides FSD10, FSD18, FSD19, FSD21, FSD22, or FSD23 and incubated with HeLa, THP-1 or NK cells for 90 sec in PBS, or for 1 h in medium without serum, or for 48 h in medium with serum, using the transduction protocols as generally described in Example 3.1a. Cells were then washed with PBS and harvested to proceed with the T7E1 protocol assay as described in Example 13.4.

The sequences of the crRNAs and tracrRNAs constructed and their targets were:

```
Feldan tracrRNA:
                                       [SEQ ID NO: 77]
5'-AAACAGCAUAGCAAGUUAAAAUAAGGCUAGUCCGUUAUCAAC

UUGAAAAAGUGGCACCGAGUCGGUGCU-3'

Cas9-flanked B2M-crRNA:
                                      [SEQ ID NO: 160]
5'-GAGTAGCGCGAGCACAGCTAGUUUUAGAGCUAUGCUGUUUUG-3'

Cpf1-flanked B2M crRNA-1:
                                      [SEQ ID NO: 161]
5'-AAUUUCUACUGUUGUAGAUAUCCAUCCGACAUUGAAGUU-3'

Cpf1-flanked B2M crRNA-2:
                                      [SEQ ID NO: 162]
5'-AAUUUCUACUCUUGUAGAUCCGAUAUUCCUCAGGUACUCCA-3'
```

FIGS. 52A-52D show the results of the cleavage of the targeted genomic B2M DNA sequence after the delivery of CRISPR/Cpf1 (1.33 µM) with crRNA-1 or crRNA-2 (2 µM) in the absence ("–ctrl") or in the presence of the peptides FSD10, FSD18, FSD19, FSD21 or FSD23 used at different concentrations, exposure times, and in different types of cells: THP-1 (FIG. 52A), and NK (FIGS. 52B, 52C, 52D), after separation by agarose gel electrophoresis. FIG. 52D shows cleavage products of the genomic B2M exon 2 DNA sequence after the delivery of a CRISPR/Cpf1 complex carrying a specific single guide RNA (crRNA-1 or crRNA-2) in presence of FSD18 or FSD21, respectively. FIG. 52E shows the cleavage product of the genomic B2M exon 2 DNA sequence with CRISPR/Cas9 (2.5 µM) and crRNA (2 µM) in the absence ("–ctrl") or in the presence of the peptide FSD22 used at 10 µM for 1 h in HeLa cells, after separation by agarose gel electrophoresis. Gel lanes were loaded in duplicate. Thin dashed arrows indicate the bands corresponding to the target gene, and thick solid arrows indicate the bands corresponding to the cleavage products of this target gene, which indicate the successful transduction of fully functional CRISPR genome editing complexes. We used a Bio-Rad ImageLab™ software (Version 5.2.1, Bio-Rad, http://www.bio-rad.com/en-ca/product/image-lab-software?tab=Download) to quantify the relative signal intensities of each of the different bands directly on the gels. The sum of all the bands in a given lane corresponds to 100% of the signal, and the numerical value in italics at the bottom of each lane is the sum of the relative signals (%) of only the two cleavage product bands (thick solid arrows). No cleavage product bands were found in the negative controls ("–ctrl", i.e., to cells that were exposed to CRISPR system in the absence of FSD peptide). These results indicate the successful delivery of the CRISPR genome-editing complexes to the nucleus, resulting in cleavage of the target gene.

G.4 Different Rationally-Designed Peptide Shuttle Agents Deliver CRISPR/Cpf1 Systems for GSK3, CBLB and DNMT1 Gene Editing in NK, THP-1 and Primary Myoblasts Cells.

Cpf1-NLS recombinant protein was prepared as described in Example G.2. A mix composed of a Cpf1-NLS recombinant protein with a single guide crRNA (see below) targeting a nucleotide sequence of the GSK3, CBLB or DNMT1 genes was co-incubated with different concentrations of FSD10, FSD18, FSD19 or FSD23 and incubated with NK cells for 48 h in medium with serum, and in THP-1 or in primary myoblasts cells for 90 sec in PBS, using the transduction protocols as generally described in Example 3.1a. Cells were then washed with PBS and harvested to proceed with the T7E1 protocol assay as described in Example 13.4.

The sequences of the crRNA constructed and their targets were:

```
GSK3 crRNA:
                                      [SEQ ID NO: 163]
5'-AAUUUCUACUCUUGUAGAUCUUUCUUCCUUUAGGAGACA-3'

CBLB crRNA:
                                      [SEQ ID NO: 164]
5'-AAUUUCUACUCUUGUAGAUAAGAACUAAAAUUCCAGAUG-3'

DNMT1 crRNA:
                                      [SEQ ID NO: 157]
5'-AAUUUCUACUGUUGUAGAUCUGAUGGUCCAUGUCUGUUACUC-3'
```

FIGS. 52F-52I show the results of the cleavage of the targeted genomic GSK3, CBLB and DNMT1 DNA sequences with the CRISPR/Cpf1 (1.33 µM) and crRNA (2 µM) in absence ("–ctrl") or presence of the shuttle agents FSD10, FSD18, FSD19 or FSD23 used at different concentrations, exposure times, and in different types of cells: NK (FIGS. 52F and 52G), THP-1 (FIG. 52H) and primary myoblasts (FIG. 52I) after separation by agarose gel electrophoresis. Gel lanes were loaded in duplicate. Thin dashed arrows indicate the bands corresponding to the target gene, and thick solid arrows indicate the bands corresponding to the cleavage products of this target gene, which indicate the successful transduction of fully functional CRISPR genome editing complexes.

G.5 Different Rationally-Designed Peptide Shuttle Agents Deliver CRISPR/Cpf1 Systems for NKG2A Gene Editing in NK Cells.

Cpf1-NLS recombinant protein was prepared as described in Example G.2. A mix composed of a Cpf1-NLS recombinant protein with a single guide crRNA (see below) targeting a nucleotide sequence of the NKG2A gene was co-incubated with different concentrations of FSD10, FSD21, FSD22 or FSD23 and incubated with NK and NK-92 cells for 90 sec in PBS, using the transduction protocols as generally described in Example 3.1a. Cells were then washed with PBS and harvested to proceed with the T7E1 protocol assay as described in Example 13.4.

The sequences of the crRNA constructed and their targets were:

```
NKG2A crRNA:
                                        [SEQ ID NO: 165]
5'-AAUUUCUACUCUUGUAGAUGGGGCAGAUUCAGGUCUGAG-3'
```

FIGS. 52J-52N show the results of the cleavage of the targeted genomic NKG2A DNA sequence with the CRISPR/Cpf1 (1.33 µM) and crRNA (2 µM) in absence ("–ctrl") or presence of the shuttle agents FSD10, FSD21, FSD22 or FSD23 used at different concentrations, exposure times, and in NK and NK-92 cells after separation by agarose gel electrophoresis. Gel lanes were loaded in duplicate. Thin dashed arrows indicate the bands corresponding to the target gene, and thick solid arrows indicate the bands corresponding to the cleavage products of this target gene, which indicate the successful transduction of fully functional CRISPR genome editing complexes.

G.6 Different Rationally-Designed Peptide Shuttle Agents Co-Deliver CRISPR/Cas9 and CRISPR/Cpf1 Complexes for HPRT, DNMT1 and B2M Gene Editing in HeLa and NK Cells Cas9-NLS recombinant protein was prepared as described in Example 13.1. Cpf1-NLS recombinant protein was prepared as described in Example G.2. A mix composed of Cas9-NLS recombinant protein with its respective crRNA/tracrRNA, or Cpf1-NLS recombinant protein with its respective single guide crRNA(s) (see below) targeting a nucleotide sequence of the DNMT1, HPRT and B2M genes, was co-incubated with different concentrations of FSD10, FSD18, FSD21 or FSD23, and incubated with HeLa or NK cells for 90 sec or 2 min in PBS using the transduction protocols as generally described in Example 3.1a. Cells were then washed with PBS and harvested to proceed with the T7E1 protocol assay as described in Example 13.4.

The sequences of the crRNA and tracrRNAs constructed and their targets were:

```
Feldan tracrRNA:
                                         [SEQ ID NO: 77]
5'-AAACAGCAUAGCAAGUUAAAAUAAGGCUAGUCCGUUAUCAA
CUUGAAAAAGUGGCACCGAGUCGGUGCU-3'

HPRT crRNA:
                                        [SEQ ID NO: 103]
5'-AAUUAUGGGGAUUACUAGGAGUUUUAGAGCUAUGCU-3'

DNMT1 crRNA:
                                        [SEQ ID NO: 157]
5'-AAUUUCUACUGUUGUAGAUCUGAUGGUCCAUGUCUGUUACUC-3'

Cas9-flanked B2M-crRNA:
                                        [SEQ ID NO: 160]
5'-GAGUAGCGCGAGCACAGCUAGUUUUAGAGCUAUGCUGUUUUG-3'

Cpf1-flanked B2M crRNA-1:
                                        [SEQ ID NO: 161]
5'-AAUUUCUACUGUUGUAGAUAUCCAUCCGACAUUGAAGUU-3'

Cpf1-flanked B2M crRNA-2:
                                        [SEQ ID NO: 162]
5'-AAUUUCUACUCUUGUAGAUCCGAUAUUCCUCAGGUACUCCA-3'
```

FIGS. 53A-53C show the results of the cleavage of the targeted genomic DNMT1, HPRT and B2M DNA sequences with different CRISPR systems in the absence ("–ctrl") or in the presence of the shuttle agents FSD10, FSD18, FSD21 or FSD23 used at different concentrations, exposure times, and in HeLa and NK cells after separation by agarose gel electrophoresis. FIG. 53A shows DNMT1 (left panel) and HPRT (right panel) DNA cleavage products from the same genomic DNA extract after the co-delivery of a DNMT1-targeting CRISPR/Cpf1 (1.25 µM) complex and a HPRT-targeting CRISPR/Cas9 (1.25 µM) complex in HeLa cells. FIG. 53B shows the cleavage products of the B2M exon 2 from the same genomic DNA extract after the co-delivery of a CRISPR/Cpf1 (1.25 µM) and a CRISPR/Cas9 (1.25 µM) in HeLa cells. Each complex targeted a different locus in the B2M exon 2 via a specific crRNA flanking Cpf1 (left panel) or a specific crRNA flanking Cas9 (Right panel). FIG. 53C shows the results of the cleavage of the B2M exon 2 from genomic extracts after the co-delivery of CRISPR/Cpf1 (1.33 µM) complexes, each one carrying a specific single guide crRNA-1 or crRNA-2 (2 µM) in presence of FSD10 (upper panel), FSD21 (middle panel) or FSD23 (bottom panel). For each experiment, NK cells were exposed to CRISPR/Cpf1 with crRNA-1 or CRISPR/Cpf1 with crRNA-2, or both complexes.

G.7 Different Rationally-Designed Peptide Shuttle Agents Deliver CRISPR/Cpf1 Complexes for B2M Gene Editing in T Cells—Flow Cytometry Analysis Cpf1-NLS recombinant protein was prepared as described in Example G.2.

Unless otherwise specified, T cells used herein were obtained from healthy human blood collected in heparinized tubes. T cells were isolated using a Ficoll™ technique (Ficoll-Paque™ GE or Lymphoprep™ Stem Cell Technologies). Briefly, blood was mixed with the Ficoll™ solution in conical tubes (50 mL) and centrifuged at 2280 rpm for 20 minutes. Mononuclear cells were harvested and transferred in another conical tube (50 mL) before washing with PBS and centrifugation at 1100 rpm for 10 minutes. Cells were resuspended in 5 mL of PBS containing 20% FBS. Cells were counted and then incubated in a culture medium composed by RPMI advanced (cat: 12633012 ThermoFisher), 10% FBS, 1% Penstrep (15140122 ThermoFisher), 1% L-glutamine (25030081 ThermoFisher) 1-2 30 U/ml). Next, T cells were enriched with a Human T cell Enrichment Kit (StemCell # cat: 19051) by negative selection following the manufacturer instructions. The enriched T cells were validated using a specific anti-CD3 antibody (Biolegend # cat: 300438). At this step, collected cells were typically around 99% T cells. T cells were activated by adding IL-2 at 30 U/mL and the anti-CD28 antibody (ThermoFisher # cat: 16-0289-85) in complete medium for 5 days prior to experimentation. The activation of T cell expansion was then double-checked with both anti-CD25 and anti-CD137 antibodies.

A mix composed of a Cpf1-NLS recombinant protein with respective single guide crRNA(s) targeting a nucleotide sequence of the B2M gene was co-incubated with different concentrations of FSD21 or FSD18 peptide shuttle agents and incubated with T cells for 90 seconds in PBS using the transduction protocols as generally described in Example 3.1a. Each of the B2M crRNAs were designed to mediate CRISPR/Cpf1-based cleavage of the B2M gene, the phenotypic effects of which can be seen by the disruption of cell surface HLA, which is detectable by flow cytometry using a fluorescent APC Mouse Anti-Human HLA-ABC antibody.

The cells were then resuspended in 100 µL PBS containing 1% FBS and 4 µL of APC Mouse Anti-Human HLA-ABC antibody before an incubation period of 20 minutes, in the dark, at ambient temperature. Then, 1 mL of PBS containing 1% FBS was added to the suspension followed by a 1200 rpm centrifugation of 5 minutes. Finally, the pellet was resuspended in 100 to 200 µL of PBS containing 1% FBS before flow cytometry analysis.

Flow cytometry results based on cell size and granularity using respectively the Forward Scatter (FSC) and the Side Scatter (SSC) parameters showed that viability of the transduced T cells was not substantially affected by the co-delivery of different tested concentrations of FSD21 or FSD18 peptide shuttle agents with CRISPR/Cpf1 systems (data not shown).

Figure 54A:
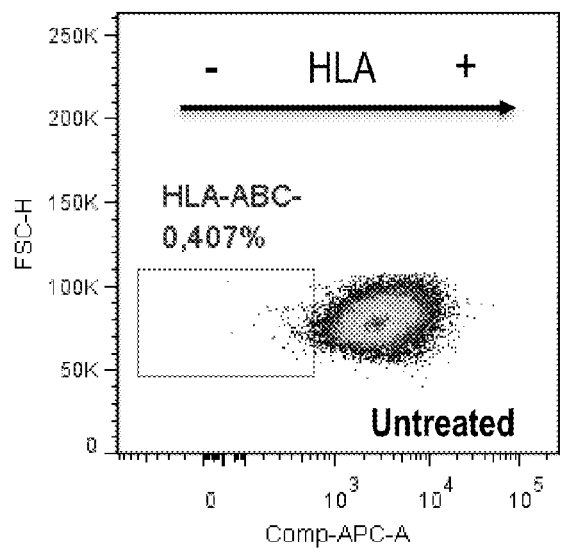
FIGS. 54A-54D show the results of flow cytometry assays in which T cells were treated with increasing concentrations of the shuttle agent FSD21 (8 µM in FIG. 54B, 10 µM in FIG. 54C, and 12 µM in FIG. 54D), 1.33 µM of CRISPR/Cpf1-NLS system and 2 µM of single guide crRNA targeting a B2M genomic DNA sequence. HLA-positive and HLA-negative (B2M knock-out) cells were identified 72 hours after treatment by using an APC-labeled Mouse Anti-Human HLA-ABC antibody. Left-shifted cell populations indicated successful inactivation of cell surface HLA receptors, resulting from inactivation of the B2M gene.
Figure 54B:
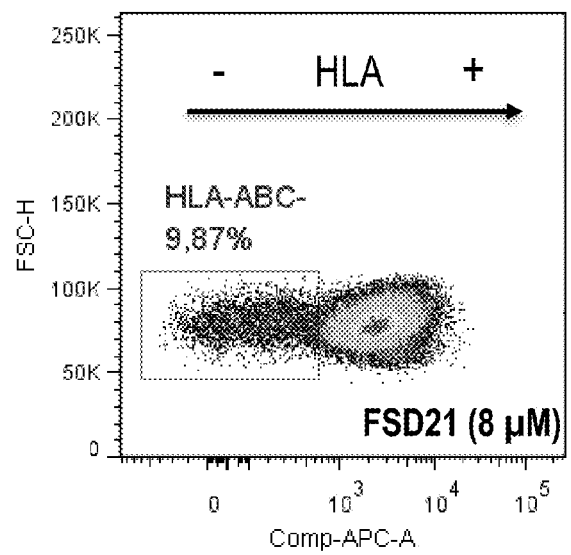
Figure 54C:
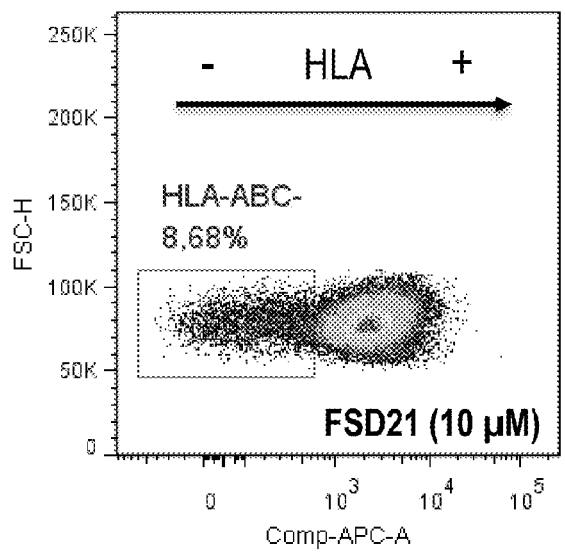
Figure 54D:
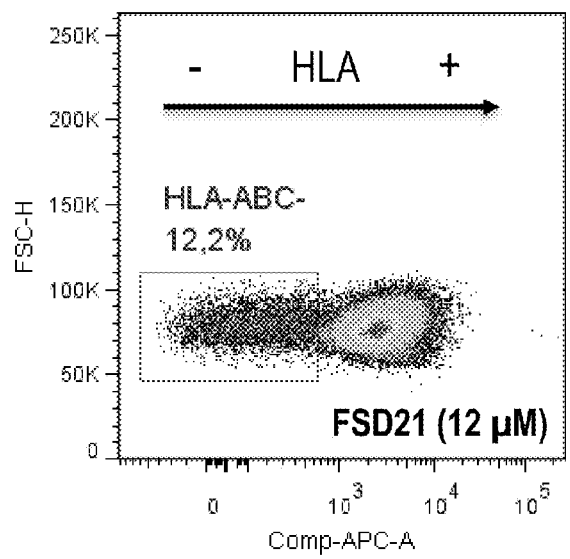
Figure 55A:
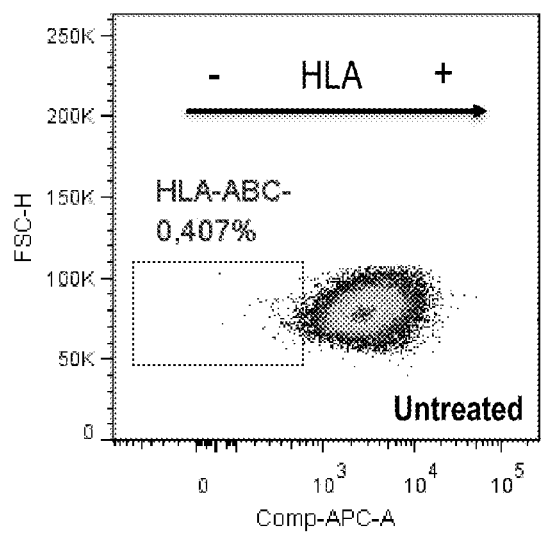
FIGS. 55A-55D show the results of flow cytometry assays in which T cells were treated with increasing concentrations of the shuttle agent FSD18 (8 µM in FIG. 55B, 10 µM in FIG. 55C, and 12 μM in FIG. 55D), 1.33 μM of CRISPR/Cpf1-NLS system and 2 μM of single guide crRNA targeting a B2M DNA sequence. HLA-positive and HLA-negative (B2M knock-out) cells were identified 72 hours after treatment by using an APC-labeled Mouse Anti-Human HLA-ABC antibody. Left-shifted cell populations indicated successful inactivation of cell surface HLA receptors, resulting from inactivation of the B2M gene.
Figure 55B:
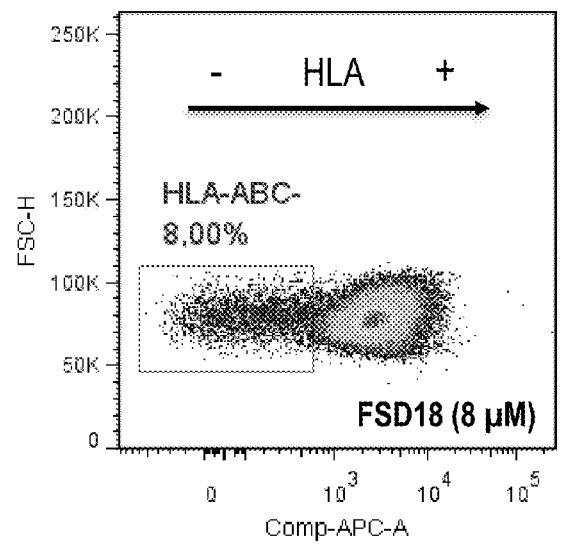
Figure 55C:
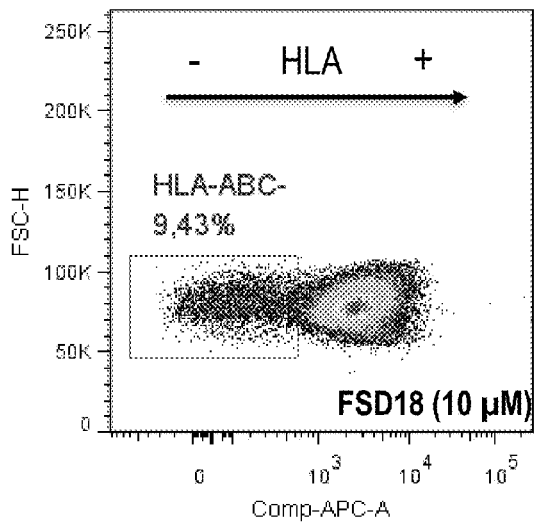
Figure 55D:
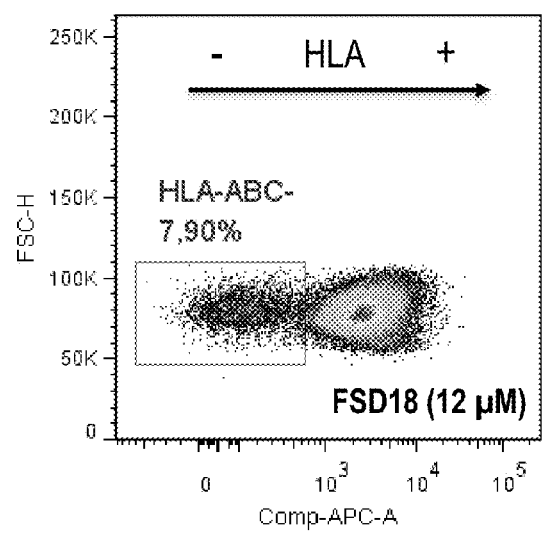

FIGS. 54A-54D and 55A-55D show delivery of CRISPR/Cpf1 genome editing complexes via the shuttle peptides FSD21 and FSD18, respectively. As seen in FIGS. 54A and 55A, "untreated" negative control cells, which were not exposed to CRISPR/Cpf1 or shuttle peptide, exhibited no significant genome editing (lack of HLA-negative cells). FIGS. 54B-54D show that FSD21 concentrations of 8, 10 and 12 µM resulted in 9.87%, 8.68%, and 12.2% of HLA-negative cells, indicating successful nuclear delivery of functional CRISPR/Cpf1 genome editing complexes and subsequent genome editing. FIGS. 55B-55D show that FSD18 concentrations of 8, 10 and 12 µM resulted in 8.0%, 9.43%, and 7.9% of HLA-negative cells, indicating successful nuclear delivery of functional CRISPR/Cpf1 genome editing complexes and subsequent genome editing.

G.8 Transduction of CRISPR/Cpf1 Complexes Containing Multiple Guide crRNA Targeting B2M in THP-1 Cell Lines Using a Single Rationally-Designed Peptide Shuttle Agent Cpf1-NLS recombinant protein was prepared as described in Example G.2. A mix composed of a Cpf1-NLS recombinant protein with a single guide crRNA (see below) targeting one of three chosen nucleotide sequences of the B2M gene was co-incubated with (3 µM) of FSD18 and incubated with THP-1 cells for 90 seconds in PBS, using the transduction protocols as generally described in Example 3.1a. The same experiments were performed using a mix composed of a Cpf1-NLS recombinant protein with three guide crRNA (see below), each targeting three different nucleotide sequences of the B2M gene. Flow cytometry experiments were performed as described in Example G.7. Also, to proceed with the T7E1 protocol assay as described in Example 13.4, cells were washed with PBS and harvested.

The sequences of the crRNA constructed and their targets were:

B2M crRNA-E:
[SEQ ID NO: 166]
5'-AAUUUCUACUCUUGUAGAUAUCCAUCCGACAUUGAAGUU-3'

B2M crRNA-J:
[SEQ ID NO: 167]
5'-AAUUUCUACUCUUGUAGAUCCGAUAUUCCUCAGGUACUCCA-3'

B2M crRNA-G:
[SEQ ID NO: 168]
5'-AAUUUCUACUCUUGUAGAUUUAGAGUCUCGUGAUGUUUAAG-3'

Flow cytometry results based on cell size and granularity using respectively the Forward Scatter (FSC) and the Side Scatter (SSC) parameters show that the viability of the transduced THP-1 cells was not substantially affected by the presence of CRISPR/Cpf1 systems comprising the guide crRNAs (RNA-E, RNA-G, RNA-J) used separately or in combination (data not shown).

Figure 56A:
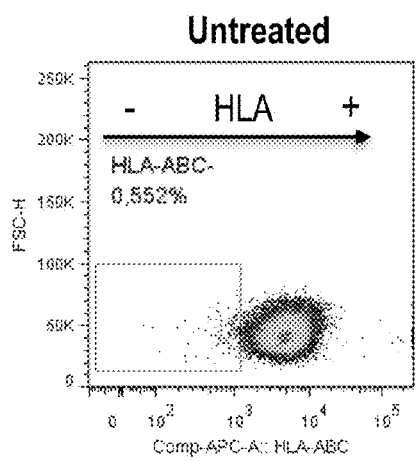
FIGS. 56A-56E show the results of flow cytometry assays in which THP-1 cells were treated (FIG. 56B-56E) or not ("untreated", FIG. 56A) with a mixture of 1.33 μM of CRISPR/Cpf1-NLS system, 2 μM of one or three guide crRNA each targeting different sites within the B2M genomic DNA sequence and 3 μM of FSD18. HLA-positive and HLA-negative (B2M knock-out) cells were identified 48 hours after treatment by using an APC-labeled Mouse Anti-Human HLA-ABC antibody in untreated cells (FIG. 56A), crRNA E treated cells (FIG. 56B), crRNA G treated cells (FIG. 56C), crRNA J treated cells (FIG. 56D) and crRNA E+G+J treated cells (FIG. 56E). Left-shifted cell populations indicated successful inactivation of cell surface HLA receptors, resulting from inactivation of the B2M gene.
Figure 56B:
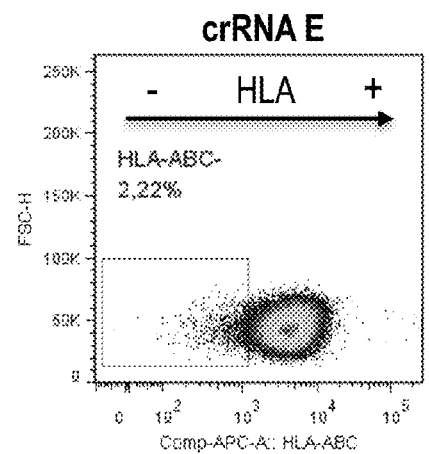
Figure 56C:
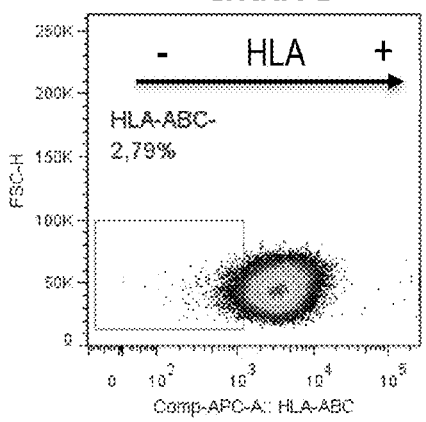
Figure 56D:
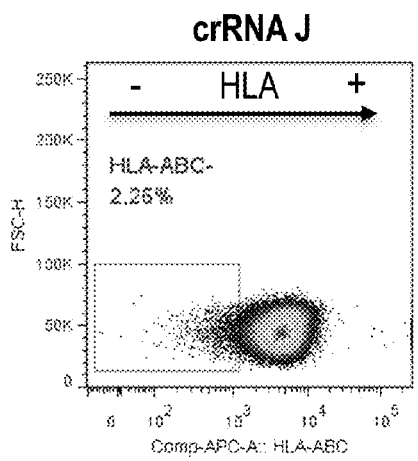
Figure 56E:
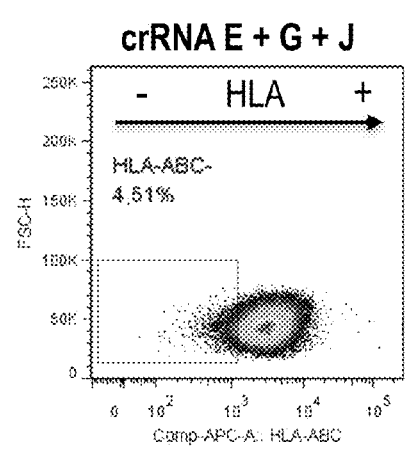

As shown in FIG. 56A, "untreated" negative control cells, which were not exposed to CRISPR/Cpf1 or shuttle peptide, exhibited no significant genome editing (lack of HLA-negative cells). FIGS. 56B-56D show that each guide crRNA (RNA-E, RNA-G, RNA-J) used separately provided comparable HLA KO efficiencies, while FIG. 56E shows the combination the three guides crRNA enhanced the HLA KO efficiency by almost a factor of two. These observations were confirmed by performing a T7E1 cleavage assay as described in Example 13.4, followed by agarose gel electrophoresis (data not shown).

G.9 Increased Cytotoxicity of NK Cells Genome-Edited to Inactive the NKG2A Gene

Figure 57A:
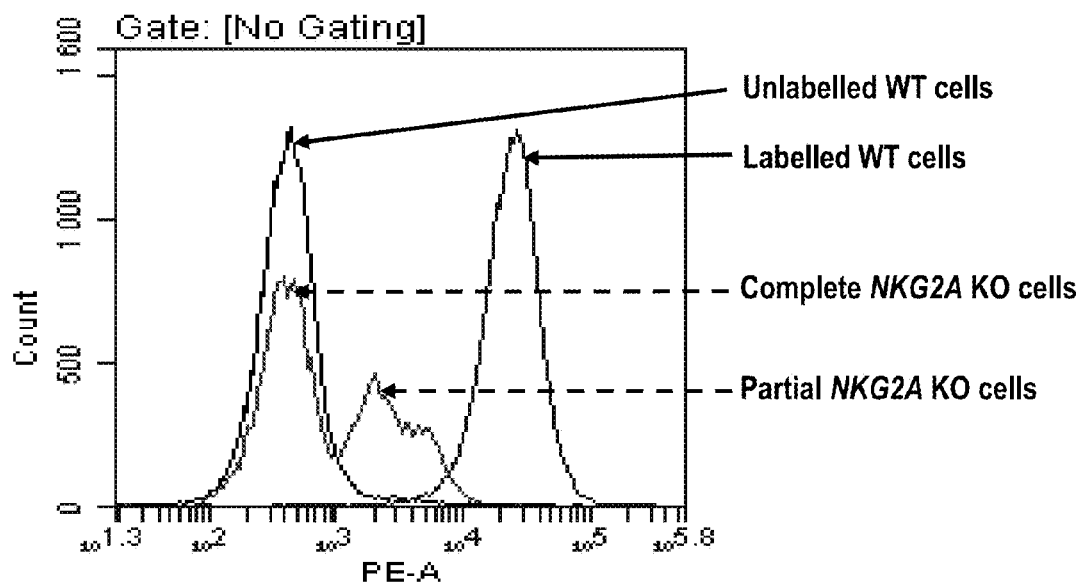
FIGS. 57A and 57B show the results of experiments in which NK-92 cells were genome-edited to determine whether inactivation of the endogenous NKG2A gene could increase their ability to kill target HeLa cells. Briefly, NK-92 cells were transduced with a CRISPR/Cpf1-NLS genome editing complex designed to cleave the NKG2A gene using the shuttle agent peptide FSD23. After transduction, NK-92 cells were immunolabelled with a phycoerythrin (PE)-labelled anti-NKG2A antibody and then analyzed by flow cytometry as shown in FIG. 57A, to verify successful inactivation of NKG2A. As controls, unlabelled wild-type NK-92 cells ("unlabelled WT cells") had no antibody signal, and labelled wild-type NK-92 cells ("labelled WT cells") had full immunolabelling signal. For NKG2A-KO NK-92 cells, two cell populations (peaks) were observed: one with a complete knock-out of NKG2A receptor expression on the cell surface ("Complete NKG2A KO cells"), and the other with a partial lack of expression ("Partial NKG2A KO cells").

Genome editing was performed in NK-92 cells to evaluate whether inactivation of the endogenous NKG2A gene could increase the cytotoxicity of the NK-92 cells. Briefly, one million NK-92 cells were incubated with Cpf1-NLS (1.5 µM) gRNA complex targeting the NKG2A gene and with FSD23 (6 µM) for 90 sec. After transduction, cells were incubated in complete medium with IL-2 (20 ng/mL) for 48 h at 37° C. NK-92 cells were then immunolabelled with a phycoerythrin (PE)-labelled anti-NKG2A antibody (Miltenyi Biotec # CD159a) following the manufacturer recommendations. NK-92 cells were then analyzed with FACS and scored as a function of their anti-NKG2A detection (PE fluorescence) level and the results are shown in FIG. 57A. As controls, unlabelled wild-type NK-92 cells ("unlabelled WT cells") had no antibody signal, and labelled wild-type NK-92 cells ("labelled WT cells") had full immunolabelling signal. For NKG2A-KO NK-92 cells, two cell populations (peaks) were observed: one with a complete knock-out of NKG2A receptor expression on the cell surface ("Complete NKG2A KO cells"), and the other with a partial lack of expression ("Partial NKG2A KO cells").

Figure 57B:
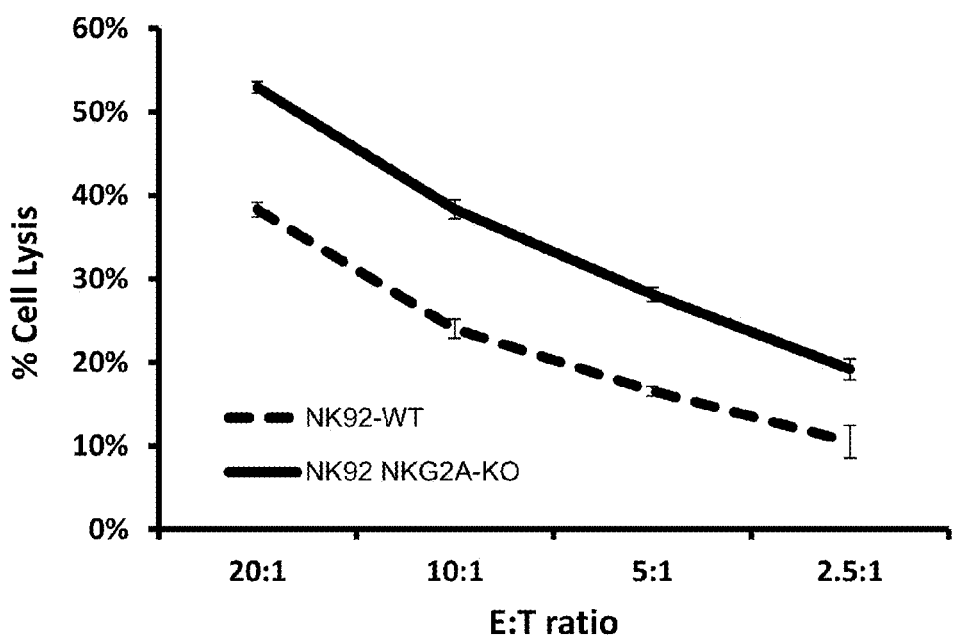

To study the effect of inactivation of the NKG2A gene on the cytotoxicity of the NK-92 cells, we evaluated the ability of WT and NKG2A KO NK-92 cells to kill target HeLa cells. The NKG2A receptor encoded by the NKG2A gene in NK cells normally binds HLA-E epitopes expressed on the surface of potential target cells, which inhibits the cytotoxic activity of the NK cells (effector). To improve this effector: target cell binding, HeLa cells were treated with interferons (50 ng/mL) to increase their HLA-E cell surface expression. Prior to being exposed to effector NK-92 cells, interferon-treated HeLa cells were exposed for 45 minutes at 37° C. to Calcein-AM (ThermoFisher # C3099), a non-fluorescent, hydrophobic compound that easily permeates intact live cells. The hydrolysis of Calcein-AM by intracellular esterases produces Calcein, a hydrophilic, strongly fluorescent compound that is well-retained in the cell cytoplasm. HeLa cells with intracellular Calcein were then centrifuged and incubated in complete medium before being exposed to WT or NKG2A-KO NK cells in a 96-well plate for 4 hrs at 37° C. Killing of the target HeLa cells by effector NK cells results in release of the intracellular Calcein into the extracellular medium. The 96-well plate was then centrifuged for 5 minutes at 1250 rpm and the Calcein signal in the supernatant was analyzed by spectrophotometry with excitation at 488 nm and detection at 510 nm. Results are shown in FIG. 57B, which presents the percentage of lysis of the target HeLa cells (measured by Calcein release) as a function of different ratios of effector NK cells to target HeLa cells (E:T ratio). The results indicate that the knock out of the NKG2A receptor expression on the surface of NK-92 cells ("NK92 NKG2A-KO") increased the cytotoxic activity of the effector cells as compared to wild-type NK-92 cells ("NK92-WT"). More specifically, NKG2A-KO NK-92 effector cells killed 10-15% more target HeLa cells than WT NK-92 cells at the different effector:target ratios (E:T ratios) tested.

Example H

Rationally Designed Peptide Shuttle Agents Enable Transduction of Transcription Factor HOXB4

Human HOXB4 recombinant protein (Example 14.1) was constructed, expressed and purified from a bacterial expression system as described in Example 1.4. THP-1 cells were cultured and tested in the protein transduction assay as generally described in Example 3.1b. Briefly, THP-1 cells were plated at 30000 cells/well one day before transduction. HOXB4-WT recombinant protein (300 nM or 50 nM) was co-incubated with FSD10 or FSD18 (1 µM) and then exposed to THP-1 cells for 30 min in the presence of serum. The cells were subjected to real time-PCR analysis as described in Example 14.2 to measure the mRNA levels of a target gene as a marker for HOXB4 activity, which was then normalized to the target gene mRNA levels detected in the negative control cells (no treatment), to obtain a "Fold over control" value. Total RNA levels (ng/µL) were also measured as a marker for cell viability. Results are shown below.

TABLE H1

HOXB4-WT transduction by FSD10 and FSD18 in THP-1 cells

| Cells | Cargo/peptide | Conc. of peptide (µM) | Conc. of HOXB4-WT (µM) | Fold over control (mean ± St. Dev) | Total RNA in ng/µL (mean ± St. Dev) |
| --- | --- | --- | --- | --- | --- |
| THP-1 | No treatment | 0 | 0 | 1 ± 0.1 | 172 ± 9.21 |
|  | HOXB4-WT alone |  | 1.5 | 2.5 ± 0.2 | 175 ± 7.05 |
|  | FSD10 alone | 1 | 0 | 1.1 ± 0.14 | 181 ± 10.7 |
|  | FSD18 alone |  |  | 1.5 ± 0.09 | 157 ± 3.9 |
|  | FSD10 + HOXB4-WT |  | 0.3 | 17.5 ± 0.21 | 159 ± 12.5 |
|  |  |  | 0.05 | 15.3 ± 0.3 | 176 ± 4.71 |
|  | FSD18 + HOXB4-WT |  | 0.3 | 15.8 ± 0.19 | 154 ± 11.24 |
|  |  |  | 0.05 | 16.7 ± 15.61 | 154 ± 3.9 |

These results show that the shuttle agents FSD10 and FSD18 are able to deliver the transcription factor HOXB4-WT to the nucleus of THP-1 cells in the presence of serum, resulting in a dose-dependent increase in mRNA transcription of the target gene.

REFERENCES

Andreu, D., Ubach, J., Boman, A., Wahlin, B., Wade, D., Merrifield, R B., and Boman, H. G. (1992) Shortened cecropin A-melittin hybrids. Significant size reduction retains potent antibiotic activity. FEBS letters 296, 190-194

Aguila, J. R, W. Liao, J. Yang, C. Avila, N. Hagag, L. Senzel and Y. Ma (2011). "SALL4 is a robust stimulator for the expansion of hematopoietic stem cells." Blood 118(3): 576-585.

Akinci, E., A. Banga, L. V. Greder, J. R Dutton and J. M. Slack (2012). "Reprogramming of pancreatic exocrine cells towards a beta (beta) cell character using Pdx1, Ngn3 and MafA." Biochem J 442(3): 539-550.

Alford et al., (2009). "Toxicity of organic fluorophores used in molecular imaging: literature review." Mol Imaging. 8(6):341-54.

Amand, H. L., B. Norden and K. Fant (2012). "Functionalization with C-terminal cysteine enhances transfection efficiency of cell-penetrating peptides through dimer formation." Biochem Biophys Res Commun 418(3): 469-474.

Aoukaty, A. & Tan, R. (2005). Role for glycogen synthase kinase-3 in NK cell cytotoxicity and X-linked lymphoproliferative disease. J Immunol 174, 4551-8.

Barrangou, R and Luciano A. Marraffini (2014). "CRISPR-Cas Systems: Prokaryotes Upgrade to Adaptive Immunity". Cell Volume 54, Issue 2, p 234-244, 24 Apr. 2014.

Bejarano, L. A. and C. Gonzalez (1999). "Motif trap: a rapid method to clone motifs that can target proteins to defined subcellular localisations." J Cell Sci 112 (Pt 23): 4207-4211.

Bikard et al., Programmable repression and activation of bacterial gene expression using an engineered CRISPR-Cas system. Nucleic Acids Res. 41, 7429-7437.

Boman, H. G., Wade, D., Boman, I. A., Wahlin, B., and Merrifield, R. B. (1989) Antibacterial and antimalarial properties of peptides that are cecropin-melittin hybrids. FEBS letters 259, 103-106.

Braud, V. M., Allan, D. S., O'Callaghan, C. A., Soderstrom, K., D'Andrea, A., Ogg, G. S., Lazetic, S., Young, N. T., Bell, J. I., Phillips, J. H., Lanier, L. L. & McMichael, A. J. (1998). HLA-E binds to natural killer cell receptors CD94/NKG2A, B and C. Nature 391, 795-9.

Buganim et al., (2014) "The Developmental Potential of iPSCs Is Greatly Influenced by Reprogramming Factor Selection". Cell stem cell. 15, 295-309.

Burstein et al., (2017), "New CRISPR-Cas systems from uncultivated microbes." *Nature.* 542(7640):237-241.

Chan, C. K. and D. A. Jans (1999). "Enhancement of polylysine-mediated transferrinfection by nuclear localization sequences: polylysine does not function as a nuclear localization sequence." Hum Gene Ther 10(10): 1695-1702.

Chan, C. K. and D. A. Jans (2001). "Enhancement of MSH receptor- and GAL4-mediated gene transfer by switching the nuclear import pathway." Gene Ther 8(2): 166-171.

Cong et al., (2013). Multiplex genome engineering using CRISPR/Cas systems. Science 339, 819-823.

Cooper, M. A., Fehniger, T. A. & Caligiuri, M. A. (2001). The biology of human natural killer-cell subsets. Trends Immunol 22, 633-40.

Cox et al. (2015). "Therapeutic genome editing: prospects and challenges". Nature medicine, 21: 121-131.

de Kruijf, E. M., Sajet, A., van Nes, J. G., Natanov, R., Putter, H., Smit, V. T., Liefers, G. J., van den Elsen, P. J., van de Velde, C. J. & Kuppen, P. J. (2010). HLA-E and HLA-G expression in classical HLA class I-negative tumors is of prognostic value for clinical outcome of early breast cancer patients. J Immunol 185, 7452-9.

Delconte, R. B., Kolesnik, T. B., Dagley, L. F., Rautela, J., Shi, W., Putz, E. M., Stannard, K., Zhang, J. G., Teh, C., Firth, M., Ushiki, T., Andoniou, C. E., Degli-Esposti, M. A., Sharp, P. P., Sanvitale, C. E., Infusini, G., Liau, N. P., Linossi, E. M., Burns, C. J., Carotta, S., Gray, D. H., Seillet, C., Hutchinson, D. S., Belz, G. T., Webb, A. I., Alexander, W. S., Li, S. S., Bullock, A. N., Babon, J. J., Smyth, M. J., Nicholson, S. E. & Huntington, N. D. (2016). CIS is a potent checkpoint in NK cell-mediated tumor immunity. Nat Immunol 17, 816-24.

Denman, C. J., Senyukov, V. V., Somanchi, S. S., Phatarpekar, P. V., Kopp, L. M., Johnson, J. L., Singh, H., Hurton, L., Maiti, S. N., Huls, M. H., Champlin, R E., Cooper, L. J. & Lee, D. A. (2012). Membrane-bound IL-21 promotes sustained ex vivo proliferation of human natural killer cells. PLoS ONE 7, e30264.

Dolfini, D., M. Minuzzo, G. Pavesi and R. Mantovani (2012). "The short isoform of NF-YA belongs to the embryonic stem cell transcription factor circuitry." Stem Cells 30(11): 2450-2459.

Drin, G., S. Cottin, E. Blanc, A. R Rees and J. Temsamani (2003). "Studies on the internalization mechanism of cationic cell-penetrating peptides." J Biol Chem 278(33): 31192-31201.

Eisenberg et al., (1982). "The helical hydrophobic moment: a measure of the amphiphilicity of a helix". Nature 299, 371-374.

El-Andaloussi, S., H. J. Johansson, T. Holm and U. Langel (2007). "A novel cell-penetrating peptide, M918, for efficient delivery of proteins and peptide nucleic acids." Mol Ther 15(10): 1820-1826.

El-Sayed, A., S. Futaki and H. Harashima (2009). "Delivery of macromolecules using arginine-rich cell-penetrating peptides: ways to overcome endosomal entrapment." AAPS J 11(1): 13-22.

Elmquist, A., M. Lindgren, T. Bartfai and U. Langel (2001). "VE-cadherin-derived cell-penetrating peptide, pVEC, with carrier functions." Exp Cell Res 269(2): 237-244.

Erazo-Oliveras et al., (2014) "Protein delivery into live cells by incubation with an endosomolytic agent." Nat Methods. (8):861-7.

Fanara, P., M. R Hodel, A. H. Corbett and A. E. Hodel (2000). "Quantitative analysis of nuclear localization signal (NLS)-importin alpha interaction through fluorescence depolarization. Evidence for auto-inhibitory regulation of NLS binding." J Biol Chem 275(28): 21218-21223.

Fasoli A et al., (2014) "Mechanistic insight into CM18-Tat11 peptide membrane-perturbing action by whole-cell patch-clamp recording." Molecules. 19(7):9228-39.

Fawell, S., J. Seery, Y. Daikh, C. Moore, L. L. Chen, B. Pepinsky and J. Barsoum (1994). "Tat-mediated delivery of heterologous proteins into cells." Proc Natl Acad Sci USA 91(2): 664-668.

Fominaya, J., C. Uherek and W. Wels (1998). "A chimeric fusion protein containing transforming growth factor-alpha mediates gene transfer via binding to the EGF receptor." Gene Ther 5(4): 521-530.

Fominaya, J. and W. Wels (1996). "Target cell-specific DNA transfer mediated by a chimeric multidomain protein. Novel non-viral gene delivery system." J Biol Chem 271(18): 10560-10568.

Fonoudi, H., M. Yeganeh, F. Fattahi, Z. Ghazizadeh, H. Rassouli, M. Alikhani, B. A. Mojarad, H. Baharvand, G. H. Salekdeh and N. Aghdami (2013). "ISL1 protein transduction promotes cardiomyocyte differentiation from human embryonic stem cells." PLoS One 8(1): e55577.

Gao et al., (2016) DNA-guided genome editing using the Natronobacterium gregoryi Argonaute. Nature Biotechnology 34, 768-773.

Giguère et al., Machine learning assisted design of highly active peptides for drug discovery. PLoS Comput Biol. 2015 Apr. 7; 11(4):e1004074.

Gilbert et al., CRISPR-mediated modular RNA-guided regulation of transcription in eukaryotes. Cell 154, 442-451.

Gilmore, T. D. and H. M. Temin (1988). "v-rel oncoproteins in the nucleus and in the cytoplasm transform chicken spleen cells." J Virol 62(3): 703-714.

Glover, D. J., S. M. Ng, A. Mechler, L. L. Martin and D. A. Jans (2009). "Multifunctional protein nanocarriers for targeted nuclear gene delivery in nondividing cells." FASEB J 23(9): 2996-3006.

Gordon, S. M., J. Chaix, L. J. Rupp, J. Wu, S. Madera, J. C. Sun, T. Lindsten and S. L. Reiner (2012). "The transcription factors T-bet and Eomes control key checkpoints of natural killer cell maturation." Immunity 36(1): 55-67.

Gottschalk, S., J. T. Sparrow, J. Hauer, M. P. Mims, F. E. Leland, S. L. Woo and L. C. Smith (1996). "A novel DNA-peptide complex for efficient gene transfer and expression in mammalian cells." Gene Ther 3(5): 448-457.

Gould, S. J., G. A. Keller, N. Hosken, J. Wilkinson and S. Subramani (1989). "A conserved tripeptide sorts proteins to peroxisomes." J Cell Biol 108(5): 1657-1664.

Green, M. and P. M. Loewenstein (1988). "Autonomous functional domains of chemically synthesized human immunodeficiency virus tat trans-activator protein." Cell 55(6): 1179-1188.

Grimes, M. L., J. Zhou, E. C. Beattie, E. C. Yuen, D. E. Hall, J. S. Valletta, K. S. Topp, J. H. LaVail, N. W. Bunnett and W. C. Mobley (1996). "Endocytosis of activated TrkA: evidence that nerve growth factor induces formation of signaling endosomes." J Neurosci 16(24): 7950-7964.

Guo, Z. Y., Lv, Y. G., Wang, L., Shi, S. J., Yang, F., Zheng, G. X., Wen, W. H. & Yang, A. G. (2015). Predictive value of HLA-G and HLA-E in the prognosis of colorectal cancer patients. Cell Immunol 293, 10-6.

Hallbrink, M., A. Floren, A. Elmquist, M. Pooga, T. Bartfai and U. Langel (2001). "Cargo delivery kinetics of cell-penetrating peptides." Biochim Biophys Acta 1515(2): 101-109.

Herce, H. D. and A. E. Garcia (2007). "Molecular dynamics simulations suggest a mechanism for translocation of the HIV-1 TAT peptide across lipid membranes." Proc Natl Acad Sci USA 104(52): 20805-20810.

Ho et al., (2001). "Synthetic protein transduction domains: enhanced transduction potential in vivo." *Cancer Research* 61: 474-477.

Homg, T., Bezbradica, J. S. & Medzhitov, R. (2007). NKG2D signaling is coupled to the interleukin 15 receptor signaling pathway. Nat Immunol 8, 1345-52.

Hurt, E. C., B. Pesold-Hurt, K. Suda, W. Oppliger and G. Schatz (1985). "The first twelve amino acids (less than half of the pre-sequence) of an imported mitochondrial protein can direct mouse cytosolic dihydrofolate reductase into the yeast mitochondrial matrix." EMBO J 4(8): 2061-2068.

Ichii, H., A. Sakamoto, Y. Kuroda and T. Tokuhisa (2004). "Bcl6 acts as an amplifier for the generation and proliferative capacity of central memory CD8+ T cells." J Immunol 173(2): 883-891.

Irie, Y., K Yamagata, Y. Gan, K. Miyamoto, E. Do, C. H. Kuo, E. Taira and N. Miki (2000). "Molecular cloning and characterization of Amida, a novel protein which interacts with a neuron-specific immediate early gene product arc, contains novel nuclear localization signals, and causes cell death in cultured cells." J Biol Chem 275(4): 2647-2653.

Ishigami, S., Arigami, T., Okumura, H., Uchikado, Y., Kita, Y., Kurahara, H., Maemura, K., Kijima, Y., Ishihara, Y., Sasaki, K, Uenosono, Y. & Natsugoe, S. (2015). Human leukocyte antigen (HLA)-E and HLA-F expression in gastric cancer. Anticancer Res 35, 2279-85.

Kakudo, T., S. Chaki, S. Futaki, I. Nakase, K Akaji, T. Kawakami, K. Maruyama, H. Kamiya and H. Harashima (2004). "Transferrin-modified liposomes equipped with a pH-sensitive fusogenic peptide: an artificial viral-like delivery system." Biochemistry 43(19): 5618-5628.

Kamiely, S. and O. Pines (2005). "Single translation-dual destination: mechanisms of dual protein targeting in eukaryotes." EMBO Rep 6(5): 420-425.

Kato, G. J., W. M. Lee, L. L. Chen and C. V. Dang (1992). "Max: functional domains and interaction with c-Myc." Genes Dev 6(1): 81-92.

Kichler, A., A. J. Mason and B. Bechinger (2006). "Cationic amphipathic histidine-rich peptides for gene delivery." Biochim Biophys Acta 1758(3): 301-307.

Kichler et al., (2003). "Histidine-rich amphipathic peptide antibiotics promote efficient delivery of DNA into mammalian cells". Proc Natl Acad Sci USA. 2003 Feb. 18; 100(4): 1564-1568.

Kira et al., (2011). "Unification of Cas protein families and a simple scenario for the origin and evolution of CRISPR-Cas systems". Biol Direct. 2011; 6: 38.

Kirwan, S. E. & Burshtyn, D. N. (2005). Killer cell Ig-like receptor-dependent signaling by Ig-like transcript 2 (ILT2/CD85j/LILRB1/LIR-1). J Immunol 175, 5006-15.

Kleinschmidt, J. A. and A. Seiter (1988). "Identification of domains involved in nuclear uptake and histone binding of protein N1 of *Xenopus laevis*." EMBO J 7(6): 1605-1614.

Kohler, M., D. Gorlich, E. Hartmann and J. Franke (2001). "Adenoviral E1A protein nuclear import is preferentially mediated by importin alpha3 in vitro." Virology 289(2): 186-191.

Lamiable et al., (2016). "PEP-FOLD3: faster de novo structure prediction for linear peptides in solution and in complex" Nucleic Acids Res. 44(W1):W449-54.

Lanford, R E., P. Kanda and R. C. Kennedy (1986). "Induction of nuclear transport with a synthetic peptide homologous to the SV40 T antigen transport signal." Cell 46(4): 575-582.

Lee, N., Llano, M., Carretero, M., Ishitani, A., Navarro, F., Lopez-Botet, M. & Geraghty, D. E. (1998). HLA-E is a major ligand for the natural killer inhibitory receptor CD94/NKG2A. Proc Natl Acad Sci USA 95, 5199-204.

Levy, E. M., Bianchini, M, Von Euw, E. M, Barrio, M. M, Bravo, A. I., Furman, D., Domenichini, E., Macagno, C., Pinsky, V., Zucchini, C., Valvassori, L. & Mordoh, J. (2008). Human leukocyte antigen-E protein is overexpressed in primary human colorectal cancer. Int J Oncol 32, 633-41.

Li, W., F. Nicol and F. C. Szoka, Jr. (2004). "GALA: a designed synthetic pH-responsive amphipathic peptide with applications in drug and gene delivery." Adv Drug Deliv Rev 56(7): 967-985.

Lin, M. H., F. C. Chou, L. T. Yeh, S. H. Fu, H. Y. Chiou, K. I. Lin, D. M. Chang and H. K. Sytwu (2013). "B lymphocyte-induced maturation protein 1 (BLIMP-1) attenuates autoimmune diabetes in NOD mice by suppressing Th1 and Th17 cells." Diabetologia 56(1): 136-146.

Liu, X., P. K. Tian, D. W. Ju, M. H. Zhang, M. Yao, X. T. Cao and J. R. Gu (2003). "Systemic genetic transfer of p21WAF-1 and GM-CSF utilizing of a novel oligopeptide-based EGF receptor targeting polyplex." Cancer Gene Ther 10(7): 529-539.

Loeser, S., Loser, K., Bijker, M. S., Rangachari, M., van der Burg, S. H., Wada, T., Beissert, S., Melief, C. J. & Penninger, J. M. (2007). Spontaneous tumor rejection by cbl-b-deficient CD8+ T cells. J Exp Med 204, 879-91.

London, E. (1992). "Diphtheria toxin: membrane interaction and membrane translocation." Biochim Biophys Acta 1113(1): 25-51.

Lord-Dufour et al., (2009) "Evidence for transcriptional regulation of the glucose-6-phosphate transporter by HIF-1alpha: Targeting G6PT with mumbaistatin analogs in hypoxic mesenchymal stromal cells". Stem cells 27: 489-497.

Lorieau, J. L., J. M. Louis and A. Bax (2010). "The complete influenza hemagglutinin fusion domain adopts a tight helical hairpin arrangement at the lipid:water interface." Proc Natl Acad Sci USA 107(25): 11341-11346.

Lin, A., Yan, W. H., Xu, H. H., Gan, M. F., Cai, J. F., Zhu, M. & Zhou, M. Y. (2007). HLA-G expression in human ovarian carcinoma counteracts NK cell function. Ann Oncol 18, 1804-9.

Liu, Q., Zhou, H., Langdon, W. Y. & Zhang, J. (2014). E3 ubiquitin ligase Cbl-b in innate and adaptive immunity. Cell Cycle 13, 1875-84.

Lu, S. J., Q. Feng, Y. Ivanova, C. Luo, T. Li, F. Li, G. R. Honig and R. Lanza (2007). "Recombinant HoxB4 fusion proteins enhance hematopoietic differentiation of human embryonic stem cells." Stem Cells Dev 16(4): 547-559.

Luan et al., (2015). "Peptide amphiphiles with multifunctional fragments promoting cellular uptake and endosomal escape as efficient gene vectors." *J. Mater. Chem. B*, 3: 1068-1078.

Lutz-Nicoladoni, C., Wolf, D. & Sopper, S. (2015). Modulation of Immune Cell Functions by the E3 Ligase Cbl-b. Front Oncol 5, 58.

Mack, M., B. Luckow, P. J. Nelson, J. Cihak, G. Simmons, P. R Clapham, N. Signoret, M. Marsh, M. Stangassinger, F. Borlat, T. N. Wells, D. Schlondorff and A. E. Proudfoot (1998). "Aminooxypentane-RANTES induces CCR5 internalization but inhibits recycling: a novel inhibitory mechanism of HIV infectivity." J Exp Med 187(8): 1215-1224.

Maeng, C. H., J. H. Yi, J. Lee, J. Y. Hong, M. K. Choi, H. A. Jung, J. O. Park, S. H. Park, Y. S. Park, W. K. Kang and H. Y. Lim (2013). "Effects of single nucleotide polymorphisms on treatment outcomes and toxicity in patients treated with sunitinib." Anticancer Res 33(10): 4619-4626.

Mahlum, E., D. Mandal, C. Halder, A. Maran, M. J. Yaszemski, R B. Jenkins, M. E. Bolander and G. Sarkar (2007). "Engineering a noncarrier to a highly efficient carrier peptide for noncovalently delivering biologically active proteins into human cells." Anal Biochem 365(2): 215-221.

Makarova et al., (2011) "Evolution and classification of the CRISPR-Cas systems". Nat Rev Microbiol. 9(6):467-77.

Makkerh, J. P., C. Dingwall and R A. Laskey (1996). "Comparative mutagenesis of nuclear localization signals reveals the importance of neutral and acidic amino acids." Curr Biol 6(8): 1025-1027.

Martinez-Fong, D., I. Navarro-Quiroga, I. Ochoa, I. Alvarez-Maya, M. A. Meraz, J. Luna and J. A. Arias-Montano (1999). "Neurotensin-SPDP-poly-L-lysine conjugate: a nonviral vector for targeted gene delivery to neural cells." Brain Res Mol Brain Res 69(2): 249-262.

Matalon, O., Fried, S., Ben-Shmuel, A., Pauker, M. H., Joseph, N., Keizer, D., Piterburg, M. & Barda-Saad, M. (2016). Dephosphorylation of the adaptor LAT and phospholipase C-gamma by SHP-1 inhibits natural killer cell cytotoxicity. Sci Signal 9, ra54.

Maurer, M. and E. von Stebut (2004). "Macrophage inflammatory protein-1." Int J Biochem Cell Biol 36(10): 1882-1886.

McKay, T., P. Reynolds, S. Jezzard, D. Curiel and C. Coutelle (2002). "Secretin-mediated gene delivery, a specific targeting mechanism with potential for treatment of biliary and pancreatic disease in cystic fibrosis." Mol Ther 5(4): 447-454.

Midoux, P., A. Kichler, V. Boutin, J. C. Maurizot and M. Monsigny (1998). "Membrane permeabilization and efficient gene transfer by a peptide containing several histidines." Bioconjug Chem 9(2): 260-267.

Milenkovic, D., T. Ramming, J. M. Muller, L. S. Wenz, N. Gebert, A. Schulze-Specking, D. Stojanovski, S. Rospert and A. Chacinska (2009). "Identification of the signal directing Tim9 and Tim10 into the intermembrane space of mitochondria." Mol Biol Cell 20(10): 2530-2539.

Miyoshi, I., N. Kasai and Y. Hayashizaki (1994). "[Structure and regulation of human thyroid-stimulating hormone (TSH) gene]." Nihon Rinsho 52(4): 940-947.

Moede, T., B. Leibiger, H. G. Pour, P. Berggren and I. B. Leibiger (1999). "Identification of a nuclear localization signal, RRMKWKK, in the homeodomain transcription factor PDX-1." FEBS Lett 461(3): 229-234.

Montrose, K., Y. Yang, X. Sun, S. Wiles and G. W. Krissansen (2013). "Xentry, a new class of cell-penetrating peptide uniquely equipped for delivery of drugs." Sci Rep 3: 1661.

Moreland, R. B., G. L. Langevin, R H. Singer, R. L. Garcea and L. M. Hereford (1987). "Amino acid sequences that determine the nuclear localization of yeast histone 2B." Mol Cell Biol 7(11): 4048-4057.

Morris, M. C., L. Chaloin, M. Choob, J. Archdeacon, F. Heitz and G. Divita (2004). "Combination of a new generation of PNAs with a peptide-based carrier enables efficient targeting of cell cycle progression." Gene Ther 11(9): 757-764.

Morris, M. C., J. Depollier, J. Mery, F. Heitz and G. Divita (2001). "A peptide carrier for the delivery of biologically active proteins into mammalian cells." Nat Biotechnol 19(12): 1173-1176.

Nakanishi, A., D. Shum, H. Morioka, E. Otsuka and H. Kasamatsu (2002). "Interaction of the Vp3 nuclear localization signal with the importin alpha 2/beta heterodimer directs nuclear entry of infecting simian virus 40." J Virol 76(18): 9368-9377.

O'Keefe, D. O. (1992). "Characterization of a full-length, active-site mutant of diphtheria toxin." Arch Biochem Biophys 296(2): 678-684.

Paolino, M., Choidas, A., Wallner, S., Pranjic, B., Uribesalgo, I., Loeser, S., Jamieson, A. M., Langdon, W. Y., Ikeda, F., Fededa, J. P., Cronin, S. J., Nitsch, R., Schultz-Fademrecht, C., Eickhoff, J., Menninger, S., Unger, A., Torka, R., Gruber, T., Hinterleitner, R., Baier, G., Wolf, D., Ullrich, A., Klebl, B. M. & Penninger, J. M. (2014). The E3 ligase Cbl-b and TAM receptors regulate cancer metastasis via natural killer cells. Nature 507, 508-12.

Parente, R. A., S. Nir and F. C. Szoka, Jr. (1990). "Mechanism of leakage of phospholipid vesicle contents induced by the peptide GALA." Biochemistry 29(37): 8720-8728.

Parameswaran, R., Ramakrishnan, P., Moreton, S. A., Xia, Z., Hou, Y., Lee, D. A., Gupta, K., deLima, M., Beck, R. C. & Wald, D. N. (2016). Repression of GSK3 restores NK cell cytotoxicity in AML patients. Nat Commun 7, 11154.

Patel, P. & Woodgett, J. R (2017). Glycogen Synthase Kinase 3: A Kinase for All Pathways? Curr Top Dev Biol 123, 277-302.

Paul, R. W., K. E. Weisser, A. Loomis, D. L. Sloane, D. LaFoe, E. M. Atkinson and R. W. Overell (1997). "Gene transfer using a novel fusion protein, GAL4/invasin." Hum Gene Ther 8(10): 1253-1262.

Perez, F., A. Joliot, E. Bloch-Gallego, A. Zahraoui, A. Triller and A. Prochiantz (1992). "Antennapedia homeobox as a signal for the cellular internalization and nuclear addressing of a small exogenous peptide." J Cell Sci 102 (Pt 4): 717-722.

Pimenta, D. C., V. C. Chen, J. Chao, M. A. Juliano and L. Juliano (2000). "Alpha1-antichymotrypsin and kallistatin hydrolysis by human cathepsin D." J Protein Chem 19(5): 411-418.

Poli, A., Michel, T., Theresine, M., Andres, E., Hentges, F. & Zimmer, J. (2009). CD56 bright natural killer (NK) cells: an important NK cell subset. Immunology 126, 458-65.

Prieve, M. G. and M. L. Waterman (1999). "Nuclear localization and formation of beta-catenin-lymphoid enhancer factor 1 complexes are not sufficient for activation of gene expression." Mol Cell Biol 19(6): 4503-4515.

Rajagopalan, R., J. Xavier, N. Rangaraj, N. M. Rao and V. Gopal (2007). "Recombinant fusion proteins TAT-Mu, Mu and Mu-Mu mediate efficient non-viral gene delivery." J Gene Med 9(4): 275-286.

Riddell et al., (2014) "Reprogramming committed murine blood cells to induced hematopoietic stem cells with defined factors". Cell, 157: 549-564

Salomone, F., F. Cardarelli, M. Di Luca, C. Boccardi, R. Nifosi, G. Bardi, L. Di Bari, M. Serresi and F. Beltram (2012). "A novel chimeric cell-penetrating peptide with membrane-disruptive properties for efficient endosomal escape." J Control Release 163(3): 293-303.

Salomone F., Cardarelli F, Signore G, Boccardi C, Beltram F. (2013) "In vitro efficient transfection by $CM_{18}$-$Tat_{11}$ hybrid peptide: a new tool for gene-delivery applications." PLoS One. 8(7):e70108.

Schneider, H., R P. Harbottle, Y. Yokosaki, J. Kunde, D. Sheppard and C. Coutelle (1998). "A novel peptide, PLAEIDGIELTY, for the targeting of alpha9beta1-integrins." FEBS Lett 429(3): 269-273.

Schreiber, V., M. Molinete, H. Boeuf, G. de Murcia and J. Menissier-de Murcia (1992). "The human poly(ADP-ribose) polymerase nuclear localization signal is a bipartite element functionally separate from DNA binding and catalytic activity." EMBO J 11(9): 3263-3269.

Schuster, M. J., G. Y. Wu, C. M. Walton and C. H. Wu (1999). "Multicomponent DNA carrier with a vesicular stomatitis virus G-peptide greatly enhances liver-targeted gene expression in mice." Bioconjug Chem 10(6): 1075-1083.

Scott, M. S., F. M. Boisvert, M. D. McDowall, A. I. Lamond and G. J. Barton (2010). "Characterization and prediction of protein nucleolar localization sequences." Nucleic Acids Res 38(21): 7388-7399.

Shaw, P. A., I. R. Catchpole, C. A. Goddard and W. H. Colledge (2008). "Comparison of protein transduction domains in mediating cell delivery of a secreted CRE protein." Biochemistry 47(4): 1157-1166.

Shawe-Taylor J, Cristianini N (2004) Kernel methods for pattern analysis. Cambridge university press.

Shen et al., (2014) "Improved PEP-FOLD approach for peptide and miniprotein structure prediction". J. Chem. Theor. Comput. 10:4745-4758.

Shoya, Y., T. Kobayashi, T. Koda, K. Ikuta, M. Kakinuma and M. Kishi (1998). "Two proline-rich nuclear localization signals in the amino- and carboxyl-terminal regions of the Borna disease virus phosphoprotein." J Virol 72(12): 9755-9762.

Somasekaram, A., A. Jarmuz, A. How, J. Scott and N. Navaratnam (1999). "Intracellular localization of human cytidine deaminase. Identification of a functional nuclear localization signal." J Biol Chem 274(40): 28405-28412.

Stojanovski, D., M. Bohnert, N. Pfanner and M. van der Laan (2012). "Mechanisms of protein sorting in mitochondria." Cold Spring Harb Perspect Biol 4(10).

Sudbeck, P. and G. Scherer (1997). "Two independent nuclear localization signals are present in the DNA-binding high-mobility group domains of SRY and SOX9." J Biol Chem 272(44): 27848-27852.

Sung, M. S., J. Y. Mun, O. Kwon, K. S. Kwon and D. B. Oh (2013). "Efficient myogenic differentiation of human adipose-derived stem cells by the transduction of engineered MyoD protein." Biochem Biophys Res Commun 437(1): 156-161.

Takahashi, K. and S. Yamanaka (2006). "Induction of pluripotent stem cells from mouse embryonic and adult fibroblast cultures by defined factors." Cell 126(4): 663-676.

Takeda, A., C. Goolsby and N. R. Yaseen (2006). "NUP98-HOXA9 induces long-term proliferation and blocks differentiation of primary human CD34+ hematopoietic cells." Cancer Res 66(13): 6628-6637.

Tan, Y., Z. Xie, M. Ding, Z. Wang, Q. Yu, L. Meng, H. Zhu, X. Huang, L. Yu, X. Meng and Y. Chen (2010). "Increased levels of FoxA1 transcription factor in pluripotent P19 embryonal carcinoma cells stimulate neural differentiation." Stem Cells Dev 19(9): 1365-1374.

Tan, Y. X., C. Chen, Y. L. Wang, S. Lin, Y. Wang, S. B. Li, X. P. Jin, H. W. Gao, F. S. Du, F. Gong and S. P. Ji (2012). "Truncated peptides from melittin and its analog with high lytic activity at endosomal pH enhance branched polyethylenimine-mediated gene transfection." J Gene Med 14(4): 241-250.

Thévenet et al., "PEP-FOLD: an updated de novo structure prediction server for both linear and disulfide bonded cyclic peptides." Nucleic Acids Res. 2012. 40, W288-293.

Uherek, C., J. Fominaya and W. Wels (1998). "A modular DNA carrier protein based on the structure of diphtheria toxin mediates target cell-specific gene delivery." J Biol Chem 273(15): 8835-8841.

Varkouhi, A. K., M. Scholte, G. Storm and H. J. Haisma (2011). "Endosomal escape pathways for delivery of biologicals." J Control Release 151(3): 220-228.

Veach, R. A., D. Liu, S. Yao, Y. Chen, X. Y. Liu, S. Downs and J. Hawiger (2004). "Receptor/transporter-independent targeting of functional peptides across the plasma membrane." J Biol Chem 279(12): 11425-11431.

Vives, E., P. Brodin and B. Lebleu (1997). "A truncated HIV-1 Tat protein basic domain rapidly translocates through the plasma membrane and accumulates in the cell nucleus." J Biol Chem 272(25): 16010-16017.

Wagstaff, K. M., D. J. Glover, D. J. Tremethick and D. A. Jans (2007). "Histone-mediated transduction as an efficient means for gene delivery." Mol Ther 15(4): 721-731.

Warr, M. R, M. Binnewies, J. Flach, D. Reynaud, T. Garg, R Malhotra, J. Debnath and E. Passegue (2013). "FOXO3A directs a protective autophagy program in haematopoietic stem cells." Nature 494(7437): 323-327.

Welch, K., J. Franke, M. Kohler and I. G. Macara (1999). "RanBP3 contains an unusual nuclear localization signal that is imported preferentially by importin-alpha3." Mol Cell Biol 19(12): 8400-8411.

Wiedenheft et al., (2011). RNA-guided complex from a bacterial immune system enhances target recognition through seed sequence interactions. Proc. Natl. Acad. Sci. USA 108, 10092-10097.

Witzel, I., M. Graeser, T. Karn, M. Schmidt, R. Wirtz, D. Schutze, A. Rausch, F. Janicke, K. Milde-Langosch and V. Muller (2013). "Androgen receptor expression is a predictive marker in chemotherapy-treated patients with endocrine receptor-positive primary breast cancers." J Cancer Res Clin Oncol 139(5): 809-816.

Wu, J., L. Zhou, K. Tonissen, R Tee and K. Artzt (1999). "The quaking I-5 protein (QKI-5) has a novel nuclear localization signal and shuttles between the nucleus and the cytoplasm." J Biol Chem 274(41): 29202-29210.

Wu, D., Kuiaste, I., Moreau, P., Carosella, E. & Yotnda, P. (2015). Rescuing lymphocytes from HLA-G immunosuppressive effects mediated by the tumor microenvironment. Oncotarget 6, 37385-97.

Wyman, T. B., F. Nicol, O. Zelphati, P. V. Scaria, C. Plank and F. C. Szoka, Jr. (1997). "Design, synthesis, and characterization of a cationic peptide that binds to nucleic acids and permeabilizes bilayers." Biochemistry 36(10): 3008-3017.

Ye, S. R, Yang, H., Li, K., Dong, D. D., Lin, X. M. & Yie, S. M. (2007a). Human leukocyte antigen G expression: as a significant prognostic indicator for patients with colorectal cancer. Mod Pathol 20, 375-83.

Yie, S. M., Yang, H., Ye, S. R, Li, K., Dong, D. D. & Lin, X. M. (2007b). Expression of human leukocyte antigen G (HLA-G) correlates with poor prognosis in gastric carcinoma. Ann Surg Oncol 14, 2721-9.

Yie, S. M., Yang, H., Ye, S. R, Li, K., Dong, D. D. & Lin, X. M. (2007c). Expression of human leucocyte antigen G (HLA-G) is associated with prognosis in non-small cell lung cancer. Lung Cancer 58, 267-74.

Yie, S. M., Yang, H., Ye, S. R, Li, K., Dong, D. D. & Lin, X. M. (2007d). Expression of HLA-G is associated with prognosis in esophageal squamous cell carcinoma. Am J Clin Pathol 128, 1002-9.

Yu, Z., C. H. Lee, C. Chinpaisal and L. N. Wei (1998). "A constitutive nuclear localization signal from the second zinc-finger of orphan nuclear receptor TR2." J Endocrinol 159(1): 53-60.

Zetsche et al., (2015). "Cpf1 Is a Single RNA-Guided Endonuclease of a Class 2 CRISPR-Cas System". Cell. 25. pii: S0092-8674(15)01200-3 [http://dx.doi.org/10.1016/j.cell.2015.09.038].

Zhang, J. K., J. Cui, Y. J. Lv and H. Yan (2006). "[Analysis of reasons for eye trauma in construction workers and visual acuity after treatment]." Zhonghua Lao Dong Wei Sheng Zhi Ye Bing Za Zhi 24(6): 371-372.

Zhen, Z. J., Ling, J. Y., Cai, Y., Luo, W. B. & He, Y. J. (2013). Impact of HLA-E gene polymorphism on HLA-E expression in tumor cells and prognosis in patients with stage m colorectal cancer. Med Oncol 30, 482.

Zhou, H., S. Wu, J. Y. Joo, S. Zhu, D. W. Han, T. Lin, S. Trauger, G. Bien, S. Yao, Y. Zhu, G. Siuzdak, H. R. Scholer, L. Duan and S. Ding (2009). "Generation of induced pluripotent stem cells using recombinant proteins." Cell Stem Cell 4(5): 381-384.

---

What is claimed is:

1. A method for protein transduction comprising contacting target eukaryotic cells with an independent polypeptide cargo and a concentration of a shuttle agent sufficient to increase the percentage or proportion of the population of target eukaryotic cells into which the independent polypeptide cargo is delivered, as compared to in the absence of the shuttle agent, wherein the shuttle agent is
  (1) a peptide having an overall length of between 20 and 100 amino acid residues comprising
  (2) an amphipathic alpha-helical motif having
  (3) a positively-charged hydrophilic outer face, and a hydrophobic outer face,
wherein at least five of the following parameters (4) to (15) are respected:
  (4) the hydrophobic outer face comprises a highly hydrophobic core consisting of spatially adjacent L, I, F, V, W, and/or M amino acids representing 12 to 50% of the amino acids of the peptide, based on an open cylindrical representation of the alpha-helix having 3.6 residues per turn;
  (5) the peptide has a hydrophobic moment ($\mu$) of 3.5 to 11;
  (6) the peptide has a predicted net charge of at least +4 at physiological pH;
  (7) the peptide has an isoelectric point (pI) of 8 to 13;
  (8) the peptide is composed of 35% to 65% of any combination of the amino acids: A, C, G, I, L, M, F, P, W, Y, and V;
  (9) the peptide is composed of 0% to 30% of any combination of the amino acids: N, Q, S, and T;
  (10) the peptide is composed of 35% to 85% of any combination of the amino acids: A, L, K, or R;
  (11) the peptide is composed of 20% to 45% of any combination of the amino acids: A and L, provided there being at least 5% of L in the peptide;
  (12) the peptide is composed of 20% to 45% of any combination of the amino acids: K and R;
  (13) the peptide is composed of 0% to 10% of any combination of the amino acids: D and E;
  (14) the difference between the percentage of A and L residues in the peptide (% A+L), and the percentage of K and R residues in the peptide (K+R), is less than or equal to 10%; and
  (15) the peptide is composed of 10 to 45% of any combination of the amino acids: Q, Y, W, P, I, S, G, V, F, E, D, C, M, N, T, and H, and
wherein the shuttle agent comprises an amino acid sequence which is at least 50%, 55%, 60%, 65%, 70%, 75%, 80%, 85%, 90%, or 95% identical to the amino acid sequence of any one of SEQ ID NOs: 104, 105, 107, 108, 110-131, 133-135, 138, 140, 142, 145, 148, 151, and 152, and wherein the shuttle agent increases the transduction efficiency and cytosolic delivery of the independent polypeptide cargo in the target eukaryotic cells.

2. The method of claim 1, wherein the shuttle agent respects at least six, at least seven, at least eight, at least nine, at least ten, at least eleven, or all of parameters (4) to (15).

3. The method of claim 1, wherein said shuttle agent comprises a hydrophobic moment (μ) between a lower limit of 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, and an upper limit of 9.5, 9.6, 9.7, 9.8, 9.9, 10.0, 10.1, 10.2, 10.3, 10.4, or 10.5.

4. The method of claim 1, wherein:
(i) the positively-charged hydrophilic outer face comprises:
(a) at least two, three, or four adjacent positively-charged K and/or R residues upon helical wheel projection; and/or
(b) a segment of six adjacent residues comprising three to five K and/or R residues upon helical wheel projection; and/or
(ii) the hydrophobic outer face comprises:
(a) at least two adjacent L residues upon helical wheel projection; and/or
(b) a segment often adjacent residues comprising at least five hydrophobic residues selected from: L, I, F, V, W, and M, upon helical wheel projection,
based on an alpha helix having angle of rotation between consecutive amino acids of 100 degrees and/or an alpha-helix having 3.6 residues per turn.

5. The method of claim 4, wherein said hydrophobic outer face comprises a highly hydrophobic core consisting of spatially adjacent L, I, F, V, W, and/or M amino acids representing from 12.5%, 13%, 13.5%, 14%, 14.5%, 15%, 15.5%, 16%, 16.5%, 17%, 17.5%, 18%, 18.5%, 19%, 19.5%, or 20%, to 25%, 30%, 35%, 40%, or 45% of the amino acids of the shuttle agent.

6. The method of claim 1, wherein said shuttle agent has a predicted net charge of between +5, +6, +7, +8, or +9, to +10, +11, +12, +13, +14, or +15, and has a predicted pI of 10-13.

7. The method of claim 1, wherein said shuttle agent further respects at least one, at least two, at least three, at least four, at least five, at least six, or all of the following parameters:
(8) the peptide is composed of 36% to 64%, 37% to 63%, 38% to 62%, 39% to 61%, or 40% to 60% of any combination of the amino acids: A, C, G, I, L, M, F, P, W, Y, and V;
(9) the peptide is composed of 1% to 29%, 2% to 28%, 3% to 27%, 4% to 26%, 5% to 25%, 6% to 24%, 7% to 23%, 8% to 22%, 9% to 210%, or 10% to 20% of any combination of the amino acids: N, Q, S, and T;
(10) the peptide is composed of 36% to 80%, 37% to 75%, 38% to 70%, 39% to 65%, or 40% to 60% of any combination of the amino acids: A, L, K, or R;
(11) the peptide is composed of 20% to 40%, 20 to 35%, or 20 to 30% of any combination of the amino acids: A and L;
(12) the peptide is composed of 20% to 40%, 20 to 35%, or 20 to 30% of any combination of the amino acids: K and R;
(13) the peptide is composed of 5 to 10% of any combination of the amino acids: D and E;
(14) the difference between the percentage of A and L residues in the peptide (% A+L), and the percentage of K and R residues in the peptide (K+R), is less than or equal to 9%, 8%, 7%, 6%, or 5%; and
(15) the peptide is composed of 15 to 40%, 20% to 35%, or 20% to 30% of any combination of the amino acids: Q, Y, W, P, I, S, G, V, F, E, D, C, M, N, T, and H.

8. The method of claim 1, wherein said shuttle agent further comprises a histidine-rich domain positioned towards the N terminus and/or towards the C terminus of the shuttle agent, wherein said histidine-rich domain is a stretch of at least 3, at least 4, at least 5, or at least 6 amino acids comprising at least 50%, at least 55%, at least 60%, at least 65%, at least 70%, at least 75%, at least 80%, at least 85%, or at least 90% histidine residues; and/or comprises at least 2, at least 3, at least 4, at least 5, at least 6, at least 7, at least 8, or at least 9 consecutive histidine residues.

9. The method of claim 1, wherein said shuttle agent further comprises a flexible linker domain rich in serine and/or glycine residues.

10. The method of claim 1, wherein the independent polypeptide cargo is or comprises a nuclease, a transcription factor, a cytokine, a hormone, a growth factor, or an antibody.

11. The method of claim 10, wherein:
(a) said nuclease is: an RNA-guided endonuclease, a CRISPR endonuclease, a type I CRISPR endonuclease, a type II CRISPR endonuclease, a type III CRISPR endonuclease, a type IV CRISPR endonuclease, a type V CRISPR endonuclease, a type VI CRISPR endonuclease, CRISPR associated protein 9 (Cas9), Cpf1, CasY, CasX, a zinc-finger nuclease (ZFNs), a Transcription activator-like effector nucleases (TALENs), a homing endonuclease, a meganuclease, a DNA-guided nuclease, *Natronobacterium gregoryi* Argonaute (NgAgo), or any combination thereof;
(b) said transcription factor is: HOXB4, NUP98-HOXA9, Oct3/4, Sox2, Sox9, Klf4, c-Myc, MyoD, Pdx1, Ngn3, MafA, Blimp-1, Eomes, T-bet, FOXO3A, NF-YA, SALL4, ISL1, FoxA1, Nanog, Esrrb, Lin28, HIF1-alpha, H1f, Runxlt1, Pbx1, Lmo2, Zfp37, Prdm5, Bcl-6, or any combination thereof; and/or
(c) said antibody that recognizes an intracellular antigen.

12. The method of claim 11, wherein said nuclease is Cas9, Cpf1, CasX, CasY, or any combination thereof, and further comprises a guide RNA, a crRNA, a tracrRNA, or both a crRNA and a tracrRNA.

13. The method of claim 1, wherein the target eukaryotic cells are stem cells, primary cells, immune cells, T cells, NK cells, or dendritic cells.

14. A method for protein transduction comprising contacting target eukaryotic cells with an independent polypeptide cargo and a concentration of a shuttle agent sufficient to increase the percentage or proportion of the population of target eukaryotic cells into which the independent polypeptide cargo is delivered, as compared to in the absence of the shuttle agent, wherein the shuttle agent is
(1) a peptide having an overall length of between 20 and 100 amino acid residues comprising
(2) an amphipathic alpha-helical motif having
(3) a positively-charged hydrophilic outer face, and a hydrophobic outer face, wherein
(4) the hydrophobic outer face comprises a highly hydrophobic core consisting of spatially adjacent L, I, F, V, W, and/or M amino acids representing 12 to 50% of the amino acids of the peptide, based on an open cylindrical representation of the alpha-helix having 3.6 residues per turn;
(5) the peptide has a hydrophobic moment (μ) of 3.5 to 11;
(6) the peptide has a predicted net charge of at least +4 at physiological pH;
(7) the peptide has an isoelectric point (pI) of 8 to 13;
(8) the peptide is composed of 35% to 65% of any combination of the amino acids: A, C, G, I, L, M, F, P, W, Y, and V;
(9) the peptide is composed of 0% to 30% of any combination of the amino acids: N, Q, S, and T; and
(10) the peptide is composed of 35% to 85% of any combination of the amino acids: A, L, K, or wherein at least two of the following parameters (11) to (15) are respected:
(11) the peptide is composed of 20% to 45% of any combination of the amino acids: A and L, provided there being at least 5% of L in the peptide;
(12) the peptide is composed of 20% to 45% of any combination of the amino acids: K and R;
(13) the peptide is composed of 0% to 10% of any combination of the amino acids: D and E;
(14) the difference between the percentage of A and L residues in the peptide (% A+L), and the percentage of K and R residues in the peptide (K+R), is less than or equal to 10%; and
(15) the peptide is composed of 10 to 45% of any combination of the amino acids: Q, Y, W, P, I, S, G, V, F, E, D, C, M, N, T, and H, and wherein the shuttle agent increases the transduction efficiency and cytosolic delivery of the independent polypeptide cargo in the target eukaryotic cells.

15. The method of claim 14, wherein said shuttle agent further comprises:
(a) a histidine-rich domain positioned towards the N terminus and/or towards the C terminus of the shuttle agent, wherein said histidine-rich domain is a stretch of at least 3, at least 4, at least 5, or at least 6 amino acids comprising at least 50%, at least 55%, at least 60%, at least 65%, at least 70%, at least 75%, at least 80%, at least 85%, or at least 90% histidine residues; and/or comprises at least 2, at least 3, at least 4, at least 5, at least 6, at least 7, at least 8, or at least 9 consecutive histidine residues; and/or
(b) a flexible linker domain rich in serine and/or glycine residues.

16. The method of claim 14, wherein the independent polypeptide cargo is or comprises a nuclease, a transcription factor, a cytokine, a hormone, a growth factor, or an antibody.

17. The method of claim 16, wherein:
(a) said nuclease is: an RNA-guided endonuclease, a CRISPR endonuclease, a type I CRISPR endonuclease, a type II CRISPR endonuclease, a type III CRISPR endonuclease, a type IV CRISPR endonuclease, a type V CRISPR endonuclease, a type VI CRISPR endonuclease, CRISPR associated protein 9 (Cas9), Cpf1, CasY, CasX, a zinc-finger nuclease (ZFNs), a Transcription activator-like effector nucleases (TALENs), a homing endonuclease, a meganuclease, a DNA-guided nuclease, *Natronobacterium gregoryi* Argonaute (NgAgo), or any combination thereof;

(b) said transcription factor is: HOXB4, NUP98-HOXA9, Oct3/4, Sox2, Sox9, Klf4, c-Myc, MyoD, Pdx1, Ngn3, MafA, Blimp-1, Eomes, T-bet, FOXO3A, NF-YA, SALL4, ISL1, FoxA1, Nanog, Esrrb, Lin28, HIF1-alpha, Hlf, Runxlt1, Pbx1, Lmo2, Zfp37, Prdm5, Bcl-6, or any combination thereof; and/or
(c) said antibody that recognizes an intracellular antigen.

18. The method of claim 16, wherein said nuclease is CRISPR associated protein 9 (Cas9), Cpf1, CasX, CasY, or any combination thereof, and further comprises a guide RNA, a crRNA, a tracrRNA, or both a crRNA and a tracrRNA.

19. The method of claim 14, wherein the target eukaryotic cells are stem cells, primary cells, immune cells, T cells, NK cells, or dendritic cells.

20. A method for protein transduction comprising contacting target eukaryotic cells with an independent polypeptide cargo and a concentration of a shuttle agent sufficient to increase the percentage or proportion of the population of target eukaryotic cells into which the independent polypeptide cargo is delivered, as compared to in the absence of the shuttle agent, wherein the shuttle agent is
(1) a peptide having an overall length of between 20 and 100 amino acid residues comprising
(2) an amphipathic alpha-helical motif having
(3) a positively-charged hydrophilic outer face, and a hydrophobic outer face, wherein:
(4) the hydrophobic outer face comprises a highly hydrophobic core consisting of spatially adjacent L, I, F, V, W, and/or M amino acids representing 12 to 50% of the amino acids of the peptide, based on an open cylindrical representation of the alpha-helix having 3.6 residues per turn;
(5) the peptide has a hydrophobic moment (μ) of 3.5 to 11;
(6) the peptide has a predicted net charge of at least +4 at physiological pH;
(7) the peptide has an isoelectric point (pI) of 8 to 13;
(8) the peptide is composed of 35% to 65% of any combination of the amino acids: A, C, G, I, L, M, F, P, W, Y, and V;
(9) the peptide is composed of 0% to 30% of any combination of the amino acids: N, Q, S, and T;
(10) the peptide is composed of 35% to 85% of any combination of the amino acids: A, L, K, or R;
(11) the peptide is composed of 20% to 45% of any combination of the amino acids: A and L, provided there being at least 5% of L in the peptide;
(12) the peptide is composed of 20% to 45% of any combination of the amino acids: K and R;
(13) the peptide is composed of 0% to 10% of any combination of the amino acids: D and E;
(14) the difference between the percentage of A and L residues in the peptide (% A+L), and the percentage of K and R residues in the peptide (K+R), is less than or equal to 10%; and
(15) the peptide is composed of 10 to 45% of any combination of the amino acids: Q, Y, W, P, I, S, G, V, F, E, D, C, M, N, T, and H, wherein the shuttle agent increases the transduction efficiency and cytosolic delivery of the independent polypeptide cargo in the target eukaryotic cells.

* * * * *

SEQUENCE LISTING

<160> NUMBER OF SEQ ID NOS: 168

<210> SEQ ID NO 1
<211> LENGTH: 18
<212> TYPE: PRT
<213> ORGANISM: Artificial sequence
<220> FEATURE:
<223> OTHER INFORMATION: CM18

<400> SEQUENCE: 1

Lys Trp Lys Leu Phe Lys Lys Ile Gly Ala Val Leu Lys Val Leu Thr
1               5                   10                  15

Thr Gly

<210> SEQ ID NO 2
<211> LENGTH: 189
<212> TYPE: PRT
<213> ORGANISM: Artificial sequence
<220> FEATURE:
<223> OTHER INFORMATION: Diphtheria toxin T domain (DT)

<400> SEQUENCE: 2

Val Gly Ser Ser Leu Ser Cys Ile Asn Leu Asp Trp Asp Val Ile Arg
1               5                   10                  15

Asp Lys Thr Lys Thr Lys Ile Glu Ser Leu Lys Glu His Gly Pro Ile
                20                  25                  30

Lys Asn Lys Met Ser Glu Ser Pro Asn Lys Thr Val Ser Glu Glu Lys
            35                  40                  45

Ala Lys Gln Tyr Leu Glu Glu Phe His Gln Thr Ala Leu Glu His Pro
        50                  55                  60

Glu Leu Ser Glu Leu Lys Thr Val Thr Gly Thr Asn Pro Val Phe Ala
65                  70                  75                  80

Gly Ala Asn Tyr Ala Ala Trp Ala Val Asn Val Ala Gln Val Ile Asp
                85                  90                  95

Ser Glu Thr Ala Asp Asn Leu Glu Lys Thr Thr Ala Ala Leu Ser Ile
            100                 105                 110

Leu Pro Gly Ile Gly Ser Val Met Gly Ile Ala Asp Gly Ala Val His
        115                 120                 125

His Asn Thr Glu Glu Ile Val Ala Gln Ser Ile Ala Leu Ser Ser Leu
    130                 135                 140

Met Val Ala Gln Ala Ile Pro Leu Val Gly Glu Leu Val Asp Ile Gly
145                 150                 155                 160

Phe Ala Ala Tyr Asn Phe Val Glu Ser Ile Ile Asn Leu Phe Gln Val
                165                 170                 175

Val His Asn Ser Tyr Asn Arg Pro Ala Tyr Ser Pro Gly
            180                 185

<210> SEQ ID NO 3
<211> LENGTH: 30
<212> TYPE: PRT
<213> ORGANISM: Artificial sequence
<220> FEATURE:
<223> OTHER INFORMATION: GALA

<400> SEQUENCE: 3

```
Trp Glu Ala Ala Leu Ala Glu Ala Leu Ala Glu Ala Leu Ala His
1               5                   10                  15

Leu Ala Glu Ala Leu Ala Glu Ala Leu Glu Ala Leu Ala Ala
            20                  25                  30
```

<210> SEQ ID NO 4
<211> LENGTH: 115
<212> TYPE: PRT
<213> ORGANISM: Artificial sequence
<220> FEATURE:
<223> OTHER INFORMATION: PEA

<400> SEQUENCE: 4

```
Val Leu Ala Gly Asn Pro Ala Lys His Asp Leu Asp Ile Lys Pro Thr
1               5                   10                  15

Val Ile Ser His Arg Leu His Phe Pro Glu Gly Gly Ser Leu Ala Ala
            20                  25                  30

Leu Thr Ala His Gln Ala Cys His Leu Pro Leu Glu Thr Phe Thr Arg
        35                  40                  45

His Arg Gln Pro Arg Gly Trp Glu Gln Leu Glu Gln Cys Gly Tyr Pro
    50                  55                  60

Val Gln Arg Leu Val Ala Leu Tyr Leu Ala Ala Arg Leu Ser Trp Asn
65                  70                  75                  80

Gln Val Asp Gln Val Ile Arg Asn Ala Leu Ala Ser Pro Gly Ser Gly
                85                  90                  95

Gly Asp Leu Gly Glu Ala Ile Arg Glu Gln Pro Glu Gln Ala Arg Leu
            100                 105                 110

Ala Leu Thr
        115
```

<210> SEQ ID NO 5
<211> LENGTH: 24
<212> TYPE: PRT
<213> ORGANISM: Artificial sequence
<220> FEATURE:
<223> OTHER INFORMATION: INF-7

<400> SEQUENCE: 5

```
Gly Leu Phe Glu Ala Ile Glu Gly Phe Ile Glu Asn Gly Trp Glu Gly
1               5                   10                  15

Met Ile Asp Gly Trp Tyr Gly Cys
            20
```

<210> SEQ ID NO 6
<211> LENGTH: 26
<212> TYPE: PRT
<213> ORGANISM: Artificial sequence
<220> FEATURE:
<223> OTHER INFORMATION: LAH4

<400> SEQUENCE: 6

```
Lys Lys Ala Leu Leu Ala Leu Ala Leu His His Leu Ala His Leu Ala
1               5                   10                  15
```

Leu His Leu Ala Leu Ala Leu Lys Lys Ala
            20                  25

<210> SEQ ID NO 7
<211> LENGTH: 24
<212> TYPE: PRT
<213> ORGANISM: Artificial sequence
<220> FEATURE:
<223> OTHER INFORMATION: HGP

<400> SEQUENCE: 7

Leu Leu Gly Arg Arg Gly Trp Glu Val Leu Lys Tyr Trp Trp Asn Leu
1               5                   10                  15

Leu Gln Tyr Trp Ser Gln Glu Leu
            20

<210> SEQ ID NO 8
<211> LENGTH: 23
<212> TYPE: PRT
<213> ORGANISM: Artificial sequence
<220> FEATURE:
<223> OTHER INFORMATION: H5WYG

<400> SEQUENCE: 8

Gly Leu Phe His Ala Ile Ala His Phe Ile His Gly Gly Trp His Gly
1               5                   10                  15

Leu Ile His Gly Trp Tyr Gly
            20

<210> SEQ ID NO 9
<211> LENGTH: 23
<212> TYPE: PRT
<213> ORGANISM: Artificial sequence
<220> FEATURE:
<223> OTHER INFORMATION: HA2

<400> SEQUENCE: 9

Gly Leu Phe Gly Ala Ile Ala Gly Phe Ile Glu Asn Gly Trp Glu Gly
1               5                   10                  15

Met Ile Asp Gly Trp Tyr Gly
            20

<210> SEQ ID NO 10
<211> LENGTH: 23
<212> TYPE: PRT
<213> ORGANISM: Artificial sequence
<220> FEATURE:
<223> OTHER INFORMATION: EB1

<400> SEQUENCE: 10

Leu Ile Arg Leu Trp Ser His Leu Ile His Ile Trp Phe Gln Asn Arg
1               5                   10                  15

Arg Leu Lys Trp Lys Lys Lys
            20

<210> SEQ ID NO 11
<211> LENGTH: 25
<212> TYPE: PRT
<213> ORGANISM: Artificial sequence
<220> FEATURE:
<223> OTHER INFORMATION: VSVG

<400> SEQUENCE: 11

Lys Phe Thr Ile Val Phe Pro His Asn Gln Lys Gly Asn Trp Lys Asn

```
1               5                   10                  15
Val Pro Ser Asn Tyr His Tyr Cys Pro
            20                  25
```

<210> SEQ ID NO 12
<211> LENGTH: 115
<212> TYPE: PRT
<213> ORGANISM: Artificial sequence
<220> FEATURE:
<223> OTHER INFORMATION: Pseudomonas toxin

<400> SEQUENCE: 12

```
Glu Gly Gly Ser Leu Ala Ala Leu Thr Ala His Gln Ala Cys His Leu
1               5                   10                  15

Pro Leu Glu Thr Phe Thr Arg His Arg Gln Pro Arg Gly Trp Glu Gln
            20                  25                  30

Leu Glu Gln Cys Gly Tyr Pro Val Gln Arg Leu Val Ala Leu Tyr Leu
        35                  40                  45

Ala Ala Arg Leu Ser Trp Asn Gln Val Asp Gln Val Ile Arg Asn Ala
    50                  55                  60

Leu Ala Ser Pro Gly Ser Gly Gly Asp Leu Gly Glu Ala Ile Arg Glu
65                  70                  75                  80

Gln Pro Glu Gln Ala Arg Leu Ala Leu Thr Leu Ala Ala Ala Glu Ser
                85                  90                  95

Glu Arg Phe Val Arg Gln Gly Thr Gly Asn Asp Glu Ala Gly Ala Ala
            100                 105                 110

Asn Ala Asp
        115
```

<210> SEQ ID NO 13
<211> LENGTH: 26
<212> TYPE: PRT
<213> ORGANISM: Artificial sequence
<220> FEATURE:
<223> OTHER INFORMATION: Melittin

<400> SEQUENCE: 13

```
Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25
```

<210> SEQ ID NO 14
<211> LENGTH: 30
<212> TYPE: PRT
<213> ORGANISM: Artificial sequence
<220> FEATURE:
<223> OTHER INFORMATION: KALA

<400> SEQUENCE: 14

```
Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30
```

<210> SEQ ID NO 15
<211> LENGTH: 20
<212> TYPE: PRT
<213> ORGANISM: Artificial sequence
<220> FEATURE:
<223> OTHER INFORMATION: JST-1

```
<400> SEQUENCE: 15

Gly Leu Phe Glu Ala Leu Leu Glu Leu Leu Glu Ser Leu Trp Glu Leu
1               5                   10                  15

Leu Leu Glu Ala
            20

<210> SEQ ID NO 16
<211> LENGTH: 16
<212> TYPE: PRT
<213> ORGANISM: Artificial sequence
<220> FEATURE:
<223> OTHER INFORMATION: SP

<400> SEQUENCE: 16

Ala Ala Val Ala Leu Leu Pro Ala Val Leu Leu Ala Leu Leu Ala Pro
1               5                   10                  15

<210> SEQ ID NO 17
<211> LENGTH: 11
<212> TYPE: PRT
<213> ORGANISM: Artificial sequence
<220> FEATURE:
<223> OTHER INFORMATION: TAT

<400> SEQUENCE: 17

Tyr Gly Arg Lys Lys Arg Arg Gln Arg Arg
1               5                   10

<210> SEQ ID NO 18
<211> LENGTH: 16
<212> TYPE: PRT
<213> ORGANISM: Artificial sequence
<220> FEATURE:
<223> OTHER INFORMATION: Penetratin (Antennapedia)

<400> SEQUENCE: 18

Arg Gln Ile Lys Ile Trp Phe Gln Asn Arg Arg Met Lys Trp Lys Lys
1               5                   10                  15

<210> SEQ ID NO 19
<211> LENGTH: 18
<212> TYPE: PRT
<213> ORGANISM: Artificial sequence
<220> FEATURE:
<223> OTHER INFORMATION: pVEC

<400> SEQUENCE: 19

Leu Leu Ile Ile Leu Arg Arg Arg Ile Arg Lys Gln Ala His Ala His
1               5                   10                  15

Ser Lys

<210> SEQ ID NO 20
<211> LENGTH: 22
<212> TYPE: PRT
<213> ORGANISM: Artificial sequence
<220> FEATURE:
<223> OTHER INFORMATION: M918

<400> SEQUENCE: 20

Met Val Thr Val Leu Phe Arg Arg Leu Arg Ile Arg Arg Ala Cys Gly
1               5                   10                  15

Pro Pro Arg Val Arg Val
            20
```

```
<210> SEQ ID NO 21
<211> LENGTH: 21
<212> TYPE: PRT
<213> ORGANISM: Artificial sequence
<220> FEATURE:
<223> OTHER INFORMATION: Pep-1

<400> SEQUENCE: 21

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 22
<211> LENGTH: 21
<212> TYPE: PRT
<213> ORGANISM: Artificial sequence
<220> FEATURE:
<223> OTHER INFORMATION: Pep-2

<400> SEQUENCE: 22

Lys Glu Thr Trp Phe Glu Thr Trp Phe Thr Glu Trp Ser Gln Pro Lys
1               5                   10                  15

Lys Lys Arg Lys Val
            20

<210> SEQ ID NO 23
<211> LENGTH: 7
<212> TYPE: PRT
<213> ORGANISM: Artificial sequence
<220> FEATURE:
<223> OTHER INFORMATION: Xentry

<400> SEQUENCE: 23

Leu Cys Leu Arg Pro Val Gly
1               5

<210> SEQ ID NO 24
<211> LENGTH: 9
<212> TYPE: PRT
<213> ORGANISM: Artificial sequence
<220> FEATURE:
<223> OTHER INFORMATION: Arginine stretch

<400> SEQUENCE: 24

Arg Arg Arg Arg Arg Arg Arg Arg Arg
1               5

<210> SEQ ID NO 25
<211> LENGTH: 26
<212> TYPE: PRT
<213> ORGANISM: Artificial sequence
<220> FEATURE:
<223> OTHER INFORMATION: Transportan

<400> SEQUENCE: 25

Trp Thr Leu Asn Ser Ala Gly Tyr Leu Leu Gly Lys Ile Asn Leu Lys
1               5                   10                  15

Ala Leu Ala Ala Leu Ala Lys Lys Ile Leu
            20                  25

<210> SEQ ID NO 26
<211> LENGTH: 18
<212> TYPE: PRT
<213> ORGANISM: Artificial sequence
<220> FEATURE:
```

-continued

<223> OTHER INFORMATION: SynB1

<400> SEQUENCE: 26

```
Arg Gly Gly Arg Leu Ser Tyr Ser Arg Arg Phe Ser Thr Ser Thr
1               5                   10                  15

Gly Arg
```

<210> SEQ ID NO 27
<211> LENGTH: 10
<212> TYPE: PRT
<213> ORGANISM: Artificial sequence
<220> FEATURE:
<223> OTHER INFORMATION: SynB3

<400> SEQUENCE: 27

```
Arg Arg Leu Ser Tyr Ser Arg Arg Arg Phe
1               5                   10
```

<210> SEQ ID NO 28
<211> LENGTH: 5
<212> TYPE: PRT
<213> ORGANISM: Artificial sequence
<220> FEATURE:
<223> OTHER INFORMATION: E1a

<400> SEQUENCE: 28

```
Lys Arg Pro Arg Pro
1               5
```

<210> SEQ ID NO 29
<211> LENGTH: 7
<212> TYPE: PRT
<213> ORGANISM: Artificial sequence
<220> FEATURE:
<223> OTHER INFORMATION: SV40 T-Ag

<400> SEQUENCE: 29

```
Pro Lys Lys Lys Arg Lys Val
1               5
```

<210> SEQ ID NO 30
<211> LENGTH: 9
<212> TYPE: PRT
<213> ORGANISM: Artificial sequence
<220> FEATURE:
<223> OTHER INFORMATION: c-myc

<400> SEQUENCE: 30

```
Pro Ala Ala Lys Arg Val Lys Leu Asp
1               5
```

<210> SEQ ID NO 31
<211> LENGTH: 22
<212> TYPE: PRT
<213> ORGANISM: Artificial sequence
<220> FEATURE:
<223> OTHER INFORMATION: Op-T-NLS

<400> SEQUENCE: 31

```
Ser Ser Asp Asp Glu Ala Thr Ala Asp Ser Gln His Ala Ala Pro Pro
1               5                   10                  15

Lys Lys Lys Arg Lys Val
            20
```

<210> SEQ ID NO 32

```
<211> LENGTH: 5
<212> TYPE: PRT
<213> ORGANISM: Artificial sequence
<220> FEATURE:
<223> OTHER INFORMATION: Vp3

<400> SEQUENCE: 32

Lys Lys Lys Arg Lys
1               5

<210> SEQ ID NO 33
<211> LENGTH: 16
<212> TYPE: PRT
<213> ORGANISM: Artificial sequence
<220> FEATURE:
<223> OTHER INFORMATION: Nucleoplasmin

<400> SEQUENCE: 33

Lys Arg Pro Ala Ala Thr Lys Lys Ala Gly Gln Ala Lys Lys Lys Lys
1               5                   10                  15

<210> SEQ ID NO 34
<211> LENGTH: 10
<212> TYPE: PRT
<213> ORGANISM: Artificial sequence
<220> FEATURE:
<223> OTHER INFORMATION: Histone 2B NLS

<400> SEQUENCE: 34

Asp Gly Lys Lys Arg Lys Arg Ser Arg Lys
1               5                   10

<210> SEQ ID NO 35
<211> LENGTH: 24
<212> TYPE: PRT
<213> ORGANISM: Artificial sequence
<220> FEATURE:
<223> OTHER INFORMATION: Xenopus N1

<400> SEQUENCE: 35

Val Arg Lys Lys Arg Lys Thr Glu Glu Glu Ser Pro Leu Lys Asp Lys
1               5                   10                  15

Asp Ala Lys Lys Ser Lys Gln Glu
            20

<210> SEQ ID NO 36
<211> LENGTH: 19
<212> TYPE: PRT
<213> ORGANISM: Artificial sequence
<220> FEATURE:
<223> OTHER INFORMATION: PARP

<400> SEQUENCE: 36

Lys Arg Lys Gly Asp Glu Val Asp Gly Val Asp Glu Cys Ala Lys Lys
1               5                   10                  15

Ser Lys Lys

<210> SEQ ID NO 37
<211> LENGTH: 7
<212> TYPE: PRT
<213> ORGANISM: Artificial sequence
<220> FEATURE:
<223> OTHER INFORMATION: PDX-1

<400> SEQUENCE: 37

Arg Arg Met Lys Trp Lys Lys
```

```
<210> SEQ ID NO 38
<211> LENGTH: 7
<212> TYPE: PRT
<213> ORGANISM: Artificial sequence
<220> FEATURE:
<223> OTHER INFORMATION: QKI-5

<400> SEQUENCE: 38

Arg Val His Pro Tyr Gln Arg
1               5

<210> SEQ ID NO 39
<211> LENGTH: 24
<212> TYPE: PRT
<213> ORGANISM: Artificial sequence
<220> FEATURE:
<223> OTHER INFORMATION: HCDA

<400> SEQUENCE: 39

Lys Arg Pro Ala Cys Thr Leu Lys Pro Glu Cys Val Gln Gln Leu Leu
1               5                   10                  15

Val Cys Ser Gln Glu Ala Lys Lys
            20

<210> SEQ ID NO 40
<211> LENGTH: 7
<212> TYPE: PRT
<213> ORGANISM: Artificial sequence
<220> FEATURE:
<223> OTHER INFORMATION: H2B

<400> SEQUENCE: 40

Gly Lys Lys Arg Ser Lys Ala
1               5

<210> SEQ ID NO 41
<211> LENGTH: 6
<212> TYPE: PRT
<213> ORGANISM: Artificial sequence
<220> FEATURE:
<223> OTHER INFORMATION: v-Rel

<400> SEQUENCE: 41

Lys Ala Lys Arg Gln Arg
1               5

<210> SEQ ID NO 42
<211> LENGTH: 5
<212> TYPE: PRT
<213> ORGANISM: Artificial sequence
<220> FEATURE:
<223> OTHER INFORMATION: Amida

<400> SEQUENCE: 42

Arg Lys Arg Arg Arg
1               5

<210> SEQ ID NO 43
<211> LENGTH: 9
<212> TYPE: PRT
<213> ORGANISM: Artificial sequence
<220> FEATURE:
<223> OTHER INFORMATION: RanBP3

<400> SEQUENCE: 43
```

```
Pro Pro Val Lys Arg Glu Arg Thr Ser
1               5

<210> SEQ ID NO 44
<211> LENGTH: 10
<212> TYPE: PRT
<213> ORGANISM: Artificial sequence
<220> FEATURE:
<223> OTHER INFORMATION: Pho4p

<400> SEQUENCE: 44

Pro Tyr Leu Asn Lys Arg Lys Gly Lys Pro
1               5                   10

<210> SEQ ID NO 45
<211> LENGTH: 9
<212> TYPE: PRT
<213> ORGANISM: Artificial sequence
<220> FEATURE:
<223> OTHER INFORMATION: LEF-1

<400> SEQUENCE: 45

Lys Lys Lys Lys Arg Lys Arg Glu Lys
1               5

<210> SEQ ID NO 46
<211> LENGTH: 9
<212> TYPE: PRT
<213> ORGANISM: Artificial sequence
<220> FEATURE:
<223> OTHER INFORMATION: TCF-1

<400> SEQUENCE: 46

Lys Lys Lys Arg Arg Ser Arg Glu Lys
1               5

<210> SEQ ID NO 47
<211> LENGTH: 8
<212> TYPE: PRT
<213> ORGANISM: Artificial sequence
<220> FEATURE:
<223> OTHER INFORMATION: BDV-P

<400> SEQUENCE: 47

Pro Arg Pro Arg Lys Ile Pro Arg
1               5

<210> SEQ ID NO 48
<211> LENGTH: 20
<212> TYPE: PRT
<213> ORGANISM: Artificial sequence
<220> FEATURE:
<223> OTHER INFORMATION: TR2

<400> SEQUENCE: 48

Lys Asp Cys Val Ile Asn Lys His His Arg Asn Arg Cys Gln Tyr Cys
1               5                   10                  15

Arg Leu Gln Arg
            20

<210> SEQ ID NO 49
<211> LENGTH: 5
<212> TYPE: PRT
<213> ORGANISM: Artificial sequence
<220> FEATURE:
<223> OTHER INFORMATION: SOX9
```

```
<400> SEQUENCE: 49

Pro Arg Arg Arg Lys
1               5

<210> SEQ ID NO 50
<211> LENGTH: 8
<212> TYPE: PRT
<213> ORGANISM: Artificial sequence
<220> FEATURE:
<223> OTHER INFORMATION: Max

<400> SEQUENCE: 50

Pro Gln Ser Arg Lys Lys Leu Arg
1               5

<210> SEQ ID NO 51
<211> LENGTH: 9
<212> TYPE: PRT
<213> ORGANISM: Artificial sequence
<220> FEATURE:
<223> OTHER INFORMATION: Mitochondrial signal sequence from Tim9

<400> SEQUENCE: 51

Asn Leu Val Glu Arg Cys Phe Thr Asp
1               5

<210> SEQ ID NO 52
<211> LENGTH: 12
<212> TYPE: PRT
<213> ORGANISM: Artificial sequence
<220> FEATURE:
<223> OTHER INFORMATION: Mitochondrial signal sequence from Yeast
      cytochrome c oxidase subunit IV

<400> SEQUENCE: 52

Met Leu Ser Leu Arg Gln Ser Ile Arg Phe Phe Lys
1               5                   10

<210> SEQ ID NO 53
<211> LENGTH: 16
<212> TYPE: PRT
<213> ORGANISM: Artificial sequence
<220> FEATURE:
<223> OTHER INFORMATION: Mitochondrial signal sequence from 18S rRNA

<400> SEQUENCE: 53

Met Leu Ile Ser Arg Cys Lys Trp Ser Arg Phe Pro Gly Asn Gln Arg
1               5                   10                  15

<210> SEQ ID NO 54
<211> LENGTH: 3
<212> TYPE: PRT
<213> ORGANISM: Artificial sequence
<220> FEATURE:
<223> OTHER INFORMATION: Peroxisome signal sequence - PTS1

<400> SEQUENCE: 54

Ser Lys Leu
1

<210> SEQ ID NO 55
<211> LENGTH: 17
<212> TYPE: PRT
<213> ORGANISM: Artificial sequence
<220> FEATURE:
<223> OTHER INFORMATION: Nucleolar signal sequence from BIRC5
```

```
<400> SEQUENCE: 55

Met Gln Arg Lys Pro Thr Ile Arg Arg Lys Asn Leu Arg Leu Arg Arg
1               5                   10                  15

Lys

<210> SEQ ID NO 56
<211> LENGTH: 11
<212> TYPE: PRT
<213> ORGANISM: Artificial sequence
<220> FEATURE:
<223> OTHER INFORMATION: Nucleolar signal sequence from RECQL4

<400> SEQUENCE: 56

Lys Gln Ala Trp Lys Gln Lys Trp Arg Lys Lys
1               5                   10

<210> SEQ ID NO 57
<211> LENGTH: 29
<212> TYPE: PRT
<213> ORGANISM: Artificial sequence
<220> FEATURE:
<223> OTHER INFORMATION: CM18-TAT

<400> SEQUENCE: 57

Lys Trp Lys Leu Phe Lys Lys Ile Gly Ala Val Leu Lys Val Leu Thr
1               5                   10                  15

Thr Gly Tyr Gly Arg Lys Lys Arg Arg Gln Arg Arg Arg
            20                  25

<210> SEQ ID NO 58
<211> LENGTH: 34
<212> TYPE: PRT
<213> ORGANISM: Artificial sequence
<220> FEATURE:
<223> OTHER INFORMATION: CM18-Penetratin

<400> SEQUENCE: 58

Lys Trp Lys Leu Phe Lys Lys Ile Gly Ala Val Leu Lys Val Leu Thr
1               5                   10                  15

Thr Gly Arg Gln Ile Lys Ile Trp Phe Gln Asn Arg Arg Met Lys Trp
            20                  25                  30

Lys Lys

<210> SEQ ID NO 59
<211> LENGTH: 36
<212> TYPE: PRT
<213> ORGANISM: Artificial sequence
<220> FEATURE:
<223> OTHER INFORMATION: His-CM18-TAT

<400> SEQUENCE: 59

Met His His His His His His Lys Trp Lys Leu Phe Lys Lys Ile Gly
1               5                   10                  15

Ala Val Leu Lys Val Leu Thr Thr Gly Tyr Gly Arg Lys Lys Arg Arg
            20                  25                  30

Gln Arg Arg Arg
        35

<210> SEQ ID NO 60
<211> LENGTH: 290
<212> TYPE: PRT
<213> ORGANISM: Artificial sequence
```

```
<220> FEATURE:
<223> OTHER INFORMATION: GFP

<400> SEQUENCE: 60

Met His His His His His Gly Gly Gly Ser Gly Gly Gly Gly
1               5                   10                  15

Ser Gly Gly Ala Ser Thr Gly Thr Gly Ile Arg Met Val Ser Lys Gly
                20                  25                  30

Glu Glu Leu Phe Thr Gly Val Val Pro Ile Leu Val Glu Leu Asp Gly
            35                  40                  45

Asp Val Asn Gly His Lys Phe Ser Val Ser Gly Glu Gly Glu Gly Asp
        50                  55                  60

Ala Thr Tyr Gly Lys Leu Thr Leu Lys Phe Ile Cys Thr Thr Gly Lys
65                  70                  75                  80

Leu Pro Val Pro Trp Pro Thr Leu Val Thr Thr Leu Thr Tyr Gly Val
                85                  90                  95

Gln Cys Phe Ser Arg Tyr Pro Asp His Met Lys Gln His Asp Phe Phe
            100                 105                 110

Lys Ser Ala Met Pro Glu Gly Tyr Val Gln Glu Arg Thr Ile Phe Phe
        115                 120                 125

Lys Asp Asp Gly Asn Tyr Lys Thr Arg Ala Glu Val Lys Phe Glu Gly
    130                 135                 140

Asp Thr Leu Val Asn Arg Ile Glu Leu Lys Gly Ile Asp Phe Lys Glu
145                 150                 155                 160

Asp Gly Asn Ile Leu Gly His Lys Leu Glu Tyr Asn Tyr Asn Ser His
                165                 170                 175

Asn Val Tyr Ile Met Ala Asp Lys Gln Lys Asn Gly Ile Lys Val Asn
            180                 185                 190

Phe Lys Ile Arg His Asn Ile Glu Asp Gly Ser Val Gln Leu Ala Asp
        195                 200                 205

His Tyr Gln Gln Asn Thr Pro Ile Gly Asp Gly Pro Val Leu Leu Pro
    210                 215                 220

Asp Asn His Tyr Leu Ser Thr Gln Ser Ala Leu Ser Lys Asp Pro Asn
225                 230                 235                 240

Glu Lys Arg Asp His Met Val Leu Leu Glu Phe Val Thr Ala Ala Gly
                245                 250                 255

Ile Thr Leu Gly Met Asp Glu Leu Tyr Lys Gly Gly Ser Gly Gly Gly
            260                 265                 270

Ser Gly Gly Gly Ser Gly Trp Ile Arg Ala Ser Ser Gly Gly Arg Glu
        275                 280                 285

Ile Ser
    290

<210> SEQ ID NO 61
<211> LENGTH: 317
<212> TYPE: PRT
<213> ORGANISM: Artificial sequence
<220> FEATURE:
<223> OTHER INFORMATION: TAT-GFP

<400> SEQUENCE: 61

Met His His His His His Gly Gly Gly Ser Gly Gly Gly Gly
1               5                   10                  15

Ser Gly Gly Ala Ser Thr Gly Thr Gly Arg Lys Lys Arg Arg Gln Arg
                20                  25                  30

Arg Arg Pro Pro Gln Gly Gly Gly Gly Ser Gly Gly Gly Gly Ser Gly
```

```
            35                  40                  45
Gly Gly Thr Gly Ile Arg Met Val Ser Lys Gly Glu Glu Leu Phe Thr
 50                  55                  60
Gly Val Val Pro Ile Leu Val Glu Leu Asp Gly Asp Val Asn Gly His
 65                  70                  75                  80
Lys Phe Ser Val Ser Gly Glu Gly Glu Gly Asp Ala Thr Tyr Gly Lys
                 85                  90                  95
Leu Thr Leu Lys Phe Ile Cys Thr Thr Gly Lys Leu Pro Val Pro Trp
            100                 105                 110
Pro Thr Leu Val Thr Thr Leu Thr Tyr Gly Val Gln Cys Phe Ser Arg
        115                 120                 125
Tyr Pro Asp His Met Lys Gln His Asp Phe Phe Lys Ser Ala Met Pro
    130                 135                 140
Glu Gly Tyr Val Gln Glu Arg Thr Ile Phe Phe Lys Asp Asp Gly Asn
145                 150                 155                 160
Tyr Lys Thr Arg Ala Glu Val Lys Phe Glu Gly Asp Thr Leu Val Asn
                165                 170                 175
Arg Ile Glu Leu Lys Gly Ile Asp Phe Lys Glu Asp Gly Asn Ile Leu
            180                 185                 190
Gly His Lys Leu Glu Tyr Asn Tyr Asn Ser His Asn Val Tyr Ile Met
        195                 200                 205
Ala Asp Lys Gln Lys Asn Gly Ile Lys Val Asn Phe Lys Ile Arg His
    210                 215                 220
Asn Ile Glu Asp Gly Ser Val Gln Leu Ala Asp His Tyr Gln Gln Asn
225                 230                 235                 240
Thr Pro Ile Gly Asp Gly Pro Val Leu Leu Pro Asp Asn His Tyr Leu
                245                 250                 255
Ser Thr Gln Ser Ala Leu Ser Lys Asp Pro Asn Glu Lys Arg Asp His
            260                 265                 270
Met Val Leu Leu Glu Phe Val Thr Ala Ala Gly Ile Thr Leu Gly Met
        275                 280                 285
Asp Glu Leu Tyr Lys Gly Gly Ser Gly Gly Gly Ser Gly Gly Gly Ser
    290                 295                 300
Gly Trp Ile Arg Ala Ser Ser Gly Gly Arg Glu Ile Ser
305                 310                 315

<210> SEQ ID NO 62
<211> LENGTH: 327
<212> TYPE: PRT
<213> ORGANISM: Artificial sequence
<220> FEATURE:
<223> OTHER INFORMATION: GFP-NLS

<400> SEQUENCE: 62

Met His His His His His His Gly Gly Gly Ser Gly Gly Gly Gly
 1               5                  10                  15
Ser Gly Gly Ala Ser Thr Gly Ile Arg Met Val Ser Lys Gly Glu Glu
            20                  25                  30
Leu Phe Thr Gly Val Val Pro Ile Leu Val Glu Leu Asp Gly Asp Val
        35                  40                  45
Asn Gly His Lys Phe Ser Val Ser Gly Glu Gly Glu Gly Asp Ala Thr
    50                  55                  60
Tyr Gly Lys Leu Thr Leu Lys Phe Ile Cys Thr Thr Gly Lys Leu Pro
 65                  70                  75                  80
Val Pro Trp Pro Thr Leu Val Thr Thr Leu Thr Tyr Gly Val Gln Cys
```

```
                85                  90                  95
Phe Ser Arg Tyr Pro Asp His Met Lys Gln His Asp Phe Phe Lys Ser
            100                 105                 110

Ala Met Pro Glu Gly Tyr Val Gln Glu Arg Thr Ile Phe Phe Lys Asp
        115                 120                 125

Asp Gly Asn Tyr Lys Thr Arg Ala Glu Val Lys Phe Glu Gly Asp Thr
    130                 135                 140

Leu Val Asn Arg Ile Glu Leu Lys Gly Ile Asp Phe Lys Glu Asp Gly
145                 150                 155                 160

Asn Ile Leu Gly His Lys Leu Glu Tyr Asn Tyr Asn Ser His Asn Val
                165                 170                 175

Tyr Ile Met Ala Asp Lys Gln Lys Asn Gly Ile Lys Val Asn Phe Lys
            180                 185                 190

Ile Arg His Asn Ile Glu Asp Gly Ser Val Gln Leu Ala Asp His Tyr
        195                 200                 205

Gln Gln Asn Thr Pro Ile Gly Asp Gly Pro Val Leu Leu Pro Asp Asn
    210                 215                 220

His Tyr Leu Ser Thr Gln Ser Ala Leu Ser Lys Asp Pro Asn Glu Lys
225                 230                 235                 240

Arg Asp His Met Val Leu Leu Glu Phe Val Thr Ala Ala Gly Ile Thr
                245                 250                 255

Leu Gly Met Asp Glu Leu Tyr Lys Gly Gly Ser Gly Gly Gly Ser Gly
            260                 265                 270

Gly Gly Ser Gly Trp Ile Arg Ala Ser Ser Gly Gly Arg Ser Ser Asp
        275                 280                 285

Asp Glu Ala Thr Ala Asp Ser Gln His Ala Ala Pro Pro Lys Lys Lys
    290                 295                 300

Arg Lys Val Gly Gly Ser Gly Gly Gly Ser Gly Gly Ser Gly Gly Gly
305                 310                 315                 320

Gly Arg Gly Thr Glu Ile Ser
                325

<210> SEQ ID NO 63
<211> LENGTH: 14
<212> TYPE: PRT
<213> ORGANISM: Artificial Sequence
<220> FEATURE:
<223> OTHER INFORMATION: C(LLKK)3C

<400> SEQUENCE: 63

Cys Leu Leu Lys Lys Leu Leu Lys Lys Leu Leu Lys Lys Cys
1               5                   10

<210> SEQ ID NO 64
<211> LENGTH: 14
<212> TYPE: PRT
<213> ORGANISM: Artificial Sequence
<220> FEATURE:
<223> OTHER INFORMATION: G(LLKK)3G

<400> SEQUENCE: 64

Gly Leu Leu Lys Lys Leu Leu Lys Lys Leu Leu Lys Lys Gly
1               5                   10

<210> SEQ ID NO 65
<211> LENGTH: 11
<212> TYPE: PRT
<213> ORGANISM: Artificial Sequence
<220> FEATURE:
```

```
<223> OTHER INFORMATION: PTD4

<400> SEQUENCE: 65

Tyr Ala Arg Ala Ala Ala Arg Gln Ala Arg Ala
 1               5                  10

<210> SEQ ID NO 66
<211> LENGTH: 30
<212> TYPE: PRT
<213> ORGANISM: Artificial Sequence
<220> FEATURE:
<223> OTHER INFORMATION: TAT-CM18

<400> SEQUENCE: 66

Tyr Gly Arg Lys Lys Arg Arg Gln Arg Arg Arg Cys Lys Trp Lys Leu
 1               5                  10                  15

Phe Lys Lys Ile Gly Ala Val Leu Lys Val Leu Thr Thr Gly
            20                  25                  30

<210> SEQ ID NO 67
<211> LENGTH: 42
<212> TYPE: PRT
<213> ORGANISM: Artificial Sequence
<220> FEATURE:
<223> OTHER INFORMATION: TAT-KALA

<400> SEQUENCE: 67

Tyr Gly Arg Lys Lys Arg Arg Gln Arg Arg Arg Cys Trp Glu Ala Lys
 1               5                  10                  15

Leu Ala Lys Ala Leu Ala Lys Ala Leu Ala Lys His Leu Ala Lys Ala
            20                  25                  30

Leu Ala Lys Ala Leu Lys Ala Cys Glu Ala
        35                  40

<210> SEQ ID NO 68
<211> LENGTH: 35
<212> TYPE: PRT
<213> ORGANISM: Artificial Sequence
<220> FEATURE:
<223> OTHER INFORMATION: His-CM18-PTD4

<400> SEQUENCE: 68

His His His His His His Lys Trp Lys Leu Phe Lys Lys Ile Gly Ala
 1               5                  10                  15

Val Leu Lys Val Leu Thr Thr Gly Tyr Ala Arg Ala Ala Ala Arg Gln
            20                  25                  30

Ala Arg Ala
        35

<210> SEQ ID NO 69
<211> LENGTH: 33
<212> TYPE: PRT
<213> ORGANISM: Artificial Sequence
<220> FEATURE:
<223> OTHER INFORMATION: His-CM18-9Arg

<400> SEQUENCE: 69

His His His His His His Lys Trp Lys Leu Phe Lys Lys Ile Gly Ala
 1               5                  10                  15

Val Leu Lys Val Leu Thr Thr Gly Arg Arg Arg Arg Arg Arg Arg Arg
            20                  25                  30

Arg
```

<210> SEQ ID NO 70
<211> LENGTH: 50
<212> TYPE: PRT
<213> ORGANISM: Artificial Sequence
<220> FEATURE:
<223> OTHER INFORMATION: His-CM18-Transportan

<400> SEQUENCE: 70

His His His His His His Lys Trp Lys Leu Phe Lys Lys Ile Gly Ala
1               5                   10                  15

Val Leu Lys Val Leu Thr Thr Gly Gly Trp Thr Leu Asn Ser Ala Gly
            20                  25                  30

Tyr Leu Leu Lys Ile Asn Leu Lys Ala Leu Ala Ala Leu Ala Lys Lys
        35                  40                  45

Ile Leu
    50

<210> SEQ ID NO 71
<211> LENGTH: 43
<212> TYPE: PRT
<213> ORGANISM: Artificial Sequence
<220> FEATURE:
<223> OTHER INFORMATION: His-LAH4-PDT4

<400> SEQUENCE: 71

His His His His His His Lys Lys Ala Leu Leu Ala Leu Ala Leu His
1               5                   10                  15

His Leu Ala His Leu Ala Leu His Leu Ala Leu Ala Leu Lys Lys Ala
            20                  25                  30

Tyr Ala Arg Ala Ala Ala Arg Gln Ala Arg Ala
        35                  40

<210> SEQ ID NO 72
<211> LENGTH: 31
<212> TYPE: PRT
<213> ORGANISM: Artificial Sequence
<220> FEATURE:
<223> OTHER INFORMATION: His-C(LLKK)3C-PDT4

<400> SEQUENCE: 72

His His His His His His Cys Leu Leu Lys Lys Leu Leu Lys Lys Leu
1               5                   10                  15

Leu Lys Lys Cys Tyr Ala Arg Ala Ala Ala Arg Gln Ala Arg Ala
            20                  25                  30

<210> SEQ ID NO 73
<211> LENGTH: 324
<212> TYPE: PRT
<213> ORGANISM: Artificial Sequence
<220> FEATURE:
<223> OTHER INFORMATION: mCherry-NLS

<400> SEQUENCE: 73

Met His His His His His His Gly Gly Gly Ser Gly Gly Gly Gly
1               5                   10                  15

Ser Gly Gly Ala Ser Thr Gly Ile Arg Met Val Ser Lys Cys Glu Glu
            20                  25                  30

Asp Asn Met Ala Ile Ile Lys Glu Phe Met Arg Phe Lys Val His Met
        35                  40                  45

Glu Gly Ser Val Asn Gly His Glu Phe Glu Ile Glu Gly Glu Gly Glu
    50                  55                  60

```
Gly Arg Pro Tyr Glu Gly Thr Gln Thr Ala Lys Leu Lys Val Thr Lys
 65                  70                  75                  80

Gly Gly Pro Leu Pro Phe Ala Trp Asp Ile Leu Ser Pro Gln Phe Met
                 85                  90                  95

Tyr Gly Ser Lys Ala Tyr Val Lys His Pro Ala Asp Ile Pro Asp Tyr
            100                 105                 110

Leu Lys Leu Ser Phe Pro Glu Gly Phe Lys Trp Glu Arg Val Met Asn
        115                 120                 125

Phe Glu Asp Gly Gly Val Val Thr Val Thr Gln Asp Ser Ser Leu Gln
    130                 135                 140

Asp Gly Glu Phe Ile Tyr Lys Val Lys Leu Arg Gly Thr Asn Phe Pro
145                 150                 155                 160

Ser Asp Gly Gln Val Met Gln Lys Lys Thr Met Gly Trp Glu Ala Ser
                165                 170                 175

Ser Glu Arg Met Tyr Pro Glu Asp Gly Ala Leu Lys Gly Glu Ile Lys
            180                 185                 190

Gln Arg Leu Lys Leu Lys Asp Gly Gly His Tyr Asp Ala Glu Val Lys
        195                 200                 205

Thr Thr Tyr Lys Ala Lys Lys Pro Val Gln Leu Pro Gly Ala Tyr Asn
    210                 215                 220

Val Asn Ile Lys Leu Asp Ile Thr Ser His Asn Glu Asp Tyr Thr Ile
225                 230                 235                 240

Val Glu Gln Tyr Glu Arg Ala Glu Gly Arg His Ser Thr Gly Gly Met
                245                 250                 255

Asp Glu Leu Tyr Lys Gly Gly Ser Gly Gly Ser Gly Gly Ser Gly Ser
            260                 265                 270

Gly Trp Ile Arg Ala Ser Ser Gly Arg Ser Ser Asp Asp Glu Ala
        275                 280                 285

Thr Ala Asp Ser Gln His Ala Ala Pro Pro Lys Lys Arg Lys Val
    290                 295                 300

Gly Gly Ser Gly Gly Gly Ser Gly Gly Gly Ser Gly Gly Gly Arg Gly
305                 310                 315                 320

Thr Glu Ile Ser

<210> SEQ ID NO 74
<211> LENGTH: 1414
<212> TYPE: PRT
<213> ORGANISM: Artificial Sequence
<220> FEATURE:
<223> OTHER INFORMATION: Cas9-NLS

<400> SEQUENCE: 74

Met Asp Lys Lys Tyr Ser Ile Gly Leu Asp Ile Gly Thr Asn Ser Val
 1               5                  10                  15

Gly Trp Ala Val Ile Thr Asp Glu Tyr Lys Val Pro Ser Lys Lys Phe
             20                  25                  30

Lys Val Leu Gly Asn Thr Asp Arg His Ser Ile Lys Lys Asn Leu Ile
         35                  40                  45

Gly Ala Leu Leu Phe Asp Ser Gly Glu Thr Ala Glu Ala Thr Arg Leu
     50                  55                  60

Lys Arg Thr Ala Arg Arg Arg Tyr Thr Arg Arg Lys Asn Arg Ile Cys
 65                  70                  75                  80

Tyr Leu Gln Glu Ile Phe Ser Asn Glu Met Ala Lys Val Asp Asp Ser
                 85                  90                  95

Phe Phe His Arg Leu Glu Glu Ser Phe Leu Val Glu Glu Asp Lys Lys
```

```
                100             105              110
His Glu Arg His Pro Ile Phe Gly Asn Ile Val Asp Glu Val Ala Tyr
            115                 120             125

His Glu Lys Tyr Pro Thr Ile Tyr His Leu Arg Lys Lys Leu Val Asp
            130                 135             140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
            195                 200                 205

Lys Ala Ile Leu Ser Ala Arg Leu Ser Lys Ser Arg Arg Leu Glu Asn
            210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
            290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
            370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
            450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525
```

```
Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
    755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
    835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
    915                 920                 925

Lys His Val Ala Gln Ile Leu Asp Ser Arg Met Asn Thr Lys Tyr Asp
930                 935                 940
```

```
Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
```

```
            1340                1345                1350
Gly Leu Tyr Glu Thr Arg Ile Asp Leu Ser Gln Leu Gly Gly Asp
        1355                1360                1365

Gly Gly Arg Ser Ser Asp Asp Glu Ala Thr Ala Asp Ser Gln His
    1370                1375                1380

Ala Ala Pro Pro Lys Lys Lys Arg Lys Val Gly Gly Ser Gly
1385                1390                1395

Gly Ser Gly Gly Gly Ser Gly Gly Gly Arg His His His His His
    1400                1405                1410

His

<210> SEQ ID NO 75
<211> LENGTH: 42
<212> TYPE: RNA
<213> ORGANISM: Artificial Sequence
<220> FEATURE:
<223> OTHER INFORMATION: crRNA (Example 13.3)

<400> SEQUENCE: 75
gaguccgagc agaagaagaa guuuuagagc uaugcuguuu ug                    42

<210> SEQ ID NO 76
<211> LENGTH: 69
<212> TYPE: RNA
<213> ORGANISM: Artificial Sequence
<220> FEATURE:
<223> OTHER INFORMATION: tracrRNA (Example 13.3)

<400> SEQUENCE: 76
aaacagcaua gcaaguuaaa auaaggcuag uccguuauca acuugaaaaa guggcaccga    60
gucggugcu                                                            69

<210> SEQ ID NO 77
<211> LENGTH: 69
<212> TYPE: RNA
<213> ORGANISM: Artificial Sequence
<220> FEATURE:
<223> OTHER INFORMATION: tracrRNA (Example 13.5)

<400> SEQUENCE: 77
aaacagcaua gcaaguuaaa auaaggcuag uccguuauca acuugaaaaa guggcaccga    60
gucggugcu                                                            69

<210> SEQ ID NO 78
<211> LENGTH: 42
<212> TYPE: RNA
<213> ORGANISM: Artificial Sequence
<220> FEATURE:
<223> OTHER INFORMATION: PPIB crRNA (Example 13.5)

<400> SEQUENCE: 78
guguauuuug accuacgaau guuuuagagc uaugcuguuu ug                    42

<210> SEQ ID NO 79
<211> LENGTH: 74
<212> TYPE: RNA
<213> ORGANISM: Artificial Sequence
<220> FEATURE:
<223> OTHER INFORMATION: PPIB tracrRNA (Example 13.5)

<400> SEQUENCE: 79
aacagcauag caaguuaaaa uaaggcuagu ccguuaucaa cuugaaaaag uggcaccgag    60
```
ucggugcuuu uuuu                                                74

<210> SEQ ID NO 80
<211> LENGTH: 246
<212> TYPE: PRT
<213> ORGANISM: Artificial Sequence
<220> FEATURE:
<223> OTHER INFORMATION: HOXB4-WT

<400> SEQUENCE: 80

Met His His His His His Met Ala Met Ser Ser Phe Leu Ile Asn
1               5                   10                  15

Ser Asn Tyr Val Asp Pro Lys Phe Pro Pro Cys Glu Glu Tyr Ser Gln
            20                  25                  30

Ser Asp Tyr Leu Pro Ser Asp His Ser Pro Gly Tyr Tyr Ala Gly Gly
        35                  40                  45

Gln Arg Arg Glu Ser Ser Phe Gln Pro Glu Ala Gly Phe Gly Arg Arg
    50                  55                  60

Ala Ala Cys Thr Val Gln Arg Tyr Pro Pro Pro Pro Pro Pro Pro
65                  70                  75                  80

Pro Pro Gly Leu Ser Pro Arg Ala Pro Ala Pro Pro Ala Gly Ala
                85                  90                  95

Leu Leu Pro Glu Pro Gly Gln Arg Cys Glu Ala Val Ser Ser Pro
                100                 105                 110

Pro Pro Pro Pro Cys Ala Gln Asn Pro Leu His Pro Ser Pro Ser His
            115                 120                 125

Ser Ala Cys Lys Glu Pro Val Val Tyr Pro Trp Met Arg Lys Val His
    130                 135                 140

Val Ser Thr Val Asn Pro Asn Tyr Ala Gly Gly Glu Pro Lys Arg Ser
145                 150                 155                 160

Arg Thr Ala Tyr Thr Arg Gln Gln Val Leu Glu Leu Glu Lys Glu Phe
                165                 170                 175

His Tyr Asn Arg Tyr Leu Thr Arg Arg Arg Val Glu Ile Ala His
            180                 185                 190

Ala Leu Cys Leu Ser Glu Arg Gln Ile Lys Ile Trp Phe Gln Asn Arg
        195                 200                 205

Arg Met Lys Trp Lys Lys Asp His Lys Leu Pro Asn Thr Lys Ile Arg
    210                 215                 220

Ser Gly Gly Ala Ala Gly Ser Ala Gly Pro Gly Arg Pro Asn
225                 230                 235                 240

Gly Gly Pro Arg Ala Leu
                245

<210> SEQ ID NO 81
<211> LENGTH: 17
<212> TYPE: PRT
<213> ORGANISM: Artificial Sequence
<220> FEATURE:
<223> OTHER INFORMATION: His-PTD4

<400> SEQUENCE: 81

His His His His His His Tyr Ala Arg Ala Ala Ala Arg Gln Ala Arg
1               5                   10                  15

Ala

<210> SEQ ID NO 82
<211> LENGTH: 41

```
<212> TYPE: PRT
<213> ORGANISM: Artificial Sequence
<220> FEATURE:
<223> OTHER INFORMATION: PTD4-KALA

<400> SEQUENCE: 82

Tyr Ala Arg Ala Ala Ala Arg Gln Ala Arg Ala Trp Glu Ala Lys Leu
1               5                   10                  15

Ala Lys Ala Leu Ala Lys Ala Leu Ala Lys His Leu Ala Lys Ala Leu
            20                  25                  30

Ala Lys Ala Leu Lys Ala Cys Glu Ala
        35                  40

<210> SEQ ID NO 83
<211> LENGTH: 39
<212> TYPE: PRT
<213> ORGANISM: Artificial Sequence
<220> FEATURE:
<223> OTHER INFORMATION: 9Arg-KALA

<400> SEQUENCE: 83

Arg Arg Arg Arg Arg Arg Arg Arg Arg Trp Glu Ala Lys Leu Ala Lys
1               5                   10                  15

Ala Leu Ala Lys Ala Leu Ala Lys His Leu Ala Lys Ala Leu Ala Lys
            20                  25                  30

Ala Leu Lys Ala Cys Glu Ala
        35

<210> SEQ ID NO 84
<211> LENGTH: 51
<212> TYPE: PRT
<213> ORGANISM: Artificial Sequence
<220> FEATURE:
<223> OTHER INFORMATION: Pep1-KALA

<400> SEQUENCE: 84

Lys Glu Thr Trp Trp Glu Thr Trp Trp Thr Glu Trp Ser Gln Pro Lys
1               5                   10                  15

Lys Lys Arg Lys Val Trp Glu Ala Lys Leu Ala Lys Ala Leu Ala Lys
            20                  25                  30

Ala Leu Ala Lys His Leu Ala Lys Ala Leu Ala Lys Ala Leu Lys Ala
        35                  40                  45

Cys Glu Ala
    50

<210> SEQ ID NO 85
<211> LENGTH: 37
<212> TYPE: PRT
<213> ORGANISM: Artificial Sequence
<220> FEATURE:
<223> OTHER INFORMATION: Xentry-KALA

<400> SEQUENCE: 85

Leu Cys Leu Arg Pro Val Gly Trp Glu Ala Lys Leu Ala Lys Ala Leu
1               5                   10                  15

Ala Lys Ala Leu Ala Lys His Leu Ala Lys Ala Leu Ala Lys Ala Leu
            20                  25                  30

Lys Ala Cys Glu Ala
        35

<210> SEQ ID NO 86
<211> LENGTH: 40
```

```
<212> TYPE: PRT
<213> ORGANISM: Artificial Sequence
<220> FEATURE:
<223> OTHER INFORMATION: SynB3-KALA

<400> SEQUENCE: 86

Arg Arg Leu Ser Tyr Ser Arg Arg Arg Phe Trp Glu Ala Lys Leu Ala
1               5                   10                  15

Lys Ala Leu Ala Lys Ala Leu Ala Lys His Leu Ala Lys Ala Leu Ala
            20                  25                  30

Lys Ala Leu Lys Ala Cys Glu Ala
        35                  40

<210> SEQ ID NO 87
<211> LENGTH: 36
<212> TYPE: PRT
<213> ORGANISM: Artificial Sequence
<220> FEATURE:
<223> OTHER INFORMATION: VSVG-PTD4

<400> SEQUENCE: 87

Lys Phe Thr Ile Val Phe Pro His Asn Gln Lys Gly Asn Trp Lys Asn
1               5                   10                  15

Val Pro Ser Asn Tyr His Tyr Cys Pro Tyr Ala Arg Ala Ala Ala Arg
            20                  25                  30

Gln Ala Arg Ala
        35

<210> SEQ ID NO 88
<211> LENGTH: 34
<212> TYPE: PRT
<213> ORGANISM: Artificial Sequence
<220> FEATURE:
<223> OTHER INFORMATION: EB1-PTD4

<400> SEQUENCE: 88

Leu Ile Arg Leu Trp Ser His Leu Ile His Ile Trp Phe Gln Asn Arg
1               5                   10                  15

Arg Leu Lys Trp Lys Lys Lys Tyr Ala Arg Ala Ala Ala Arg Gln Ala
            20                  25                  30

Arg Ala

<210> SEQ ID NO 89
<211> LENGTH: 31
<212> TYPE: PRT
<213> ORGANISM: Artificial Sequence
<220> FEATURE:
<223> OTHER INFORMATION: JST-PTD4

<400> SEQUENCE: 89

Gly Leu Phe Glu Ala Leu Leu Glu Leu Leu Glu Ser Leu Trp Glu Leu
1               5                   10                  15

Leu Leu Glu Ala Tyr Ala Arg Ala Ala Ala Arg Gln Ala Arg Ala
            20                  25                  30

<210> SEQ ID NO 90
<211> LENGTH: 29
<212> TYPE: PRT
<213> ORGANISM: Artificial Sequence
<220> FEATURE:
<223> OTHER INFORMATION: CM18-PTD4

<400> SEQUENCE: 90
```

Lys Trp Lys Leu Phe Lys Lys Ile Gly Ala Val Leu Lys Val Leu Thr
1               5                   10                  15

Thr Gly Tyr Ala Arg Ala Ala Ala Arg Gln Ala Arg Ala
            20                  25

<210> SEQ ID NO 91
<211> LENGTH: 35
<212> TYPE: PRT
<213> ORGANISM: Artificial Sequence
<220> FEATURE:
<223> OTHER INFORMATION: 6Cys-CM18-PTD4

<400> SEQUENCE: 91

Cys Cys Cys Cys Cys Cys Lys Trp Lys Leu Phe Lys Lys Ile Gly Ala
1               5                   10                  15

Val Leu Lys Val Leu Thr Thr Gly Tyr Ala Arg Ala Ala Ala Arg Gln
            20                  25                  30

Ala Arg Ala
        35

<210> SEQ ID NO 92
<211> LENGTH: 32
<212> TYPE: PRT
<213> ORGANISM: Artificial Sequence
<220> FEATURE:
<223> OTHER INFORMATION: CM18-L1-PTD4

<400> SEQUENCE: 92

Lys Trp Lys Leu Phe Lys Lys Ile Gly Ala Val Leu Lys Val Leu Thr
1               5                   10                  15

Thr Gly Gly Gly Ser Tyr Ala Arg Ala Ala Ala Arg Gln Ala Arg Ala
            20                  25                  30

<210> SEQ ID NO 93
<211> LENGTH: 36
<212> TYPE: PRT
<213> ORGANISM: Artificial Sequence
<220> FEATURE:
<223> OTHER INFORMATION: CM18-L2-PTD4

<400> SEQUENCE: 93

Lys Trp Lys Leu Phe Lys Lys Ile Gly Ala Val Leu Lys Val Leu Thr
1               5                   10                  15

Thr Gly Gly Gly Ser Gly Gly Gly Ser Tyr Ala Arg Ala Ala Ala Arg
            20                  25                  30

Gln Ala Arg Ala
        35

<210> SEQ ID NO 94
<211> LENGTH: 41
<212> TYPE: PRT
<213> ORGANISM: Artificial Sequence
<220> FEATURE:
<223> OTHER INFORMATION: CM18-L3-PTD4

<400> SEQUENCE: 94

Lys Trp Lys Leu Phe Lys Lys Ile Gly Ala Val Leu Lys Val Leu Thr
1               5                   10                  15

Thr Gly Gly Gly Ser Gly Gly Gly Ser Gly Gly Ser Gly Tyr Ala
            20                  25                  30

Arg Ala Ala Ala Arg Gln Ala Arg Ala
        35                  40

```
<210> SEQ ID NO 95
<211> LENGTH: 35
<212> TYPE: PRT
<213> ORGANISM: Artificial Sequence
<220> FEATURE:
<223> OTHER INFORMATION: His-CM18-TAT

<400> SEQUENCE: 95

His His His His His His Lys Trp Lys Leu Phe Lys Lys Ile Gly Ala
1               5                   10                  15

Val Leu Lys Val Leu Thr Thr Gly Tyr Gly Arg Lys Lys Arg Arg Gln
            20                  25                  30

Arg Arg Arg
        35

<210> SEQ ID NO 96
<211> LENGTH: 41
<212> TYPE: PRT
<213> ORGANISM: Artificial Sequence
<220> FEATURE:
<223> OTHER INFORMATION: His-CM18-PTD4-6Cys

<400> SEQUENCE: 96

His His His His His His Lys Trp Lys Leu Phe Lys Lys Ile Gly Ala
1               5                   10                  15

Val Leu Lys Val Leu Thr Thr Gly Tyr Ala Arg Ala Ala Ala Arg Gln
            20                  25                  30

Ala Arg Ala Cys Cys Cys Cys Cys Cys
        35                  40

<210> SEQ ID NO 97
<211> LENGTH: 32
<212> TYPE: PRT
<213> ORGANISM: Artificial Sequence
<220> FEATURE:
<223> OTHER INFORMATION: 3His-CM18-PTD4

<400> SEQUENCE: 97

His His His Lys Trp Lys Leu Phe Lys Lys Ile Gly Ala Val Leu Lys
1               5                   10                  15

Val Leu Thr Thr Gly Tyr Ala Arg Ala Ala Ala Arg Gln Ala Arg Ala
            20                  25                  30

<210> SEQ ID NO 98
<211> LENGTH: 41
<212> TYPE: PRT
<213> ORGANISM: Artificial Sequence
<220> FEATURE:
<223> OTHER INFORMATION: 12His-CM18-PTD4

<400> SEQUENCE: 98

His His His His His His His His His His His His Lys Trp Lys Leu
1               5                   10                  15

Phe Lys Lys Ile Gly Ala Val Leu Lys Val Leu Thr Thr Gly Tyr Ala
            20                  25                  30

Arg Ala Ala Ala Arg Gln Ala Arg Ala
        35                  40

<210> SEQ ID NO 99
<211> LENGTH: 36
<212> TYPE: PRT
<213> ORGANISM: Artificial Sequence
<220> FEATURE:
```

<223> OTHER INFORMATION: HA-CM18-PTD4

<400> SEQUENCE: 99

His His His Ala His His His Lys Trp Lys Leu Phe Lys Lys Ile Gly
1               5                   10                  15

Ala Val Leu Lys Val Leu Thr Thr Gly Tyr Ala Arg Ala Ala Ala Arg
            20                  25                  30

Gln Ala Arg Ala
        35

<210> SEQ ID NO 100
<211> LENGTH: 38
<212> TYPE: PRT
<213> ORGANISM: Artificial Sequence
<220> FEATURE:
<223> OTHER INFORMATION: 3HA-CM18-PTD4

<400> SEQUENCE: 100

His Ala His His Ala His His Ala His Lys Trp Lys Leu Phe Lys Lys
1               5                   10                  15

Ile Gly Ala Val Leu Lys Val Leu Thr Thr Gly Tyr Ala Arg Ala Ala
            20                  25                  30

Ala Arg Gln Ala Arg Ala
        35

<210> SEQ ID NO 101
<211> LENGTH: 35
<212> TYPE: PRT
<213> ORGANISM: Artificial Sequence
<220> FEATURE:
<223> OTHER INFORMATION: CM18-His-PTD4

<400> SEQUENCE: 101

Lys Trp Lys Leu Phe Lys Lys Ile Gly Ala Val Leu Lys Val Leu Thr
1               5                   10                  15

Thr Gly His His His His His His Tyr Ala Arg Ala Ala Ala Arg Gln
            20                  25                  30

Ala Arg Ala
        35

<210> SEQ ID NO 102
<211> LENGTH: 41
<212> TYPE: PRT
<213> ORGANISM: Artificial Sequence
<220> FEATURE:
<223> OTHER INFORMATION: His-CM18-PTD4-His

<400> SEQUENCE: 102

His His His His His His Lys Trp Lys Leu Phe Lys Lys Ile Gly Ala
1               5                   10                  15

Val Leu Lys Val Leu Thr Thr Gly Tyr Ala Arg Ala Ala Ala Arg Gln
            20                  25                  30

Ala Arg Ala His His His His His
        35                  40

<210> SEQ ID NO 103
<211> LENGTH: 36
<212> TYPE: RNA
<213> ORGANISM: Artificial Sequence
<220> FEATURE:
<223> OTHER INFORMATION: HPRT crRNA

<400> SEQUENCE: 103
aauuaugggg auuacuagga guuuuagagc uaugcu					36

<210> SEQ ID NO 104
<211> LENGTH: 38
<212> TYPE: PRT
<213> ORGANISM: Artificial Sequence
<220> FEATURE:
<223> OTHER INFORMATION: FSD1

<400> SEQUENCE: 104

His His His His His His Lys Trp Lys Leu Leu Arg Arg Ala Ala Lys
1               5                   10                  15

Lys Ala Ala Arg Arg Tyr Leu Lys Leu Leu Leu Lys Gln Leu Lys Leu
            20                  25                  30

His His His His His His
        35

<210> SEQ ID NO 105
<211> LENGTH: 38
<212> TYPE: PRT
<213> ORGANISM: Artificial Sequence
<220> FEATURE:
<223> OTHER INFORMATION: FSD2

<400> SEQUENCE: 105

His His His His His His Trp Leu Lys Leu Leu Arg Arg Ala Ala Lys
1               5                   10                  15

Lys Ala Ala Arg Leu Tyr Arg Lys Leu Leu Arg Lys Ala Arg Lys Leu
            20                  25                  30

His His His His His His
        35

<210> SEQ ID NO 106
<211> LENGTH: 38
<212> TYPE: PRT
<213> ORGANISM: Artificial Sequence
<220> FEATURE:
<223> OTHER INFORMATION: FSD3

<400> SEQUENCE: 106

His His His His His His Lys Arg Lys Lys Lys Arg Arg Ala Lys Lys
1               5                   10                  15

Lys Arg Ala Trp Leu Tyr Leu Ala Leu Leu Leu Trp Ala Leu Ala Leu
            20                  25                  30

His His His His His His
        35

<210> SEQ ID NO 107
<211> LENGTH: 38
<212> TYPE: PRT
<213> ORGANISM: Artificial Sequence
<220> FEATURE:
<223> OTHER INFORMATION: FSD4

<400> SEQUENCE: 107

His His His His His His Lys Arg Gln Leu Lys Arg Lys Leu Arg Lys
1               5                   10                  15

Trp Lys Arg Leu Leu Arg Leu Leu Arg Leu Ala Arg Leu Trp Leu
            20                  25                  30

His His His His His His
        35

<210> SEQ ID NO 108
<211> LENGTH: 37
<212> TYPE: PRT
<213> ORGANISM: Artificial Sequence
<220> FEATURE:
<223> OTHER INFORMATION: FSD5

<400> SEQUENCE: 108

His His His His His His Leu Leu Lys Leu Trp Ser Arg Leu Leu Lys
1               5                   10                  15

Leu Trp Thr Gln Gly Arg Arg Leu Lys Ala Lys Arg Ala Lys Ala His
            20                  25                  30

His His His His His
        35

<210> SEQ ID NO 109
<211> LENGTH: 34
<212> TYPE: PRT
<213> ORGANISM: Artificial Sequence
<220> FEATURE:
<223> OTHER INFORMATION: FSD6

<400> SEQUENCE: 109

His His His His His His Trp Tyr Leu Ala Leu Leu Ala Leu Tyr Trp
1               5                   10                  15

Gln Arg Ala Lys Ala Lys Thr Arg Gln Arg Arg Arg His His His His
            20                  25                  30

His His

<210> SEQ ID NO 110
<211> LENGTH: 33
<212> TYPE: PRT
<213> ORGANISM: Artificial Sequence
<220> FEATURE:
<223> OTHER INFORMATION: FSD7

<400> SEQUENCE: 110

His His His His His His Trp Ala Arg Leu Ala Arg Ala Phe Ala Arg
1               5                   10                  15

Ala Ile Lys Lys Leu Tyr Ala Arg Ala Leu Arg Arg Gln Ala Arg Thr
            20                  25                  30

Gly

<210> SEQ ID NO 111
<211> LENGTH: 33
<212> TYPE: PRT
<213> ORGANISM: Artificial Sequence
<220> FEATURE:
<223> OTHER INFORMATION: FSD8

<400> SEQUENCE: 111

His His His His His His Lys Trp Lys Leu Ala Arg Ala Phe Ala Arg
1               5                   10                  15

Ala Ile Lys Lys Leu Tyr Ala Arg Ala Leu Arg Arg Gln Ala Arg Thr
            20                  25                  30

Gly

<210> SEQ ID NO 112
<211> LENGTH: 39
<212> TYPE: PRT
<213> ORGANISM: Artificial Sequence
<220> FEATURE:

```
<223> OTHER INFORMATION: FSD8

<400> SEQUENCE: 112

His His His His His His Lys Trp Lys Leu Ala Arg Ala Phe Ala Arg
1               5                   10                  15

Ala Ile Lys Lys Leu Tyr Ala Arg Ala Leu Arg Arg Gln Ala Arg Thr
            20                  25                  30

Gly His His His His His His
        35

<210> SEQ ID NO 113
<211> LENGTH: 34
<212> TYPE: PRT
<213> ORGANISM: Artificial Sequence
<220> FEATURE:
<223> OTHER INFORMATION: FSD10

<400> SEQUENCE: 113

Lys Trp Lys Leu Ala Arg Ala Phe Ala Arg Ala Ile Lys Lys Leu Gly
1               5                   10                  15

Gly Ser Gly Gly Gly Ser Tyr Ala Arg Ala Leu Arg Arg Gln Ala Arg
            20                  25                  30

Thr Gly

<210> SEQ ID NO 114
<211> LENGTH: 36
<212> TYPE: PRT
<213> ORGANISM: Artificial Sequence
<220> FEATURE:
<223> OTHER INFORMATION: FSD11

<400> SEQUENCE: 114

His His His His His His Lys Trp Lys Leu Ala Arg Ala Phe Ala Arg
1               5                   10                  15

Ala Leu Arg Ala Ile Lys Lys Leu Tyr Ala Arg Ala Leu Arg Arg Gln
            20                  25                  30

Ala Arg Thr Gly
        35

<210> SEQ ID NO 115
<211> LENGTH: 27
<212> TYPE: PRT
<213> ORGANISM: Artificial Sequence
<220> FEATURE:
<223> OTHER INFORMATION: FSD12

<400> SEQUENCE: 115

Lys Trp Lys Leu Ala Arg Ala Phe Ala Arg Ala Ile Lys Lys Leu Tyr
1               5                   10                  15

Ala Arg Ala Leu Arg Arg Gln Ala Arg Thr Gly
            20                  25

<210> SEQ ID NO 116
<211> LENGTH: 40
<212> TYPE: PRT
<213> ORGANISM: Artificial Sequence
<220> FEATURE:
<223> OTHER INFORMATION: FSD13

<400> SEQUENCE: 116

His His His His His His Lys Trp Ala Lys Leu Leu Arg Ala Phe Ala
1               5                   10                  15
```

Lys Ala Ile Lys Lys Leu Tyr Ala Arg Leu Ala Arg Arg Gln Ala Arg
            20                  25                  30

Thr Gly His His His His His His
            35                  40

<210> SEQ ID NO 117
<211> LENGTH: 38
<212> TYPE: PRT
<213> ORGANISM: Artificial Sequence
<220> FEATURE:
<223> OTHER INFORMATION: FSD14

<400> SEQUENCE: 117

His His His His His His Leu Ala Leu Ala Arg Trp Ala Arg Tyr Phe
1               5                   10                  15

Arg Ile Leu Ala Lys Leu Lys Arg Thr Lys Arg Gly Gln Ala Lys Ala
            20                  25                  30

His His His His His His
            35

<210> SEQ ID NO 118
<211> LENGTH: 39
<212> TYPE: PRT
<213> ORGANISM: Artificial Sequence
<220> FEATURE:
<223> OTHER INFORMATION: FSD15

<400> SEQUENCE: 118

His His His His His His Lys Trp Lys Ile Ala Arg Ala Phe Ala Arg
1               5                   10                  15

Ser Leu Lys Lys Leu Tyr Ala Arg Leu Leu Ala Arg Gln Ala Lys Thr
            20                  25                  30

Gly His His His His His His
            35

<210> SEQ ID NO 119
<211> LENGTH: 31
<212> TYPE: PRT
<213> ORGANISM: Artificial Sequence
<220> FEATURE:
<223> OTHER INFORMATION: FSD16

<400> SEQUENCE: 119

His His His His His His Leu Leu Lys Leu Trp Ser Arg Leu Leu Lys
1               5                   10                  15

Leu Trp Thr Gln Gly Arg Arg Leu Lys Ala Lys Arg Ala Lys Ala
            20                  25                  30

<210> SEQ ID NO 120
<211> LENGTH: 37
<212> TYPE: PRT
<213> ORGANISM: Artificial Sequence
<220> FEATURE:
<223> OTHER INFORMATION: FSD17

<400> SEQUENCE: 120

His His His His His His Leu Ala Lys Leu Phe Lys Trp Leu Arg Ala
1               5                   10                  15

Leu Ile Arg Gln Gly Ala Lys Arg Lys Thr Lys Arg Ala Ser Ala His
            20                  25                  30

His His His His His
            35

<210> SEQ ID NO 121
<211> LENGTH: 32
<212> TYPE: PRT
<213> ORGANISM: Artificial Sequence
<220> FEATURE:
<223> OTHER INFORMATION: FSD18

<400> SEQUENCE: 121

Leu Leu Lys Leu Trp Ser Arg Leu Leu Lys Leu Trp Thr Gln Gly Gly
1               5                   10                  15

Ser Gly Gly Gly Ser Gly Arg Arg Leu Lys Ala Lys Arg Ala Lys Ala
            20                  25                  30

<210> SEQ ID NO 122
<211> LENGTH: 42
<212> TYPE: PRT
<213> ORGANISM: Artificial Sequence
<220> FEATURE:
<223> OTHER INFORMATION: FSD19

<400> SEQUENCE: 122

His His His His His His Leu Leu Lys Leu Trp Ser Arg Leu Leu Lys
1               5                   10                  15

Thr Trp Thr Gln Gly Arg Arg Leu Lys Ala Lys Ser Ala Gln Ala Ser
            20                  25                  30

Thr Arg Gln Ala His His His His His
        35                  40

<210> SEQ ID NO 123
<211> LENGTH: 33
<212> TYPE: PRT
<213> ORGANISM: Artificial Sequence
<220> FEATURE:
<223> OTHER INFORMATION: FSD20

<400> SEQUENCE: 123

His His His His Ala Ala Val Leu Lys Leu Trp Lys Arg Leu Leu Lys
1               5                   10                  15

Leu Phe Arg Lys Gly Arg Arg Leu Lys Ala Lys Arg Ala Lys Ala Lys
            20                  25                  30

Arg

<210> SEQ ID NO 124
<211> LENGTH: 31
<212> TYPE: PRT
<213> ORGANISM: Artificial Sequence
<220> FEATURE:
<223> OTHER INFORMATION: FSD21

<400> SEQUENCE: 124

His His His His His His Phe Leu Lys Ile Trp Ser Arg Leu Ile Lys
1               5                   10                  15

Ile Trp Thr Gln Gly Arg Arg Lys Gly Ala Gln Ala Ala Phe Arg
            20                  25                  30

<210> SEQ ID NO 125
<211> LENGTH: 38
<212> TYPE: PRT
<213> ORGANISM: Artificial Sequence
<220> FEATURE:
<223> OTHER INFORMATION: FSD22

<400> SEQUENCE: 125

His His His His His His Val Leu Lys Leu Trp Ser Arg Ile Leu Lys
1               5                   10                  15

Ala Phe Thr Gln Gly Arg Arg Met Ala Ala Lys Arg Ala Lys Cys Asn
            20                  25                  30

His His His His His His
        35

<210> SEQ ID NO 126
<211> LENGTH: 37
<212> TYPE: PRT
<213> ORGANISM: Artificial Sequence
<220> FEATURE:
<223> OTHER INFORMATION: FSD23

<400> SEQUENCE: 126

His His His His His His Leu Leu Lys Leu Trp Ser Arg Leu Leu Lys
1               5                   10                  15

Glu Trp Thr Gln Gly Arg Arg Leu Glu Ala Lys Arg Ala Glu Ala His
            20                  25                  30

His His His His His
        35

<210> SEQ ID NO 127
<211> LENGTH: 34
<212> TYPE: PRT
<213> ORGANISM: Artificial Sequence
<220> FEATURE:
<223> OTHER INFORMATION: FSD24

<400> SEQUENCE: 127

His His His His His His Leu Leu Cys Leu Trp Ser Arg Leu Leu Lys
1               5                   10                  15

Leu Trp Thr Gln Gly Glu Arg Leu Lys Ala Lys Cys Ala Lys Ala Cys
            20                  25                  30

Glu Arg

<210> SEQ ID NO 128
<211> LENGTH: 35
<212> TYPE: PRT
<213> ORGANISM: Artificial Sequence
<220> FEATURE:
<223> OTHER INFORMATION: FSD25

<400> SEQUENCE: 128

His His His His His His Val Trp Lys Leu Phe Trp Thr Leu Leu Ala
1               5                   10                  15

Ala Ile Tyr Gly Arg Gly Lys Ala Arg Gln Lys Arg Ala Lys Arg Gln
            20                  25                  30

Ala Arg Gly
        35

<210> SEQ ID NO 129
<211> LENGTH: 35
<212> TYPE: PRT
<213> ORGANISM: Artificial Sequence
<220> FEATURE:
<223> OTHER INFORMATION: FSD26

<400> SEQUENCE: 129

Ala Leu Leu Gly Leu Phe Ile Lys Trp Val Lys Lys Val Gly Thr Leu
1               5                   10                  15

Phe Arg Lys Ala Lys Ala Gly Ala Gln Asn Arg Arg Ala Lys Ala Gln

```
            20                  25                  30

Lys Gly Lys
        35

<210> SEQ ID NO 130
<211> LENGTH: 37
<212> TYPE: PRT
<213> ORGANISM: Artificial Sequence
<220> FEATURE:
<223> OTHER INFORMATION: FSN1

<400> SEQUENCE: 130

His His His His His His Lys Arg Lys Arg Ser Lys Lys Arg Lys
1               5                   10                  15

Leu Trp Thr Gln Gly Trp Leu Leu Leu Ala Leu Leu Ala Leu Ala His
            20                  25                  30

His His His His His
        35

<210> SEQ ID NO 131
<211> LENGTH: 37
<212> TYPE: PRT
<213> ORGANISM: Artificial Sequence
<220> FEATURE:
<223> OTHER INFORMATION: FSN2

<400> SEQUENCE: 131

His His His His His His Lys Leu Lys Leu Arg Ser Arg Leu Lys Trp
1               5                   10                  15

Gly Arg Thr Gln Leu Trp Arg Ala Leu Ala Lys Lys Ala Leu Leu His
            20                  25                  30

His His His His His
        35

<210> SEQ ID NO 132
<211> LENGTH: 36
<212> TYPE: PRT
<213> ORGANISM: Artificial Sequence
<220> FEATURE:
<223> OTHER INFORMATION: FSN3

<400> SEQUENCE: 132

His His His His His His Gln Phe Leu Cys Phe Trp Leu Asn Lys Met
1               5                   10                  15

Gly Lys His Asn Thr Val Trp His Gly Arg His Leu Lys Cys His Lys
            20                  25                  30

Arg Gly Lys Gly
        35

<210> SEQ ID NO 133
<211> LENGTH: 35
<212> TYPE: PRT
<213> ORGANISM: Artificial Sequence
<220> FEATURE:
<223> OTHER INFORMATION: FSN4

<400> SEQUENCE: 133

His His His His His His Leu Leu Tyr Leu Trp Arg Arg Leu Leu Lys
1               5                   10                  15

Phe Trp Cys Ala Gly Arg Arg Val Tyr Ala Lys Cys Ala Lys Ala Tyr
            20                  25                  30

Gly Cys Phe
```

<210> SEQ ID NO 134
<211> LENGTH: 39
<212> TYPE: PRT
<213> ORGANISM: Artificial Sequence
<220> FEATURE:
<223> OTHER INFORMATION: FSN5

<400> SEQUENCE: 134

His His His His His His Leu Leu Lys Leu Trp Arg Arg Leu Leu Lys
1               5                   10                  15

Leu Phe Arg Lys Ala Leu Arg Ala Leu Ala Lys Arg Ala Lys Ser Ala
            20                  25                  30

Leu Lys Arg Ala Gln Ala Ala
        35

<210> SEQ ID NO 135
<211> LENGTH: 39
<212> TYPE: PRT
<213> ORGANISM: Artificial Sequence
<220> FEATURE:
<223> OTHER INFORMATION: FSN6

<400> SEQUENCE: 135

His His His His His His Leu Leu Lys Leu Trp Ser Arg Leu Leu Lys
1               5                   10                  15

Leu Trp Thr Gln Ala Leu Arg Ala Leu Ala Lys Arg Ala Lys Ala Leu
            20                  25                  30

Ala His His His His His His
        35

<210> SEQ ID NO 136
<211> LENGTH: 31
<212> TYPE: PRT
<213> ORGANISM: Artificial Sequence
<220> FEATURE:
<223> OTHER INFORMATION: FSN7

<400> SEQUENCE: 136

Leu Ile Lys Leu Trp Ser Arg Phe Ile Lys Phe Trp Thr Gln Gly Arg
1               5                   10                  15

Arg Ile Lys Ala Lys Leu Ala Arg Ala Gly Gln Ser Trp Phe Gly
            20                  25                  30

<210> SEQ ID NO 137
<211> LENGTH: 19
<212> TYPE: PRT
<213> ORGANISM: Artificial Sequence
<220> FEATURE:
<223> OTHER INFORMATION: FSN8

<400> SEQUENCE: 137

His His His His His His Phe Arg Lys Leu Trp Leu Ala Ile Val Arg
1               5                   10                  15

Ala Lys Lys

<210> SEQ ID NO 138
<211> LENGTH: 35
<212> TYPE: PRT
<213> ORGANISM: Artificial Sequence
<220> FEATURE:
<223> OTHER INFORMATION: FSD27

```
<400> SEQUENCE: 138

His His His His His His Lys Trp Lys Leu Phe Trp Glu Ala Lys Leu
1               5                   10                  15

Ala Lys Tyr Ala Arg Ala Ala Ala Arg Gln Ala Arg Ala Ala Arg Gln
            20                  25                  30

Ala Arg Ala
        35

<210> SEQ ID NO 139
<211> LENGTH: 35
<212> TYPE: PRT
<213> ORGANISM: Artificial Sequence
<220> FEATURE:
<223> OTHER INFORMATION: FSD28

<400> SEQUENCE: 139

His His His His His His His Met Ala His Leu Trp Glu Ser Asn Ala
1               5                   10                  15

Arg Lys Phe Trp Lys Lys Ala Phe Ala Gln His Ala Ala Ala His Ile
            20                  25                  30

Ala Glu Ala
        35

<210> SEQ ID NO 140
<211> LENGTH: 35
<212> TYPE: PRT
<213> ORGANISM: Artificial Sequence
<220> FEATURE:
<223> OTHER INFORMATION: FSD29

<400> SEQUENCE: 140

Leu His His His Ser His His Leu Ile His Ile Trp Leu Leu Phe Lys
1               5                   10                  15

Leu Lys Leu Lys Lys Lys Lys Ala Ala Arg Arg Ala Arg Arg Ala Arg
            20                  25                  30

Arg His His
        35

<210> SEQ ID NO 141
<211> LENGTH: 35
<212> TYPE: PRT
<213> ORGANISM: Artificial Sequence
<220> FEATURE:
<223> OTHER INFORMATION: FSD30

<400> SEQUENCE: 141

His His His His His His Cys Leu Leu Lys Lys Trp Glu Ala Lys Leu
1               5                   10                  15

Ala Lys Lys Ile Gly Gly Gly Gly Arg Gln Ala Arg Ala Lys Ala Leu
            20                  25                  30

Ala Lys Ala
        35

<210> SEQ ID NO 142
<211> LENGTH: 35
<212> TYPE: PRT
<213> ORGANISM: Artificial Sequence
<220> FEATURE:
<223> OTHER INFORMATION: FSD31

<400> SEQUENCE: 142

Tyr His His His His His Lys Trp Lys Lys Arg Trp Glu Ala Lys Leu
```

```
1               5                   10                  15
Ala Lys Ala Leu Arg Ala Ala Gly Arg Gln Ala Arg Ala Lys Ala Leu
                20                  25                  30

Ala Lys Ala
        35

<210> SEQ ID NO 143
<211> LENGTH: 35
<212> TYPE: PRT
<213> ORGANISM: Artificial Sequence
<220> FEATURE:
<223> OTHER INFORMATION: FSD32

<400> SEQUENCE: 143

Ile Val Arg His Glu His Cys Met Ile His Leu Trp Tyr Lys Asn Leu
1               5                   10                  15

Ala Lys Tyr Cys Ser Thr Ser His Ala Arg Arg Leu Ala Arg Arg Arg
                20                  25                  30

Ala His His
        35

<210> SEQ ID NO 144
<211> LENGTH: 35
<212> TYPE: PRT
<213> ORGANISM: Artificial Sequence
<220> FEATURE:
<223> OTHER INFORMATION: FSD33

<400> SEQUENCE: 144

His His His His His His His His Arg Gln Arg Arg Arg Trp Glu Ala
1               5                   10                  15

Arg Gly Gly Phe Leu Gly Gly Gly Gly Tyr Ala Arg Ala Ala Arg Gln
                20                  25                  30

Ala Arg Ala
        35

<210> SEQ ID NO 145
<211> LENGTH: 35
<212> TYPE: PRT
<213> ORGANISM: Artificial Sequence
<220> FEATURE:
<223> OTHER INFORMATION: FSD34

<400> SEQUENCE: 145

His His His His His His Lys Leu Ile His Ile Trp Glu Ala Lys Leu
1               5                   10                  15

Phe Lys Lys Ile Arg Ala Ala Ala Arg Gln Ala Arg Ala Arg Arg Ala
                20                  25                  30

Ala Lys Ala
        35

<210> SEQ ID NO 146
<211> LENGTH: 35
<212> TYPE: PRT
<213> ORGANISM: Artificial Sequence
<220> FEATURE:
<223> OTHER INFORMATION: FSD35

<400> SEQUENCE: 146

His His His His His His Lys Leu Leu Lys Arg Trp Glu Ala Lys Leu
1               5                   10                  15

Ala Lys Ala Leu Ala Lys Ala Leu Ala Lys His Leu Ala Lys Ala Leu
```

```
                    20                  25                  30

Ala Lys Ala
        35

<210> SEQ ID NO 147
<211> LENGTH: 35
<212> TYPE: PRT
<213> ORGANISM: Artificial Sequence
<220> FEATURE:
<223> OTHER INFORMATION: FSD36

<400> SEQUENCE: 147

His His His His His His Cys Leu Ile His Ile Trp Glu Ala Lys Leu
1               5                   10                  15

Ala Lys Lys Cys Gly Gly Gly Gly Tyr Ala Arg Ala Ala Ala Arg Gln
            20                  25                  30

Ala Arg Ala
        35

<210> SEQ ID NO 148
<211> LENGTH: 35
<212> TYPE: PRT
<213> ORGANISM: Artificial Sequence
<220> FEATURE:
<223> OTHER INFORMATION: FSD37

<400> SEQUENCE: 148

Arg Leu His His Ser His His Leu Ile His Ile Trp Leu Leu Phe Lys
1               5                   10                  15

Leu Lys Leu Lys Lys Lys Lys Arg Ala Ala Arg Arg Ala Arg Arg His
            20                  25                  30

His His Leu
        35

<210> SEQ ID NO 149
<211> LENGTH: 35
<212> TYPE: PRT
<213> ORGANISM: Artificial Sequence
<220> FEATURE:
<223> OTHER INFORMATION: FSD38

<400> SEQUENCE: 149

Gly His His His His His His His Leu Ile His Ile Trp Glu Ala Lys
1               5                   10                  15

Leu Ala Lys Leu Ala Lys Ala Leu Ala Arg Ala Ala Ala Arg Gln Ala
            20                  25                  30

Arg Ala Lys
        35

<210> SEQ ID NO 150
<211> LENGTH: 35
<212> TYPE: PRT
<213> ORGANISM: Artificial Sequence
<220> FEATURE:
<223> OTHER INFORMATION: FSD39

<400> SEQUENCE: 150

His His His His His His His His Arg Gln Arg Arg Arg Trp Glu Ala
1               5                   10                  15

Arg Gly Phe Leu Gly Gly Gly Gly Tyr Ala Arg Ala Ala Ala Arg Gln Ala
            20                  25                  30

Arg Ala Ala
```

-continued

```
<210> SEQ ID NO 151
<211> LENGTH: 35
<212> TYPE: PRT
<213> ORGANISM: Artificial Sequence
<220> FEATURE:
<223> OTHER INFORMATION: FSD40

<400> SEQUENCE: 151

Tyr Gly Arg Lys Lys Arg Tyr Met Leu Arg Leu Trp Tyr Gln Asn Leu
1               5                   10                  15

Arg Met Tyr Cys Lys Lys Ala Tyr Ala Gln His Arg Ala Arg Gln His
            20                  25                  30

Ala Lys Leu
        35

<210> SEQ ID NO 152
<211> LENGTH: 35
<212> TYPE: PRT
<213> ORGANISM: Artificial Sequence
<220> FEATURE:
<223> OTHER INFORMATION: FSD41

<400> SEQUENCE: 152

Leu His His His His His Lys Leu Ile His Ile Trp Glu Ala Lys Leu
1               5                   10                  15

Ala Lys Ala Leu Ala Lys Ala Leu Ala Arg Arg Ala Ala Ala Arg Gln
            20                  25                  30

Ala Arg Ala
        35

<210> SEQ ID NO 153
<211> LENGTH: 35
<212> TYPE: PRT
<213> ORGANISM: Artificial Sequence
<220> FEATURE:
<223> OTHER INFORMATION: FSD42

<400> SEQUENCE: 153

His His His His His His Cys Met Lys Val Val Trp Glu Ile Val Leu
1               5                   10                  15

Ala Lys Tyr Lys Gly Gly Gly Gly Arg Ala Arg Ala Ala Ser Arg Arg
            20                  25                  30

Ala Arg Ala
        35

<210> SEQ ID NO 154
<211> LENGTH: 72
<212> TYPE: DNA
<213> ORGANISM: Artificial Sequence
<220> FEATURE:
<223> OTHER INFORMATION: Short DNA template

<400> SEQUENCE: 154
tgaaatggag agctaaatta tggggattac aagcttgata gcgaaggggc agcaatgagt      60
tgacactaca ga                                                          72

<210> SEQ ID NO 155
<211> LENGTH: 1353
<212> TYPE: PRT
<213> ORGANISM: Artificial Sequence
<220> FEATURE:
```

-continued

<223> OTHER INFORMATION: Cpf1-NLS

<400> SEQUENCE: 155

```
Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
        355                 360                 365

Lys Lys Leu Glu Thr Ile Ser Ser Ala Leu Cys Asp His Trp Asp Thr
    370                 375                 380

Leu Arg Asn Ala Leu Tyr Glu Arg Arg Ile Ser Glu Leu Thr Gly Lys
385                 390                 395                 400
```

-continued

```
Ile Thr Lys Ser Ala Lys Glu Lys Val Gln Arg Ser Leu Lys His Glu
            405                 410                 415

Asp Ile Asn Leu Gln Glu Ile Ile Ser Ala Ala Gly Lys Glu Leu Ser
        420                 425                 430

Glu Ala Phe Lys Gln Lys Thr Ser Glu Ile Leu Ser His Ala His Ala
            435                 440                 445

Ala Leu Asp Gln Pro Leu Pro Thr Leu Lys Lys Gln Glu Glu Lys
    450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
        515                 520                 525

Glu Lys Phe Lys Leu Asn Phe Gln Met Pro Thr Leu Ala Ser Gly Trp
    530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
        595                 600                 605

Ser Thr Gln Leu Lys Ala Val Thr Ala His Phe Gln Thr His Thr Thr
    610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
        675                 680                 685

Lys Thr Thr Ser Ile Asp Leu Ser Ser Leu Arg Pro Ser Ser Gln Tyr
    690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
        755                 760                 765

Phe Ser Pro Glu Asn Leu Ala Lys Thr Ser Ile Lys Leu Asn Gly Gln
    770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
```

```
                820             825             830
Arg Leu Ser His Asp Leu Ser Asp Glu Ala Arg Ala Leu Leu Pro Asn
            835             840             845

Val Ile Thr Lys Glu Val Ser His Glu Ile Ile Lys Asp Arg Arg Phe
850             855             860

Thr Ser Asp Lys Phe Phe Phe His Val Pro Ile Thr Leu Asn Tyr Gln
865             870             875             880

Ala Ala Asn Ser Pro Ser Lys Phe Asn Gln Arg Val Asn Ala Tyr Leu
            885             890             895

Lys Glu His Pro Glu Thr Pro Ile Ile Gly Ile Asp Arg Gly Glu Arg
            900             905             910

Asn Leu Ile Tyr Ile Thr Val Ile Asp Ser Thr Gly Lys Ile Leu Glu
            915             920             925

Gln Arg Ser Leu Asn Thr Ile Gln Gln Phe Asp Tyr Gln Lys Lys Leu
            930             935             940

Asp Asn Arg Glu Lys Glu Arg Val Ala Ala Arg Gln Ala Trp Ser Val
945             950             955             960

Val Gly Thr Ile Lys Asp Leu Lys Gln Gly Tyr Leu Ser Gln Val Ile
            965             970             975

His Glu Ile Val Asp Leu Met Ile His Tyr Gln Ala Val Val Val Leu
            980             985             990

Glu Asn Leu Asn Phe Gly Phe Lys Ser Lys Arg Thr Gly Ile Ala Glu
            995             1000            1005

Lys Ala Val Tyr Gln Gln Phe Glu Lys Met Leu Ile Asp Lys Leu
            1010            1015            1020

Asn Cys Leu Val Leu Lys Asp Tyr Pro Ala Glu Lys Val Gly Gly
            1025            1030            1035

Val Leu Asn Pro Tyr Gln Leu Thr Asp Gln Phe Thr Ser Phe Ala
            1040            1045            1050

Lys Met Gly Thr Gln Ser Gly Phe Leu Phe Tyr Val Pro Ala Pro
            1055            1060            1065

Tyr Thr Ser Lys Ile Asp Pro Leu Thr Gly Phe Val Asp Pro Phe
            1070            1075            1080

Val Trp Lys Thr Ile Lys Asn His Glu Ser Arg Lys His Phe Leu
            1085            1090            1095

Glu Gly Phe Asp Phe Leu His Tyr Asp Val Lys Thr Gly Asp Phe
            1100            1105            1110

Ile Leu His Phe Lys Met Asn Arg Asn Leu Ser Phe Gln Arg Gly
            1115            1120            1125

Leu Pro Gly Phe Met Pro Ala Trp Asp Ile Val Phe Glu Lys Asn
            1130            1135            1140

Glu Thr Gln Phe Asp Ala Lys Gly Thr Pro Phe Ile Ala Gly Lys
            1145            1150            1155

Arg Ile Val Pro Val Ile Glu Asn His Arg Phe Thr Gly Arg Tyr
            1160            1165            1170

Arg Asp Leu Tyr Pro Ala Asn Glu Leu Ile Ala Leu Leu Glu Glu
            1175            1180            1185

Lys Gly Ile Val Phe Arg Asp Gly Ser Asn Ile Leu Pro Lys Leu
            1190            1195            1200

Leu Glu Asn Asp Asp Ser His Ala Ile Asp Thr Met Val Ala Leu
            1205            1210            1215

Ile Arg Ser Val Leu Gln Met Arg Asn Ser Asn Ala Ala Thr Gly
            1220            1225            1230
```

| Glu | Asp | Tyr | Ile | Asn | Ser | Pro | Val | Arg | Asp | Leu | Asn | Gly | Val | Cys |
| --- | --- | --- | --- | --- | --- | --- | --- | --- | --- | --- | --- | --- | --- | --- |
| 1235 | | | | | 1240 | | | | | 1245 | | | | |

| Phe | Asp | Ser | Arg | Phe | Gln | Asn | Pro | Glu | Trp | Pro | Met | Asp | Ala | Asp |
| --- | --- | --- | --- | --- | --- | --- | --- | --- | --- | --- | --- | --- | --- | --- |
| 1250 | | | | | 1255 | | | | | 1260 | | | | |

| Ala | Asn | Gly | Ala | Tyr | His | Ile | Ala | Leu | Lys | Gly | Gln | Leu | Leu | Leu |
| --- | --- | --- | --- | --- | --- | --- | --- | --- | --- | --- | --- | --- | --- | --- |
| 1265 | | | | | 1270 | | | | | 1275 | | | | |

| Asn | His | Leu | Lys | Glu | Ser | Lys | Asp | Leu | Lys | Leu | Gln | Asn | Gly | Ile |
| --- | --- | --- | --- | --- | --- | --- | --- | --- | --- | --- | --- | --- | --- | --- |
| 1280 | | | | | 1285 | | | | | 1290 | | | | |

| Ser | Asn | Gln | Asp | Trp | Leu | Ala | Tyr | Ile | Gln | Glu | Leu | Arg | Asn | Gly |
| --- | --- | --- | --- | --- | --- | --- | --- | --- | --- | --- | --- | --- | --- | --- |
| 1295 | | | | | 1300 | | | | | 1305 | | | | |

| Gly | Arg | Ser | Ser | Asp | Asp | Glu | Ala | Thr | Ala | Asp | Ser | Gln | His | Ala |
| --- | --- | --- | --- | --- | --- | --- | --- | --- | --- | --- | --- | --- | --- | --- |
| 1310 | | | | | 1315 | | | | | 1320 | | | | |

| Ala | Pro | Pro | Lys | Lys | Lys | Arg | Lys | Val | Gly | Gly | Ser | Gly | Gly | Gly |
| --- | --- | --- | --- | --- | --- | --- | --- | --- | --- | --- | --- | --- | --- | --- |
| 1325 | | | | | 1330 | | | | | 1335 | | | | |

| Ser | Gly | Gly | Gly | Ser | Gly | Gly | Gly | Arg | His | His | His | His | His | His |
| --- | --- | --- | --- | --- | --- | --- | --- | --- | --- | --- | --- | --- | --- | --- |
| 1340 | | | | | 1345 | | | | | 1350 | | | | |

<210> SEQ ID NO 156
<211> LENGTH: 1631
<212> TYPE: DNA
<213> ORGANISM: Artificial Sequence
<220> FEATURE:
<223> OTHER INFORMATION: GFP coding DNA template

<400> SEQUENCE: 156

| aagtaatcaa ttacggggtc attagttcat agcccatata tggagttccg cgttacataa | 60 |
| --- | --- |
| cttacggtaa atggcccgcc tggctgaccg cccaacgacc cccgcccatt gacgtcaata | 120 |
| atgacgtatg ttcccatagt aacgccaata gggactttcc attgacgtca atgggtggag | 180 |
| tatttacggt aaactgccca cttggcagta catcaagtgt atcatatgcc aagtacgccc | 240 |
| cctattgacg tcaatgacgg taaatggccc gcctggcatt atgcccagta catgacctta | 300 |
| tgggactttc ctacttggca gtacatctac gtattagtca tcgctattac catggtgatg | 360 |
| cggttttggc agtacatcaa tgggcgtgga tagcggtttg actcacgggg atttccaagt | 420 |
| ctccacccca ttgacgtcaa tgggagtttg ttttggcacc aaaatcaacg ggactttcca | 480 |
| aaatgtcgta caactccgcc ccattgacg caaatgggcg gtaggcgtgt acggtgggag | 540 |
| gtctatataa gcagagctgg tttagtgaac cgtcagatcc gctagcgcta ccggtcgcca | 600 |
| ccatggtgag caagggcgag gagctgttca ccggggtggt gcccatcctg gtcgagctgg | 660 |
| acggcgacgt aaacggccac aagttcagcg tgtccggcga gggcgagggc gatgccacct | 720 |
| acggcaagct gaccctgaag ttcatctgca ccaccggcaa gctgcccgtg ccctggccca | 780 |
| ccctcgtgac caccctgacc tacggcgtgc agtgcttcag ccgctacccc gaccacatga | 840 |
| agcagcacga cttcttcaag tccgccatgc ccgaaggcta cgtccaggag cgcaccatct | 900 |
| tcttcaagga cgacggcaac tacaagaccc gcgccgaggt gaagttcgag ggcgacaccc | 960 |
| tggtgaaccg catcgagctg aagggcatcg acttcaagga ggacggcaac atcctgggc | 1020 |
| acaagctgga gtacaactac aacagccaca cgtctatat catggccgac aagcagaaga | 1080 |
| acggcatcaa ggtgaacttc aagatccgcc acaacatcga ggacggcagc gtgcagctcg | 1140 |
| ccgaccacta ccagcagaac accccatcg cgacggccc cgtgctgctg cccgacaacc | 1200 |
| actacctgag cacccagtcc gccctgagca agacccaa cgagaagcgc gatcacatgg | 1260 |
| tcctgctgga gttcgtgacc gccgcgggga tcactctcgg catggacgag ctgtacaagt | 1320 |

```
ccggactcag atctcgagct caagcttcga attctgcagt cgacggtacc gcgggcccgg    1380
gatccaccgg atctagataa ctgatcataa tcagccatac cacatttgta gaggttttac    1440
ttgctttaaa aaacctccca cacctccccc tgaacctgaa acataaaatg aatgcaattg    1500
ttgttgttaa cttgtttatt gcagcttata atggttacaa ataaagcaat agcatcacaa    1560
atttcacaaa taaagcattt ttttcactgc attctagttg tggtttgtcc aaactcatca    1620
atgtatctta a                                                        1631
```

```
<210> SEQ ID NO 157
<211> LENGTH: 42
<212> TYPE: RNA
<213> ORGANISM: Artificial Sequence
<220> FEATURE:
<223> OTHER INFORMATION: DNMT1 crRNA

<400> SEQUENCE: 157 aauucuacu guguagauc ugauggucca ugucuguuac uc                          42

<210> SEQ ID NO 158
<211> LENGTH: 14
<212> TYPE: PRT
<213> ORGANISM: Artificial Sequence
<220> FEATURE:
<223> OTHER INFORMATION: FSD5, FSD16, FSD18, FSD19, FSD20, FSD22, and
      FSD23 consensus
<220> FEATURE:
<221> NAME/KEY: MISC_FEATURE
<222> LOCATION: (5)..(5)
<223> OTHER INFORMATION: N, Q, S, T, K, R, H, D, E, C, Y
      (polar/hydrophilic residues)
<220> FEATURE:
<221> NAME/KEY: MISC_FEATURE
<222> LOCATION: (7)..(7)
<223> OTHER INFORMATION: G, A, V, L, I, P, Y, F, W, M, C
      (non-polar/hydrophobic)
<220> FEATURE:
<221> NAME/KEY: MISC_FEATURE
<222> LOCATION: (10)..(10)
<223> OTHER INFORMATION: Any amino acid other than proline
<220> FEATURE:
<221> NAME/KEY: MISC_FEATURE
<222> LOCATION: (11)..(11)
<223> OTHER INFORMATION: N, Q, S, T, K, R, H, D, E, C, Y
      (polar/hydrophilic residues)
<220> FEATURE:
<221> NAME/KEY: MISC_FEATURE
<222> LOCATION: (12)..(12)
<223> OTHER INFORMATION: N, Q, S, T, K, R, H, D, E, C, Y
      (polar/hydrophilic residues)
<220> FEATURE:
<221> NAME/KEY: MISC_FEATURE
<222> LOCATION: (13)..(13)
<223> OTHER INFORMATION: N, Q, S, T, K, R, H, D, E, C, Y
      (polar/hydrophilic residues)
<220> FEATURE:
<221> NAME/KEY: MISC_FEATURE
<222> LOCATION: (13)..(13)
<223> OTHER INFORMATION: N, Q, S, T, K, R, H, D, E, C, Y
      (polar/hydrophilic residues)

<400> SEQUENCE: 158

Leu Lys Leu Trp Asn Arg Asn Leu Lys Asn Asn Asn Asn Gly
1               5                   10

<210> SEQ ID NO 159
<211> LENGTH: 8
<212> TYPE: PRT
<213> ORGANISM: Artificial Sequence
<220> FEATURE:
<223> OTHER INFORMATION: FSD5, FSD16, FSD18, FSD19, FSD20, FSD22, FSD23
```

```
                              concensus
<220> FEATURE:
<221> NAME/KEY: MISC_FEATURE
<222> LOCATION: (3)..(3)
<223> OTHER INFORMATION: G, A, V, L, I, P, Y, F, W, M, C
      (non-polar/hydrophbic)
<220> FEATURE:
<221> NAME/KEY: MISC_FEATURE
<222> LOCATION: (4)..(4)
<223> OTHER INFORMATION: Any amino acid other than proline
<220> FEATURE:
<221> NAME/KEY: MISC_FEATURE
<222> LOCATION: (7)..(7)
<223> OTHER INFORMATION: N, Q, S, T, K, R, H, D, E, C, Y
      (polar/hydrophilic)

<400> SEQUENCE: 159

Arg Arg Asn Asn Ala Lys Asn Ala
1               5

<210> SEQ ID NO 160
<211> LENGTH: 42
<212> TYPE: RNA
<213> ORGANISM: Artificial Sequence
<220> FEATURE:
<223> OTHER INFORMATION: B2M crRNA (Cas9)

<400> SEQUENCE: 160
gaguagcgcg agcacagcua guuuuagagc uaugcuguuu ug                    42

<210> SEQ ID NO 161
<211> LENGTH: 39
<212> TYPE: RNA
<213> ORGANISM: Artificial Sequence
<220> FEATURE:
<223> OTHER INFORMATION: B2M exon 2 crRNA-1 (Cpf1)

<400> SEQUENCE: 161
aauuucuacu guuguagaua uccauccgac auugaaguu                        39

<210> SEQ ID NO 162
<211> LENGTH: 41
<212> TYPE: RNA
<213> ORGANISM: Artificial Sequence
<220> FEATURE:
<223> OTHER INFORMATION: B2M exon 2 crRNA-2 (Cpf1)

<400> SEQUENCE: 162
aauuucuacu cuuguagauc cgauauuccu cagguacucc a                     41

<210> SEQ ID NO 163
<211> LENGTH: 39
<212> TYPE: RNA
<213> ORGANISM: Artificial Sequence
<220> FEATURE:
<223> OTHER INFORMATION: CBLB crRNA

<400> SEQUENCE: 163
aauuucuacu cuuguagauc uuucuuccuu uaggagaca                        39

<210> SEQ ID NO 164
<211> LENGTH: 39
<212> TYPE: RNA
<213> ORGANISM: Artificial Sequence
<220> FEATURE:
<223> OTHER INFORMATION: GSK3 crRNA

<400> SEQUENCE: 164
```

```
aauuucuacu cuuguagaua agaacuaaaa uuccagaug                                39

<210> SEQ ID NO 165
<211> LENGTH: 39
<212> TYPE: RNA
<213> ORGANISM: Artificial Sequence
<220> FEATURE:
<223> OTHER INFORMATION: NKG2A crRNA

<400> SEQUENCE: 165
aauuucuacu cuuguagaug gggcagauuc aggucugag                                39

<210> SEQ ID NO 166
<211> LENGTH: 39
<212> TYPE: RNA
<213> ORGANISM: Artificial Sequence
<220> FEATURE:
<223> OTHER INFORMATION: B2M crRNA-E

<400> SEQUENCE: 166
aauuucuacu cuuguagaua uccauccgac auugaaguu                                39

<210> SEQ ID NO 167
<211> LENGTH: 41
<212> TYPE: RNA
<213> ORGANISM: Artificial Sequence
<220> FEATURE:
<223> OTHER INFORMATION: B2M crRNA-J

<400> SEQUENCE: 167
aauuucuacu cuuguagauc cgauauuccu cagguacucc a                             41

<210> SEQ ID NO 168
<211> LENGTH: 41
<212> TYPE: RNA
<213> ORGANISM: Artificial Sequence
<220> FEATURE:
<223> OTHER INFORMATION: B2M crRNA-G

<400> SEQUENCE: 168
aauuucuacu cuuguagauu uagagucucg ugauguuuaa g                             41
```

UNITED STATES PATENT AND TRADEMARK OFFICE
CERTIFICATE OF CORRECTION

PATENT NO. : 9,982,267 B2  
APPLICATION NO. : 15/666139  
DATED : May 29, 2018  
INVENTOR(S) : Thomas Del'Guidice, Jean-Pascal Lepetit-Stoffaes and David Guay Page 1 of 1

It is certified that error appears in the above-identified patent and that said Letters Patent is hereby corrected as shown below:

In the Claims

Column 253, Line 14, Claim 14:  
Replace "combination of the amino acids: A, L, K, or"  
With --combination of the amino acids: A, L, K, or R;--

Signed and Sealed this  
Tenth Day of September, 2019

Andrei Iancu  
*Director of the United States Patent and Trademark Office*